(12) United States Patent
Pharkya et al.

(10) Patent No.: US 10,487,342 B2
(45) Date of Patent: Nov. 26, 2019

(54) MICROORGANISMS AND METHODS FOR THE PRODUCTION OF BUTADIENE USING ACETYL-COA

(71) Applicant: Genomatica, Inc., San Diego, CA (US)

(72) Inventors: Priti Pharkya, San Diego, CA (US); Anthony P. Burgard, Bellefonte, PA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 15/325,396

(22) PCT Filed: Jul. 2, 2015

(86) PCT No.: PCT/US2015/038945
§ 371 (c)(1),
(2) Date: Jan. 10, 2017

(87) PCT Pub. No.: WO2016/007365
PCT Pub. Date: Jan. 14, 2016

(65) Prior Publication Data
US 2017/0191085 A1    Jul. 6, 2017

Related U.S. Application Data

(60) Provisional application No. 62/023,786, filed on Jul. 11, 2014.

(51) Int. Cl.
| | | |
|---|---|---|
| *C12P 5/02* | (2006.01) | |
| *C12N 15/52* | (2006.01) | |
| *C12P 3/00* | (2006.01) | |
| *C12P 7/40* | (2006.01) | |
| *C01B 3/00* | (2006.01) | |
| *C08F 36/06* | (2006.01) | |
| *C08F 36/14* | (2006.01) | |
| *C12N 9/04* | (2006.01) | |
| *C12N 9/02* | (2006.01) | |
| *C12N 9/10* | (2006.01) | |
| *C12N 9/12* | (2006.01) | |

(52) U.S. Cl.
CPC ............. *C12P 5/026* (2013.01); *C01B 3/00* (2013.01); *C08F 36/06* (2013.01); *C08F 36/14* (2013.01); *C12N 9/0006* (2013.01); *C12N 9/0008* (2013.01); *C12N 9/0067* (2013.01); *C12N 9/10* (2013.01); *C12N 9/12* (2013.01); *C12N 15/52* (2013.01); *C12P 3/00* (2013.01); *C12P 7/40* (2013.01); *C12Y 101/02007* (2013.01); *C12Y 101/03013* (2013.01); *C12Y 102/99003* (2013.01); *Y02E 50/343* (2013.01); *Y02E 60/324* (2013.01)

(58) Field of Classification Search
None
See application file for complete search history.

(56) References Cited

U.S. PATENT DOCUMENTS

| | | | |
|---|---|---|---|
| 4,570,029 | A | 2/1986 | Kulprathipanja et al. |
| 4,703,007 | A | 10/1987 | Mulholland et al. |
| 4,740,222 | A | 4/1988 | Mehra |
| 5,958,745 | A | 9/1999 | Gruys et al. |
| 6,686,194 | B1 | 2/2004 | Mutzel et al. |
| 7,127,379 | B2 | 10/2006 | Palsson et al. |
| 2002/0012939 | A1 | 1/2002 | Palsson |
| 2002/0168654 | A1 | 11/2002 | Maranas et al. |
| 2003/0059792 | A1 | 3/2003 | Palsson et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2009/0047719 | A1 | 2/2009 | Burgard et al. |
| 2010/0330635 | A1* | 12/2010 | Burgard ................ C12N 15/52 435/158 |
| 2011/0000125 | A1 | 1/2011 | McDaniel et al. |

(Continued)

FOREIGN PATENT DOCUMENTS

| | | | |
|---|---|---|---|
| EP | 2017344 A1 | 1/2009 | |
| WO | WO 2002/055995 A2 | 7/2002 | |

(Continued)

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Draths et al. Environmentally Compatible Synthesis of Adipic Acid from D-Glucose. J. Am. Chem. Soc. 1994, 116: 399-400.*

(Continued)

*Primary Examiner* — Iqbal H Chowdhury
(74) *Attorney, Agent, or Firm* — Jones Day

(57) ABSTRACT

The invention provides non-naturally occurring microbial organisms containing butadiene or 2,4-pentadienoate pathways comprising at least one exogenous nucleic acid encoding a butadiene or 2,4-pentadienoate pathway enzyme expressed in a sufficient amount to produce butadiene or 2,4-pentadienoate. The organism can further contain a hydrogen synthesis pathway. The invention additionally provides methods of using such microbial organisms to produce butadiene or 2,4-pentadienoate by culturing a non-naturally occurring microbial organism containing butadiene or 2,4-pentadienoate pathways as described herein under conditions and for a sufficient period of time to produce butadiene or 2,4-pentadienoate. Hydrogen can be produced together with the production of butadiene or 2,4-pentadienoate.

23 Claims, 5 Drawing Sheets

(56) References Cited

U.S. PATENT DOCUMENTS

| | | | |
|---|---|---|---|
| 2011/0207203 A1 | 8/2011 | Reppas et al. | |
| 2011/0300597 A1* | 12/2011 | Burk | C12N 15/52 435/167 |
| 2012/0003652 A1 | 1/2012 | Reeves et al. | |
| 2012/0021478 A1* | 1/2012 | Osterhout | C12N 15/52 435/167 |
| 2012/0156735 A1* | 6/2012 | Dauner | C12N 9/0008 435/115 |
| 2013/0109064 A1 | 5/2013 | Osterhout et al. | |
| 2014/0058056 A1* | 2/2014 | Burgard | C12P 7/18 528/85 |
| 2014/0106424 A1* | 4/2014 | Marrs | C12N 9/0004 435/160 |
| 2014/0155567 A1 | 6/2014 | Burk et al. | |

FOREIGN PATENT DOCUMENTS

| | | |
|---|---|---|
| WO | WO 2003/106998 A1 | 12/2003 |
| WO | WO 2004/024876 A2 | 3/2004 |
| WO | WO 2007/141208 A2 | 12/2007 |
| WO | WO 2008/119735 A1 | 10/2008 |
| WO | WO 2009/014437 A1 | 1/2009 |
| WO | WO 2010/068953 A2 | 6/2010 |
| WO | WO 2011/076691 A1 | 6/2011 |
| WO | WO 2011/140171 A2 | 11/2011 |
| WO | WO 2013/057194 A1 | 4/2013 |
| WO | WO 2013/090915 A1 | 6/2013 |
| WO | WO 2013/192183 A1 | 12/2013 |
| WO | WO 2014/055649 A1 | 4/2014 |
| WO | WO 2014/063156 A2 | 4/2014 |

OTHER PUBLICATIONS

Aberhart et al., "Stereospecific hydrogen loss in the conversion of [2H7]isobutyrate to beta-hydroxyisobutyrate in Pseudomonas putida. The stereochemistry of beta-hydroxyisobutyrate dehydrogenase," *J. Chem. Soc. Perkin* 1, 6:1404-1406 (1979).
Alber et al., "Malonyl-Coenzyme A Reductase in the Modified 3-Hydroxypropionate Cycle for Autotrophic Carbon Fixation in Archaeal Metallosphaera and *Sulfolobus* spp," *J. Bacteriol.*, 188(24):8551-8559 (2006).
Alber et al., "Study of an alternate glyoxylate cycle for acetate assimilation by Rhodobacter sphaeroides," *Mol. Microbiol.*, 61(2):297-309 (2006).
Alhapel et al., "Molecular and functional analysis of nicotinate catabolism in Eubacterium barkeri," *Proc. Natl. Acad. Sci.*, 103:12341-12346 (2006).
Andreesen et al., "Formate dehydrogenase of Clostridium thermoaceticum: incorporation of selenium-75, and the effects of selenite, molybdate, and tungstate on the enzyme," *J. Bacteriol.*, 116(2):867-873 (1973).
Angov, "Codon usage: Mature's roadmap to expression and folding of proteins," *Biotechnol. J.*, 6(6):650-659 (2011).
Araujo et al., "Before it gets started: Regulating Translation at the 5' UTR," *Comparative and Functional Genomics*, Article ID 475731, 8 pages (2012).
Arraiano et al., "The critical role of RNA processing and degredation in the control of gene expression," *FEMS Microbiol. Rev.*, 34(5):883-932 (2010).
Atsumi et al., "Metabolic engineering of *Escherichia coli* for 1-butanol production," *Metabol. Eng.*, 10:305-311 (2008).
Atsumi et al., "Non-fermentative pathways for synthesis of branched-chain higher alcohols as biofuels," *Nature*, 451:86-89 (2008).
Atteia et al., "Pyruvate Formate-lyase and a Novel Route of Eukaryotic ATP Synthesis in Chlamydomonas Mitochondria," *J. Biol. Chem.*, 281:9909-9918 (2006).
Azcarate-Peril et al., "Transcriptional and functional analysis of oxalyl-coenzyme A (CoA) decarboxylase and formyl-CoA transferase genes from Lactobacillus acidophilus," *Appl. Environ. Microbiol.*, 72(3):1891-1899 (2006).

Baetz et al., "Purification and characterization of formyl-coenzyme A transferase from Oxalobacter formigenes," *J. Bacteriol.*, 172(7):3537-3540 (1990).
Baker et al., "Substrate specificity, substrate channeling, and allostery in BphJ: an acylating aldehyde dehydrogenase associated with the pyruvate aldolase BphI," *Biochemistry*, 51(22):4558-4567 (2012).
Barker et al., "Butyryl-CoA: acetoacetate CoA-transferase from a lysine-fermenting Clostridium," *J. Biol. Chem.*, 253(4):1219-1225 (1978).
Barker et al., "Pathway of lysine degradation in Fusobacterium nucleatum," *J. Bacteriol.*, 152(1):201-207 (1982).
Barthelmebs et al., "Expression in *Escherichia coli* of Native and Chimeric Phenolic Acid Decarboxylases with Modified Enzymatic Activities and Method for Screening Recombinant *E. coli* Strains Expressing These Enzymes," *Appl. Environ. Microbiol.*, 67(3):1063-1069 (2001).
Basson et al., "*Saccharomyces cerevisiae* contains two functional genes encoding 3-hydroxy-3-methylglutaryl-coenzyme A reductase," *Proc. Natl. Acad. Sci. USA*, 83(15):5563-5567 (1986).
Berg et al., "A 3-Hydroxypropionate/4-Hydroxybutyrate Autotrophic Carbon Dioxide Assimilation Pathway in Archaea," *Science*, 318:1782-1786 (2007).
Bergquist et al., "Degenerate oligonucleotide gene shuffling (DOGS) and random drift mutagenesis (RNDM): Two complementary techniques for enzyme evolution," *Biomol. Eng.*, 22:63-72 (2005).
Bergquist et al., "Degenerate Oligonucleotide Gene Shuffling," *Methods Mol. Biol.*, 352:191-204 (2007).
Bernhard et al., "Functional and structural role of the cytochrome b subunit of the membrane-bound hydrogenase complex of Alcaligenes eutrophus H16," *Eur. J Biochem.*, 248:179-186 (1997).
Bianchi et al., "*Escherichia coli* ferredoxin NADP+ reductase: activation of *E. coli* anaerobic ribonucleotide reduction, cloning of the gene (fpr), and overexpression of the protein," *Biochemistry*, 175(6):1590-1595 (1993).
Binstock et al., "Fatty Acid Oxidation Complex from *Escherichia coli*," *Methods Enzymol.*, 71:403-411 (1981).
Blanco et al., "Critical catalytic functional groups in the mechanism of aspartate-ß-semialdehyde dehydrogenase," *Acta Crystallogr. D Biol. Crystallogr.*, 60:1808-1815 (2004).
Blanco et al., "The role of substrate-binding groups in the mechanism of aspartate-ß-semialdehyde dehydrogenase," *Acta Crystallogr. D Biol. Crystallogr.*, 60:1388-1395 (2004).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.*, 123(3):563-569 (1982).
Bleykasten-Grosshans et al., "Transposable elements in yeasts," *C. R. Biologies*, 334:679-686 (2011).
Bochar et al., "3-Hydroxy-3-Methylglutaryl Coenzyme A Reductase of Sulfolobus solfataricus: DNA Sequence, Phylogeny, Expression in *Escherichia coli* of the hmgA Gene, and Purification and Kinetic Characterization of the Gene Product," *J. Bacteriol.*, 179:3632-3638 (1997).
Bock et al., "Purification and Characterization of Two Extremely Thermostable Enzymes, Phosphate Acetyltransferase and Acetate Kinase, from the Hyperthermophilic Eubacterium Thermotoga maritima," *J. Bacteriol.*, 181(6):1861-1867 (1999).
Boles et al., "Characterization of a Glucose-Repressed Pyruvate Kinase (Pyk2p) in *Saccharomyces cerevisiae* That is Catalytically Insensitive to Fructose-1,6-Bisphosphate," *J. Bacteriol.*, 179(9):2987-2993 (1997).
Bonnarme et al., "Itaconate Biosynthesis in Aspergillus terreus," *J. Baceriol.*, 177:3573-3578 (1995).
Bose et al., "Genetic Analysis of the Methanol- and Methylamine-Specific Methyltransferase 2 Genes of Methanosarcina acetivorans C2A," *J. Bacteriol.*, 190(11):4017-4026 (2008).
Bower et al., "Cloning, Sequencing, and Characterization of the Bacillus subtilis Biotin Biosynthetic Operon," *J. Bacteriol.*, 178(14):4122-4130 (1996).
Boynton et al., "Cloning, Sequencing, and Expression of Clustered Genes Encoding ß-Hydroxybutyryl-Coenzyme a (CoA) Dehydrogenase, Crotonase, and Butyryl-CoA Dehydrogenase from Clostridium acetobutylicum ATCC 824," *J. Bacteriol.*, 178(11):3015-3024 (1996).

(56) References Cited

OTHER PUBLICATIONS

Branlant et al., "Nucleotide sequence of the *Escherichia coli* gap gene: Different evolutionary behavior of the NAD+-binding domain and of the catalytic domain of D-glyceraldehyde-3-phosphate dehydrogenase," *Eur. J. Biochem.*, 150:61-66 (1985).

Brasen et al., "Unusual ADP-forming acetyl-coenzyme A synthetases from the mesophilic halophilic euryarchaeon Haloarcula marismortui and from the hyperthermophilic crenarchaeon Pyrobaculum aerophilum," *Arch. Microbiol.*, 182:277-287 (2004).

Bravo et al., "Reliable, Sensitive, Rapid and Quantitative Enzyme-Based Assay for Gamma-Hydroxybutyric Acid (GHB)," *J. Forensic Sci.*, 49(2):379-387 (2004).

Breitkreuz et al., "A Novel gamma-Hydroxybutyrate Dehydrogenase: identification and expression of an *Arabidopsis* cDNA and potential role under oxygen deficiency," *J. Biol. Chem.*, 278(42):41552-41556 (2003).

Brizio et al., "Over-expression in *Escherichia coli*, functional characterization and refolding of rat dimethylglycine dehydrogenase," *Protein Expr. Purif.*, 37(2):434-442 (2004).

Brown et al., "The enzymic interconversion of acetate and acetyl-coenzyme A in *Escherichia coli*," *J. Gen. Microbiol.*, 102:327-336 (1977).

Brugger et al., "Characteristics of fungal phytases from Aspergillus fumigatus and Sartorya fumigate," *Appl. Microbiol. Biotechnol.*, 63:383-389 (2004).

Buck et al., "Primary structure of the succinyl-CoA synthetase of *Escherichia coli*," *Biochem.*, 24:6245-6252 (1985).

Buckel et al., "ATP-driven electron transfer in enzymatic radical reactions," *Curr. Opin. Chem. Biol.*, 8:462-467 (2004).

Buckel et al., "Radical Enzymes in Anaerobes," *Annu. Rev. Microbiol.*, 60:27-49 (2006).

Buckel et al., "Radical-mediated dehydration reactions in anaerobic bacteria," *Biol. Chem.*, 386:951-959 (2005).

Buckel, "Unusual enzymes involved in five pathways of glutamate fermentation," *Appl. Microbiol. Biotechnol.*, 57(3):263-273 (2001).

Burgard et al., "Minimal Reaction Sets for *Escherichia coli* Metabolism under Different Growth Requirements and Uptake Environments," *Biotechnol. Prog.*, 17:791-797 (2001).

Burgard et al., "OptKnock: A Bilevel Programming Framework for Identifying Gene Knockout Strategies for Microbial Strain Optimization," *Biotechnol. Bioeng.*, 84(6):647-657 (2003).

Burgdorf et al., "The Soluble NAD+-Reducing [NiFe]-Hydrogenase from Ralstonia eutropha H16 Consists of Six Subunits and Can Be Specifically Activated by NADPH," *J. Bacteriol.*, 187(9):3122-3132 (2005).

Burke et al., "The isolation, characterization, and sequence of the pyruvate kinase gene of *Saccharomyces cerevisiae*," *J. Biol. Chem.*, 258(4):2193-2201 (1983).

Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.*, 120(31):7665-7675 (1998).

Buu et al., "Functional Characterization and Localization of Acetyl-CoA Hydrolase, Ach1p, in *Saccharomyces cerevisiae*," *J. Biol. Chem.*, 278(19):17203-17209 (2003).

Cahyanto et al., "Regulation of aspartokinase, aspartate semialdehyde dehydrogenase, dihydrodipicolinate synthase and dihydrodipicolinate reductase in Lactobacillus plantarum," *Microbiology*, 152:105-112 (2006).

Campbell et al., "A new *Escherichia coli* metabolic competency: growth on fatty acids by a novel anaerobic b-oxidation pathway," *Mol Microbiol.*, 47(3):793-805 (2003).

Carter et al., "Ferrous ion-dependent L-serine dehydratase from Clostridium acidiurici," *J. Bacteriol.*, 109(2):757-763 (1972).

Cary et al., "Cloning and expression of Clostridium acetobutylicum ATCC 824 acetoacetyl-coenzyme A:acetate/butyrate:coenzyme A-transferase in *Escherichia coli*," *Appl. Environ. Microbiol.*, 56(6):1576-1583 (1990).

Casas et al., "Pentadiene production from potassium sorbate by osmotolerant yeasts," *Int. J. Food Microbiol.*, 94(1):93-96 (2004).

Castel et al., "RNA interference in the nucleus: roles for small RNAs in transcription, epigenetics and beyond," *Nat. Rev. Genet.*, 14(2):100-112 (2013).

Castillo et al., "A Mutant D-Fructose-6-Phosphate Aldolase (Ala129Ser) with Improved Affinity towards Dihydroxyacetone for the Synthesis of Polyhydroxylated Compounds," *Adv. Synth. Catalys.*, 352(6):1039-1046 (2010).

Chao et al., "The Effects of Wall Populations on Coexistence of Bacteria in the Liquid Phase of Chemostat Cultures," *J. Gen. Microbiol.*, 131:1229-1236 (1985).

Chen et al., "Malonate uptake and metabolism in *Saccharomyces cerevisiae*," *Appl. Biochem. Biotechnol.*, 171(1):44-62 (2013).

Chistoserdova et al., "Genetics of the serine cycle in Methylobacterium extorquens AM1: cloning, sequence, mutation, and physiological effect of glyA, the gene for serine hydroxymethyltransferase," *J. Bacteriol.*, 176(21):6759-6762 (1994).

Chopra et al., "Expression, purification, and biochemical characterization of *Mycobacterium tuberculosis* aspartate decarboxylase, PanD," *Protein Expr. Purif.*, 25:533-540 (2002).

Chowdhury et al., "3-Hydroxyisobutyrate dehydrogenase from Pseudomonas putida E23: purification and characterization," *Biosci. Biotechnol. Biochem.*, 60(12):2043-2047 (1996).

Chowdhury et al., "Cloning and Overexpression of the 3-Hydroxyisobutyrate Dehydrogenase Gene from Pseudomonas putida E23," *Biosci. Boiotechnol. Biochem.*, 67(2):438-441 (2003).

Cicchillo et al., "*Escherichia coli* L-serine deaminase requires a [4Fe-4S] cluster in catalysis," *J. Biol. Chem.*, 279(31):32418-32425 (2004).

Clark et al., "Purification and properties of 5,10-methylenetetrahydrofolate reductase, an iron-sulfur flavoprotein from Clostridium formicoaceticum," *J. Biol. Chem.*, 259(17):10845-10849 (1984).

Clausen et al., "PAD1 encodes phenylacrylic acid decarboxylase which confers resistance to cinnamic acid in *Saccharomyces cerevisiae*," *Gene*, 142:107-112 (1994).

Coco et al., "DNA shuffling method for generating highly recombined genes and evolved enzymes," *Nat. Biotechnol.*, 19:354-359 (2001).

Colonna et al., "Synthesis and radiocarbon evidence of terephthalate polyesters completely prepared from renewable resources," *Green Chem.*, 13:2543-2548 (2011).

Coppi et al., "The hydrogenases of Geobacter sulfurreducens: a comparative genomic perspective," *Microbiol.*, 151:1239-1254 (2005).

Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.*, 272(41):25659-25667 (1997).

Cracknell et al., "A kinetic and thermodynamic understanding of O2 tolerance in [NiFe]-hydrogenases," *Proc. Natl. Acad. Sci. USA*, 106(49):20681-20686 (2009).

Crosby et al., "Structure-guided expansion of the substrate range of methylmalonyl coenzyme A synthetase (MatB) of Rhodopseudomonas palustris," *Appl. Environ. Microbiol.*, 78(18):6619-6629 (2012).

Currie et al., "Authentication and dating of biomass componenets of industrial materials; links to sustainable technology," *Nucl. Instr. Methods Phys. Res. B*, 172:281-287 (2000).

D'Ari et al., "Purification, characterization, cloning, and amino acid sequence of the bifunctional enzyme 5,10-methylenetetrahydrofolate dehydrogenase/5,10-methenyltetrahydrofolate cyclohydrolase from *Escherichia coli*," *J. Biol. Chem.*, 266(35):23953-23958 (1991).

Daigaku et al., "Loss of heterozygosity in yeast can occur by ultraviolet irradiation during the S phase of the cell cycle," *Mutation Research*, 600:177-183 (2006).

Das et al., "Characterization of a Corrinoid Protein Involved in the C1 Metabolism of Strict Anaerobic Bacterium Moorella thermoacetica," *Proteins*, 67:167-176 (2007).

Datsenko et al., "One-step inactivation of chromosomal genes in *Escherichia coli* K-12 using PCR products," *Proc. Natl. acad. Sci. USA*, 97(12):6640-6645 (2000).

Davis et al., "Overproduction of Acetyl-CoA Carboxylase Activity Increases the Rate of Fatty Acid Biosynthesis in *Escherichia coli*," *J. Biol. Chem.*, 275(37):28593-28598 (2000).

(56) References Cited

OTHER PUBLICATIONS

De Bok et al., "Two W-containing formate dehydrogenases (CO2-reductases) involved in syntrophic propionate oxidation by Syntrophobacter fumaroxidans," *Eur. J. Biochem.*, 270:2476-2485 (2003).
De Crecy et al., "Development of a novel continuous culture device for experimental evolution of bacterial populations," *Appl. Microbiol. Biotechnol.*, 77:489-496 (2007).
Deana, "Substrate specificity of a dicarboxyl-CoA: dicarboxylic acid coenzyme A transferase from rat liver mitochondria," *Biochem. Int.*, 26(4):767-773 (1992).
Di Gennaro et al., "Styrene lower catabolic pathway in Pseudomonas Xuorescens ST: identification and characterization of genes for phenylacetic acid degradation," *Arch. Microbiol.*, 188:117-125 (2007).
Diaz et al., "Characterization of the hca Cluster Encoding the Dioxygenolytic Pathway for Initial Catabolism of 3-Phenylpropionic Acid in *Escherichia coli* K-12," *J. Bacteriol.*, 180(11):2915-2923 (1998).
Dietrich et al., "High-Throughput Metabolic Engineering: Advances in Small-Molecule Screening and Selection," *Annu. Rev. Biochem.*, 79:563-590 (2010).
Dobbek et al., "Crystal structure of a carbon monoxide dehydrogenase reveals a [Ni—4Fe—5S] cluster," *Science*, 293:1281-1285 (2001).
Donovan et al., "Review: Optimizing inducer and culture conditions for expression of foreign proteins under the control of the lac promoter," *J. Ind. Microbiol.*, 16(3):145-154 (1996).
Doten et al., "Cloning and genetic organization of the pca gene cluster from Acinetobacter calcoaceticus," *J. Bacteriol.*, 169(7):3168-3174 (1987).
Drake et al., "Acetogenesis, Acetogenic Bacteria, and the Acetyl-CoA 'Woof/LjungdahL' Pathway: Past and Currect Perspectives," *Acetogenesis*, Chapman & Hall, New York, NY, pp. 3-60 (1994).
Drake et al., "Demonstration of hydrogenase in extracts of the homoacetate-fermenting bacterium Clostridium thermoaceticum," *J. Bacteriol.*, 150(2):702-709 (1982).
Drake et al., "Physiology of the thermophilic acetogen Moorella thermoacetica," *Res. Microbiol.*, 155:869-883 (2004).
Drevland et al., "Enzymology and Evolution of the Pyruvate Pathway to 2-Oxobutyrate in Methanocaldococcus jannaschii," *J. Bacteriol.*, 189(12):4391-4400 (2007).
Duncan et al., "Acetate Utilization and Butyryl Coenzyme A (CoA):Acetate-CoA Transferase in Butyrate-Producing Bacteria from the Human Large Intestine," *Appl. Environ. Microbiol.*, 68(10):5186-5190 (2002).
Dusch et al., "Expression of the Corynebacterium glutamicum panD Gene Encoding L-Aspartate-α-Decarboxylase Leads to Pantothenate Overproduction in *Escherichia coli,*" *Appl. Environ. Microbiol.*, 65(4):1530-1539 (1999).
Dwiarti et al., "Purification and Characterization of cis-Aconitic Acid Decarboxylase from Aspergillus terreus TN484-M1," *J. Biosci. Bioeng.*, 94(1):29-33 (2002).
Dykhuizen, "Chemostats Used for Studying Natural Selection and Adaptive Evoluation," *Methods Enzymol.*, 613-631 (1993).
Eaton, "p-Cumate Catabolic Pathway in Pseudomonas putida F1: Cloning and Characterization of DNA Carrying the cmt Operon," *J. Bacteriol.*, 178(5):1351-1362 (1996).
Eikmanns et al., "Crystallization and preliminary X-ray diffraction study of the green flavoenzyme 5-hydroxyvaleryl-CoA dehydratase/dehydrogenase from Clostridium aminovalericum," *Proteins*, 19(3):269-271 (1994).
Eikmanns et al., "Cystalline green 5-hydroxyvaleryl-CoA dehydratase from Clostridium aminovalericum," *Eur. J. Biochem.*, 197:661-668 (1991).
Faehnle et al., "A New Branch in the Family: Structure of Aspartate-ß-semialdehyde Dehydrogenase from Methanococcus jannaschii," *J. Mol. Biol.*, 353:1055-1068 (2005).
Fernandez-Valverde et al., "Purification of Pseudomonas putida acyl coenzyme A ligase active with a range of aliphatic and aromatic substrates," *Appl. Environ. Microbiol.*, 59:1149-1154 (1993).

Ferrandez et al., "Genetic characterization and expression in heterologous hosts of the 3-(3-hydroxyphenyl)propionate catabolic pathway of *Escherichia coli* K-12," *J. Bacteriol.*, 179(8):2573-2581 (1997).
Fong et al., "Description and Interpretation of Adaptive Evolution of *Escherichia coli* K-12 MG1655 by Using a Genome-Scale in Silico Metabolic Model," *J. Bacteriol.*, 185(21):6400-6408 (2003).
Fong et al., "In Silico Design and Adaptive Evolution of *Escherichia coli* for Production of Lactic Acid," *Biotechnol. Bioeng.*, 91:643-648 (2005).
Fong et al., "Metabolic gene-deletion strains of *Escherichia coli* evolve to computationally predicted growth phenotypes," *Nat. Genet.*, 36(10):1056-1058 (2004).
Fontaine et al., "Molecular Characterization and Transcriptional Analysis of adhE2, the Gene Encoding the NADH-Dependent Aldehyde/Alcohol Dehydrogenase Responsible for Butanol Production in Alcohologenic Cultures of Clostridium acetobutylicum ATCC 824," *J. Bacteriol.*, 184(3):821-830 (2002).
Ford et al., "Molecular properties of the lysl+gene and the regulation of alpha-aminoadipate reductase in Schizosaccharomyces pombe," *Curr. Gemet.*, 28:131-137 (1995).
Fox et al., "Characterization of the Region Encoding the CO-Induced Hydrogenase of Rhodospirillum rubrum," *J. Bacteriol.*, 178(21):6200-6208 (1996).
Fox et al., "Isolation and characterization of homogeneous acetate kinase from *Salmonella typhimurium* and *Escherichia coli,*" *J. Biol. Chem.*, 261(29):13487-13497 (1986).
Fuchs, "Alternative pathways of carbon dioxide fixation: insights into the early evolution of life?," *Annu. Rev. Microbiol.*, 65:631-658 (2011).
Fujii et al., "Error-prone rolling circle amplification: the simplest random mutagenesis protocol," *Nat. Protocols*, 1(5):2493-2497 (2006).
Fujii et al., "One-step random mutagenesis by error-prone rolling circle amplification," *Nucleic Acids Res.*, 32(19):e145 (2004).
Fujii et al., "The crystal structure of zinc-containing ferredoxin from the thermoacidophilic archaeon *Sulfolobus* sp. strain 7," *Biochemistry*, 36(6):1505-1513 (1997).
Fujinaga et al., "Cloning and expression in *Escherichia coli* of the gene encoding the [2Fe—2S] ferredoxin from Clostridium pasteurianum," *Biochem. Biophys. Res. Commun.*, 192(3):1115-1122 (1993).
Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics*, 68:144-151 (2000).
Furdui et al., "The Role of Pyruvate Ferredoxin Oxidoreductase in Pyruvate Synthesis during Autotrophic Growth by the Wood-Ljungdahl Pathway," *J. Biol. Chem.*, 275(37):28494-28499 (2000).
Galagan et al., "The Genome of M. acetivorans Reveals Extensive Metabolic and Physiological Diversity," *Genome Res.*, 12:532-542 (2002).
Germer et al., "Overexpression, Isolation, and Spectroscopic Characterization of the Bidirectional [NiFe] Hydrogenase from *Synechocystis* sp. PCC 6803," *J. Biol. Chem.*, 284(52):36462-36472 (2009).
Gibbs et al., "Degenerate oligonucleotide gene shuffling (DOGS): a method for enhancing the frequency of recombination with family shuffling," *Gene*, 271:13-20 (2001).
Goenrich et al., "A glutathione-dependent formaldehyde-activating enzyme (Gfa) from Paracoccus denitrificans detected and purified via two-dimensional proton exchange NMR spectroscopy," *J. Biol. Chem.*, 277(5):3069-3072 (2002).
Gonzalez et al., "Genetic analysis of Carboxydothermus hydrogenoformans carbon monoxide dehydrogenase genes cooF and cooS," *FEMS Microbiol. Lett.*, 191:243-247 (2000).
Grill et al., "Characterization of fructose 6 phosphate phosphoketolases purified from Bifidobacterium species," *Curr. Microbiol.*, 31(1):49-54 (1995).
Guest et al., "The fumarase genes of *Escherichia coli*: location of the fumB gene and discovery of a new gene (fumC)," *J. Gen. Mirobiol.*, 131:2971-2984 (1985).
Guirard et al., "Purification and Properties of Ornithine Decarboxylase from *Lactobacillus* sp. 30a," *J. Biol. Chem.*, 255:5960-5964 (1980).

(56) References Cited

OTHER PUBLICATIONS

Gulick et al., "The 1.75 Å Crystal Structure of Acetyl-CoA Synthetase Bound to Adenosine-5'-propylphosphate and Coenzyme A," *Biochemistry*, 42:2866-2873 (2003).
Guo et al., "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from Schizosaccharomyces pombe," *Yeast*, 21:1279-1288 (2004).
Guo et al., "Site-directed mutational analysis of the novel catalytic domains of α-aminoadipate reductase (Lys2P) from Candida albicans," *Mol. Gen. Genomics*, 269:271-279 (2003).
Gutierrez et al., "Structure-guided redesign of D-fructose-6-phosphate aldolase from *E. coli*: remarkable activity and selectivity towards acceptor substrates by two-point mutation," *Chem. Commun. (Camb).*, 47(20):5762-5764 (2011).
Hadfield et al., "Active Site Analysis of the Potential Antimicrobial Target Aspartate Semialdehyde Dehydrogenase," *Biochemistry*, 40:14475-14483 (2001).
Hadfield et al., "Structure of Aspartate-b-semialdehyde Dehydrogenase from *Escherichia coli*, a Key Enzyme in the Aspartate Family of Amino Acid Biosynthesis," *J. Mol. Biol.*, 289:991-1002 (1999).
Hagemeier et al., "Insight into the mechanism of biological methanol activation based on the crystal structure of the methanol-cobalamin methyltransferase complex," *Proc. Natl. Acad. Sci. USA*, 103:18917-18922 (2006).
Hakobyan et al., "Proton translocation coupled to formate oxidation in anaerobically grown fermenting *Escherichia coli*," *Biophys. Chem.*, 115(1):55-61 (2005).
Hanai et al., "Engineered Synthetic Pathway for Isopropanol Production in *Escherichia coli*," *Appl. Environ. Microbiol.*, 73(24):7814-7818 (2007).
Hansen et al., "The Effect of the lacY Gene on the Induction of IPTG Inducible Promoters, Studied in *Escherichia coli* and Pseudomonas fluorescens," *Curr. Microbiol.*, 36(6):341-347 (1998).
Harms et al., "Methylcobalamin:Coenzyme M Methyltransferase Isoenzymes MtaA and MtbA from Methanosarcina barkeri," *Eur. J. Biochem.*, 235:653-659 (1996).
Harrison et al., "The pimFABCDE operon from Rhodopseudomonas palustris mediates dicarboxylic acid degradation and participates in anaerobic benzoate degradation," *Microbiol.*, 151:727-736 (2005).
Hartmanis et al., "Butyrate kinase from Clostridium acetobutylicum," *J. Biol. Chem.*, 262(2):617-621 (1987).
Harwood et al., "Identification of the pcaRKF gene cluster from Pseudomonas putida: involvement in chemotaxis, biodegradation, and transport of 4-hydroxybenzoate," *J. Bacteriol.*, 176(21):6479-6488 (1994).
Hasegawa et al., "Transcriptional regulation of ketone body-utilizing enzyme, acetoacetyl-CoA synthetase, by C/EBPα during adipocyte differentiation," *Biochim. Biophys. Acta*, 1779:414-419 (2008).
Hashidoko et al., "Cloning of a DNA Fragment Carrying the 4-Hydroxycinnamate Decarboxylase (pofK) Gene from Klebsiella oxytoca, and Its Constitutive Expression in *Escherichia coli* JM109 Cells," *Biosci. Biotech. Biochem.*, 58(1):217-218 (1994).
Hatrongjit et al., "A novel NADP+-dependent formate dehydrogenase from Burkholderia stabilis 15516: Screening, purification and characterization," *Enzym. Microbiol. Tech.*, 46:557-561 (2010).
Hawes et al., "Mammalian 3-hydroxyisobutyrate dehydrogenase," *Methods Enzymol.*, 324:218-228 (2000).
Hayes et al., "Combining computational and experimental screening for rapid optimization of protein properties," *Proc. Natl. Acad. Sci. USA*, 99(25):15926-15931 (2002).
Hayes, "Transposon-based strategies for microbial functional genomics and proteomics," *Annu. Rev. Genet.*, 37:3-29 (2003).
Hayman et al., "Purification and characterization of a tartrate-resistant acid phosphatase from human osteoclastomas," *Biochem. J.*, 261:601-609 (1989).
Haywood et al., "Characterization of two 3-ketothiolases possessing differing substrate specificities in the polyhydroxyalkanoate synthesizing organism Alcaligenes eutrophus," *FEMS Microbiol. Lett.*, 52:91-96 (1988).
Heggeset et al., "Genome Sequence of Thermotolerant Bacillus methanolicus: Features and Regulation Related to Methylotrophy and Production of L-Lysine and L-Glutamate from Methanol," *Appl. Environ. Microbiol.*, 78(15):5170-5181 (2012).
Heil et al., "Glycine binds the transcriptional accessory protein GcvR to disrupt a GcvA/GcvR interaction and allow GcvA-mediated activation of the *Escherichia coli* gcvTHP operon," *Microbiol.*, 148:2203-2214 (2002).
Hemschemeier et al., "Biochemical and Physiological Characterization of the Pyruvate Formate-Lyase Pfl1 of Chlamydomonas reinhardtii, a Typically Bacterial Enzyme in a Eukaryotic Alga," *Eukaryot. Cell*, 7(3):518-526 (2008).
Herrmann et al., "Energy Conservation via Electron-Transferring Flavoprotein in Anaerobic Bacteria," *J. Bacteriol.*, 190:784-791 (2008).
Hesslinger et al., "Novel keto acid formate-lyase and propionate kinase enzymes are components of an anaerobic pathway in *Escherichia coli* that degrades L-threonine to propionate," *Mol. Microbiol.*, 27(2):477-492 (1998).
Hibbert et al., "Directed evolution of biocatalytic processes," *Biomol. Eng.*, 22:11-19 (2005).
Hijarrubia et al., "Domain Structure Characterization of the Multifunctional alpha-Aminoadipate Reductase from Penicillium chrysogenum by Limited Proteolysis," *J. Biol. Chem.*, 278(10):8250-8256 (2003).
Hillmer et al., "Particulate nature of enzymes involved in the fermentation of ethanol and acetate by Clostridium kluyveri," *FEBS Lett.*, 21(3):351-354 (1972).
Hillmer et al., "Solubilization and Partial Characterization of Particulate Dehydrogenases From Clostridium Kluyveri," *Biochim. Biophys. Acta*, 334:12-23 (1974).
Hiser et al., "ERG10 from *Saccharomyces cerevisiae* encodes acetoacetyl-CoA thiolase," *J. Biol. Chem.*, 269:31383-31389 (1994).
Hochstrasser, "Ubiquitin-Dependent Protein Degradation," *Annu. Rev. Genet.*, 30:405-439 (1996).
Hoffmeister et al., "Mitochondrial trans-2-Enoyl-CoA Reductase of Wax Ester Fermentation from Euglena gracilis Defines a New Family of Enzymes Involved in Lipid Synthesis," *J. Biol. Chem.*, 280(6):4329-4338 (2005).
Hofmeister et al., "(R)-lactyl-CoA dehydratase from Clostridium propionicum: Stereochemistry of the dehydration of (R)-2-hydroxybutyryl-CoA to crotonyl-CoA," *Eur. J. Biochem.*, 206:547-552 (1992).
Hofvander et al., "A prokaryotic acyl-CoA reductase performing reduction of fatty acyl-CoA to fatty alcohol," *FEBS Lett.*, 3538-3543 (2011).
Horiguchi et al., "Peroxisomal catalase in the methylotrophic yeast Candida boidinii: transport efficiency and metabolic significance," *J. Bacteriol.*, 183(21):6372-6383 (2001).
Houseley et al., "The Many Pathways of RNA Degradation," *Cell*, 136(4):763-776 (2009).
Huang et al., "Purification and characterization of a ferulic acid decarboxylase from Pseudomonas fluorescens," *J. Bacteriol.*, 176(19):5912-5918 (1994).
Hughes et al., "Evidence for isofunctional enzymes in the degradation of phenol, m- and p-toluate, and p-cresol via catechol meta-cleavage pathways in Alcaligenes eutrophus," *J. Bacteriol.*, 158(1):79-83 (1984).
Hugler et al., "Malonyl-CoenzymeAa Reductase from Chloroflexus aurantiacus, a Key Enzyme of the 3-Hydroxypropionate Cycle for Autotrophic CO2 Fixation," *J. Bacteriol.*, 184(8):2404-2410 (2002).
Huisman et al., "Enzyme evolution for chemical process applications," R.N. Patel (ed.), *Biocatalysis in the pharmaceutical and biotechnology industries*, CRC Press, p. 717-742 (2007).
Ibarra et al., "*Escherichia coli* K-12 undergoes adaptive evolution to achieve in silico predicted optimal growth," *Nature*, 420:186-189 (2002).

(56) References Cited

OTHER PUBLICATIONS

Ingram-Smith et al., "AMP-forming acetyl-CoA synthetases in Archaea show unexpected diversity in substrate utilization," *Archaea*, 2:95-107 (2007).
Ingram-Smith et al., "Characterization of the Acetate Binding Pocket in the Methanosarcina thermophila Acetate Kinase," *J. Bacteriol.*, 187(7):2386-2394 (2005).
Ishige et al., "Wax Ester Production from n-Alkanes by *Acinetobacter* sp. Strain M-1: Ultrastructure of Cellular Inclusions and Role of Acyl Coenzyme A Reductase," *Appl. Environ. Microbiol.*, 68(3):1192-1195 (2002).
Ismaiel et al., "Purification and characterization of a primary-secondary alcohol dehydrogenase from two strains of Clostridium beijerinckii," *J. Bacteriol.*, 175(16):5097-5105 (1993).
Ismail et al., "Functional genomics by NMR spectroscopy," *Eur. J. Biochem.*, 270:3047-3054 (2003).
Ito et al., "Cloning and high-level expression of the glutathione-independent formaldehyde dehydrogenase gene from Pseudomonas putida," *J. Bacteriol.*, 176(9):2483-2493 (1994).
Izumi et al., "Structure and Mechanism of HpcG, a Hydratase in the Homoprotocatechuate Degradation Pathway of *Escherichia coli*," *J. Mol. Biol.*, 370:899-911 (2007).
Jacobi et al., "The hyp operon gene products are required for the maturation of catalytically active hydrogenase isoenzymes in *Escherichia coli*," *Arch. Microbiol.*, 158:444-451 (1992).
Jacques et al., "Characterization of yeast homoserine dehydrogenase, an antifungal target: the invariant histidine 309 is important for enzyme integrity," *Boichim. Et Biophys. Acta*, 1544:28-41 (2001).
James et al., "Production and Characterization of Bifunctional Enzymes. Domain Swapping to Produce New Bifunctional Enzymes in the Aspartate Pathway," *Biochemistry*, 41:3720-3725 (2002).
Jeon et al., "Heterologous expression of the alcohol dehydrogenase (adhI) gene from Geobacillus thermoglucosidasius strain M10EXG," *J. Biotechnol.*, 135:127-133 (2008).
Jeong et al., "Cloning and characterization of a gene encoding phosphoketolase in a Lactobacillus paraplantarum isolated from Kimchi," *J. Microbiol. Biotechnol.*, 17(5):822-829 (2007).
Jerome et al., "Development of a fed-batch process for the production of a dye-linked formaldehyde dehydrogenase in Hyphomicrobium zavarzinii ZV 580," *Appl. Microbiol. Biotechnol.*, 77:779-788 (2007).
Jogl et al., "Crystal Structure of Yeast Acetyl-Coenzyme A Synthetase in Complex with AMP," *Biochemistry*, 43:1425-1431 (2004).
Jojima et al., "Production of isopropanol by metabolically engineered *Escherichia coli*," *Appl. Microbiol. Biotechnol.*, 77:1219-1224 (2008).
Jones et al., "Acetone-Butanol Fermentation Revisted," *Microbiol. Rev.*, 50(4):484-524 (1986).
Kallen et al., "The mechanism of the condensation of formaldehyde with tetrahydrofolic acid," *J. Biol. Chem.*, 241(24):5851-5863 (1966).
Kanamasa et al., "Cloning and functional characterization of the cis-aconitic acid decarboxylase (CAD) gene from Aspergillus terreus," *Appl. Microbiol. Biotechnol.*, 80:223-229 (2008).
Kapatral et al., "Genome Sequence and Analysis of the Oral Bacterium Fusobacterium nucleatum Strain ATCC 25586," *J. Bacteriol.*, 184(7):2005-2018 (2002).
Karlen et al., "Absolute determination of the activity of the two C14 dating standards," *Arkiv Geofysik*, 4:465-147 (1964).
Kaschabek et al., "Degradation of Aromatics and Chloroaromatics by *Pseudomonas* sp. Strain B13: Purification and Characterization of 3-Oxoadipate:Succinyl-Coenzyme A (CoA) Transferase and 3-Oxoadipyl-CoA Thiolase," *J. Bacteriol.*, 184(1):207-215 (2002).
Kato et al., "3-Methylaspartate ammonia-lyase as a marker enzyme of the mesaconate pathway for (S)-glutamate fermentation in Enterobacteriaceae," *Arch. Microbiol.*, 168:457-463 (1997).
Kato et al., "The physiological role of the ribulose monophosphate pathway in bacteria and archaea," *Biosci. Biotechnol. Biochem.*, 70(1):10-21 (2006).
Kawasaki et al., "Transcriptional gene silencing by short interfering RNAs," *Curr. Opin. Mol. Ther.*, 7(2):125-131 (2005).

Kazahaya et al., "Aerobic dissimilation of glucose by heterolactic bacteria," *J. Gen. Appl. Microbiol.*, 18:43-55 (1972).
Kellum et al., "Effects of cultivation gas phase on hydrogenase of the acetogen Clostridium thermoaceticum," *J. Bacteriol.*, 160(1):466-469 (1984).
Kessler et al., "Pyruvate-formate-lyase-deactivase and acetyl-CoA reductase activities of *Escherichia coli* reside on a polymeric protein particle encoded by adhE," *FEBS Lett.*, 281:59-63 (1991).
Kikuchi et al., "Glycine cleavage system: reaction mechanism, physiological significance, and hyperglycinemia," *Proc. Jpn. Acad. Ser.*, 84(7):246-263 (2008).
Kim et al., "2-Hydroxyisocaproyl-CoA dehydratase and its activator from Clostridium difficile," *FEBS J.*, 272:550-561 (2005).
Kim et al., "A model of nitrogen flow by malonamate in *Rhizobium japonicum*-soybean symbiosis," *Biochem. Biophys. Res. Commun.*, 169(2):692-699 (1990).
Kim et al., "Construction of an *Escherichia coli* K-12 Mutant for Homoethanologenic Fermentation of Glucose or Xylose without Foreign Genes," *Appl. Environ. Microbiol.*, 73:1766-1771 (2007).
Kim et al., "Dehydration of (R)-2-hydroxyacyl-CoA to enoyl-CoA in the fermentation of a-amino acids by anaerobic bacteria," *FEMS Microbiol. Rev.*, 28:455-468 (2004).
Kim et al., "Dihydrolipoamide Dehydrogenase Mutation Alters the NADH Sensitivity of Pyruvate Dehydrogenase Complex of *Escherichia coli* K-12," *J. Bacteriol.*, 190(11):3851-3858 (2008).
Kim et al., "Studies of the hyperthermophile Thermotoga maritima by random sequencing of cDNA and genomic libraries. Identification and sequencing of the trpEG (D) operon," *J. Mol. Biol.*, 321:960-981 (1993).
Kinderlerer et al., "Fungal metabolites of sorbic acid," *Food Addit. Contam.*, 7(5):657-669 (1990).
Kinoshita et al., "Purification of two alcohol dehydrogenases from Zymomonas mobilis and their properties," *Appl. Microbiol. Biotechnol.*, 22:249-254 (1985).
Klatt et al., "Comparative genomics provides evidence for the 3-hydroxypropionate autotrophic pathway in filamentous anoxygenic phototrophic bacteria and in hot spring microbial mats," *Environ. Microbiol.*, 9(8):2067-2078 (2007).
Kloosterman et al., "Molecular, Biochemical, and Functional Characterization of a Nudix Hydrolase Protein That Stimulates the Activity of a Nicotinoprotein Alcohol Dehydrogenase," *J. Biol. Chem.*, 277(38):34785-34792 (2002).
Knappe et al., "Post-translational activation introduces a free radical into pyruvate formate-lyase," *Proc. Natl. Acad. Sci. USA*, 81:1332-1335 (1984).
Kobayashi et al., "Physicochemical, catalytic, and immunochemical properties of fumarases crystallized separately from mitochondrial and cytosolic fractions of rat liver," *J. Biochem.*, 89:1923-1931 (1981).
Kocharin et al., "Improved polyhydroxybutyrate production by *Saccharomyces cerevisiae* through the use of the phosphoketolase pathway," *Biotechnol. Bioeng.*, 110(8):2216-2224 (2013).
Kollmann-Koch et al., "Nicotinic Acid Metabolism," *Hoppe-Seylers Z. Physiol. Chem.*, 365:847-857 (1984).
Koo et al., "Cloning and characterization of the bifunctional alcohol/acetaldehyde dehydrogenase gene (adhE) in Leuconostoc mesenteroides isolated from kimchi," *Biotechnol. Lett.*, 27:505-510 (2005).
Korolev et al., "Autotracing of *Escherichia coli* acetate CoA-transferase a-subunit structure using 3.4 A MAD and 1.9 A native data," *Acta Crystallogr. D. Biol. Crystallogr.*, 58:2116-2121 (2002).
Kosaka et al., "Characterization of the sol Operon in Butanol-Hyperproducing Clostridium saccharoperbutylacetonicum Strain N1-4 and Its Degeneration Mechanism," *Biosci. Biotechnol. Biochem.*, 71(1):58-68 (2007).
Kosjek et al., "Purification and Characterization of a Chemotolerant Alcohol Dehydrogenase Applicable to Coupled Redox Reactions," *Biotechnol. Bioeng.*, 86:55-62 (2004).
Koutz et al., "Structural comparison of the Pichia pastoris alcohol oxidase genes," *Yeast*, 5(3):167-177 (1989).
Kovachy et al., "Recognition, Isolation, and Characterization of Rat Liver D-Methylmalonyl Coenzyme A Hydrolase," *J. Biol. Chem.*, 258(18):11415-11421 (1983).

(56) References Cited

OTHER PUBLICATIONS

Kreimeyer et al., "Identification of the Last Unknown Genes in the Fermentation Pathway of Lysine," *J. Biol. Chem.*, 282(10):7191-7197 (2007).
Kretz et al., "Gene Site Saturation Mutagenesis: A Comprehensive Mutagenesis Approach," *Methods Enzymol.*, 388:3-11 (2004).
Kuchta et al., "Lactate Reduction in Clostridium propionicum," *J. Biol. Chem.*, 260(24):13181-13189 (1985).
Kukor et al., "Genetic organization and regulation of a meta cleavage pathway for catechols produced from catabolism of toluene, benzene, phenol, and cresols by Pseudomonas pickettii PKO1," *J. Bacteriol.*, 173(15):4587-4594 (1991).
Kurdistani et al., "Histone acetylation and deacetylation in yeast," *Nat. Rev. Mol. Cell Biol.*, 4(4):276-284 (2003).
Kuznetsova et al., "Enzyme genomics: Application of general enzymatic screens to discover new enzymes," *FEMS Microbiol. Rev.*, 29(2):263-279 (2005).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.*, 395:147-155 (2006).
Lamed et al., "Novel NADP-linked alcohol—aldehyde/ketone oxidoreductase in thermophilic ethanologenic bacteria," *Biochem. J.*, 195:183-190 (1981).
Lametschwandtner et al., "The difference in recognition of terminal tripeptides as peroxisomal targeting signal 1 between yeast and human is due to different affinities of their receptor Pex5p to the cognate signal and to residues adjacent to it," *J. Biol. Chem.*, 273(50):33635-33643 (1998).
Lau et al., "Sequence and expression of the todGIH genes involved in the last three steps of toluene degradation by Pseudomonas putida F1," *Gene*, 146(1):7-13 (1994).
Leal et al., "PduP is a coenzyme-a-acylating propionaldehyde dehydrogenase associated with the polyhedral bodies involved in B12-dependent 1,2-propanediol degradation by *Salmonella enterica* serovar Typhimurium LT2," *Arch. Microbiol.*, 180:353-361 (2003).
Learned et al., "3-Hydroxy-3-methylglutaryl-coenzyme A reductase from *Arabidopsis thaliana* is structurally distinct from the yeast and animal enzymes," *Proc. Natl. Acad. Sci. USA*, 86:2779-2783 (1989).
Ledeboer et al., "Molecular cloning and characterization of a gene coding for methanol oxidase in Hansenula polymorpha," *Nucelic Acids Res.*, 13(9):3063-3082 (1985).
Lee et al., "A new approach to directed gene evolution by recombined extension on truncated templates (RETT)," *J. Molec. Catalysis*, 26:119-129 (2003).
Lee et al., "Antisense technology in molecular and cellular bioengineering," *Curr. Opin. Biotechnol.*, 14(5):505-511 (2003).
Lee et al., "Cloning and characterization of the gene encoding phosphoketolase in Leuconostoc mesenteroides isolated from kimchi," *Biotechnol. Lett.*, 27(12):853-858 (2005).
Lee et al., "Cysteine-286 as the site of acylation of the Lux-specific fatty acyl-CoA reductase," *Biochim. Biophys. Acta*, 1388(2):215-222 (1997).
Lee et al., "Identification of essential active-site residues in ornithine decarboxylase of Nicotiana glutinosa decarboxylating both L-ornithine and L-lysine," *Biochem. J.*, 360:657-665 (2001).
Lee et al., "Phylogenetic Diversity and the Structural Basis of Substrate Specificity in the ß/α-Barrel Fold Basic Amino Acid Decarboxylases," *J. Biol. Chem.*, 282(37):27115-27125 (2007).
Lehtio et al., "Crystal Structure of a Glycyl Radical Enzyme from Archaeoglobus fulgidus," *J. Mol. Biol.*, 357:221-235 (2006).
Lehtio et al., "The pyruvate formate lyase family: sequences, structures and activation," *Prot. Eng. Des. Sel.*, 17(6):545-552 (2004).
Lemonnier et al., "Expression of the second lysine decarboxylase gene of *Escherichia coli*," *Microbiol.*, 144:751-760 (1998).
Lenski et al., "Dynamics of adaptation and diversification: a 10,000-generation experiment with bacterial populations," *Proc. Natl. Acad. Sci. USA*, 91:6808-6814 (1994).

Leppanen et al., "Pyruvate formate lyase is structurally homologous to type I ribonucleotide reductase," *Structure*, 7(7): 733-744 (1999).
Lessner et al., "An unconventional pathway for reduction of CO2 to methane in CO-grown Methanosarcina acetivorans revealed by proteomics," *Proc. Natl. Acad. Sci. USA*, 103:17921-17926 (2006).
Leys et al., "Channelling and formation of 'active' formaldehyde in dimethylglycine oxidase," *EMBO J.*, 22(16):4038-4048 (2003).
Li et al., "Properties of Nicotinamide Adenine Dinucleotide Phosphate-Dependent Formate Dehydrogenase from Clostridium thermoaceticum," *J. Bacteriol.*, 92(2):405-412 (1966).
Lian et al., "Stereochemical and isotopic labeling studies of 4-oxalocrotonate decarboxylase and vinylpyruvate hydratase: analysis and mechanistic implications," *J. Am. Chem. Soc.*, 116:10403-10411 (1994).
Lin et al., "Fed-Batch Culture of a Metabolically Engineered *Escherichia coli* Strain Designed for High-Level Succinate Production and Yield Under Aerobic Conditions," *Biotech. Bioeng.*, 90:775-779 (2005).
Lokanath et al., "Crystal Structure of Novel NADP-dependent 3-Hydroxyisobutyrate Dehydrogenase from Thermus thermophilus HB8," *J. Mol. Biol.*, 352:905-917 (2005).
Louie et al., "Cloning and characterization of the gamma-glutamyl phosphate reductase gene of Campylobacter jejuni," *Mol. Gen. Genet.*, 240:29-35 (1993).
Louis et al., "Restricted Distribution of the Butyrate Kinase Pathway among Butyrate-Producing Bacteria from the Human Colon," *J. Bacteriol.*, 186(7):2099-2106 (2004).
Lovell et al., "Cloning and expression in *Escherichia coli* of the *Clostridium thermoaceticum* gene encoding thermostable formyltetrahydrofolate synthetase," *Arch. Microbiol.*, 149:280-285 (1988).
Lovell et al., "Primary structure of the thermostable formyltetrahydrofolate synthetase from Clostridium thermoaceticum," *Biochemistry*, 29:5687-5694 (1990).
Low et al., "Mimicking Somatic Hypermutation: Affinity Maturation of Antibodies Displayed on Bacteriophage Using a Bacterial Mutator Strain," *J. Mol. Biol.*, 260:359-368 (1996).
Lu et al., "Sequence and expression of the gene encoding the corrinoid/iron-sulfur protein from Clostridium thermoaceticum and reconstitution of the recombinant protein to full activity," *J. Biol. Chem.*, 268(8):5605-5614 (1993).
Luers et al., "The Pichia pastoris dihydroxyacetone kinase is a PTS1-containing, but cytosolic, protein that is essential for growth on methanol," *Yeast*, 14:759-771 (1998).
Lukey et al., "How *Escherichia coli* is Equipped to Oxidize Hydrogen under Different Redox Conditions," *J. Biol. Chem.*, 285(6):3928-3938 (2010).
Luo et al., "Identification and characterization of the propanediol utilization protein PduP of Lactobacillus reuteri for 3-hydroxypropionic acid production from glycerol," *Appl. Microbiol. Biotechnol.*, 89(3):697-703 (2011).
Lutz et al., "Dissecting the functional program of *Escherichia coli* promoters: the combined mode of action of Lac repressor and AraC activator," *Proc. Natl. Acad. Sci. USA*, 98:11248-11253 (2001).
Lutz et al., "Independent and tight regulation of transcriptional units in *Escherichia coli* via the LacR/O, the TetR/O and AraC/I1-I2 regulatory elements," *Nucl. Acids Res.*, 25(6):1203-1210 (1997).
Lutz et al., "Rapid generation of incremental truncation libraries for protein engineering using alpa-phosphothioate nucleotides," *Nucleic Acids Res.*, 29(4):e16 (2001).
Ma et al., "Nucleotide Sequence of Plasmid pCNB1 from Comamonas Strain CNB-1 Reveals Novel Genetic Organization and Evolution for 4-Chloronitrobenzene Degradation," *Appl. Environ. Microbiol.*, 73(14):4477-4483 (2007).
Maaheimo et al., "Central carbon metabolism of *Saccharomyces cerevisiae* explored by biosynthetic fractional (13)C labeling of common amino acids," *Eur. J. Biochem.*, 268(8):2464-2479 (2001).
Mack et al., "Conversion of glutaconate CoA-transferase from Acidaminococcus fermentans into an acyl-CoA hydrolase by site-directed mutagenesis," *FEBS Lett.*, 402(2):209-212 (1997).
Maeda et al., "Enhanced hydrogen production from glucose by metabolically engineered *Escherichia coli*," *Appl. Microbiol. Biotechnol.*, 77:879-890 (2007).

(56) References Cited

OTHER PUBLICATIONS

Maeder et al., "The Methanosarcina barkeri Genome: Comparative Analysis with Methanosarcina acetivorans and Methanosarcina mazei Reveals Extensive Rearrangement within Methanosarcinal Genomes," *J. Bacteriol.*, 188(22):7922-7931 (2006).
Mahan et al., "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.*, 156(3):1249-1262 (1983).
Manjasetty et al., "Crystallization and preliminary X-ray analysis of dmpFG-encoded 4-hydroxy-2-ketovalerate aldolase±aldehyde dehydrogenase (acylating) from *Pseudomonas* sp. strain CF600," *Acta Crystallogr. D. Biol. Crystallogr.*, 57:582-585 (2001).
Mann et al., "Protemic analysis of post-translational modifications," *Nature Biotech.*, 21:255-261 (2003).
Mann, "An international reference material for radiocarbon dating," *Radiocarbon*, 25(2):519-527 (1983).
Manning et al., "Tracer studies of the interconversion of R- and S-methylmalonic semialdehydes in man," *Biochem. J.*, 231:481-484 (1985).
Marks et al., "Molecular cloning and characterization of (R)-3-hydroxybutyrate dehydrogenase from human heart," *J. Biol. Chem.*, 267:15459-15463 (1992).
Marolewski et al., "Cloning and characterization of a new purine biosynthetic enzyme: a non-folate glycinamide ribonucleotide transformylase from *E. coli,*" *Biochemistry*, 33(9):2531-2537 (1994).
Martin et al., "Engineering a mevalonate pathway in *Escherichia coli* for production of terpenoids," *Nat. Biotechnol.*, 21:796-802 (2003).
Martinez-Blanco et al., "Purification and Biochemical Characterization of Phenylacetyl-CoA Ligase from Pseudomonas putida," *J. Biol. Chem.*, 265(12):7084-7090 (1990).
Mattevi et al., "Atomic structure of the cubic core of the pyruvate dehydrogenase multienzyme complex," *Science*, 255:1544-1550 (1992).
Matthies et al., "Reciprocal isomerization of butyrate and isobutyrate by the strictly anaerobic bacterium strain WoG13 and methanogenic isobutyrate degradation by a defined triculture," *Appl. Environ. Microbiol.*, 58(5):1435-1439 (1992).
McCue et al., "Gene expression and stress response mediated by the epigenetic regulation of a transposable element small RNA," *PLoS Genet.*, 8(2):e1002474 (2012).
McNeil et al., "Cloning and molecular characterization of three genes, including two genes encoding serine hydroxymethyltransferases, whose inactivation is required to render yeast auxotrophic for glycine," *J. Biol. Chem.*, 269(12):9155-9165 (1994).
Meile et al., "Characterization of the D-xylulose 5-phosphate/D-fructose 6-phosphate phosphoketolase gene (xfp) from Bifidobacterium lactis," *J. Bacteriol.*, 183(9):2929-2936 (2001).
Melchiorsen et al., "The level of pyruvate-formate lyase controls the shift from homolactic to mixed-acid product formation in Lactococcus lactis," *Appl. Microbiol. Biotechnol.*, 58:338-344 (2002).
Menon et al., "Mechanism of the Clostridium thermoaceticum Pyruvate:Ferredoxin Oxidoreductase: Evidence for the Common Catalytic Intermediacy of the Hydroxyethylthiamine Pyropyrosphate Radical," *Biochemistry*, 36:8484-8494 (1997).
Menzel et al., "Characterization of Anaerobic Fermentative Growth of Bacillus subtilis: Identification of Fermentation End Products and Genes Required for Growth," *J. Biotechnol.*, 56:135-142 (1997).
Merkel et al., "Characterization and sequence of the *Escherichia coli* panBCD gene cluster," *FEMS Microbiol. Lett.*, 143:247-252 (1996).
Metz et al., "Purification of a Jojoba Embryo Fatty Acyl-Coenzyme A Reductase and Expression of Its cDNA in High Erucic Acid Rapeseed," *Plant Physiol.*, 122:635-644 (2000).
Mitsui et al., "Formaldehyde Fixation Contributes to Detoxification for Growth of a Nonmethylotroph, Burkholderia cepacia TM1, on Vanillic Acid," *Appl. Environ. Microbiol.*, 69(10):6128-6132 (2003).

Mizobata et al., "Purification and characterization of a thermostable class II fumarase from Thermus thermophiles," *Arch. Biohem. Biophys.*, 35(1):49-55 (1998).
Mko, "Phenotype Variability: Penetrance and Expressivity," *Nature Education*, 1(1):137 (2008).
Molin et al., "Dihydroxyacetone Kinases in *Saccharomyces cerevisiae* are Involved in Detoxification of Dihydroxyacetone," *J. Biol. Chem.*, 278(3):1415-1423 (2003).
Momany et al., "Crystallographic Structure of a PLP-Dependent Ornithine Decarboxylase from Lactobacillus 30a to 3.0 Å Resolution," *J. Mol. Biol.*, 252:643-655 (1995).
Moore et al., "Expression and purification of aspartate beta-semialdehyde dehydrogenase from infectious microorganisms," *Protein Expr. Purif.*, 25:189-194 (2002).
Morita et al., "Bacterial distribution of glycolaldehyde dehydrogenase in relation to vitamin B6 biosynthesis," *Agric. Biol. Chem.*, 43:185-186 (1979).
Morris et al., "Nucleotide sequence of the LYS2 gene of *Saccharomyces cerevisiae*: homology to Bacillus brevis tyrocidine synthetase 1," *Gene*, 98:141-145 (1991).
Morton et al., "The primary structure of the subunits of carbon monoxide dehydrogenase/acetyl-CoA synthase from Clostridium thermoaceticum," *J. Biol. Chem.*, 266(35):23824-23828 (1991).
Mukhopadhyay et al., "The fdxA ferredoxin gene can down-regulate frxA nitroreductase gene expression and is essential in many strains of Helicobacter pylori," *J. Bacteriol.*, 185(9):2927-2935 (2003).
Muller et al., "Activation of (R)-2-hydroxyglutaryl-CoA dehydratase from Acidaminococcus fermentans," *Eur. J. Biochem.*, 230:698-704 (1995).
Muller et al., "Nucleotide exchange and excision technology (NExT) DNA shuffling: a robust method for DNA fragmentation and directed evolution," *Nucleic Acids Res.*, 33(13):e117 (2005).
Musfeldt et al., "Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcus jannaschii," *J. Bacteriol.*, 184(3):636-644 (2002).
Myronova et al., "Three-Dimensional Structure Determination of a Protein Supercomplex That Oxidizes Methane to Formaldehyde in Methylococcus capsulatus (Bath)," *Biochemistry*, 45:11905-11914 (2006).
Naggert et al., "Cloning, sequencing, and characterization of *Escherichia coli* thioesterase II," *J. Biol. Chem.*, 266(17):11044-11050 (1991).
Nagy et al., "Formyltetrahydrofolate Hydrolase, a Regulatory Enzyme That Functions to Balance Pools of Tetrahydrofolate and One-Carbon Tetrahydrofolate Adducts in *Escherichia coli,*" *J. Bacteriol.*, 177(5):1292-1298(1995).
Naidu et al., "Characterization of a Three-Component Vanillate O-Demethylase from Moorella thermoacetica," *J. Bacteriol.*, 183(11):3276-2381 (2001).
Nakagawa et al., "Analysis of alcohol oxidase isozymes in gene-disrupted strains of methylotrophic yeast Pichia methanolica," *J. Biosci. Bioeng.*, 91(2):225-227 (2001).
Nakahigashi et al., "Nucleotide sequence of the fadA and fadB genes from *Escherichia coli,*" *Nucelic Acids Res.*, 18(16):4937 (1990).
Nakai et al., "A Knowledge Base for Predicting Protein Localization Sites in Eukaryotic Cells," *Genomics*, 14(4):897-911 (1992).
Nakano et al., "Characterization of Anaerobic Fermentative Growth of Bacillus subtilis: Identification of Fermentation End Products and Genes Required for Growth," *J. Bacteriol.*, 179(21):6749-6755 (1997).
Nakazawa et al., "Pyruvate:NADP+ oxidoreductase is stabilized by its cofactor, thiamin pyrophosphate, in mitochondria of Euglena gracilis," *Arch. Biochem. Biophys.*, 411(2):183-188 (2003).
Nashizawa et al., "Regulation of inducible gene expression by natural antisense transcripts," *Front. Biosci.*, 17:938-958 (2012).
Ness et al., "Synthetic shuffling expands functional protein diversity by allowing amino acids to recombine independently," *Nat. Biotechnol.*, 20:1251-1255 (2002).

(56) References Cited

OTHER PUBLICATIONS

Netzer et al., "Cometabolism of a nongrowth substrate: L-serine utilization by Corynebacterium glutamicum," *Appl. Environ. Microbiol.*, 70(12):7148-7155 (2004).
Neuberger et al., "Prediction of peroxisomal targeting signal 1 containing proteins from amino acid sequence," *J. Mol. Biol.*, 328(3):581-592 (2003).
Nogales et al., "Characterization of the last step of the aerobic phenylacetic acid degradation pathway," *Microbiol.*, 153:357-365 (2007).
Nunn et al., "The nucleotide sequence and deduced amino acid sequence of the genes for cytochrome cL and a hypothetical second subunit of the methanol dehydrogenase of Methylobacterium AM1," *Nucl. Acids Res.*, 16(15):7722 (1988).
O'Brien et al., "Chemical, physical and enzymatic comparisons of formyltetrahydrofolate synthetases from thermo- and mesophilic Clostridia," *Experienia Suppl.*, 26:249-262 (1976).
O'Reilly et al., "Sequence and analysis of the citrulline biosynthetic operon argC-F from Bacillus subtilis," *Microbiol.*, 140:1023-1025 (1994).
O'Sullivan, "Aptasensors—the future of biosensing?," *Anal. Bioanal. Chem.*, 372(1):44-48 (2002).
Oh et al., "Structural analysis of the fds operon encoding the NAD+-linked formate dehydrogenase of Ralstonia eutropha," *J. Biol. Chem.*, 273(41):26349-26360 (1998).
Ohgami et al., "Expression of acetoacetyl-CoA synthetase, a novel cytosolic ketone body-utilizing enzyme, in human brain," *Biochem. Pharm.*, 65:989-994 (2003).
Okamura-Ikeda et al., "Cloning and nucleotide sequence of the gcv operon encoding the *Escherichia coli* glycine-cleavage system," *Eur. J. Biochem.*, 216(2):539-548 (1993).
Olivera et al., "Molecular characterization of the phenylacetic acid catabolic pathway in Pseudomonas putida U: The phenylacetyl-CoA catabolon," *Proc. Natl. Acad. Sci. USA*, 95:6419-6424 (1998).
Ordonez et al., "Methylene reductase: responsible for the in vitro formation of formaldehyde from 5-methyltetrahydrofolic acid," *Psychopharmacol. Commun.*, 1(3):253-260 (1975).
Orita et al., "Bifunctional enzyme fusion of 3-hexulose-6-phosphate synthase and 6-phospho-3-hexuloisomerase," *Appl. Microbiol. Biotechnol.*, 76:439-445 (2007).
Oshima et al., "Regulation of phosphatase synthesis in *Saccharomyces cerevisiae*—a review," *Gene*, 179:171-177 (1996).
Ostermeier et al., "A combinatorial approach to hybrid enzymes independent of DNA homology," *Nat. Biotechnol.*, 17:1205-1209 (1999).
Ostermeier et al., "Combinatorial protein engineering by incremental truncation," *Proc. Natl. Acad. Sci. USA*, 96:3562-3567 (1999).
Otten et al., "Directed evolution: selecting today's biocatalysts," *Biomol. Eng.*, 22:1-9 (2005).
Papini et al., "Physiological characterization of recombinant *Saccharomyces cerevisiae* expressing the Aspergillus nidulans phosphoketolase pathway: validation of activity through 13C-based metabolic flux analysis," *Appl. Microbiol. Biotechnol.*, 95(4):1001-1010 (2012).
Parizzi et al., "The genome sequence of Propionibacterium acidipropionici provides insights into its biotechnological and industrial potential," *BMC Genomics*, 13:562 (2012).
Park et al., "Biosynthesis of Poly(3-hydroxybutyrateco-3-hydroxyalkanoates) by Metabolically Engineered *Escherichia coli* Strains," *Appl. Biochem. Biotechnol.*, 113-116:335-346 (2004).
Park et al., "Growth of Mycobacteria on Carbon Monoxide and Methanol," *J. Bacteriol.*, 185(1):142-147 (2003).
Park et al., "Identification and Characterization of a New Enoyl Coenzyme A Hydratase Involved in Biosynthesis of Medium-Chain-Length Polyhydroxyalkanoates in Recombinant *Escherichia coli*," *J. Bacteriol.*, 185(18):5391-5397 (2003).
Park et al., "New FadB Homologous Enzymes and Their Use in Enhanced Biosynthesis of Medium-Chain-Length Polyhydroxyalkanoates in fadB Mutant *Escherichia coli*," *Biotechnol. Bioeng.*, 86(6):681-686 (2004).
Park et al., "Purifications and Characterizations of a Ferredoxin and Its Related 2-Oxoacid:Ferredoxin Oxidoreductase from the Hyperthermophilic Archaeon, Sulfolobus solfataricus P1," *J. Biochem. Mol. Biol.*, 39(1):46-54 (2006).
Parkin et al., "Rapid and Efficient Electrocatalytic CO2/CO Interconversions by Carboxydothermus hydrogenoformans CO Dehydrogenase I on an Electrode," *J. Am. Chem. Soc.*, 129:10328-10329 (2007).
Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene*, 68:275-283 (1988).
Pasquinelli et al., "MicroRNAs and their targets: recognition, regulation and an emerging reciprocal relationship," *Nat. Rev. Genet.*, 13(4):271-282 (2012).
Pauli et al., "ato Operon: a highly inducible system for acetoacetate and butyrate degradation in *Escherichia coli*," *Eur. J. Biochem.*, 29:553-562 (1972).
Pauwels et al., "The N-acetylglutamate synthase/N-acetylglutamate kinase metabolon of *Saccharomyces cerevisiae* allows co-ordinated feedback regulation of the first two steps in arginine biosynthesis," *Eur. J. Biochem.*, 270:1014-1024 (2003).
Paxton et al., "Role of branched-chain 2-oxo acid dehydrogenase and pyruvate dehydrogenase in 2-oxobutyrate metabolism," *Biochem. J.*, 234(2):295-303 (1986).
Peoples et al., "Fine structural analysis of the Zoogloea ramigera phbA-phbB locus encoding beta-ketothiolase and acetoacetyl-CoA reductase: nucleotide sequence of phbB," *Mol. Microbiol.*, 3(3):349-357 (1989).
Peretz et al., "Amino acid sequence of alcohol dehydrogenase from the thermophilic bacterium Thermoanaerobium brockii," *Biochemistry*, 28:6549-6555 (1989).
Perez et al., "*Escherichia coli* YqhD Exhibits Aldehyde Reductase Activity and Protects from the Harmful Effect of Lipid Peroxidation-derived Aldehydes," *J. Biol. Chem.*, 283(12):7346-7353 (2008).
Pierce et al., "The Complete Genome Sequence of Moorella thermoacetica (f. *Clostridium thermoaceticum*)," *Environ. Microbiol.*, 10(1):2550-2573 (2008).
Pieulle et al., "Isolation and Analysis of the Gene Encoding the Pyruvate-Ferredoxin Oxidoreductase of Desulfovibrio africanus, Production of the Recombinant Enzyme in *Escherichia coli*, and Effect of Carboxy-Terminal Deletions on Its Stability," *J. Bacteriol.*, 179(18):5684-5692 (1997).
Pinches et al., "Production in food of 1,3-pentadiene and styrene by Trichoderma species," *Int. J. Food. Microbiol.*, 116:182-185 (2007).
Plamann et al., "Characterization of the *Escherichia coli* gene for serine hydroxymethyltransferase," *Gene*, 22(1):9-18 (1983).
Ploux et al., "The NADPH-linked acetoacetyl-CoA reductase from Zoogloea ramigera. Characterization and mechanistic studies of the cloned enzyme over-produced in *Escherichia coli*," *Eur. J. Biochem.*, 174:177-182 (1988).
Plumridge et al., "The decarboxylation of the weak-acid preservative, sorbic acid, is encoded by linked genes in *Aspergillus* spp," *Fung. Genet. Bio.*, 47:683-692 (2010).
Poehlein et al., "An Ancient Pathway Combining Carbon Dioxide Fixation with the Generation and Utilization of a Sodium Ion Gradient for ATP Synthesis," *PLoS One*, 7(3):e33439 (2012).
Pohl et al., "Remarkably Broad Substrate Tolerance of Malonyl-CoA Synthetase, an Enzyme Capable of Intracellular Synthesis of Polyketide Precursors," *J. Am. Chem. Soc.*, 123:5822-5823 (2001).
Pollard et al., "Purification, characterisation and reaction mechanism of monofunctional 2-hydroxypentadienoic acid hydratase from *Escherichia coli*," *Eur. J. Biochem.*, 251:98-106 (1998).
Pollard et al., "Substrate Selectivity and Biochemical Properties of 4-Hydroxy-2-Keto-Pentanoic Acid Aldolase from *Escherichia coli*," *Appl. Environ. Microbiol.*, 64(10):4093-4094 (1998).
Porter et al., "Enzymatic properties of dimethylglycine dehydrogenase and sarcosine dehydrogenase from rat liver," *Arch. Biochem. Biophys.*, 243(2):396-407 (1985).
Postma et al., "Phosphoenolpyruvate:carbohydrate phosphotransferase systems of bacteria," *Microbiol. Rev.*, 57(3):543-594 (1993).
Powlowski et al., "Purification and properties of the physically associated meta-cleavage pathway enzymes 4-hydroxy-2-

(56) References Cited

OTHER PUBLICATIONS ketovalerate aldolase and aldehyde dehydrogenase (acylating) from *Pseudomonas* sp. strain CF600," *J. Bacteriol.*, 175(2):377-385 (1993).
Priefert et al., "Identification and molecular characterization of the acetyl coenzyme A synthetase gene (acoE) of Alcaligenes eutrophus," *J. Bacteriol.*, 174(20):6590-6599 (1992).
Prieto et al., "Molecular Characterization of the 4-Hydroxyphenylacetate Catabolic Pathway of *Escherichia coli* W: Engineering a Mobile Aromatic Degradative Cluster," *J. Bacteriol.*, 178(1):111-120 (1996).
Pritchard et al., "A general model of error-prone PCR," *J. Theor. Biol.*, 234:497-509 (2005).
Pritchett et al., "Genetic, physiological and biochemical characterization of multiple methanol methyltransferase isozymes in Methanosarcina acetivorans C2A," *Mol. Microbiol.*, 56(5):1183-1194 (2005).
Pronk et al., "Pyruvate metabolism in *Saccharomyces cerevisiae*," *Yeast*, 12:1607-1633 (1996).
Qi et al., "Functional expression of prokaryotic and eukaryotic genes in *Escherichia coli* for conversion of glucose to p-hydroxystyrene," *Metab. Eng.*, 9:268-276 (2007).
Rado et al., "Phosphotransacetylase from Bacillus subtilis: purification and physiological studies," *Biochim. Biophys. Acta*, 321:114-125 (1973).
Ragsdale et al., "Pyruvate Ferredoxin Oxidoreductase and Its Radical Intermediate," *Chem. Rev.*, 103:2333-2346 (2003).
Ragsdale, "Enzymology of the Wood—Ljungdahl Pathway of Acetogenesis," *Ann. NY Acad. Sci.*, 1125:129-136 (2008).
Ragsdale, "Life with Carbon Monoxide," *Crit. Rev. Biochem. Mol. Biol.*, 39:165-195 (2004).
Rajpal et al., "A general method for greatly improving the affinity of antibodies by using combinatorial libraries," *Proc. Natl. Acad. Sci. USA*, 102:8466-8471 (2005).
Rakhely et al., "Cyanobacterial-Type, Heteropentameric, NAD+-Reducing NiFe Hydrogenase in the Purple Sulfur Photosynthetic Bacterium Thiocapsa roseopersicina," *Appl. Environ. Microbiol.*, 70(2):722-728 (2004).
Ramjee et al., "*Escherichia coli* L-aspartate-a-decarboxylase: preprotein processing and observation of reaction intermediates by electrospray mass spectrometry," *Biochem. J.*, 323:661-669 (1997).
Ramos-Vera et al., "Autotrophic Carbon Dioxide Assimilation in Thermoproteales Revisited," *J. Bacteriol.*, 191(13):4286-4297 (2009).
Ramos-Vera et al., "Regulation of autotrophic CO2 fixation in the archaeon Thermoproteus neutrophilus," *J. Bacteriol.*, 192(20):5329-4340 (2010).
Rangarajan et al., "Structure of [NiFe] Hydrogenase Maturation Protein HypE from *Escherichia coli* and Its Interaction with HypF," *J. Bacteriol.*, 190(4):1447-1458 (2008).
Rathinasabapathi, "Propionate, a souce of beta-alanine, is an inhibitor of beta-alanine methylation in Limonium latifolium, Plumbaginaceae," *J. Plant Physol.*, 159:671-674 (2002).
Reda et al., "Reversible interconversion of carbon dioxide and formate by an electroactive enzyme," *Proc. Natl. Acad. Sci. USA*, 105(31):10654-10658 (2008).
Reetz et al., "Directed Evolution of an Enantioselective Enzyme through Combinatorial Multiple-Cassette Mutagenesis," *Angew. Chem. Int. Ed. Engl.*, 40:3589-3591 (2001).
Reetz et al., "Iterative saturation mutagenesis (ISM) for rapid directed evolution of functional enzymes," *Nat. Protocols*, 2:891-903 (2007).
Reetz et al., "Iterative Saturation Mutagenesis on the Basis of B Factors as a Strategy for Increasing Protein Thermostability," *Angew. Chem. Int. Ed. Engl.*, 45:7745-7751 (2006).
Reidhaar-Olson et al., "Combinatorial Cassette Mutagenesis as a Probe of the Informational Content of Protein Sequences," *Science*, 241:53-57 (1988).
Reidhaar-Olson et al., "Random Mutagenesis of Protein Sequences Using Oligonucleotide Cassettes," *Methods Enzymol.*, 208:564-586 (1991).

Reiser et al., "Isolation of Mutants of Acinetobacter calcoaceticus Deficient in Wax Ester Synthesis and Complementation of One Mutation with a Gene Encoding a Fatty Acyl Coenzyme A Reductase," *J. Bacteriol.*, 179(9):2969-2975 (1997).
Ricagno et al., "Formyl-CoA transferase encloses the CoA binding site at the interface of an interlocked dimer," *EMBO J.*, 22(13):3210-3219 (2003).
Ringner et al., "Folding free energies of 5'-UTRs impact post-transcriptional regulation on a genomic scale in yeast," *PLoS Comput. Biol.*, 1(7):e72 (2005).
Riviere et al., "Acetyl: Succinate CoA-transferase in Procyclic Trypanosoma brucei," *J. Biol. Chem.*, 279(44):45337-45346 (2004).
Ro et al., "Dihydroxyacetone Synthase from a Methanol-Utilizing Carboxydobacterium, *Acinetobacter* sp. Strain JC1 DSM 3803," *J. Bacteriol.*, 179(19):6041-6047 (1997).
Roberts et al., "Cloning and expression of the gene cluster encoding key proteins involved in acetyl-CoA synthesis in Clostridium thermoaceticum: CO dehydrogenase, the corrinoid/Fe—S protein, and methyltransferase," *Proc. Natl. Acad. Sci. USA*, 86:32-36 (1989).
Roberts et al., "The role of enoyl-coa hydratase in the metabolism of isoleucine by Pseudomonas putida," *Arch. Microbiol.*, 117:99-108 (1978).
Robinson et al., "Studies on rat brain acyl-coenzyme a hydrolase (short chain)," *Biochem. Biophys. Res. Comm.*, 71(4):959-965 (1976).
Rodriguez et al., "Characterization of the p-Coumaric Acid Decarboxylase from Lactobacillus plantarum CECT 748$^T$," *J. Agric. Food Chem.*, 56:3068-3072 (2008).
Roper et al., "Sequence of the hpcC and hpcG genes of the meta-fission homoprotocatechuic acid pathway of *Escherichia coli* C: nearly 40% amino-acid identity with the analogous enzymes of the catechol pathway," *Gene*, 156:47-51 (1995).
Rother et al., "Anaerobic growth of Methanosarcina acetivorans C2A on carbon monoxide: An unusual way of life for a methanogenic archaeon," *Proc. Natl. Acad. Sci. USA*, 101:16929-16934 (2004).
Rother et al., "Genetic and proteomic analyses of CO utilization by Methanosarcina acetivorans," *Arch. Microbiol.*, 188:463-472 (2007).
Russel et al., "Peptide Signals Encode Protein Localization," *J. Bact.*, 189(21):7581-7585 (2007).
Sabo et al., "Purification and physical properties of inducible *Escherichia coli* lysine decarboxylase," *Biochem.*, 13:662-670 (1974).
Sakai et al., "Cloning and sequencing of the alcohol oxidase-encoding gene (AOD1) from the formaldehyde-producing asporogeneous methylotrophic yeast, Candida boidinii S2," *Gene*, 114(1):67-73 (1992).
Sariaslani, "Development of a Combined Biological and Chemical Process for Production of Industrial Aromatics from Renewable Resources," *Annu. Rev. Microbiol.*, 61:51-69 (2007).
Sato et al., "Poly[(R)-3-Hydroxybutyrate] Formation in *Escherichia coli* from Glucose through an Enoyl-CoA Hydratase-Mediated Pathway," *J. Biosci. Bioeng.*, 103:38-44 (2007).
Sauer et al., "Methanol:coenzyme M methyltransferase from Methanosarcina barkeri. Zinc dependence and thermodynamics of the methanol:cob(I)alamin methyltransferase reaction," *Eur. J. Biochem.*, 243:670-677 (1997).
Sawers et al., "Characterization and physiological roles of membrane-bound hydrogenase isoenzymes from Salmonella typhimurium," *J. Bacteriol.*, 168(1):398-404 (1986).
Sawers et al., "Differential expression of hydrogenase isoenzymes in *Escherichia coli* K-12: evidence for a third isoenzyme," *J. Bacteriol.*, 164(3):1324-1331 (1985).
Sawers et al., "Purification and properties of membrane-bound hydrogenase isoenzyme 1 from anaerobically grown *Escherichia coli* K12," *Eur. J. Biochem.*, 156(2):265-275 (1986).
Sawers et al., "The hydrogenases and formate dehydrogenases of *Escherichia coli*," *Antonie van Leeuwenhowek*, 66:57-88 (1994).
Schink et al., "The membrane-bound hydrogenase of Alcaligenes eutrophus. I. Solubilization, purification, and biochemical properties," *Biochim. Biophys. Acta*, 567(2):315-324 (1979).
Schirmer et al., "Microbial Biosynthesis of Alkanes," *Science*, 329:559-562 (2010).

(56) References Cited

OTHER PUBLICATIONS

Schmitz et al., "HoxE—a subunit specific for the pentameric bidirectional hydrogenase complex (HoxEFUYH) of cyanobacteria," *Biochim. Biophys. Acta*, 1554(1-2):66-74 (2002).
Schmitzberger et al., "Structural constraints on protein self-processing in L-aspartate-α-decarboxylase," *EMBO J.*, 22:6193-6204 (2003).
Schneider et al., "Purification and properties of soluble hydrogenase from Alcaligenes eutrophus H 16," *Biochim. Biophys. Acta*, 452:66-80 (1976).
Schurmann et al., "Fructose-6-phosphate Aldolase is a Novel Class I Aldolase from *Escherichia coli* and is Related to a Novel Group of Bacterial Transaldolases," *J. Biol. Chem.*, 276(14):11055-11061 (2001).
Schweiger et al., "Purification of 2-hydroxyglutaryl-CoA dehydratase from Acidaminococcus fermentans:An iron-sulfur protein," *Eur. J. Biochem.*, 169:441-448 (1987).
Schweitzer et al., "The serine hydroxymethyltransferase gene glyA in Corynebacterium glutamicum is controlled by GlyR," *J. Biotechnol.*, 139(3):214-221 (2009).
Seedorf et al., "The genome of Clostridium kluyveri, a strict anaerobe with unique metabolic features," *Proc. Natl. Acad. Sci. USA*, 105(6):2128-2133 (2008).
Selifonova et al., "Rapid Evolution of Novel Traits in Microorganisms," *Appl. Environ. Microbiol.*, 67:3645-3649 (2001).
Selmer et al., "Propionate CoA-transferase from Clostridium propionicum: Cloning of the gene and identification of glutamate 324 at the active site," *Eur. J. Biochem.*, 269:372-380 (2002).
Sen et al., "Developments in Directed Evolution for Improving Enzyme Functions," *Appl. Biochem. Biotechnol.*, 143:212-223 (2007).
Servinsky et al., "Arabinose is metabolized via a phosphoketolase pathway in Clostridium acetobutylicum AtCC 824," *J. Ind. Microbiol. Biotechnol.*, 39:1859-1867 (2012).
Sgorbati et al., "Purification and properties of two fructose-6-phosphate phosphoketolases in Bifidobacterium," *Antonie Van Leeuwenhoek*, 42(1-2):49-57 (1976).
Shafiani et al., "Cloning and characterization of aspartate-ß-semialdehyde dehydrogenase from *Mycobacterium tuberculosis* H37 Rv," *J. Appl. Microbiol.*, 89:832-838 (2005).
Shah et al., "Repressible Alkaline Phosphatase of *Staphylococcus aureus*," *J. Bacteriol.*, 94(3):780-781 (1967).
Shames et al., "Interaction of aspartate and aspartate-derived antimetabolites with the enzymes of the threonine biosynthetic pathway of *Escherichia coli*," *J. Biol. Chem.*, 259(24):15331-15339 (1984).
Shao et al., "Random-priming in vitro recombination: an effective tool for directed evolution," *Nucleic Acids Res.*, 26(2):681-683 (1998).
Sheppard et al., "Purification and Properties of NADH-Dependent 5,10-Methylenetetrahydrofolate Reductase (MetF) from *Escherichia coli*," *J. Bacteriol.*, 181(3):718-725 (1999).
Shimomura et al., "3-hydroxyisobutyryl-CoA hydrolase," *Meth. Enzymol.*, 324:229-240 (2000).
Shimomura et al., "Purification and partial characterization of 3-hydroxyisobutyryl-coenzyme A hydrolase of rat liver," *J. Biol. Chem.*, 269(19):14248-14253 (1994).
Shimoyama et al., "MmcBC inPelotomaculum thermopropionicum represents a novel group of prokaryotic fumarases," *FEMS Microbiol. Lett.*, 270:207-213 (2007).
Shingler et al., "Nucleotide sequence and functional analysis of the complete phenol/3,4-dimethylphenol catabolic pathway of *Pseudomonas* sp. strain CF600," *J. Bacteriol.*, 174(3):711-724 (1992).
Sibilli et al., "Two regions of the bifunctional protein aspartokinase I-homoserine dehydrogenase I are connected by a short hinge," *J. Biol. Chem.*, 256(20):10228-10230 (1981).
Sieber et al., "Libraries of hybrid proteins related sequenc efrsom distantly," *Nat. Biotechnol.*, 19:456-460 (2001).
Simanshu et al., "Structure and function of enzymes involved in the anaerobic degradation of L-threonine to propionate," *J. Biosci.*, 32(6):1195-1206 (2007).
Simicevic et al., "DNA-centered approaches to characterize regulatory protein-DNA interaction complexes," *Mol Biosyst.*, 6(3):462-468 (2010).
Skarstedt et al., "*Escherichia coli* acetate kinase mechanism studied by net initial rate, equilibrium, and independent isotopic exchange kinetics," *J. Biol. Chem.*, 251(21):6775-6783 (1976).
Slater et al., "Multiple b-Ketothiolases Mediate Poly(b-Hydroxyalkanoate) Copolymer Synthesis in Ralstonia eutropha," *J. Bacteriol.*, 180(8):1979-1987 (1998).
Smith et al., "Fumarate metabolism and the microaerophily of *Campylobacter* species," *Int. J. Biochem. Cell Biol.*, 31:961-975 (1999).
Smith et al., "Purification and characteristics of a gamma-glutamyl kinase involved in *Escherichia coli* proline biosynthesis," *J. Bacteriol.*, 157(2):545-551 (1984).
Sohling et al., "Molecular Analysis of the Anaerobic Succinate Degradation Pathway in Clostridium kluyveri," *J. Bacteriol.*, 178(3):871-880 (1996).
Sohling et al., "Purification and characterization of a coenzyme-A-dependent succinate-semialdehyde dehydrogenase from Clostridium kluyveri," *Eur. J. Biochem.*, 212(1):121-127 (1993).
Soini et al., "High cell density media for *Escherichia coli* are generally designed for aerobic cultivations—consequences for large-scale bioprocesses and shake flask cultures," *Microb. Cell Fact.*, 7:26 (2008).
Song et al., "Structure, Function, and Mechanism of the Phenylacetate Pathway Hot Dog-fold Thioesterase Paal," *J. Biol. Chem.*, 281(16):11028-11038 (2006).
Speer et al., "Sequence of the gene for a NAD(P)-dependent formaldehyde dehydrogenase (class III alcohol dehydrogenase) from a marine methanotroph Methylobacter marinus A45," *FEMS Microbiol. Lett.*, 121:349-356 (1994).
Sramek et al., "Purification and properties of *Escherichia coli* coenzyme A-transferase," *Arch. Biochem. Biophys.*, 171:14-26 (1975).
St. Maurice et al., "Flavodoxin:Quinone Reductase (FqrB): a Redox Partner of Pyruvate:Ferredoxin Oxidoreductase That Reversibly Couples Pyruvate Oxidation to NADPH Production in Helicobacter pylori and Campylobacter jejuni," *J. Bacteriol.*, 189(13):4767-4773 (2007).
Stadtman, "Phosphotransacetylase from Clostridium kluyveri," *Methods Enzym.*, 1:596-599 (1955).
Stadtman, "The enzymatic synthesis of beta-alanyl coenzyme A," *J. Am. Chem. Soc.*, 77:5765-5766 (1955).
Stanley et al., "Expression and Stereochemical and Isotope Effect Studies of Active 4-Oxalocrotonate Decarboxylase," *Biochem.*, 39:3514 (2000).
Stanley et al., "Expression and Stereochemical and Isotope Effect Studies of Active 4-Oxalocrotonate Decarboxylase," *Biochem.*, 39:718-726 (2000).
Starnes et al., "Threonine-sensitive aspartokinase-homoserine dehydrogenase complex, amino acid composition, molecular weight, and subunit composition of the complex," *Biochemistry*, 1972:677-687 (1972).
Steinbuchel et al., "NAD-linked L(+)-lactate dehydrogenase from the strict aerobe alcaligenes eutrophus. 2. Kinetic properties and inhibition by oxaloacetate," *Eur. J. Biochem.*, 130(2):329-334 (1983).
Stemmer, "DNA shuffling by random fragmentation and reassembly: in vitro recombination for molecular evolution," *PRoc. Natil. Acad. Sci. USA*, 91:10747-10751 (1994).
Stemmer, "Rapid evolution of a protein in vitro by DNA shuffling," *Nature*, 370:389-391 (1994).
Stols et al., "New vectors for co-expression of proteins: Structure of Bacillus subtilis ScoAB obtained by high-throughput protocols," *Prot. Expr. Purif.*, 53:396-403 (2007).
Strauss et al., "Enzymes of a novel autotrophic CO2 fixation pathway in the phototrophic bacterium Chloroflexus aurantiacus, the 3-hydroxypropionate cycle," *Eur. J. Biochem.*, 215:633-643 (1993).
Suda et al., "Purification and properties of alpha-ketoadipate reductase, a newly discovered enzyme from human placenta," *Arch. Biochem. Biophys.*, 176(2):610-620 (1976).

(56) References Cited

OTHER PUBLICATIONS

Suda et al., "Subcellular localization and tissue distribution of alpha-ketoadipate reduction and oxidation in the rat," *Biochem. Biophys. Res. Commun.*, 77(2):586-591 (1977).
Sulzenbacher et al., "Crystal Structure of *E. coli* Alcohol Dehydrogenase YqhD: Evidence of a Covalently Modified NADP Coenzyme," *J. Mol. Biol.*, 342:489-502 (2004).
Sumper et al., "Acetyl-CoA Carboxylase from Yeast," *Methods Enzym.*, 71:34-37 (1981).
Sunga et al., "The Pichia pastoris formaldehyde dehydrogenase gene (FLD1) as a marker for selection of multicopy expression strains of P. pastoris," *Gene*, 330:39-47 (2004).
Sunohara et al., "Nascent-peptide-mediated ribosome stalling at a stop codon induces mRNA cleavage resulting in nonstop mRNA that is recognized by tmRNA," *RNA*, 10(3):378-386 (2004).
Sunohara et al., "Ribosome stalling during translation elongation induces cleavage of mRNA being translated in *Escherichia coli*," *J. Biol. Chem.*, 279(15):15368-15375 (2004).
Suzuki et al., "*Corynebacterium* sp. U-96 contains a cluster of genes of enzymes for the catabolism of sarcosine to pyruvate," *Biosci. Biotechnol. Biochem.*, 69(5):952-956 (2005).
Suzuki et al., "GriC and GriD Constitute a Carboxylic Acid Reductase Involved in Grixazone Biosynthesis in Streptomyces griseus," *J. Antibiot.*, 60(6):380-387 (2007).
Suzuki et al., "Overexpression, crystallization and preliminary X-ray analysis of xylulose-5-phosphate/fructose-6-phosphate phosphoketolase from Bifidobacterium breve," *Acta Crystallogr. Sect. F Struct. Biol. Cryst. Commun.*, 66(Pt 8):941-943 (2010).
Suzuki et al., "Phosphotransacetylase of *Escherichia coli* B, activation by pyruvate and inhibition by NADH and certain nucleotides," *Biochim. Biophys. Acta*, 191:559-569 (1969).
Svetlitchnyi et al., "A functional Ni—Ni-[4Fe—4S] cluster in the monomeric acetyl-CoA synthase from Carboxydothermus hydrogenoformans," *Proc. Natl. Acad. Sci. USA*, 101:446-451 (2004).
Svetlitchnyi et al., "Two Membrane-Associated NiFeS-Carbon Monoxide Dehydrogenases from the Anaerobic Carbon-Monoxide-Utilizing Eubacterium Carboxydothermus hydrogenoformans," *J. Bacteriol.*, 183(17):5134-5144 (2001).
Takacs et al., "Formate hydrogenlyase in the hyperthermophilic archaeon, Thermococcus litoralis," *BMC Microbiol.*, 8:88 (2008).
Takahashi et al., "Functional assignment of the ORF2-iscS-iscU-iscA-hscB-hscA-fdx-ORF3 gene cluster involved in the assembly of Fe—S clusters in *Escherichia coli*," *J. Biochem.*, 126:917-926 (1999).
Takahashi et al., "Metabolic Pathways for Cytotoxic End Product Formation from Glutamate- and Aspartate-Containing Peptides by Porphyromonas gingivalis," *J. Bacteriol.*, 182(17):4704-4710 (2000).
Takahashi-Abbe et al., "Biochemical and functional properties of a pyruvate formate-lyase (PFL)-activating system in *Streptococcus mutans*," *Oral Microbiol. Immunol.*, 18:293-297 (2003).
Takatsuka et al., "Gene Cloning and Molecular Characterization of Lysine Decarboxylase from Selenomonas ruminantium Delineate Its Evolutionary Relationship to Ornithine Decarboxylases from Eukaryotes," *J. Bacteriol.*, 182(23):6732-6741 (2000).
Takatsuka et al., "Identification of the amino acid residues conferring substrate specificity upon Selenomonas ruminantium lysine decarboxylase," *Biosci. Biotechnol. Biochem.*, 63:1843-1846 (1999).
Tallant et al., "Coenzyme M Methylase Activity of the 480-Kilodalton Corrinoid Protein from Methanosarcina barkeri," *J. Bacteriol.*, 175(5):1295-1301 (1996).
Tallant et al., "Methylthiol:Coenzyme M Methyltransferase from Methanosarcina barkeri, an Enzyme of Methanogenesis from Dimethylsulfide and Methylmercaptopropionate," *J. Bacteriol.*, 179(22):6902-6911 (1997).
Tallant et al., "The MtsA Subunit of the Methylthiol:Coenzyme M Methyltransferase of Methanosarcina barkeri Catalyses Both Half-reactions of Corrinoid-dependent Dimethylsulfide: Coenzyme M Methyl Transfer," *J. Biol. Chem.*, 276:4485-4493 (2001).

Tanaka et al., "Cloning and characterization of a human orthologue of testis-specific succinyl CoA: 3-oxo acid CoA transferase (Scot-t) cDNA," *Mol. Hum. Reprod.*, 8(1):16-23 (2002).
Tanaka et al., "Lysine decarboxylase of Vibrio parahaemolyticus: kinetics of transcription and role in acid resistance," *J. Appl. Microbiol.*, 104:1283-1293 (2008).
Tani et al., "Glycolaldehyde Dehydrogenase, Its Involvement in Vitamin $B_6$ Biosynthetic Pathway of *Escherichia coli* B," *Agric. Biol. Chem.*, 38(10):2057-2058 (1974).
Tani et al., "Separation and Characterization of Glyeolaldehyde Dehydrogenase Isozymes in *Escherichia coli* B," *Agric. Biol. Chem.*, 42(1):63-68 (1978).
Tani et al., "Thermostable NADP1-Dependent Medium-Chain Alcohol Dehydrogenase from *Acinetobacter* sp. Strain M-1: Purification and Characterization and Gene Expression in *Escherichia coli*," *Appl. Environ. Microbiol.*, 66(12):5231-5235 (2000).
Thauer, "A Fifth Pathway of Carbon Fixation," *Science*, 318:1732-1733 (2007).
Thorndike et al., "Production of formaldehyde from N5-methyltetrahydrofolate by normal and leukemic leukocytes," *Cancer Res.*, 37(4):1125-1132 (1977).
Toth et al., "The ald Gene, Encoding a Coenzyme A-Acylating Aldehyde Dehydrogenase, Distinguishes Clostridium beijerinckii and Two Other Solvent-Producing Clostridia from Clostridium acetobutylicum," *Appl. Environ. Microbiol.*, 65(11):4973-4980 (1999).
Toyota et al., "Differential Substrate Specificity and Kinetic Behavior of *Escherichia coli* YfdW and Oxalobacter formigenes Formyl Coenzyme A Transferase," *J. Bacteriol.*, 190(7):2556-2564 (2008).
Tseng et al., "Oxygen- and Growth Rate-Dependent Regulation of *Escherichia coli* Fumarase (FumA, FumB, and FumC) Activity," *J. Bacteriol.*, 183(2):461-467 (2001).
Uchiyama et al., "Identification of the 4-Hydroxycinnamate Decarboxylase (PAD) Gene of *Klebsiella oxytoca*," *Biosci. Biotechnol. Biochem.*, 72(1):116-123 (2008).
Vamecq et al., "The microsomal dicarboxykyk-CoA synthetase," *Biochem. J.*, 230:683-693 (1985).
Van Der Klei et al., "The Hansenula polymorpha per6 mutant is affected in two adjacent genes which encode dihydroxyacetone kinase and a novel protein, Pak1p, involved in peroxisome integrity," *Curr. Genet.*, 34:1-11 (1998).
Van Der Oost et al., "Genetic and biochemical characterization of a short-chain alcohol dehydrogenase from the hyperthermophilic archaeon Pyrococcus furiosus," *Eur. J. Biochem.*, 268:3062-3068 (2001).
Van Grinsven et al., "Acetate:Succinate CoA-transferase in the Hydrogenosomes of Trichomonas vaginalis," *J. Biol. Chem.*, 283:1411-1418 (2008).
Van Mourik et al., "Functional analysis of a Campylobacter jejuni alkaline phosphatase secreted via the Tat export machinery," *Microbiol.*, 154:584-592 (2008).
Van Vliet et al., "The iron-induced ferredoxin FdxA of Campylobacter jejuni is involved in aerotolerance," *FEMS Microbiol. Lett.*, 196:189-193 (2001).
Vanderwinkel et al., "Growth of *Escherichia coli* on fatty acids: requirement for coenzyme A transferase activity," *Biochem. Biophys. Res. Commun.*, 33(6):902-908 (1968).
Vardar-Schara et al., "Metabolically engineered bacteria for producing hydrogen via fermentation," *Microb. Biotechnol.*, 1(2):107-125 (2008).
Vazquez et al., "Phosphotransbutyrylase Expression in Bacillus megaterium," *Curr. Microbiol.*, 42:345-349 (2001).
Venkitasubramanian et al., "Reduction of Carboxylic Acids by Nocardia Aldehyde Oxidoreductase Requires a Phosphopantetheinylated Enzyme," *J. Biol. Chem.*, 282(1):478-485 (2007).
Venkitasubramanian et al., *Biocatalysis in the Pharmaceutical and Biotechnology Industries*, "Biocatalytic Reduction of Carboxylic Acids: Mechanism and Applications," *CRC Press LLC*, Boca Raton, Florida, chapter 15, pp. 425-440 (2006).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).

(56) References Cited

OTHER PUBLICATIONS

Vorholt et al., "Novel Formaldehyde-Activating Enzyme in Methylobacterium extorquens AM1 Required for Growth on Methanol," *J. Bacteriol.*, 182(23):6645-6650 (2000).
Wakil et al., "Studies on the fatty acid oxidizing system of animal tissues: beta-Hydroxyacyl coenzyme A dehydrogenase," *J. Biol. Chem.*, 207(2):631-638 (1954).
Walter et al., "Molecular characterization of two Clostridium acetobutylicum ATCC 824 butanol dehydrogenase isozyme genes," *J. Bacteriol.*, 174(22):7149-7158 (1992).
Walter et al., "Sequence and arrangement of two genes of the butyrate-synthesis pathway of Clostridium acetobutylicum ATCC 824," *Gene*, 107-111 (1993).
Wang et al., "Activation of Silent Genes by Transposons Tn5 and Tn10," *Genetics*, 120(4):875-885 (1988).
Wang et al., "Determination of the metal ion dependence and substrate specificity of a hydratase involved in the degradation pathway of biphenyl/chlorobiphenyl," *FEBS J.*, 272:966-974 (2005).
Wang et al., "Molecular cloning and functional identification of a novel phenylacetyl-CoA ligase gene from Penicillium chrysogenum," *Biochem. Biophys. Res. Comm.*, 360:453-458 (2007).
Wang et al., "NADP+ Reduction with Reduced Ferredoxin and NADP+ Reduction with NADH Are Coupled via an Electron-Bifurcating Enzyme Complex in Clostridium kluyveri," *J. Bacteriol.*, 192(19):5115-5123 (2010).
Wang et al., "Overview of Regulatory Strategies and Molecula Elements in Metabolic Engineering of Bacteria," *Mol. Biotechnol.*, 52(2):300-308 (2012).
Weaver et al., "Structure of free fumarase C from *Escherichia coli*," *Acta Crystallogr. D. Biol. Crystallogr.*, 61:1395-1401 (2005).
Weidner et al., "Molecular Characterization of the Genes Encoding Pyruvate Formate-Lyase and Its Activating Enzyme of Clostridium pasteurianum," *J. Bacteriol.*, 178(8):2440-2444 (1996).
Westin et al., "The Identification of a Succinyl-CoA Thioesterase Suggests a Novel Pathway for Succinate Production in Peroxisomes," *J. Biol. Chem.*, 280(46):38125-38132 (2005).
Whitehead et al., "Cloning and expression in *Escherichia coli* of the gene for 10-formyltetrahydrofolate synthetase from Clostridium acidiurici ("Clostridium acidi-urici")," *J. Bacteriol.*, 167(1):205-209 (1986).
Whitehead et al., "Nucleotide sequence of the Clostridium acidiurici ("Clostridium acidi-urici") gene for 10-formyltetrahydrofolate synthetase shows extensive amino acid homology with the trifunctional enzyme C1-tetrahydrofolate synthase from *Saccharomyces cerevisiae*," *J. Bacteriol.*, 170(7):3255-3261 (1988).
Wieland et al., "Engineering of ribozyme-based riboswitches for mammalian cells," *Methods*, 56(3):351-357 (2012).
Wiesenborn et al., "Coenzyme AA transferase from Clostridium acetobutylicum ATCC 824 and its role in the uptake of acids," *Appl. Environ. Microbiol.*, 55(2):323-329 (1989).
Wiesenborn et al., "Phosphotransbutyrylase from Clostridium acetobutylicum ATCC 824 and its role in acidogenesis," *Appl. Environ. Microbiol.*, 55(2):317-322 (1989).
Willke et al., "Biotechnological production of itaconic acid," *Appl. Microbial. Biotechnol.*, 56:289-295 (2001).
Winzer et al., "Acetate kinase from Clostridium acetobutylicum: a highly specific enzyme that is actively transcribed during acidogenesis and solventogenesis," *Microbiol.*, 143:3279-3286 (1997).
Winzer et al., "Differential Regulation of Two Thiolase Genes from Clostridium acetobutylicum DSM 792," *J. Mol. Microbiol. Biotechnol.*, 2(4):531-541 (2000).
Wolff et al., "Purification and Characterization of the Oxygen-Sensitive 4-Hydroxybutanoate Dehydrogenase from Clostridium kluyveri," *Prot. Exp. Purif.*, 6:206-212 (1995).
Wong et al., "Molecular properties of pyruvate formate-lyase activating enzyme," *Biochemistry*, 32(51):14102-14110 (1993).
Wong et al., "Sequence saturation mutagenesis (SeSaM): a novel method for directed evolution," *Nucelic Acids Res.*, 32(3):e26 (2004).
Wong et al., "Sequence saturation mutagenesis with tunable mutation frequencies," *Anal. Biocehm.*, 341:187-189 (2005).
Wong et al., "Transversion-enriched sequence saturation mutagenesis (SeSaM-Tv+): A random mutagenesis method with consecutive nucleotide exchanges that complements the bias of error-prone PCR," *Biotechnol. J.*, 3:74-82 (2008).
Woods et al., "Two biochemically distinct classes of fumarase in *Escherichia coli*," *Biochim. Biophys. Acta*, 954:14-26 (1988).
Wu et al., "Life in Hot Carbon Monoxide: The Complete Genome Sequence of Carboxydothermus hydrogenoformans Z-2901," *PLoS Genet.*, 1:e65 (2005).
Yabutani et al., "Analysis of beta-ketothiolase and acetoacetyl-CoA reductase genes of a methylotrophic bacterium, Paracoccus denitrificans, and their expression in *Escherichia coli*," *FEMS Microbiol. Lett.*, 133:85-90 (1995).
Yamamoto et al., "Carboxylation reaction catalyzed by 2-oxoglutarate:ferredoxin oxidoreductases from Hydrogenobacter thermophiles," *Extremophiles*, 14:79-85 (2010).
Yamamoto et al., "Purification and properties of NADP-dependent formate dehydrogenase from Clostridium thermoaceticum, a tungsten-selenium-iron protein," *J. Biol. Chem.*, 258(3):1826-1832 (1983).
Yang et al., "Collaborative spirit of histone deacetylases in regulating chromatin structure and gene expression," *Curr. Opin. Genet. Dev.*, 13(2):143-153 (2003).
Yang et al., "Nucleotide sequence of the promoter and fadB gene of the fadBA operon and primary structure of the multifunctional fatty acid oxidation protein from *Escherichia coli*," *Biochemistry*, 30(27):6788-6795 (1991).
Yang, "Location of the fadBA operon on the physical map of *Escherichia coli*," *J. Bacteriol.*, 173:7405-7406 (1991).
Yarlett et al., "Trichomonas vaginalis: characterization of ornithine decarboxylase," *Biochem. J.*, 293:487-493 (1993).
Yasueda et al., "Bacillus subtilis yckG and yckF Encode Two Key Enzymes of the Ribulose Monophosphate Pathway Used by Methylotrophs, and yckH is Required for Their Expression," *J. Bacteriol.*, 181(23):7154-7160 (1999).
Yin et al., "The gene encoding xylulose-5-phosphate/fructose-6-phosphate phosphoketolase (xfp) is conserved among *Bifidobacterium* species within a more variable region of the genome and both are useful for strain identification," *FEMS Microbiol. Lett.*, 246(2):251-257 (2005).
Ylianttila et al., "Crystal Structure of Yeast Peroxisomal Multifunctional Enzyme: Structural Basis for Substrate Specificity o (3R)-hydroxyacyl-CoA Dehydrogenase Units," *J. Mol. Biol.*, 358:1286-1295 (2006).
Ylianttila et al., "Site-directed mutagenesis to enable and improve crystallizability of Candida tropicalis (3R)-hydroxyacyl-CoA dehydrogenase," *Biochem. Biophys. Res. Commun.*, 324:25-30 (2004).
Yoon et al., "Purification and characterization of pyruvate:ferredoxin oxidoreductase from Hydrogenobacter thermophilus TK-6," *Arch. Microbiol.*, 167(5):275-279 (1997).
Youngleson et al., "Homology between hydroxybutyryl and hydroxyacyl coenzyme A dehydrogenase enzymes from Clostridium acetobutylicum fermentation and vertebrate fatty acid beta-oxidation pathways," *J. Bacteriol.*, 171(12):6800-6807 (1989).
Yuan et al., "Prokaryotic ubiquitin-like ThiS fusion enhances the heterologous protein overexpression and aggregation in *Escherichia coli*," *PLoS One*, 8(4):e62529 (2013).
Zeiher et al., "Identification and Characterization of Mitochondrial Acetyl-Coenzyme A Hydrolase from Pisum sativum L. Seedlings," *Plant Physiol.*, 94:20-27 (1990).
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," *Microboil.*, 145:2323-2334 (1999).
Zhao et al., "Molecular evolution by staggered extension process (StEP) in vitro recombination," *Nat. Biotechnol.*, 16(3):258-261 (1998).
Zhou et al., "Engineering a native homoethanol pathway in *Escherichia coli* B for ethanol production," *Biotechnol. Lett.*, 30:335-342 (2008).

(56) References Cited

OTHER PUBLICATIONS

Zhou et al., "Isolation, crystallization and preliminary X-ray analysis of a methanol-induced corrinoid protein from Moorella thermoacetica," *Acta Crystallogr. Sect. F. Struct. Biol. Cryst. Commun.*, 61:537-540 (2005).

Zhou et al., "The remarkable structural and functional organization of the eukaryotic pyruvate dehydrogenase complexes," *Proc. Natl. Acad. Sci. USA*, 98(26):14802-14807 (2001).

\* cited by examiner

MICROORGANISMS AND METHODS FOR THE PRODUCTION OF BUTADIENE USING ACETYL-COA

CROSS-REFERENCE TO RELATED APPLICATION

This application is a United States National Stage Application under 35 U.S.C. § 371 of International Patent Application No. PCT/US2015/038945, filed Jul. 2, 2015, which claims the benefit of priority of U.S. Provisional Application No. 62/023,786, filed Jul. 11, 2014, the entire contents of each of which are incorporated herein by reference.

BACKGROUND OF THE INVENTION

The present invention relates generally to biosynthetic processes, and more specifically to organisms having 2,4-pentadienoate or butadiene biosynthetic capability.

Over 25 billion pounds of butadiene (1,3-butadiene, BD) are produced annually and is applied in the manufacture of polymers such as synthetic rubbers and ABS resins, and chemicals such as hexamethylenediamine and 1,4-butanediol. Butadiene is typically produced as a by-product of the steam cracking process for conversion of petroleum feedstocks such as naphtha, liquefied petroleum gas, ethane or natural gas to ethylene and other olefins. The ability to manufacture butadiene from alternative and/or renewable feedstocks would represent a major advance in the quest for more sustainable chemical production processes.

One possible way to produce butadiene renewably involves fermentation of sugars or other feedstocks to produce diols, such as 1,4-butanediol or 1,3-butanediol, which are separated, purified, and then dehydrated to butadiene in a second step involving metal-based catalysis. Direct fermentative production of butadiene from renewable feedstocks would obviate the need for dehydration steps and butadiene gas (bp −4.4° C.) would be continuously emitted from the fermenter and readily condensed and collected. Developing a fermentative production process would eliminate the need for fossil-based butadiene and would allow substantial savings in cost, energy, and harmful waste and emissions relative to petrochemically-derived butadiene.

2,4-pentadienoate is a useful substituted butadiene derivative in its own right and a valuable intermediate en route to other substituted 1,3-butadiene derivatives, including, for example, 1-carbamoyl-1,3-butadienes which are accessible via Curtius rearrangement. The resultant N-protected-1,3-butadiene derivatives can be used in Diels alder reactions for the preparation of substituted anilines. 2,4-Pentadienoate can be used in the preparation of various polymers and co-polymers.

Thus, there exists a need for alternative methods for effectively producing commercial quantities of compounds such as 2,4-pentadienoate or butadiene. The present invention satisfies this need and provides related advantages as well.

SUMMARY OF INVENTION

The invention provides non-naturally occurring microbial organisms containing butadiene or 2,4-pentadienoate pathways having at least one exogenous nucleic acid encoding a butadiene or 2,4-pentadienoate pathway enzyme expressed in a sufficient amount to produce butadiene or 2,4-pentadienoate. The invention additionally provides methods of using such microbial organisms to produce butadiene or 2,4-pentadienoate by culturing a non-naturally occurring microbial organism containing butadiene or 2,4-pentadienoate pathways as described herein under conditions and for a sufficient period of time to produce butadiene or 2,4-pentadienoate.

In some embodiments, provided herein is a non-naturally occurring microbial organism containing a butadiene or a 2,4-pentadienoate pathway described herein and further having an acetyl-CoA pathway, a formaldehyde fixation pathway, a methanol metabolic pathway, a formate assimilation pathway, a methanol oxidation pathway, a hydrogenase, a carbon monoxide dehydrogenase, or any combination thereof. In some aspects, the organism includes at least one exogenous nucleic acid encoding at least an enzyme of the acetyl-CoA pathway, the formaldehyde fixation pathway, the methanol metabolic pathway, the formate assimilation pathway, the methanol oxidation pathway, the hydrogenase, or any combination thereof, that is expressed in a sufficient amount to enhance the availability of acetyl-CoA or reducing equivalents. Such organisms of the invention advantageously enhance the production of substrates and/or pathway intermediates for the production of butadiene, 2,4-pentadienoate or hydrogen.

In some embodiments, provided herein is a non-naturally occurring microbial organism containing a butadiene or a 2,4-pentadienoate pathway described herein and further includes attenuation of one or more endogenous enzymes, which enhances carbon flux through acetyl-CoA, or a gene disruption of one or more endogenous nucleic acids encoding such enzymes. For example, in some aspects, the endogenous enzyme can be selected from DHA kinase, methanol oxidase, PQQ-dependent methanol dehydrogenase, DHA synthase or any combination thereof.

In some embodiments, provided herein is a non-naturally occurring microbial organism containing a butadiene or a 2,4-pentadienoate pathway described herein and further having a hydrogen synthesis pathway catalyzing the synthesis of hydrogen from a reducing equivalent, wherein the hydrogen synthesis pathway includes an enzyme selected from the group consisting of a hydrogenase, a formate-hydrogene lyase and ferredoxin: NADP+ oxidoreductase. In one aspect, the reducing equivalent is selected from the group consisting of NADH, NADPH, FADH, reduced quinones, reduced ferredoxins, reduced flavodoxins or reduced thioredoxins In some embodiments, provided herein is a method for producing a combination of butadiene and hydrogen or of 2,4-pentadienoate and hydrogen including culturing a non-naturally occurring microbial organism disclosed herein under conditions and for a sufficient period of time to produce a butadiene and hydrogen or 2,4-pentadienoate and hydrogen.

In some embodiments, provided herein is bioderived butadiene, 2,4-pentadienoate or hydrogen produced according to a method disclosed herein. In some embodiments, provided herein is a biobased product having the bioderived butadiene, 2,4-pentadienoate or hydrogen.

In some embodiments, provided herein is a process for producing hydrogen including (a) culturing a non-naturally culturing microbial organism disclosed herein in a substantially anaerobic culture medium under a condition to produce hydrogen; (b) separating the produced hydrogen from the culture medium; and (c) collecting the separated hydrogen.

Acetaldehyde dehydrogenase, B. 4-hydroxy 2-oxovalerate aldolase, C. 4-hydroxy 2-oxovalerate dehydratase, D. 2-oxopentenoate reductase, E. 2-hydroxypentenoate dehydratase, F. 2,4-pentadienoate decarboxylase, G. 2-oxopentenoate ligase, H. 2-oxopentenoate:acetyl CoA CoA transferase, I. 2-oxopentenoyl-CoA reductase, J. 2-hydroxypentenoate ligase, K. 2-hydroxypentenoate:acetyl-CoA CoA transferase, L. 2-hydroxypentenoyl-CoA dehydratase, M. 2,4-Pentadienoyl-CoA hydrolase, N. 2,4-Pentadienoyl-CoA: acetyl CoA CoA transferase.

Figure 2:
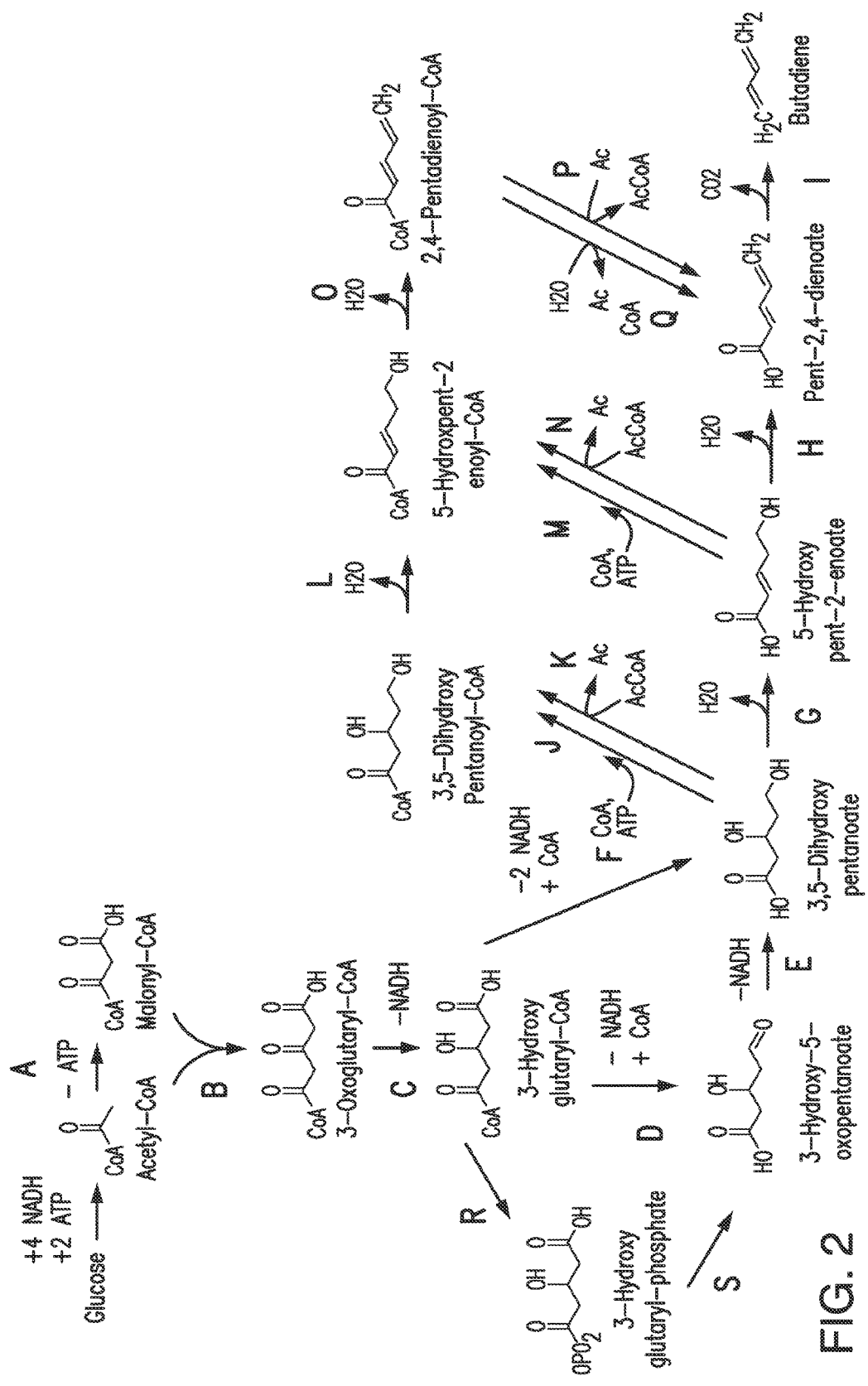

FIG. 2 shows exemplary pathways to form butadiene and 2,4-pentadienoate via 3-oxoglutaryl-CoA. The enzymes are: A. Acetyl-CoA carboxylase, B. malonyl-CoA:acetyl-CoA acyltransferase, C. 3-Oxoglutaryl-CoA reductase (ketone-reducing), D. 3-hydroxyglutaryl-CoA reductase (aldehyde forming), E. 3-hydroxy-5-oxopentanoate reductase, F. 3-hydroxyglutaryl-CoA reductase (alcohol forming), G. 3,5-dihydroxypentanoate dehydratase, H. 5-hydroxypent-2-enoate dehydratase, I. 2,4-pentadienoate decarboxylase, J. 3,5-dihydroxypentanoate ligase, K. 3,5-dihydroxypentanoate: acetyl-CoA CoA transferase, L. 3,5-dihydroxypentanoyl-CoA dehydratase, M. 5-hydroxypent-2-enoate ligase, N. 5-hydroxypent-2-enoate:acetyl-CoA CoA transferase, O. 5-hydroxypent-2-enoyl-CoA hydrolase, P. 2,4-pentadienoyl-CoA CoA hydrolase, Q. 2,4-pentadienoyl-CoA:acetyl-CoA CoA transferase, R. Phosphate-3-hydroxyglutaryl transferase, S. 3-hydroxy-5-oxopentanoate synthase.

Figure 3:
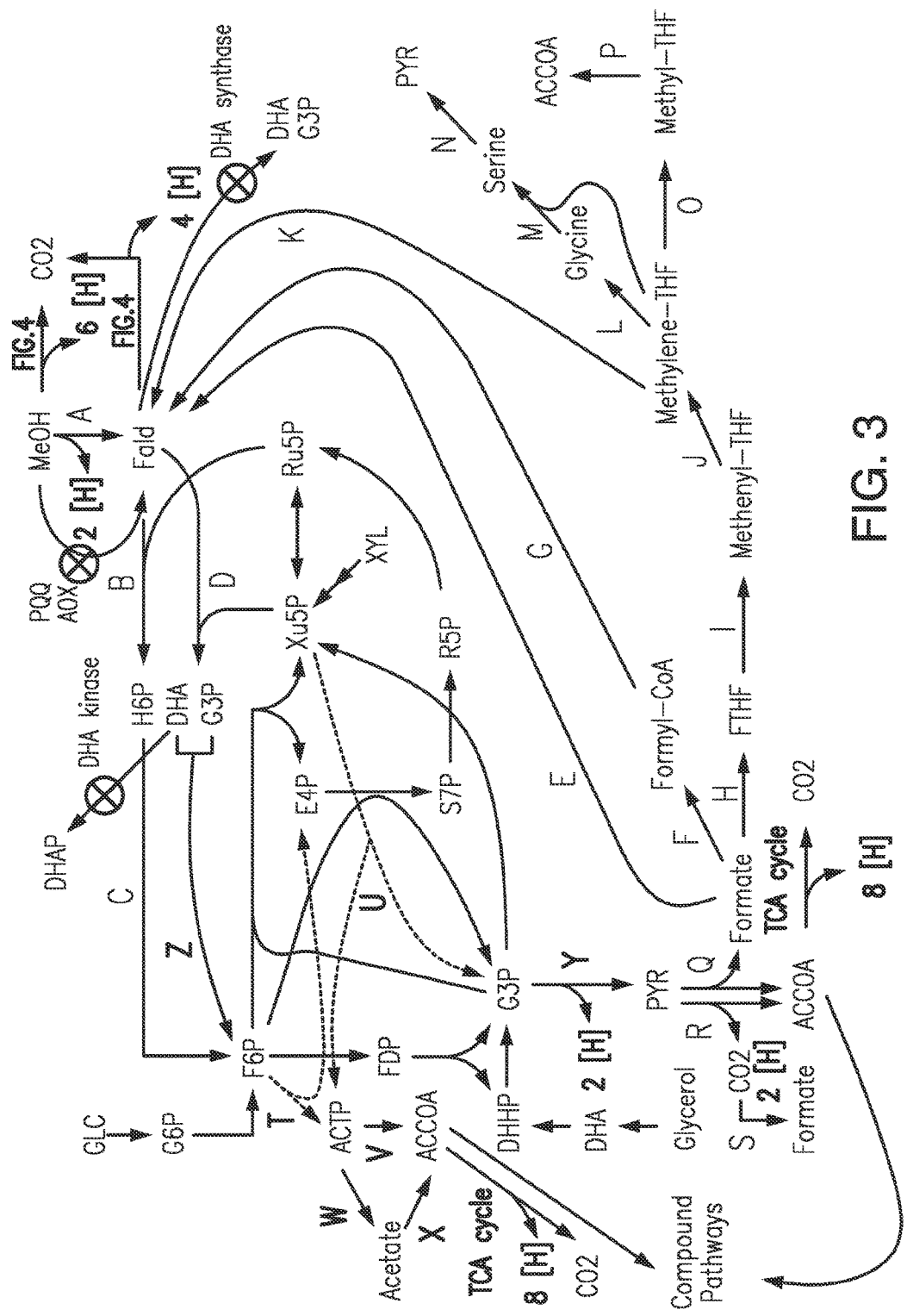

FIG. 3 shows exemplary metabolic pathways enabling the conversion of CO2, formate, formaldehyde (Fald), methanol (MeOH), glycerol, xylose (XYL) and glucose (GLC) to acetyl-CoA (ACCOA) and exemplary endogenous enzyme targets for optional attenuation or disruption. The exemplary pathways can be combined with bioderived compound pathways, including the pathways depicted herein that utilize ACCOA, such as those depicted in FIGS. 1-2. The enzyme targets are indicated by arrows having "X" markings. The endogenous enzyme targets include DHA kinase, methanol oxidase (AOX), PQQ-dependent methanol dehydrogenase (PQQ) and/or DHA synthase. The enzymes are: A. methanol dehydrogenase, B. 3-hexulose-6-phosphate synthase, C. 6-phospho-3-hexuloisomerase, D. dihydroxyacetone synthase, E. formate reductase, F. formate ligase, formate transferase, or formate synthetase, G. formyl-CoA reductase, H. formyltetrahydrofolate synthetase, I. methenyltetrahydrofolate cyclohydrolase, J. methylenetetrahydrofolate dehydrogenase, K. spontaneous or formaldehyde-forming enzyme, L. glycine cleavage system, M. serine hydroxymethyltransferase, N. serine deaminase, O. methylenetetrahydrofolate reductase, P. acetyl-CoA synthase, Q. pyruvate formate lyase, R. pyruvate dehydrogenase, pyruvate ferredoxin oxidoreductase, or pyruvate:NADP+ oxidoreductase, S. formate dehydrogenase, T. fructose-6-phosphate phosphoketolase, U. xylulose-5-phosphate phosphoketolase, V. phosphotransacetylase, W. acetate kinase, X. acetyl-CoA transferase, synthetase, or ligase, Y. lower glycolysis including glyceraldehyde-3-phosphate dehydrogenase, Z. fructose-6-phosphate aldolase.

Figure 4:
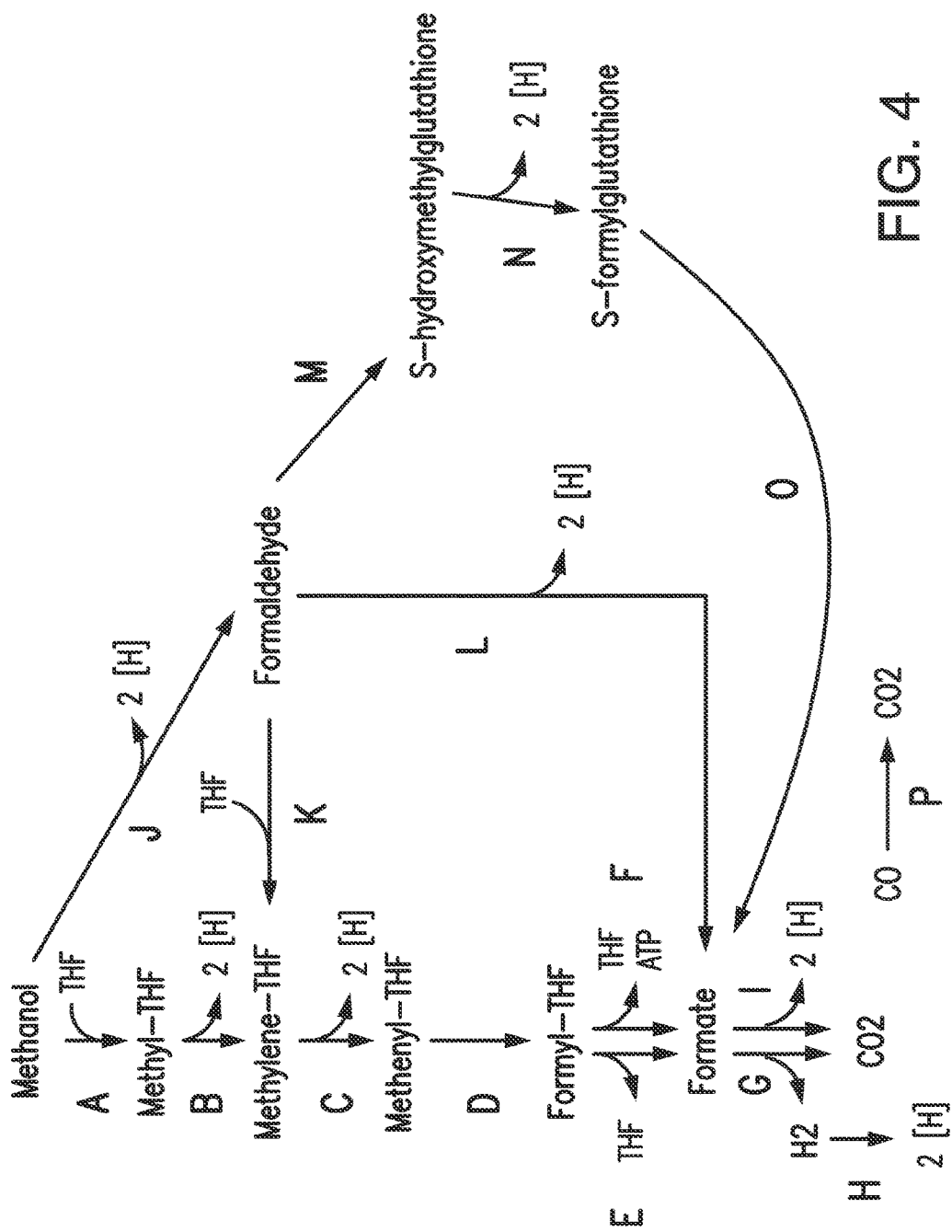

FIG. 4 shows exemplary metabolic pathways that provide the extraction of reducing equivalents from methanol, hydrogen, or carbon monoxide. The enzymes are: A. methanol methyltransferase, B. methylenetetrahydrofolate reductase, C. methylenetetrahydrofolate dehydrogenase, D. methenyltetrahydrofolate cyclohydrolase, E. formyltetrahydrofolate deformylase, F. formyltetrahydrofolate synthetase, G. formate hydrogen lyase, H. hydrogenase, I. formate dehydrogenase, J. methanol dehydrogenase, K. spontaneous or formaldehyde activating enzyme, L. formaldehyde dehydrogenase, M. spontaneous or S-(hydroxymethyl)glutathione synthase, N. Glutathione-Dependent Formaldehyde Dehydrogenase, O. S-formylglutathione hydrolase, P. carbon monoxide dehydrogenase. See abbreviation list below for compound names.

Figure 5:
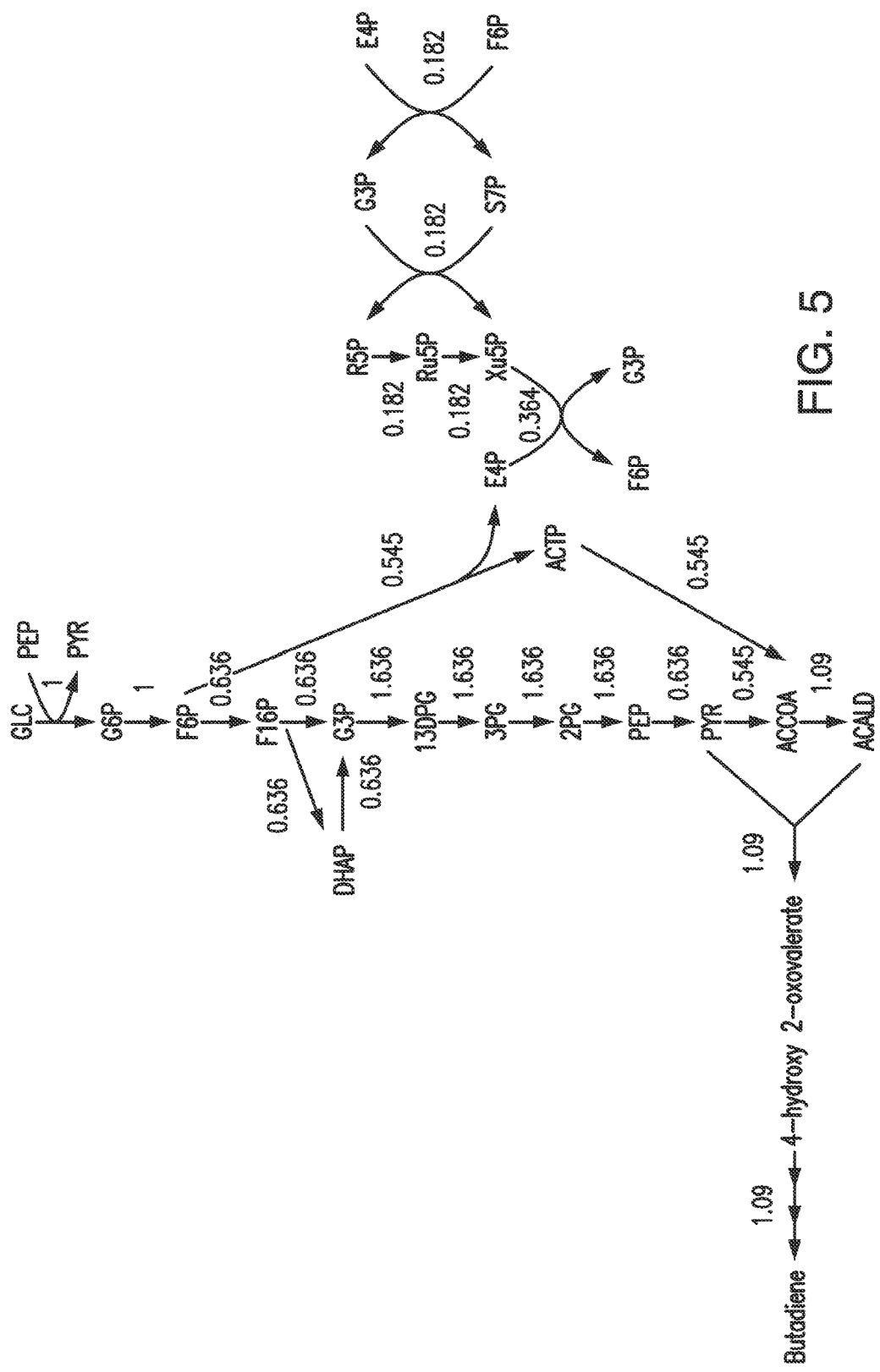

FIG. 5 shows the carbon flux distribution of a butadiene pathway via 4-hydroxy 2-oxovalerate when incorporating the phoshoketolase pathway. The theoretical yield of the pathway is improved from 1 mol butadiene per mole glucose to 1.09 mole butadiene per mole glucose. See abbreviation list below for compound names.

DETAILED DESCRIPTION OF THE INVENTION

Provided herein is the design and production of cells and organisms having biosynthetic production capabilities for butadiene or 2,4-pentadienoate. The invention, in particular, relates to the design of microbial organisms capable of producing butadiene or 2,4-pentadienoate by introducing one or more nucleic acids encoding a butadiene or 2,4-pentadienoate pathway enzyme.

The following is a list of abbreviations and their corresponding compound or composition names. These abbreviations, which are used throughout the disclosure and the figures. It is understood that one of ordinary skill in the art can readily identify these compounds/compositions by such nomenclature: MeOH or MEOH=methanol; Fald=formaldehyde; GLC=glucose; G6P=glucose-6-phosphate; H6P=hexulose-6-phosphate; F6P=fructose-6-phosphate; FDP=fructose diphosphate or fructose-1,6-diphosphate; DHA=dihydroxyacetone; DHAP=dihydroxyacetone phosphate; G3P=glyceraldehyde-3-phosphate; PYR=pyruvate; ACTP=acetyl-phosphate; ACCOA=acetyl-CoA; AACOA=acetoacetyl-CoA; MALCOA=malonyl-CoA; FTHF=formyltetrahydrofolate; THF=tetrahydrofolate; E4P=erythrose-4-phosphate: Xu5P=xyulose-5-phosphate; Ru5P=ribulose-5-phosphate; S7P=sedoheptulose-7-phosphate: R5P=ribose-5-phosphate; XYL=xylose; TCA=tricarboxylic acid; PEP=Phosphoenolpyruvate; OAA=Oxaloacetate; MAL=malate.

Pathways identified herein, and particularly pathways exemplified in specific combinations presented herein, are superior over other pathways based in part on the applicant's ranking of pathways based on attributes including maximum theoretical yield, maximal carbon flux, maximal production of reducing equivalents, minimal production of CO2, pathway length, number of non-native steps, thermodynamic feasibility, number of enzymes active on pathway substrates or structurally similar substrates, and having steps with currently characterized enzymes, and furthermore, the latter pathways are even more favored by having in addition at least the fewest number of non-native steps required, the most enzymes known active on pathway substrates or structurally similar substrates, and the fewest total number of steps from central metabolism.

In one embodiment, the invention utilizes in silico stoichiometric models of *Escherichia coli* metabolism that identify metabolic designs for biosynthetic production of butadiene or 2,4-pentadienoate. The results described herein indicate that metabolic pathways can be designed and recombinantly engineered to achieve the biosynthesis of butadiene or 2,4-pentadienoate in *Escherichia coli* and other cells or organisms. Biosynthetic production of butadiene or 2,4-pentadienoate, for example, for the in silico designs can be confirmed by construction of strains having the designed metabolic genotype. These metabolically engineered cells or organisms also can be subjected to adaptive evolution to further augment butadiene or 2,4-pentadienoate biosynthesis, including under conditions approaching theoretical maximum growth.

In certain embodiments, the butadiene or 2,4-pentadienoate biosynthesis characteristics of the designed strains make them genetically stable and particularly useful in continuous bioprocesses. Separate strain design strategies were identified with incorporation of different non-native or heterologous reaction capabilities into E. coli or other host organisms leading to butadiene or 2,4-pentadienoate producing metabolic pathways from acetyl-CoA. In silico metabolic designs were identified that resulted in the biosynthesis of butadiene or 2,4-pentadienoate in microorganisms from each of these substrates or metabolic intermediates.

Strains identified via the computational component of the platform can be put into actual production by genetically engineering any of the predicted metabolic alterations, which lead to the biosynthetic production of butadiene or 2,4-pentadienoate or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a butadiene or 2,4-pentadienoate biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring microorganisms of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a butadiene or 2,4-pentadienoate of the invention, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of butadiene or 2,4-pentadienoate of the invention, but does not necessarily mimic complete disruption of the enzyme or protein.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having butadiene or 2,4-pentadienoate biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionarily related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Figure 1:
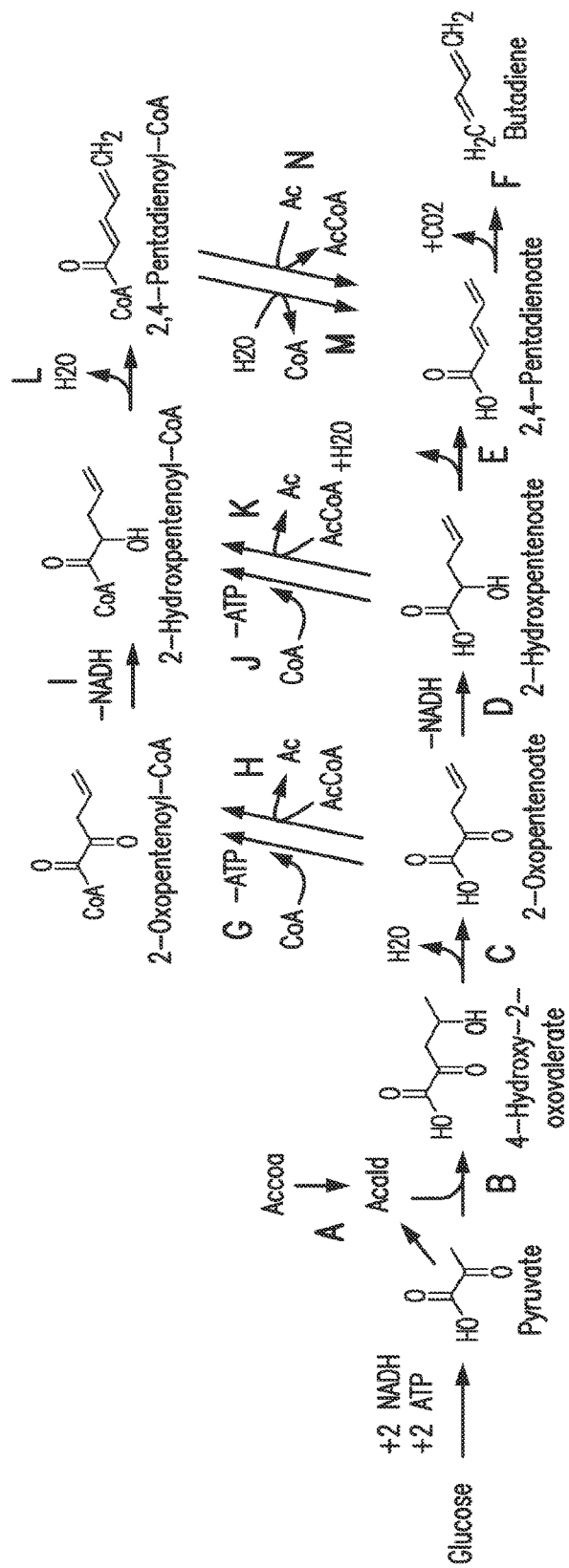
FIG. 1 shows exemplary pathways to form butadiene and 2,4-pentadienoate via 2-oxopentenoate. The enzymes are: A.

In some embodiments, the invention provides a non-naturally occurring microbial organism having a butadiene pathway, having at least one exogenous nucleic acid encoding a butadiene pathway enzyme expressed in a sufficient amount to produce butadiene, wherein the butadiene pathway includes a pathway shown in FIGS. 1 and 2 selected from: (1) 1A, 1B, 1C, 1G, 1I, 1L, 1M, and 1F; (2) 1A, 1B, 1C, 1G, 1I, 1L, 1N, and 1F; (3) 1A, 1B, 1C, 1H, 1I, 1L, 1M, and 1F; (4) 1A, 1B, 1C, 1H, 1I, 1L, 1N, and 1F; (5) 1A, 1B, 1C, 1D, 1J, 1L, 1M, and 1F; (6) 1A, 1B, 1C, 1D, 1J, 1L, 1N, and 1F; (7) 1A, 1B, 1C, 1D, 1K, 1L, 1M, and 1F; (8) 1A, 1B, 1C, 1D, 1K, 1L, 1N, and 1F; (9) 1B, 1C, 1G, 1I, 1L, 1M, and 1F; (10) 1B, 1C, 1G, 1I, 1L, 1N, and 1F; (11) 1B, 1C, 1H, 1I, 1L, 1M, and 1F; (12) 1B, 1C, 1H, 1I, 1L, 1N, and 1F; (13) 1B, 1C, 1D, 1J, 1L, 1M, and 1F; (14) 1B, 1C, 1D, 1J, 1L, 1N, and 1F; (15) 1B, 1C, 1D, 1K, 1L, 1M, and 1F; (16) 1B, 1C, 1D, 1K, 1L, 1N, and 1F; (17) 2A, 2B, 2C, 2R, 2S, 2E, 2J, 2L, 2O, 2Q, and 2; (18) 2A, 2B, 2C, 2R, 2S, 2E, 2J, 2L, 2O, 2P, and 2I; (19) 2A, 2B, 2C, 2R, 2S, 2E, 2K, 2L, 2O, 2Q, and 2I; (20) 2A, 2B, 2C, 2R, 2S, 2E, 2K, 2L, 2O, 2P, and 2I; (21) 2A, 2B, 2C, 2R, 2S, 2E, 2G, 2M, 2O, 2Q, and 2I; (22) 2A, 2B, 2C, 2R, 2S, 2E, 2G, 2M, 2O, 2P, and 2I; (23) 2A, 2B, 2C, 2R, 2S, 2E, 2G, 2N, 2O, 2Q, and 2I; (24) 2A, 2B, 2C, 2R, 2S, 2E, 2G, 2N, 2O, 2P, and 2I; (25) 2A, 2B, 2C, 2R, 2S, 2E, 2G, 2H, and 2I; (26) 2A, 2B, 2C, 2D, 2E, 2J, 2L, 2O, 2Q, and 2I; (27) 2A, 2B, 2C, 2D, 2E; 2J, 2L, 2O, 2P, and 2I; (28) 2A, 2B, 2C, 2D, 2E, 2K, 2L, 2O, 2Q, and 2I; (29) 2A, 2B, 2C, 2D, 2E, 2K, 2L, 2O, 2P, and 2I; (30) 2A, 2B, 2C, 2D, 2E, 2G, 2M, 2O, 2Q, and 2I; (31) 2A, 2B, 2C, 2D, 2E, 2G, 2M, 2O, 2P, and 2I; (32) 2A, 2B, 2C, 2D, 2E, 2G, 2N, 2O, 2Q, and 2I; (33) 2A, 2B, 2C, 2D, 2E, 2G, 2N, 2O, 2P, and 2I; (34) 2A, 2B, 2C, 2F, 2J, 2L, 2O, 2Q, and 2I; (35) 2A, 2B, 2C, 2F, 2J, 2L, 2O, 2P, and 2I; (36) 2A, 2B, 2C, 2F, 2K, 2L, 2O, 2Q, and 2I; (37) 2A, 2B, 2C, 2F, 2K, 2L, 2O, 2P, and 2I; (38) 2A, 2B, 2C, 2F, 2G, 2M, 2O, 2Q, and 2I; (39) 2A, 2B, 2C, 2F, 2G, 2M, 2O, 2P, and 2I; (40) 2A, 2B, 2C, 2F, 2G, 2N, 2O, 2Q, and 2I; (41) 2A, 2B, 2C, 2F, 2G, 2N, 2O, 2P, and 2I; (42) 2B, 2C, 2R, 2S, 2E, 2J, 2L, 2O, 2Q, and 2I; (43) 2B, 2C, 2R, 2S, 2E, 2J, 2L, 2O, 2P, and 2I; (44) 2B, 2C, 2R, 2S, 2E, 2K, 2L, 2O, 2Q, and 2I; (45) 2B, 2C, 2R, 2S, 2E, 2K, 2L, 2O, 2P, and 2I; (46) 2B, 2C, 2R, 2S, 2E, 2G, 2M, 2O, 2Q, and 2I; (47) 2B, 2C, 2R, 2S, 2E, 2G, 2M, 2O, 2P, and 2I; (48) 2B, 2C, 2R, 2S, 2E, 2G, 2N, 2O, 2Q, and 2I; (49) 2B, 2C, 2R, 2S, 2E, 2G, 2N, 2O, 2P, and 2I; (50) 2B, 2C, 2R, 2S, 2E, 2G, 2H, and 2I; (51) 2B, 2C, 2D, 2E, 2J, 2L, 2O, 2Q, and 2I; (52) 2B, 2C, 2D, 2E, 2J, 2L, 2O, 2P, and 2I; (53) 2B, 2C, 2D, 2E, 2K, 2L, 2O, 2Q, and 2I; (54) 2B, 2C, 2D, 2E, 2K, 2L, 2O, 2P, and 2I; (55) 2B, 2C, 2D, 2E, 2G, 2M, 2O, 2Q, and 2I; (56) 2B, 2C, 2D, 2E, 2G, 2M, 2O, 2P, and 2I; (57) 2B, 2C, 2D, 2E, 2G, 2N, 2O, 2Q, and 2I; (58) 2B, 2C, 2D, 2E, 2G, 2N, 2O, 2P, and 2I; (59) 2B, 2C, 2F, 2J, 2L, 2O, 2Q, and 2I; (60) 2B, 2C, 2F, 2J, 2L, 2O, 2P, and 2I; (61) 2B, 2C, 2F, 2K, 2L, 2O, 2Q, and 2I; (62) 2B, 2C, 2F, 2K, 2L, 2O, 2P, and 2I; (63) 2B, 2C, 2F, 2G, 2M, 2O, 2Q, and 2I; (64) 2B, 2C, 2F, 2G, 2M, 2O, 2P, and 2I; (65) 2B, 2C, 2F, 2G, 2N, 2O, 2Q, and 2I; (66) 2B, 2C, 2F, 2G, 2N, 2O, 2P, and 2I; (67) 1C, 1G, 1I, 1L, 1M, and 1F; (68) 1C, 1G, 1I, 1L, 1N, and 1F; (69) 1C, 1H, 1I, 1L, 1M, and 1F; (70) 1C, 1H, 1I, 1L, 1N, and 1F; (71) 1C, 1D, 1J, 1L, 1M, and 1F; (72) 1C, 1D, 1J, 1L, 1N, and 1F; (73) 1C, 1D, 1K, 1L, 1M, and 1F; (74) 1C, 1D, 1K, 1L, 1N, and 1F; (75) 2C, 2R, 2S, 2E, 2J, 2L, 2O, 2Q, and 2I; (76) 2C, 2R, 2S, 2E, 2J, 2L, 2O, 2P, and 2I; (77) 2C, 2R, 2S, 2E, 2K, 2L, 2O, 2Q, and 2I; (78) 2C, 2R, 2S, 2E, 2K, 2L, 2O, 2P, and 2I; (79) 2C, 2R, 2S, 2E, 2G, 2M, 2O, 2Q, and 2I; (80) 2C, 2R, 2S, 2E, 2G, 2M, 2O, 2P, and 2I; (81) 2C, 2R, 2S, 2E, 2G, 2N, 2O, 2Q, and 2I; (82) 2C, 2R, 2S, 2E, 2G, 2N, 2O, 2P, and 2I; (83) 2C, 2R, 2S, 2E, 2G, 2H, and 2I; (84) 2C, 2D, 2E, 2J, 2L, 2O, 2Q, and 2I; (85) 2C, 2D, 2E, 2J, 2L, 2O, 2P, and 2I; (86) 2C, 2D, 2E, 2K, 2L, 2O, 2Q, and 2I; (87) 2C, 2D, 2E, 2K, 2L, 2O, 2P, and 2I; (88) 2C, 2D, 2E, 2G, 2M, 2O, 2Q, and 2I; (89) 2C, 2D, 2E, 2G, 2M, 2O, 2P, and 2I; (90) 2C, 2D, 2E, 2G, 2N, 2O, 2Q, and 2I; (91) 2C, 2D, 2E, 2G, 2N, 2O, 2P, and 2I; (92) 2C, 2F, 2J, 2L, 2O, 2Q, and 2I; (93) 2C, 2F, 2J, 2L, 2O, 2P, and 2I; (94) 2C, 2F, 2K, 2L, 2O, 2Q, and 2I; (95) 2C, 2F, 2K, 2L, 2O, 2P, and 2I; (96) 2C, 2F, 2G, 2M, 2O, 2Q, and 2I; (97) 2C, 2F, 2G, 2M, 2O, 2P, and 2I; (98) 2C, 2F, 2G, 2N, 2O, 2Q, and 2I; and (99) 2C, 2F, 2G, 2N, 2O, 2P, and 2I, wherein 1A is an acetaldehyde dehydrogenase, wherein 1B is a 4-hydroxy 2-oxovalerate aldolase, wherein 1C is a 4-hydroxy 2-oxovalerate dehydratase, wherein 1D is a 2-oxopentenoate reductase, wherein 1E is a 2-hydroxypentenoate dehydratase, wherein 1F is a 2,4-pentadienoate decarboxylase, wherein 1G is a 2-oxopentenoate ligase, wherein 1H is a 2-oxopentenoate: acetyl CoA CoA transferase, wherein 1I is a 2-oxopentenoyl-CoA reductase, wherein 1J is a 2-hydroxypentenoate ligase, wherein 1K is a 2-hydroxypentenoate:acetyl-CoA CoA transferase, wherein 1L is a 2-hydroxypentenoyl-CoA dehydratase, wherein 1M is a 2,4-Pentadienoyl-CoA hydrolase, wherein 1N is a 2,4-Pentadienoyl-CoA:acetyl CoA CoA transferase, wherein 2A is an acetyl-CoA carboxylase, wherein 2B is a malonyl-CoA:acetyl-CoA acyltransferase, wherein 2C is a 3-Oxoglutaryl-CoA reductase (ketone-reducing), wherein 2D is a 3-hydroxyglutaryl-CoA reductase (aldehyde forming), wherein 2E is a 3-hydroxy-5-oxopentanoate reductase, wherein 2F is a 3-hydroxyglutaryl-CoA reductase (alcohol forming), wherein 2G is a 3,5-dihydroxypentanoate dehydratase, wherein 2H is a 5-hydroxypent-2-enoate dehydratase, wherein 2I is a 2,4-pentadienoate decarboxylase, wherein 2J is a 3,5-dihydroxypentanoate ligase, wherein 2K is a 3,5-dihydroxypentanoate: acetyl-CoA CoA transferase, wherein 2L is a 3,5-dihydroxypentanoyl-CoA dehydratase, wherein 2M is a 5-hydroxypent-2-enoate ligase, wherein 2N is a 5-hydroxypent-2-enoate:acetyl-CoA CoA transferase, wherein 2O is a 5-hydroxypent-2-enoyl-CoA hydrolase, wherein 2P is a 2,4-pentadienoyl-CoA hydrolase, wherein 2Q is a 2,4-pentadienoyl-CoA:acetyl-CoA CoA transferase, wherein 2R is a Phosphate-3-hydroxyglutaryl transferase, and wherein 2S is a 3-hydroxy-5-oxopentanoate synthase.

In some embodiments, the butadiene pathway includes (1) 1A, 1B, 1C, 1G, 1I, 1L, 1M, and 1F. In some embodiments, the butadiene pathway includes (2) 1A, 1B, 1C, 1G, 1I, 1L, 1N, and 1F. In some embodiments, the butadiene pathway includes (3) 1A, 1B, 1C, 1H, 1I, 1L, 1M, and 1F. In some embodiments, the butadiene pathway includes (4) 1A, 1B, 1C, 1H, 1I, 1L, 1N, and 1F. In some embodiments, the butadiene pathway includes (5) 1A, 1B, 1C, 1D, 1J, 1L, 1M, and 1F. In some embodiments, the butadiene pathway includes (6) 1A, 1B, 1C, 1D, 1J, 1L, 1N, and 1F. In some embodiments, the butadiene pathway includes (7) 1A, 1B, 1C, 1D, 1K, 1L, 1M, and 1F. In some embodiments, the butadiene pathway includes (8) 1A, 1B, 1C, 1D, 1K, 1L, 1N, and 1F. In some embodiments, the butadiene pathway includes (9) 1B, 1C, 1G, 1I, 1L, 1M, and 1F. In some embodiments, the butadiene pathway includes (10) 1B, 1C, 1G, 1I, 1L, 1N, and 1F. In some embodiments, the butadiene pathway includes (11) 1B, 1C, 1H, 1I, 1L, 1M, and 1F. In some embodiments, the butadiene pathway includes (12) 1B, 1C, 1H, 1I, 1L, 1N, and 1F. In some embodiments, the butadiene pathway includes (13) 1B, 1C, 1D, 1J, 1L, 1M, and 1F. In some embodiments, the butadiene pathway includes (14) 1B, 1C, 1D, 1J, 1L, 1N, and 1F. In some embodiments, the butadiene pathway includes (15) 1B, 1C, 1D, 1K, 1L, 1M, and 1F. In some embodiments, the butadiene pathway includes (16) 1B, 1C, 1D, 1K, 1L, 1N, and 1F. In some embodiments, the butadiene pathway includes (17) 2A, 2B, 2C, 2R, 2S, 2E, 2J, 2L, 2O, 2Q, and 2I. In some embodiments, the butadiene pathway includes (18) 2A, 2B, 2C, 2R, 2S, 2E, 2J, 2L, 2O, 2P, and 2I. In some embodiments, the butadiene pathway includes (19) 2A, 2B, 2C, 2R, 2S, 2E, 2K, 2L, 2O, 2Q, and 2I. In some embodiments, the butadiene pathway includes (20) 2A, 2B, 2C, 2R, 2S, 2E, 2K, 2L, 2O, 2P, and 2I. In some embodiments, the butadiene pathway includes (21) 2A, 2B, 2C, 2R, 2S, 2E, 2G, 2M, 2O, 2Q, and 2I. In some embodiments, the butadiene pathway includes (22) 2A, 2B, 2C, 2R, 2S, 2E, 2G, 2M, 2O, 2P, and 2I. In some embodiments, the butadiene pathway includes (23) 2A, 2B, 2C, 2R, 2S, 2E, 2G, 2N, 2O, 2Q, and 2I. In some embodiments, the butadiene pathway includes (24)

2A, 2B, 2C, 2R, 2S, 2E, 2G, 2N, 2O, 2P, and 2I. In some embodiments, the butadiene pathway includes (25) 2A, 2B, 2C, 2R, 2S, 2E, 2G, 2H, and 2I. In some embodiments, the butadiene pathway includes (26) 2A, 2B, 2C, 2D, 2E, 2J, 2L, 2O, 2Q, and 2I. In some embodiments, the butadiene pathway includes (27) 2A, 2B, 2C, 2D, 2E; 2J, 2L, 2O, 2P, and 2I. In some embodiments, the butadiene pathway includes (28) 2A, 2B, 2C, 2D, 2E, 2K, 2L, 2O, 2Q, and 2I. In some embodiments, the butadiene pathway includes (29) 2A, 2B, 2C, 2D, 2E, 2K, 2L, 2O, 2P, and 2I. In some embodiments, the butadiene pathway includes (30) 2A, 2B, 2C, 2D, 2E, 2G, 2M, 2O, 2Q, and 2I. In some embodiments, the butadiene pathway includes (31) 2A, 2B, 2C, 2D, 2E, 2G, 2M, 2O, 2P, and 2I. In some embodiments, the butadiene pathway includes (32) 2A, 2B, 2C, 2D, 2E, 2G, 2N, 2O, 2Q, and 2I. In some embodiments, the butadiene pathway includes (33) 2A, 2B, 2C, 2D, 2E, 2G, 2N, 2O, 2P, and 2I. In some embodiments, the butadiene pathway includes (34) 2A, 2B, 2C, 2F, 2J, 2L, 2O, 2Q, and 2I. In some embodiments, the butadiene pathway includes (35) 2A, 2B, 2C, 2F, 2J, 2L, 2O, 2P, and 2I. In some embodiments, the butadiene pathway includes (36) 2A, 2B, 2C, 2F, 2K, 2L, 2O, 2Q, and 2I. In some embodiments, the butadiene pathway includes (37) 2A, 2B, 2C, 2F, 2K, 2L, 2O, 2P, and 2I. In some embodiments, the butadiene pathway includes (38) 2A, 2B, 2C, 2F, 2G, 2M, 2O, 2Q, and 2I. In some embodiments, the butadiene pathway includes (39) 2A, 2B, 2C, 2F, 2G, 2M, 2O, 2P, and 2I. In some embodiments, the butadiene pathway includes (40) 2A, 2B, 2C, 2F, 2G, 2N, 2O, 2Q, and 2I. In some embodiments, the butadiene pathway includes (41) 2A, 2B, 2C, 2F, 2G, 2N, 2O, 2P, and 2I. In some embodiments, the butadiene pathway includes (42) 2B, 2C, 2R, 2S, 2E, 2J, 2L, 2O, 2Q, and 2I. In some embodiments, the butadiene pathway includes (43) 2B, 2C, 2R, 2S, 2E, 2J, 2L, 2O, 2P, and 2I. In some embodiments, the butadiene pathway includes (44) 2B, 2C, 2R, 2S, 2E, 2K, 2L, 2O, 2Q, and 2I. In some embodiments, the butadiene pathway includes (45) 2B, 2C, 2R, 2S, 2E, 2K, 2L, 2O, 2P, and 2I. In some embodiments, the butadiene pathway includes (46) 2B, 2C, 2R, 2S, 2E, 2G, 2M, 2O, 2Q, and 2I. In some embodiments, the butadiene pathway includes (47) 2B, 2C, 2R, 2S, 2E, 2G, 2M, 2O, 2P, and 2I. In some embodiments, the butadiene pathway includes (48) 2B, 2C, 2R, 2S, 2E, 2G, 2N, 2O, 2Q, and 2I. In some embodiments, the butadiene pathway includes (49) 2B, 2C, 2R, 2S, 2E, 2G, 2N, 2O, 2P, and 2I. In some embodiments, the butadiene pathway includes (50) 2B, 2C, 2R, 2S, 2E, 2G, 2H, and 2I. In some embodiments, the butadiene pathway includes (51) 2B, 2C, 2D, 2E, 2J, 2L, 2O, 2Q, and 2I. In some embodiments, the butadiene pathway includes (52) 2B, 2C, 2D, 2E, 2J, 2L, 2O, 2P, and 2I. In some embodiments, the butadiene pathway includes (53) 2B, 2C, 2D, 2E, 2K, 2L, 2O, 2Q, and 2I. In some embodiments, the butadiene pathway includes (54) 2B, 2C, 2D, 2E, 2K, 2L, 2O, 2P, and 2I. In some embodiments, the butadiene pathway includes (55) 2B, 2C, 2D, 2E, 2G, 2M, 2O, 2Q, and 2I. In some embodiments, the butadiene pathway includes (56) 2B, 2C, 2D, 2E, 2G, 2M, 2O, 2P, and 2I. In some embodiments, the butadiene pathway includes (57) 2B, 2C, 2D, 2E, 2G, 2N, 2O, 2Q, and 2I. In some embodiments, the butadiene pathway includes (58) 2B, 2C, 2D, 2E, 2G, 2N, 2O, 2P, and 2I. In some embodiments, the butadiene pathway includes (59) 2B, 2C, 2F, 2J, 2L, 2O, 2Q, and 2I. In some embodiments, the butadiene pathway includes (60) 2B, 2C, 2F, 2J, 2L, 2O, 2P, and 2I. In some embodiments, the butadiene pathway includes (61) 2B, 2C, 2F, 2K, 2L, 2O, 2Q, and 2I. In some embodiments, the butadiene pathway includes (62) 2B, 2C, 2F, 2K, 2L, 2O, 2P, and 2I. In some embodiments, the butadiene pathway includes (63) 2B, 2C, 2F, 2G, 2M, 2O, 2Q, and 2I. In some embodiments, the butadiene pathway includes (64) 2B, 2C, 2F, 2G, 2M, 2O, 2P, and 2I. In some embodiments, the butadiene pathway includes (65) 2B, 2C, 2F, 2G, 2N, 2O, 2Q, and 2I. In some embodiments, the butadiene pathway includes (66) 2B, 2C, 2F, 2G, 2N, 2O, 2P, and 2I. In some embodiments, the butadiene pathway includes (67) 1C, 1G, 1I, 1L, 1M, and 1F. In some embodiments, the butadiene pathway includes (68) 1C, 1G, 1I, 1L, 1N, and 1F. In some embodiments, the butadiene pathway includes (69) 1C, 1H, 1I, 1L, 1M, and 1F. In some embodiments, the butadiene pathway includes (70) 1C, 1H, 1I, 1L, 1N, and 1F. In some embodiments, the butadiene pathway includes (71) 1C, 1D, 1J, 1L, 1M, and 1F. In some embodiments, the butadiene pathway includes (72) 1C, 1D, 1J, 1L, 1N, and 1F. In some embodiments, the butadiene pathway includes (73) 1C, 1D, 1K, 1L, 1M, and 1F. In some embodiments, the butadiene pathway includes (74) 1C, 1D, 1K, 1L, 1N, and 1F. In some embodiments, the butadiene pathway includes (75) 2C, 2R, 2S, 2E, 2J, 2L, 2O, 2Q, and 2I. In some embodiments, the butadiene pathway includes (76) 2C, 2R, 2S, 2E, 2J, 2L, 2O, 2P, and 2I. In some embodiments, the butadiene pathway includes (77) 2C, 2R, 2S, 2E, 2K, 2L, 2O, 2Q, and 2I. In some embodiments, the butadiene pathway includes (78) 2C, 2R, 2S, 2E, 2K, 2L, 2O, 2P, and 2I. In some embodiments, the butadiene pathway includes (79) 2C, 2R, 2S, 2E, 2G, 2M, 2O, 2Q, and 2I. In some embodiments, the butadiene pathway includes (80) 2C, 2R, 2S, 2E, 2G, 2M, 2O, 2P, and 2I. In some embodiments, the butadiene pathway includes (81) 2C, 2R, 2S, 2E, 2G, 2N, 2O, 2Q, and 2I. In some embodiments, the butadiene pathway includes (82) 2C, 2R, 2S, 2E, 2G, 2N, 2O, 2P, and 2I. In some embodiments, the butadiene pathway includes (83) 2C, 2R, 2S, 2E, 2G, 2H, and 2I. In some embodiments, the butadiene pathway includes (84) 2C, 2D, 2E, 2J, 2L, 2O, 2Q, and 2I. In some embodiments, the butadiene pathway includes (85) 2C, 2D, 2E, 2J, 2L, 2O, 2P, and 2I. In some embodiments, the butadiene pathway includes (86) 2C, 2D, 2E, 2K, 2L, 2O, 2Q, and 2I. In some embodiments, the butadiene pathway includes (87) 2C, 2D, 2E, 2K, 2L, 2O, 2P, and 2I. In some embodiments, the butadiene pathway includes (88) 2C, 2D, 2E, 2G, 2M, 2O, 2Q, and 2I. In some embodiments, the butadiene pathway includes (89) 2C, 2D, 2E, 2G, 2M, 2O, 2P, and 2I. In some embodiments, the butadiene pathway includes (90) 2C, 2D, 2E, 2G, 2N, 2O, 2Q, and 2I. In some embodiments, the butadiene pathway includes (91) 2C, 2D, 2E, 2G, 2N, 2O, 2P, and 2I. In some embodiments, the butadiene pathway includes (92) 2C, 2F, 2J, 2L, 2O, 2Q, and 2I. In some embodiments, the butadiene pathway includes (93) 2C, 2F, 2J, 2L, 2O, 2P, and 2I. In some embodiments, the butadiene pathway includes (94) 2C, 2F, 2K, 2L, 2O, 2Q, and 2I. In some embodiments, the butadiene pathway includes (95) 2C, 2F, 2K, 2L, 2O, 2P, and 2I. In some embodiments, the butadiene pathway includes (96) 2C, 2F, 2G, 2M, 2O, 2Q, and 2I. In some embodiments, the butadiene pathway includes (97) 2C, 2F, 2G, 2M, 2O, 2P, and 2I. In some embodiments, the butadiene pathway includes (98) 2C, 2F, 2G, 2N, 2O, 2Q, and 2I. In some embodiments, the butadiene pathway includes (99) 2C, 2F, 2G, 2N, 2O, 2P, and 2I.

In some aspects of the invention, the microbial organism can include one, two, three, four, five, six, seven, eight, nine, ten, or eleven exogenous nucleic acids each encoding a butadiene pathway enzyme. In some aspects, the microbial organism includes exogenous nucleic acids encoding each of the enzymes of at least one of the pathways selected from (1)-(99). In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a 2,4-pentadienoate pathway, having at least one exogenous nucleic acid encoding a 2,4-pentadienoate pathway enzyme expressed in a sufficient amount to produce 2,4-pentadienoate, wherein the 2,4-pentadienoate pathway includes a pathway shown in FIGS. 1 and 2 selected from (1) 1A, 1B, 1C, 1G, 1I, 1L, and 1M; (2) 1A, 1B, 1C, 1G, 1I, 1L, and 1N; (3) 1A, 1B, 1C, 1H, 1I, 1L, and 1M; (4) 1A, 1B, 1C, 1H, 1I, 1L, and 1N; (5) 1A, 1B, 1C, 1D, 1J, 1L, and 1M; (6) 1A, 1B, 1C, 1D, 1J, 1L, and 1N; (7) 1A, 1B, 1C, 1D, 1K, 1L, and 1M; (8) 1A, 1B, 1C, 1D, 1K, 1L, and 1N; (9) 1B, 1C, 1G, 1I, 1L, and 1M; (10) 1B, 1C, 1G, 1I, 1L, and 1N; (11) 1B, 1C, 1H, 1I, 1L, and 1M; (12) 1B, 1C, 1H, 1I, 1L, and 1N; (13) 1B, 1C, 1D, 1J, 1L, and 1M; (14) 1B, 1C, 1D, 1J, 1L, and 1N; (15) 1B, 1C, 1D, 1K, 1L, and 1M; (16) 1B, 1C, 1D, 1K, 1L, and 1N; (17) 2A, 2B, 2C, 2R, 2S, 2E, 2J, 2L, 2O, and 2Q; (18) 2A, 2B, 2C, 2R, 2S, 2E, 2J, 2L, 2O, and 2P; (19) 2A, 2B, 2C, 2R, 2S, 2E, 2K, 2L, 2O, and 2Q; (20) 2A, 2B, 2C, 2R, 2S, 2E, 2K, 2L, 2O, and 2P; (21) 2A, 2B, 2C, 2R, 2S, 2E, 2G, 2M, 2O, and 2Q; (22) 2A, 2B, 2C, 2R, 2S, 2E, 2G, 2M, 2O, and 2P; (23) 2A, 2B, 2C, 2R, 2S, 2E, 2G, 2N, 2O, and 2Q; (24) 2A, 2B, 2C, 2R, 2S, 2E, 2G, 2N, 2O, and 2P; (25) 2A, 2B, 2C, 2R, 2S, 2E, 2G, and 2H; (26) 2A, 2B, 2C, 2D, 2E, 2J, 2L, 2O, and 2Q; (27) 2A, 2B, 2C, 2D, 2E; 2J, 2L, 2O, and 2P; (28) 2A, 2B, 2C, 2D, 2E, 2K, 2L, 2O, and 2Q; (29) 2A, 2B, 2C, 2D, 2E, 2K, 2L, 2O, and 2P; (30) 2A, 2B, 2C, 2D, 2E, 2G, 2M, 2O, and 2Q; (31) 2A, 2B, 2C, 2D, 2E, 2G, 2M, 2O, and 2P; (32) 2A, 2B, 2C, 2D, 2E, 2G, 2N, 2O, and 2Q; (33) 2A, 2B, 2C, 2D, 2E, 2G, 2N, 2O, and 2P; (34) 2A, 2B, 2C, 2F, 2J, 2L, 2O, and 2Q; (35) 2A, 2B, 2C, 2F, 2J, 2L, 2O, and 2P; (36) 2A, 2B, 2C, 2F, 2K, 2L, 2O, and 2Q; (37) 2A, 2B, 2C, 2F, 2K, 2L, 2O, and 2P; (38) 2A, 2B, 2C, 2F, 2G, 2M, 2O, and 2Q; (39) 2A, 2B, 2C, 2F, 2G, 2M, 2O, and 2P; (40) 2A, 2B, 2C, 2F, 2G, 2N, 2O, and 2Q; (41) 2A, 2B, 2C, 2F, 2G, 2N, 2O, and 2P; (42) 2B, 2C, 2R, 2S, 2E, 2J, 2L, 2O, and 2Q; (43) 2B, 2C, 2R, 2S, 2E, 2J, 2L, 2O, and 2P; (44) 2B, 2C, 2R, 2S, 2E, 2K, 2L, 2O, and 2Q; (45) 2B, 2C, 2R, 2S, 2E, 2K, 2L, 2O, and 2P; (46) 2B, 2C, 2R, 2S, 2E, 2G, 2M, 2O, and 2Q; (47) 2B, 2C, 2R, 2S, 2E, 2G, 2M, 2O, and 2P; (48) 2B, 2C, 2R, 2S, 2E, 2G, 2N, 2O, and 2Q; (49) 2B, 2C, 2R, 2S, 2E, 2G, 2N, 2O, and 2P; (50) 2B, 2C, 2R, 2S, 2E, 2G, and 2H; (51) 2B, 2C, 2D, 2E, 2J, 2L, 2O, and 2Q; (52) 2B, 2C, 2D, 2E, 2J, 2L, 2O, and 2P; (53) 2B, 2C, 2D, 2E, 2K, 2L, 2O, and 2Q; (54) 2B, 2C, 2D, 2E, 2K, 2L, 2O, and 2P; (55) 2B, 2C, 2D, 2E, 2G, 2M, 2O, and 2Q; (56) 2B, 2C, 2D, 2E, 2G, 2M, 2O, and 2P; (57) 2B, 2C, 2D, 2E, 2G, 2N, 2O, and 2Q; (58) 2B, 2C, 2D, 2E, 2G, 2N, 2O, and 2P; (59) 2B, 2C, 2F, 2J, 2L, 2O, and 2Q; (60) 2B, 2C, 2F, 2J, 2L, 2O, and 2P; (61) 2B, 2C, 2F, 2K, 2L, 2O, and 2Q; (62) 2B, 2C, 2F, 2K, 2L, 2O, and 2P; (63) 2B, 2C, 2F, 2G, 2M, 2O, and 2Q; (64) 2B, 2C, 2F, 2G, 2M, 2O, and 2P; (65) 2B, 2C, 2F, 2G, 2N, 2O, and 2Q; (66) 2B, 2C, 2F, 2G, 2N, 2O, and 2P; (67) 1C, 1G, 1I, 1L, and 1M; (68) 1C, 1G, 1I, 1L, and 1N; (69) 1C, 1H, 1I, 1L, and 1M; (70) 1C, 1H, 1I, 1L, and 1N; (71) 1C, 1D, 1J, 1L, and 1M; (72) 1C, 1D, 1J, 1L, and 1N; (73) 1C, 1D, 1K, 1L, and 1M; (74) 1C, 1D, 1K, 1L, and 1N; (75) 2C, 2R, 2S, 2E, 2J, 2L, 2O, and 2Q; (76) 2C, 2R, 2S, 2E, 2J, 2L, 2O, and 2P; (77) 2C, 2R, 2S, 2E, 2K, 2L, 2O, and 2Q; (78) 2C, 2R, 2S, 2E, 2K, 2L, 2O, and 2P; (79) 2C, 2R, 2S, 2E, 2G, 2M, 2O, and 2Q; (80) 2C, 2R, 2S, 2E, 2G, 2M, 2O, and 2P; (81) 2C, 2R, 2S, 2E, 2G, 2N, 2O, and 2Q; (82) 2C, 2R, 2S, 2E, 2G, 2N, 2O, and 2P; (83) 2C, 2R, 2S, 2E, 2G, and 2H; (84) 2C, 2D, 2E, 2J, 2L, 2O, and 2Q; (85) 2C, 2D, 2E, 2J, 2L, 2O, and 2P; (86) 2C, 2D, 2E, 2K, 2L, 2O, and 2Q; (87) 2C, 2D, 2E, 2K, 2L, 2O, and 2P; (88) 2C, 2D, 2E, 2G, 2M, 2O, and 2Q; (89) 2C, 2D, 2E, 2G, 2M, 2O, and 2P; (90) 2C, 2D, 2E, 2G, 2N, 2O, and 2Q; (91) 2C, 2D, 2E, 2G, 2N, 2O, and 2P; (92) 2C, 2F, 2J, 2L, 2O, and 2Q; (93) 2C, 2F, 2J, 2L, 2O, and 2P; (94) 2C, 2F, 2K, 2L, 2O, and 2Q; (95) 2C, 2F, 2K, 2L, 2O, and 2P; (96) 2C, 2F, 2G, 2M, 2O, and 2Q; (97) 2C, 2F, 2G, 2M, 2O, and 2P; (98) 2C, 2F, 2G, 2N, 2O, and 2Q; and (99) 2C, 2F, 2G, 2N, 2O, and 2P, wherein 1A is an acetaldehyde dehydrogenase, wherein 1B is a 4-hydroxy 2-oxovalerate aldolase, wherein 1C is a 4-hydroxy 2-oxovalerate dehydratase, wherein 1D is a 2-oxopentenoate reductase, wherein 1E is a 2-hydroxypentenoate dehydratase, wherein 1G is a 2-oxopentenoate ligase, wherein 1H is a 2-oxopentenoate: acetyl CoA CoA transferase, wherein 1I is a 2-oxopentenoyl-CoA reductase, wherein 1J is a 2-hydroxypentenoate ligase, wherein 1K is a 2-hydroxypentenoate:acetyl-CoA CoA transferase, wherein 1L is a 2-hydroxypentenoyl-CoA dehydratase, wherein 1M is a 2,4-Pentadienoyl-CoA hydrolase, wherein 1N is a 2,4-Pentadienoyl-CoA:acetyl CoA CoA transferase, wherein 2A is an acetyl-CoA carboxylase, wherein 2B is a malonyl-CoA:acetyl-CoA acyltransferase, wherein 2C is a 3-Oxoglutaryl-CoA reductase (ketone-reducing), wherein 2D is a 3-hydroxyglutaryl-CoA reductase (aldehyde forming), wherein 2E is a 3-hydroxy-5-oxopentanoate reductase, wherein 2F is a 3-hydroxyglutaryl-CoA reductase (alcohol forming), wherein 2G is a 3,5-dihydroxypentanoate dehydratase, wherein 2H is a 5-hydroxypent-2-enoate dehydratase, wherein 2J is a 3,5-dihydroxypentanoate ligase, wherein 2K is a 3,5-dihydroxypentanoate: acetyl-CoA CoA transferase, wherein 2L is a 3,5-dihydroxypentanoyl-CoA dehydratase, wherein 2M is a 5-hydroxypent-2-enoate ligase, wherein 2N is a 5-hydroxypent-2-enoate:acetyl-CoA CoA transferase, wherein 2O is a 5-hydroxypent-2-enoyl-CoA hydrolase, wherein 2P is a 2,4-pentadienoyl-CoA CoA hydrolase, wherein 2Q is a 2,4-pentadienoyl-CoA: acetyl-CoA CoA transferase, wherein 2R is a Phosphate-3-hydroxyglutaryl transferase, and wherein 2S is a 3-hydroxy-5-oxopentanoate synthase.

In some embodiments, the 2,4-pentadienoate pathway comprises (1) 1A, 1B, 1C, 1G, 1I, 1L, and 1M. In some embodiments, the 2,4-pentadienoate pathway comprises (2) 1A, 1B, 1C, 1G, 1I, 1L, and 1N. In some embodiments, the 2,4-pentadienoate pathway comprises (3) 1A, 1B, 1C, 1H, 1I, 1L, and 1M. In some embodiments, the 2,4-pentadienoate pathway comprises (4) 1A, 1B, 1C, 1H, 1I, 1L, and 1N. In some embodiments, the 2,4-pentadienoate pathway comprises (5) 1A, 1B, 1C, 1D, 1J, 1L, and 1M. In some embodiments, the 2,4-pentadienoate pathway comprises (6) 1A, 1B, 1C, 1D, 1J, 1L, and 1N. In some embodiments, the 2,4-pentadienoate pathway comprises (7) 1A, 1B, 1C, 1D, 1K, 1L, and 1M. In some embodiments, the 2,4-pentadienoate pathway comprises (8) 1A, 1B, 1C, 1D, 1K, 1L, and 1N. In some embodiments, the 2,4-pentadienoate pathway comprises (9) 1B, 1C, 1G, 1I, 1L, and 1M. In some embodiments, the 2,4-pentadienoate pathway comprises (10) 1B, 1C, 1G, 1I, 1L, and 1N. In some embodiments, the 2,4-pentadienoate pathway comprises (11) 1B, 1C, 1H, 1I, 1L, and 1M. In some embodiments, the 2,4-pentadienoate pathway comprises (12) 1B, 1C, 1H, 1I, 1L, and 1N. In some embodiments, the 2,4-pentadienoate pathway comprises (13) 1B, 1C, 1D, 1J, 1L, and 1M. In some embodiments, the 2,4-pentadienoate pathway comprises (14) 1B, 1C, 1D, 1J, 1L, and 1N. In some embodiments, the 2,4-pentadienoate pathway comprises (15) 1B, 1C, 1D, 1K, 1L, and 1M. In some embodiments, the 2,4-pentadienoate pathway comprises (16) 1B, 1C, 1D, 1K, 1L, and 1N. In some embodiments, the 2,4-pentadienoate pathway comprises (17) 2A, 2B, 2C, 2R, 2S, 2E, 2J, 2L, 2O, and 2Q. In some embodiments, the 2,4-pentadienoate pathway comprises (18) 2A, 2B, 2C, 2R, 2S, 2E, 2J, 2L, 2O, and 2P. In some embodiments, the 2,4-pentadienoate pathway comprises (19) 2A, 2B, 2C, 2R, 2S, 2E, 2K, 2L, 2O, and 2Q. In some embodiments, the 2,4-pentadienoate pathway comprises (20) 2A, 2B, 2C, 2R, 2S, 2E, 2K, 2L, 2O, and 2P. In some embodiments, the 2,4-pentadienoate pathway comprises (21) 2A, 2B, 2C, 2R, 2S, 2E, 2G, 2M, 2O, and 2Q. In some embodiments, the 2,4-pentadienoate pathway comprises (22) 2A, 2B, 2C, 2R, 2S, 2E, 2G, 2M, 2O, and 2P. In some embodiments, the 2,4-pentadienoate pathway comprises (23) 2A, 2B, 2C, 2R, 2S, 2E, 2G, 2N, 2O, and 2Q. In some embodiments, the 2,4-pentadienoate pathway comprises (24) 2A, 2B, 2C, 2R, 2S, 2E, 2G, 2N, 2O, and 2P. In some embodiments, the 2,4-pentadienoate pathway comprises (25) 2A, 2B, 2C, 2R, 2S, 2E, 2G, and 2H. In some embodiments, the 2,4-pentadienoate pathway comprises (26) 2A, 2B, 2C, 2D, 2E, 2J, 2L, 2O, and 2Q. In some embodiments, the 2,4-pentadienoate pathway comprises (27) 2A, 2B, 2C, 2D, 2E; 2J, 2L, 2O, and 2P. In some embodiments, the 2,4-pentadienoate pathway comprises (28) 2A, 2B, 2C, 2D, 2E, 2K, 2L, 2O, and 2Q. In some embodiments, the 2,4-pentadienoate pathway comprises (29) 2A, 2B, 2C, 2D, 2E, 2K, 2L, 2O, and 2P. In some embodiments, the 2,4-pentadienoate pathway comprises (30) 2A, 2B, 2C, 2D, 2E, 2G, 2M, 2O, and 2Q. In some embodiments, the 2,4-pentadienoate pathway comprises (31) 2A, 2B, 2C, 2D, 2E, 2G, 2M, 2O, and 2P. In some embodiments, the 2,4-pentadienoate pathway comprises (32) 2A, 2B, 2C, 2D, 2E, 2G, 2N, 2O, and 2Q. In some embodiments, the 2,4-pentadienoate pathway comprises (33) 2A, 2B, 2C, 2D, 2E, 2G, 2N, 2O, and 2P. In some embodiments, the 2,4-pentadienoate pathway comprises (34) 2A, 2B, 2C, 2F, 2J, 2L, 2O, and 2Q. In some embodiments, the 2,4-pentadienoate pathway comprises (35) 2A, 2B, 2C, 2F, 2J, 2L, 2O, and 2P. In some embodiments, the 2,4-pentadienoate pathway comprises (36) 2A, 2B, 2C, 2F, 2K, 2L, 2O, and 2Q. In some embodiments, the 2,4-pentadienoate pathway comprises (37) 2A, 2B, 2C, 2F, 2K, 2L, 2O, and 2P. In some embodiments, the 2,4-pentadienoate pathway comprises (38) 2A, 2B, 2C, 2F, 2G, 2M, 2O, and 2Q. In some embodiments, the 2,4-pentadienoate pathway comprises (39) 2A, 2B, 2C, 2F, 2G, 2M, 2O, and 2P. In some embodiments, the 2,4-pentadienoate pathway comprises (40) 2A, 2B, 2C, 2F, 2G, 2N, 2O, and 2Q. In some embodiments, the 2,4-pentadienoate pathway comprises (41) 2A, 2B, 2C, 2F, 2G, 2N, 2O, and 2P. In some embodiments, the 2,4-pentadienoate pathway comprises (42) 2B, 2C, 2R, 2S, 2E, 2J, 2L, 2O, and 2Q. In some embodiments, the 2,4-pentadienoate pathway comprises (43) 2B, 2C, 2R, 2S, 2E, 2J, 2L, 2O, and 2P. In some embodiments, the 2,4-pentadienoate pathway comprises (44) 2B, 2C, 2R, 2S, 2E, 2K, 2L, 2O, and 2Q. In some embodiments, the 2,4-pentadienoate pathway comprises (45) 2B, 2C, 2R, 2S, 2E, 2K, 2L, 2O, and 2P. In some embodiments, the 2,4-pentadienoate pathway comprises (46) 2B, 2C, 2R, 2S, 2E, 2G, 2M, 2O, and 2Q. In some embodiments, the 2,4-pentadienoate pathway comprises (47) 2B, 2C, 2R, 2S, 2E, 2G, 2M, 2O, and 2P. In some embodiments, the 2,4-pentadienoate pathway comprises (48) 2B, 2C, 2R, 2S, 2E, 2G, 2N, 2O, and 2Q. In some embodiments, the 2,4-pentadienoate pathway comprises (49) 2B, 2C, 2R, 2S, 2E, 2G, 2N, 2O, and 2P. In some embodiments, the 2,4-pentadienoate pathway comprises (50) 2B, 2C, 2R, 2S, 2E, 2G, and 2H. In some embodiments, the 2,4-pentadienoate pathway comprises (51) 2B, 2C, 2D, 2E, 2J, 2L, 2O, and 2Q. In some embodiments, the 2,4-pentadienoate pathway comprises (52) 2B, 2C, 2D, 2E, 2J, 2L, 2O, and 2P. In some embodiments, the 2,4-pentadienoate pathway comprises (53) 2B, 2C, 2D, 2E, 2K, 2L, 2O, and 2Q. In some embodiments, the 2,4-pentadienoate pathway comprises (54) 2B, 2C, 2D, 2E, 2K, 2L, 2O, and 2P. In some embodiments, the 2,4-pentadienoate pathway comprises (55) 2B, 2C, 2D, 2E, 2G, 2M, 2O, and 2Q. In some embodiments, the 2,4-pentadienoate pathway comprises (56) 2B, 2C, 2D, 2E, 2G, 2M, 2O, and 2P. In some embodiments, the 2,4-pentadienoate pathway comprises (57) 2B, 2C, 2D, 2E, 2G, 2N, 2O, and 2Q. In some embodiments, the 2,4-pentadienoate pathway comprises (58) 2B, 2C, 2D, 2E, 2G, 2N, 2O, and 2P. In some embodiments, the 2,4-pentadienoate pathway comprises (59) 2B, 2C, 2F, 2J, 2L, 2O, and 2Q. In some embodiments, the 2,4-pentadienoate pathway comprises (60) 2B, 2C, 2F, 2J, 2L, 2O, and 2P. In some embodiments, the 2,4-pentadienoate pathway comprises (61) 2B, 2C, 2F, 2K, 2L, 2O, and 2Q. In some embodiments, the 2,4-pentadienoate pathway comprises (62) 2B, 2C, 2F, 2K, 2L, 2O, and 2P. In some embodiments, the 2,4-pentadienoate pathway comprises (63) 2B, 2C, 2F, 2G, 2M, 2O, and 2Q. In some embodiments, the 2,4-pentadienoate pathway comprises (64) 2B, 2C, 2F, 2G, 2M, 2O, and 2P. In some embodiments, the 2,4-pentadienoate pathway comprises (65) 2B, 2C, 2F, 2G, 2N, 2O, and 2Q. In some embodiments, the 2,4-pentadienoate pathway comprises (66) 2B, 2C, 2F, 2G, 2N, 2O, and 2P. In some embodiments, the 2,4-pentadienoate pathway comprises (67) 1C, 1G, 1I, 1L, and 1M. In some embodiments, the 2,4-pentadienoate pathway comprises (68) 1C, 1G, 1I, 1L, and 1N. In some embodiments, the 2,4-pentadienoate pathway comprises (69) 1C, 1H, 1I, 1L, and 1M. In some embodiments, the 2,4-pentadienoate pathway comprises (70) 1C, 1H, 1I, 1L, and 1N. In some embodiments, the 2,4-pentadienoate pathway comprises (71) 1C, 1D, 1J, 1L, and 1M. In some embodiments, the 2,4-pentadienoate pathway comprises (72) 1C, 1D, 1J, 1L, and 1N. In some embodiments, the 2,4-pentadienoate pathway comprises (73) 1C, 1D, 1K, 1L, and 1M. In some embodiments, the 2,4-pentadienoate pathway comprises (74) 1C, 1D, 1K, 1L, and 1N. In some embodiments, the 2,4-pentadienoate pathway comprises (75) 2C, 2R, 2S, 2E, 2J, 2L, 2O, and 2Q. In some embodiments, the 2,4-pentadienoate pathway comprises (76) 2C, 2R, 2S, 2E, 2J, 2L, 2O, and 2P. In some embodiments, the 2,4-pentadienoate pathway comprises (77) 2C, 2R, 2S, 2E, 2K, 2L, 2O, and 2Q. In some embodiments, the 2,4-pentadienoate pathway comprises (78) 2C, 2R, 2S, 2E, 2K, 2L, 2O, and 2P. In some embodiments, the 2,4-pentadienoate pathway comprises (79) 2C, 2R, 2S, 2E, 2G, 2M, 2O, and 2Q. In some embodiments, the 2,4-pentadienoate pathway comprises (80) 2C, 2R, 2S, 2E, 2G, 2M, 2O, and 2P. In some embodiments, the 2,4-pentadienoate pathway comprises (81) 2C, 2R, 2S, 2E, 2G, 2N, 2O, and 2Q. In some embodiments, the 2,4-pentadienoate pathway comprises (82) 2C, 2R, 2S, 2E, 2G, 2N, 2O, and 2P. In some embodiments, the 2,4-pentadienoate pathway comprises (83) 2C, 2R, 2S, 2E, 2G, and 2H. In some embodiments, the 2,4-pentadienoate pathway comprises (84) 2C, 2D, 2E, 2J, 2L, 2O, and 2Q. In some embodiments, the 2,4-pentadienoate pathway comprises (85) 2C, 2D, 2E, 2J, 2L, 2O, and 2P. In some embodiments, the 2,4-pentadienoate pathway comprises (86) 2C, 2D, 2E, 2K, 2L, 2O, and 2Q. In some embodiments, the 2,4-pentadienoate pathway comprises (87) 2C, 2D, 2E, 2K, 2L, 2O, and 2P. In some embodiments, the 2,4-pentadienoate pathway comprises (88) 2C, 2D, 2E, 2G, 0.2M, 2O, and 2Q. In some embodiments, the 2,4-pentadienoate pathway comprises (89) 2C, 2D, 2E, 2G, 2M, 2O, and 2P. In some embodiments, the 2,4-pentadienoate pathway comprises (90) 2C, 2D, 2E, 2G, 2N, 2O, and 2Q. In some embodiments, the 2,4-pentadienoate pathway comprises (91) 2C, 2D, 2E, 2G, 2N, 2O, and 2P. In some embodiments, the 2,4-pentadienoate pathway comprises (92) 2C, 2F, 2J, 2L, 2O, and 2Q. In some embodiments, the 2,4-pentadienoate pathway comprises (93) 2C, 2F, 2J, 2L, 2O, and 2P. In some embodiments, the 2,4-pentadienoate pathway comprises (94) 2C, 2F, 2K, 2L, 2O, and 2Q. In some embodiments, the 2,4-pentadienoate pathway comprises (95) 2C, 2F, 2K, 2L, 2O, and 2P. In some embodiments, the 2,4-pentadienoate pathway comprises (96) 2C, 2F, 2G, 2M, 2O, and 2Q. In some embodiments, the 2,4-pentadienoate pathway comprises (97) 2C, 2F, 2G, 2M, 2O, and 2P. In some embodiments, the 2,4-pentadienoate pathway comprises (98) 2C, 2F, 2G, 2N, 2O, and 2Q. In some embodiments, the 2,4-pentadienoate pathway comprises (99) 2C, 2F, 2G, 2N, 2O, and 2P.

In some aspects of the invention, the microbial organism can include one, two, three, four, five, six, seven, eight, nine, or ten exogenous nucleic acids each encoding a 2,4-pentadienoate pathway enzyme. In some aspects, the microbial organism includes exogenous nucleic acids encoding each of the enzymes of at least one of the pathways selected from (1)-(99). In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a butadiene pathway or a 2,4-pentadienoate pathway having at least one exogenous nucleic acid encoding a butadiene pathway enzyme or a 2,4-pentadienoate pathway enzyme expressed in a sufficient amount to produce butadiene or 2,4-pentadienoate, wherein the butadiene pathway or the 2,4-pentadienoate pathway includes a pathway as described above, further having an acetyl-CoA pathway having a pathway shown in FIG. 3 selected from: (1) 3T and 3V; (2) 3T, 3W, and 3X; (3) 3U and 3V; (4) 3U, 3W, and 3X, wherein 3T is a fructose-6-phosphate phosphoketolase, wherein 3U is a xylulose-5-phosphate phosphoketolase, wherein 3V is a phosphotransacetylase, wherein 3W is an acetate kinase, wherein 3X is an acetyl-CoA transferase, an acetyl-CoA synthetase, or an acetyl-CoA ligase. In some embodiments, the acetyl-CoA pathway comprises (1) 3T and 3V. In some embodiments, the acetyl-CoA pathway comprises (2) 3T, 3W, and 3X. In some embodiments, the acetyl-CoA pathway comprises (3) 3U and 3V. In some embodiments, the acetyl-CoA pathway comprises (4) 3U, 3W, and 3X.

In some aspects, the microbial organism has an acetyl-CoA pathway as described above wherein an enzyme of the acetyl-CoA pathway is encoded by at least one exogenous nucleic acid and is expressed in a sufficient amount to enhance carbon flux through acetyl-CoA. In some aspects, the microbial organism has one, two, or three exogenous nucleic acids each encoding an acetyl-CoA pathway enzyme. In some aspects, the microbial organism has exogenous nucleic acids encoding each of the enzymes of at least one of the acetyl-CoA pathways described above selected from (1)-(4). In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a butadiene pathway or a 2,4-pentadienoate pathway having at least one exogenous nucleic acid encoding a butadiene pathway enzyme or a 2,4-pentadienoate pathway enzyme expressed in a sufficient amount to produce butadiene or 2,4-pentadienoate, wherein the butadiene pathway or the 2,4-pentadienoate pathway includes a pathway as described above, further having a formaldehyde fixation pathway as shown in FIG. 3 selected from: (1) 3D and 3Z; (2) 3D; or (3) 3B and 3C, wherein 3B is a 3-hexulose-6-phosphate synthase, wherein 3C is a 6-phospho-3-hexuloisomerase, wherein 3D is a dihydroxyacetone synthase, wherein 3Z is a fructose-6-phosphate aldolase. In some embodiments, the formaldehyde fixation pathway comprises (1) 3D and 3Z. In some embodiments, the formaldehyde fixation pathway comprises (2) 3D. In some embodiments, the formaldehyde fixation pathway comprises (3) 3B and 3C.

In some aspects, the microbial organism has a formaldehyde fixation pathway as described above wherein an enzyme of the formaldehyde fixation pathway is encoded by at least one exogenous nucleic acid and is expressed in a sufficient amount to enhance carbon flux through acetyl-CoA. In some aspects, the microbial organism has one or two exogenous nucleic acids each encoding a formaldehyde fixation pathway enzyme. In some aspects, the microbial organism has exogenous nucleic acids encoding each of the enzymes of at least one of the formaldehyde fixation pathways described above selected from (1)-(3). In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a butadiene pathway or a 2,4-pentadienoate pathway having at least one exogenous nucleic acid encoding a butadiene pathway enzyme or a 2,4-pentadienoate pathway enzyme expressed in a sufficient amount to produce butadiene or 2,4-pentadienoate, wherein the butadiene pathway or 2,4-pentadienoate pathway includes a pathway as described above, further having a methanol metabolic pathway as shown in FIG. 4 selected from (1) 4A and 4B; (2) 4A, 4B and 4C; (3) 4J; (4) 4J, 4K and 4C; (5) 4J, 4M, and 4N; (6) 4J and 4L; (7) 4J, 4L, and 4G; (8) 4J, 4L, and 4I; (9) 4A, 4B, 4C, 4D, and 4E; (10) 4A, 4B, 4C, 4D, and 4F; (11) 4J, 4K, 4C, 4D, and 4E; (12) 4J, 4K, 4C, 4D, and 4F; (13) 4J, 4M, 4N, and 4O; (14) 4A, 4B, 4C, 4D, 4E, and 4G; (15) 4A, 4B, 4C, 4D, 4F, and 4G; (16) 4J, 4K, 4C, 4D, 4E, and 4G; (17) 4J, 4K, 4C, 4D, 4F, and 4G; (18) 4J, 4M, 4N, 4O, and 4G; (19) 4A, 4B, 4C, 4D, 4E, and 4I; (20) 4A, 4B, 4C, 4D, 4F, and 4I; (21) 4J, 4K, 4C, 4D, 4E, and 4I; (22) 4J, 4K, 4C, 4D, 4F, and 4I; and (23) 4J, 4M, 4N, 4O, and 4I, wherein 4A is a methanol methyltransferase, wherein 4B is a methylenetetrahydrofolate reductase, wherein 4C is a methylenetetrahydrofolate dehydrogenase, wherein 4D is a methenyltetrahydrofolate cyclohydrolase, wherein 4E is a formyltetrahydrofolate deformylase, wherein 4F is a formyltetrahydrofolate synthetase, wherein 4G is a formate hydrogen lyase, wherein 4I is a formate dehydrogenase, wherein 4J is a methanol dehydrogenase, wherein 4K is a formaldehyde activating enzyme or spontaneous, wherein 4L is a formaldehyde dehydrogenase, wherein 4M is a S-(hydroxymethyl)glutathione synthase or spontaneous, wherein 4N is a glutathione-dependent formaldehyde dehydrogenase, wherein 4O is a S-formylglutathione hydrolase. In some embodiments, the methanol metabolic pathway comprises (1) 4A and 4B. In some embodiments, the methanol metabolic pathway comprises (2) 4A, 4B and 4C. In some embodiments, the methanol metabolic pathway comprises (3) 4J, 4K and 4C. In some embodiments, the methanol metabolic pathway comprises (4) 4J, 4M, and 4N. In some embodiments, the methanol metabolic pathway comprises (5) 4J and 4L. In some embodiments, the methanol metabolic pathway comprises (6) 4J, 4L, and 4G. In some embodiments, the methanol metabolic pathway comprises (7) 4J, 4L, and 4I. In some embodiments, the methanol metabolic pathway comprises (8) 4A, 4B, 4C, 4D, and 4E. In some embodiments, the methanol metabolic pathway comprises (9) 4A, 4B, 4C, 4D, and 4F. In some embodiments, the methanol metabolic pathway comprises (10) 4J, 4K, 4C, 4D, and 4E. In some embodiments, the methanol metabolic pathway comprises (11) 4J, 4K, 4C, 4D, and 4F. In some embodiments, the methanol metabolic pathway comprises (12) 4J, 4M, 4N, and 4O. In some embodiments, the methanol metabolic pathway comprises (13) 4A, 4B, 4C, 4D, 4E, and 4G; In some embodiments, the methanol metabolic pathway comprises (14) 4A, 4B, 4C, 4D, 4F, and 4G. In some embodiments, the methanol metabolic pathway comprises (15) 4J, 4K, 4C, 4D, 4E, and 4G. In some embodiments, the methanol metabolic pathway comprises (16) 4J, 4K, 4C, 4D, 4F, and 4G. In some embodiments, the methanol metabolic pathway comprises (17) 4J, 4M, 4N, 4O, and 4G. In some embodiments, the methanol metabolic pathway comprises (18) 4A, 4B, 4C, 4D, 4E, and 4I. In some embodiments, the methanol metabolic pathway comprises (19) 4A, 4B, 4C, 4D, 4F, and 4I. In some embodiments, the methanol metabolic pathway comprises (20) 4J, 4K, 4C, 4D, 4E, and 4I. In some embodiments, the methanol metabolic pathway comprises (21) 4J, 4K, 4C, 4D, 4F, and 4I. In some embodiments, the methanol metabolic pathway comprises (22) 4J, 4M, 4N, 4O, and 4I.

In some aspects, the microbial organism has a methanol metabolic pathway as described above wherein an enzyme of the methanol metabolic pathway is encoded by at least one exogenous nucleic acid. In some aspects, the microbial organism has one, two, three, four, five, or six exogenous nucleic acids each encoding a methanol metabolic pathway enzyme. In some aspects, the microbial organism has exogenous nucleic acids encoding each of the enzymes of at least one of the methanol metabolic pathways described above selected from (1)-(23). In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a butadiene pathway or a 2,4-pentadienoate pathway having at least one exogenous nucleic acid encoding a butadiene pathway enzyme or a 2,4-pentadienoate pathway enzyme expressed in a sufficient amount to produce butadiene or a 2,4-pentadienoate, wherein the butadiene pathway or the 2,4-pentadienoate pathway includes a pathway as described above, further having a formate assimilation pathway as shown in FIG. 3 selected from: (1) 3E; (2) 3F, and 3G; (3) 3H, 3I, 3J, and 3K; (4) 3H, 3I, 3J, 3L, 3M, and 3N; (5) 3E, 3H, 3I, 3J, 3L, 3M, and 3N; (6) 3F, 3G, 3H, 3I, 3J, 3L, 3M, and 3N; (7) 3K, 3H, 3I, 3J, 3L, 3M, and 3N; and (8) 3H, 3I, 3J, 3O, and 3P, wherein 3E is a formate reductase, 3F is a formate ligase, a formate transferase, or a formate synthetase, wherein 3G is a formyl-CoA reductase, wherein 3H is a formyltetrahydrofolate synthetase, wherein 3I is a methenyltetrahydrofolate cyclohydrolase, wherein 3J is a methylenetetrahydrofolate dehydrogenase, wherein 3K is a formaldehyde-forming enzyme or spontaneous, wherein 3L is a glycine cleavage system, wherein 3M is a serine hydroxymethyltransferase, wherein 3N is a serine deaminase, wherein 3O is a methylenetetrahydrofolate reductase, wherein 3P is an acetyl-CoA synthase. In some embodiments, the formate assimilation pathway comprises (1) 3E. In some embodiments, the formate assimilation pathway comprises (2) 3F, and 3G. In some embodiments, the formate assimilation pathway comprises (3) 3H, 3I, 3J, and 3K. In some embodiments, the formate assimilation pathway comprises (4) 3H, 3I, 3J, 3L, 3M, and 3N. In some embodiments, the formate assimilation pathway comprises (5) 3E, 3H, 3I, 3J, 3L, 3M, and 3N. In some embodiments, the formate assimilation pathway comprises (6) 3F, 3G, 3H, 3I, 3J, 3L, 3M, and 3N. In some embodiments, the formate assimilation pathway comprises (7) 3K, 3H, 3I, 3J, 3L, 3M, and 3N. In some embodiments, the formate assimilation pathway comprises (8) 3H, 3I, 3J, 3O, and 3P.

In some aspects, the microbial organism has a formate assimilation pathway as described above wherein an enzyme of the formate assimilation pathway is encoded by at least one exogenous nucleic acid and is expressed in a sufficient amount to enhance carbon flux through acetyl-CoA. In some aspects, the microbial organism has one, two, three, four, five, six, seven or eight exogenous nucleic acids each encoding a formate assimilation pathway enzyme. In some aspects, the microbial organism has exogenous nucleic acids encoding each of the enzymes of at least one of the formate assimilation pathways described above selected from (1)-(8). In some aspects, the at least one exogenous nucleic acid is a heterologous nucleic acid. In some aspects, the non-naturally occurring microbial organism is in a substantially anaerobic culture medium.

In some aspects, the formate assimilation pathway as described above further includes: (1) 3Q; (2) 3R and 3S; (3) 3Y and 3Q; or (4) 3Y, 3R, and 3S, wherein 3Q is a pyruvate formate lyase, wherein 3R is a pyruvate dehydrogenase, a pyruvate ferredoxin oxidoreductase, or a pyruvate:NADP+ oxidoreductase, wherein 3S is a formate dehydrogenase, wherein 3Y is a glyceraldehyde-3-phosphate dehydrogenase or an enzyme of lower glycolysis. In some aspects, the formate assimilation pathway as described above further includes (1) 3Q. In some aspects, the formate assimilation pathway as described above further includes (2) 3R and 3S. In some aspects, the formate assimilation pathway as described above further includes (3) 3Y and 3Q. In some aspects, the formate assimilation pathway as described above further includes (4) 3Y, 3R, and 3S.

In some embodiments, the invention provides a non-naturally occurring microbial organism having a butadiene pathway or a 2,4-pentadienoate pathway having at least one exogenous nucleic acid encoding a butadiene pathway enzyme or a 2,4-pentadienoate pathway enzyme expressed in a sufficient amount to produce butadiene or 2,4-pentadienoate, wherein the butadiene pathway or the 2,4-pentadienoate pathway includes a pathway as described above, further having a methanol oxidation pathway having a methanol dehydrogenase as shown in FIG. 3. In some aspects, the microbial organism has at least one exogenous nucleic acid encoding a methanol oxidation pathway enzyme expressed in a sufficient amount to produce formaldehyde in the presence of methanol. In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a butadiene pathway or a 2,4-pentadienoate pathway having at least one exogenous nucleic acid encoding a butadiene pathway enzyme or a 2,4-pentadienoate pathway enzyme expressed in a sufficient amount to produce butadiene or 2,4-pentadienoate, wherein the butadiene pathway or 2,4-pentadienoate pathway includes a pathway as described above, further having a hydrogenase or carbon monoxide dehydrogenase. In some aspects, the microbial organism has at least one exogenous nucleic acid encoding the hydrogenase or the carbon monoxide dehydrogenase. In some aspects, the at least one exogenous nucleic acid is a heterologous nucleic acid. In some aspects, the non-naturally occurring microbial organism is in a substantially anaerobic culture medium.

In some embodiments, the invention provides a non-naturally occurring microbial organism having a butadiene pathway or a 2,4-pentadienoate pathway as described herein, wherein the microbial organism further includes attenuation of one or more endogenous enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. Accordingly, in some aspects, the attenuation is of the endogenous enzyme DHA kinase. In some aspects, the attenuation is of the endogenous enzyme methanol oxidase. In some aspects, the attenuation is of the endogenous enzyme PQQ-dependent methanol dehydrogenase. In some aspects, the attenuation is of the endogenous enzyme DHA synthase. The invention also provides a microbial organism wherein attenuation is of any combination of two or three endogenous enzymes described herein. For example, a microbial organism of the invention can include attenuation of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein attenuation is of all endogenous enzymes described herein. For example, in some aspects, a microbial organism described herein includes attenuation of DHA kinase, methanol oxidase, PQQ-dependent methanol dehydrogenase and DHA synthase.

In some embodiments, the invention provides a non-naturally occurring microbial organism having a butadiene pathway or a 2,4-pentadienoate pathway as described herein, wherein the microbial organism further includes attenuation of one or more endogenous enzymes of a competing formaldehyde assimilation or dissimilation pathway. Examples of these endogenous enzymes are disclosed in FIG. 3. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes attenuation of one, two, three, four, five, six, seven, eight, nine, ten or more endogenous enzymes of a competing formaldehyde assimilation or dissimilation pathway.

In some embodiments, the invention provides a non-naturally occurring microbial organism having a butadiene pathway or a 2,4-pentadienoate pathway as described herein, wherein the microbial organism further includes a gene disruption of one or more endogenous nucleic acids encoding enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. According, in some aspects, the gene disruptiondisruption is of an endogenous nucleic acid encoding the enzyme DHA kinase. In some aspects, the gene disruptiondisruption is of an endogenous nucleic acid encoding the enzyme methanol oxidase. In some aspects, the gene disruptiondisruption is of an endogenous nucleic acid encoding the enzyme PQQ-dependent methanol dehydrogenase. In some aspects, the gene disruption is of an endogenous nucleic acid encoding the enzyme DHA synthase. The invention also provides a microbial organism wherein the gene disruption is of any combination of two or three nucleic acids encoding endogenous enzymes described herein. For example, a microbial organism of the invention can include a gene disruption of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein all endogenous nucleic acids encoding enzymes described herein are disrupted. For example, in some aspects, a microbial organism described herein includes disruption of DHA kinase, methanol oxidase, PQQ-dependent methanol dehydrogenase and DHA synthase.

In some embodiments, the invention provides a non-naturally occurring microbial organism having a butadiene pathway or a 2,4-pentadienoate as described herein, wherein the microbial organism further includes a gene disruption of one or more endogenous enzymes of a competing formaldehyde assimilation or dissimilation pathway. Examples of these endogenous enzymes are disclosed in FIG. 3. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes a gene disruption of one, two, three, four, five, six, seven, eight, nine, ten or more endogenous nucleic acids encoding enzymes of a competing formaldehyde assimilation or dissimilation pathway.

In some embodiments, the invention provides a non-naturally occurring microbial organism having a butadiene pathway or a 2,4-pentadienoate pathway as described herein, further having a hydrogen synthesis pathway catalyzing the synthesis of hydrogen from a reducing equivalent, said hydrogen synthesis pathway including an enzyme selected from the group consisting: a hydrogenase, a formate-hydrogene lyase, and ferredoxin: NADP+ oxidoreductase. In some aspects, the reducing equivalent is selected from the group consisting of NADH, NADPH, FADH, reduced quinones, reduced ferredoxins, reduced flavodoxins and reduced thioredoxins. In some aspects, the non-naturally occurring microbial organism has at least one exogenous nucleic acid encoding a hydrogen synthesis pathway enzyme expressed in a sufficient amount to produce hydrogen.

In an additional embodiment, the invention provides a non-naturally occurring microbial organism having a butadiene or 2,4-pentadienoate pathway, wherein the non-naturally occurring microbial organism has at least one exogenous nucleic acid encoding an enzyme or protein that converts a substrate to a product selected from the group consisting of acetyl CoA to acetaldehyde, pyruvate to 4-hydroxy 2-oxovalerate, 4-hydroxy 2-oxovalerate to 2-oxopentenoate, 2-oxopentenoate to 2-oxopentenoyl-CoA, 2-oxopentenoyl-CoA to 2-hydroxypentenoyl-CoA, 2-hydroxypentenoyl-CoA to 2,4-Pentadienoyl-CoA, 2,4-Pentadienoyl-CoA to 2,4-pentadienoate, 2-oxopentenoate to 2-hydroxypentenoate, 2-hydroxypentenoatet to 2,4-pentadienoate, 2-hydroxypentenoate to 2-hydroxypentenoyl-CoA, acetyl-CoA to malonyl-CoA, malonyl-CoA to 3-Oxoglutaryl-CoA, 3-Oxoglutaryl-CoA to 3-hydroxyglutaryl-CoA, 3-hydroxyglutaryl-CoA to 3-hydroxyglutaryl-phosphate, 3-hydroxyglutaryl-CoA to 3-hydroxy-5-oxopentanoate, 3-hydroxyglutaryl-CoA to 3-hydroxy-5-oxopentanoate, 3-hydroxy-5-oxopentanoate to 3,5-dihydroxypentanoate, 3-hydroxyglutaryl-CoA to 3,5-dihydroxypentanoate, 3,5-dihydroxypentanoate to 3,5-dihydroxypentanoyl-CoA, 3,5-dihydroxypentanoyl-CoA to 5-hydroxypent-2-enoyl-CoA, 5-hydroxypent-2-enoyl-CoA to 2,4-pentadienoyl-CoA, 2,4-pentadienoyl-CoA to 2,4-pentadienoate, 3,5-dihydroxypentanoate to 5-hydroxypent-2-enoate, 5-hydroxypent-2-enoate to 2,4-pentadienoate, 5-hydroxypent-2-enoate to 5-hydroxypent-2-enoyl-CoA, 2,4-pentadienoate to butadiene. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a butadiene or 2,4-pentadienoate pathway, such as that shown in FIGS. 1 and 2.

While generally described herein as a microbial organism that contains a butadiene or 2,4-pentadienoate pathway, it is understood that the invention additionally provides a non-naturally occurring microbial organism comprising at least one exogenous nucleic acid encoding a butadiene or 2,4-pentadienoate pathway enzyme expressed in a sufficient amount to produce an intermediate of a butadiene or 2,4-pentadienoate pathway. For example, as disclosed herein, a butadiene or 2,4-pentadienoate pathway is exemplified in FIGS. 1-2. Therefore, in addition to a microbial organism containing a butadiene or 2,4-pentadienoate pathway that produces butadiene or 2,4-pentadienoate, the invention additionally provides a non-naturally occurring microbial organism comprising at least one exogenous nucleic acid encoding a butadiene or 2,4-pentadienoate pathway enzyme, where the microbial organism produces a butadiene or 2,4-pentadienoate pathway intermediate, for example, 4-hydroxy-2-oxovalerate, 2-oxopentenoate, 2-oxopentenoyl-CoA, 2-hydroxypentenoyl-CoA, 2,4-Pentadienoyl-CoA, 2-hydroxypentenoate, malonyl-CoA, 3-Oxoglutaryl-CoA, 3-hydroxyglutaryl-CoA, 3-hydroxyglutaryl-phosphate, 3-hydroxy-5-oxopentanoate, 3,5-dihydroxypentanoate, 3,5-dihydroxypentanoyl-CoA, 5-hydroxypent-2-enoyl-CoA, 2,4-pentadienoyl-CoA, 3,5-dihydroxypentanoate, or 5-hydroxypent-2-enoate.

It is understood that any of the pathways disclosed herein, as described in the Examples and exemplified in the Figures, including the pathways of FIGS. 1-4, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a butadiene or 2,4-pentadienoate pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the product 2,4-pentadienoate and intermediates pyruvate, 4-hydroxy-2-oxovalerate, 2-oxopentenoate, 2-hydroxypentenoate, 3-hydroxyglutaryl-phosphate, 3-hydroxy-5-oxopentanoate, 3,5-dihydroxypentanoate, or 5-hydroxypent-2-enoate, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl 2,4-pentadienoate, ethyl 2,4-pentadienoate, and n-propyl 2,4-pentadienoate. Other biosynthetically accessible O-carboxylates can include medium to long chain groups, that is C4-C22, O-carboxylate esters derived from fatty alcohols, such as butyl, pentanoyl, hexyl, heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more butadiene or 2,4-pentadienoate biosynthetic pathways. Depending on the host microbial organism chosen for biosynthesis, nucleic acids for some or all of a particular butadiene or 2,4-pentadienoate biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve butadiene or 2,4-pentadienoate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as butadiene or 2,4-pentadienoate.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order-Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the butadiene or 2,4-pentadienoate biosynthetic pathway constituents of a selected host microbial organism, the non-naturally occurring microbial organisms of the invention will include at least one exogenously expressed butadiene or 2,4-pentadienoate pathway-encoding nucleic acid and up to all encoding nucleic acids for one or more butadiene or 2,4-pentadienoate biosynthetic pathways. For example, butadiene or 2,4-pentadienoate biosynthesis can be established in a host deficient in a pathway enzyme or protein through exogenous expression of the corresponding encoding nucleic acid. In a host deficient in all enzymes or proteins of a butadiene or 2,4-pentadienoate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of butadiene or 2,4-pentadienoate can be included, such as an acetaldehyde dehydrogenase, a 4-hydroxy 2-oxovalerate dehydratase, a 2-oxopentenoate reductase, 2-hydroxypentenoate:acetyl-CoA CoA transferase, 2-hydroxypentenoyl-CoA dehydratase, 2,4-Pentadienoyl-CoA hydrolase, and a 2,4-pentadienoate decarboxylase.

Given the teachings and guidance provided herein, those skilled in the art will understand that the number of encoding nucleic acids to introduce in an expressible form will, at least, parallel the butadiene or 2,4-pentadienoate pathway deficiencies of the selected host microbial organism. Therefore, a non-naturally occurring microbial organism of the invention can have one, two, three, four, five, six, seven, eight, nine, ten, or eleven, up to all nucleic acids encoding the enzymes or proteins constituting a butadiene or 2,4-pentadienoate biosynthetic pathway disclosed herein. In some embodiments, the non-naturally occurring microbial organisms also can include other genetic modifications that facilitate or optimize butadiene or 2,4-pentadienoate biosynthesis or that confer other useful functions onto the host microbial organism. One such other functionality can include, for example, augmentation of the synthesis of one or more of the butadiene or 2,4-pentadienoate pathway precursors such as acetyl-CoA, pyruvate, or malonyl-CoA.

Generally, a host microbial organism is selected such that it produces the precursor of a butadiene or 2,4-pentadienoate pathway, either as a naturally produced molecule or as an engineered product that either provides de novo production of a desired precursor or increased production of a precursor naturally produced by the host microbial organism. For example, acetyl-CoA, pyruvate, and malonyl-CoA are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a butadiene or 2,4-pentadienoate pathway.

In some embodiments, a non-naturally occurring microbial organism of the invention is generated from a host that contains the enzymatic capability to synthesize butadiene or 2,4-pentadienoate. In this specific embodiment it can be useful to increase the synthesis or accumulation of a butadiene or 2,4-pentadienoate pathway product to, for example, drive butadiene or 2,4-pentadienoate pathway reactions toward butadiene or 2,4-pentadienoate production.

Increased synthesis or accumulation can be accomplished by, for example, overexpression of nucleic acids encoding one or more of the above-described butadiene or 2,4-pentadienoate pathway enzymes or proteins. Overexpression of the enzyme or enzymes and/or protein or proteins of the butadiene or 2,4-pentadienoate pathway can occur, for example, through modification of an endogenous gene to overexpress the gene, exogenous expression of the endogenous gene or genes, or through exogenous expression of the heterologous gene or genes. Therefore, naturally occurring organisms can be readily generated to be non-naturally occurring microbial organisms of the invention, for example, producing butadiene or 2,4-pentadienoate, through overexpression of one, two, three, four, five, six, seven, eight, nine, ten or eleven, that is, up to all nucleic acids encoding butadiene or 2,4-pentadienoate biosynthetic pathway enzymes or proteins. In addition, a non-naturally occurring organism can be generated by mutagenesis of an endogenous gene that results in an increase in activity of an enzyme in the butadiene or 2,4-pentadienoate biosynthetic pathway. For example, the promoter region of an endogenous gene can be modified to increase the expression of the gene.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a butadiene or 2,4-pentadienoate biosynthetic pathway onto the microbial organism. Alternatively, encoding nucleic acids can be introduced to produce an intermediate microbial organism having the biosynthetic capability to catalyze some of the required reactions to confer butadiene or 2,4-pentadienoate biosynthetic capability. For example, a non-naturally occurring microbial organism having a butadiene or 2,4-pentadienoate biosynthetic pathway can comprise at least two exogenous nucleic acids encoding desired enzymes or proteins, such as the combination of 2-oxopentenoate ligase and 2,4-pentadienoate decarboxylase, or alternatively 5-hydroxypent-2-enoate dehydratase and 2,4-pentadienoate decarboxylase, or alternatively 2-hydroxypentenoate ligase and 2-hydroxypentenoyl-CoA dehydratase, or alternatively 2-hydroxypentenoate:acetyl-CoA CoA transferase and 2-hydroxypentenoyl-CoA dehydratase, or alternatively 3,5-dihydroxypentanoate ligase and 3,5-dihydroxypentanoyl-CoA dehydratase, or alternatively 3,5-dihydroxypentanoate:acetyl-CoA CoA transferase and 2-hydroxypentenoyl-CoA dehydratase, or alternatively 5-hydroxypent-2-enoate ligase and 5-hydroxypent-2-enoyl-CoA hydrolase, or alternatively 5-hydroxypent-2-enoate:acetyl-CoA CoA transferase and 5-hydroxypent-2-enoyl-CoA hydrolase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, 2-oxopentenoate ligase, 2-oxopentenoyl-CoA reductase, and 2-hydroxypentenoyl-CoA dehydratase, or alternatively 2-hydroxypentenoate ligase, 2-hydroxypentenoyl-CoA dehydratase, and 2,4-Pentadienoyl-CoA hydrolase, or alternatively 3,5-dihydroxypentanoate ligase, 3,5-dihydroxypentanoyl-CoA dehydratase, 5-hydroxypent-2-enoyl-CoA hydrolase, or alternatively 5-hydroxypent-2-enoate ligase, 5-hydroxypent-2-enoyl-CoA hydrolase, and 2,4-pentadienoyl-CoA:acetyl-CoA CoA transferase, and so forth, as desired, so long as the combination of enzymes and/or proteins of the desired biosynthetic pathway results in production of the corresponding desired product. Similarly, any combination of four, five, six, seven, eight, nine, ten, eleven or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of butadiene or 2,4-pentadienoate as described herein, the non-naturally occurring microbial organisms and methods of the invention also can be utilized in various combinations with each other and/or with other microbial organisms and methods well known in the art to achieve product biosynthesis by other routes. For example, one alternative to produce butadiene or 2,4-pentadienoate other than use of the butadiene or 2,4-pentadienoate producers is through addition of another microbial organism capable of converting a butadiene or 2,4-pentadienoate pathway intermediate to butadiene or 2,4-pentadienoate. One such procedure includes, for example, the fermentation of a microbial organism that produces a butadiene or 2,4-pentadienoate pathway intermediate. The butadiene or 2,4-pentadienoate pathway intermediate can then be used as a substrate for a second microbial organism that converts the butadiene or 2,4-pentadienoate pathway intermediate to butadiene or 2,4-pentadienoate. The butadiene or 2,4-pentadienoate pathway intermediate can be added directly to another culture of the second organism or the original culture of the butadiene or 2,4-pentadienoate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, butadiene or 2,4-pentadienoate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of butadiene or 2,4-pentadienoate can be accomplished by constructing a microbial organism that contains biosynthetic pathways for conversion of one pathway intermediate to another pathway intermediate or the product. Alternatively, butadiene or 2,4-pentadienoate also can be biosynthetically produced from microbial organisms through co-culture or co-fermentation using two organisms in the same vessel, where the first microbial organism produces a butadiene or 2,4-pentadienoate intermediate and the second microbial organism converts the intermediate to butadiene or 2,4-pentadienoate.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce butadiene or 2,4-pentadienoate.

Similarly, it is understood by those skilled in the art that a host organism can be selected based on desired characteristics for introduction of one or more gene disruptions to increase production of butadiene or 2,4-pentadienoate. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will increase butadiene or 2,4-pentadienoate biosynthesis. In a particular embodiment, the increased production couples biosynthesis of butadiene or 2,4-pentadienoate to growth of the organism, and can obligatorily couple production of butadiene or 2,4-pentadienoate to growth of the organism if desired and as disclosed herein.

Sources of encoding nucleic acids for a butadiene or 2,4-pentadienoate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acidaminococcus fermentans, Acinetobacter baumannii* Naval-82, *Acinetobacter baylyi, Acinetobacter calcoaceticus, Acinetobacter* sp. Strain M-1, *Actinobacillus succinogenes* 130Z, *Allochromatium vinosum* DSM 180, *Aminomonas aminovorus, Anaerotruncus colihominis, Aquifex aeolicus* VF5, *Arabidopsis thaliana, Archaeglubus fulgidus, Archaeoglobus fulgidus* DSM 4304, *Aspergillus niger, Aspergillus oryzae, Aspergillus terreus, Azotobacter vinelandii* DJ *Bacillus alcalophilus* ATCC 27647, *Bacillus azotoformans* LMG 9581, *Bacillus cereus, Bacillus coagulans* 36D1, *Bacillus megaterium, Bacillus methanolicus* MGA3, *Bacillus methanolicus* PB1, *Bacillus pumilus, Bacillus selenitireducens* MLS10, *Bacillus smithii, Bacillus sphaericus, Bacillus subtilis, Bacteroides capillosus, Bifidobacterium animalis lactis, Bifidobacterium breve, Biflidobacterium dentium* ATCC 27678, *Bifidobacterium pseudolongum* subsp. *Globosum, Bos taurus, Burkholderia ambifaria* AMMD, *Burkholderia phymatum, Burkholderia stabilis, Burkholderia thailandensis* E264, *Burkholderia xenovorans, Burkholderia xenovorans* LB400, butyrate-producing bacterium L2-50, *Campylobacter curvus* 525.92, *Campylobacter jejuni, Candida albicans, Candida boidinii, Candida methylica, Candida tropicalis, Carboxydothermus hydrogenoformans, Carboxydothermus hydrogenoformans* Z-2901, *Caulobacter* sp. AP07, *Chlamydomonas reinhardtii, Chloroflexus aurantiacus, Chlorobium phaeobacteroides* DSM 266, *Chloroflexus aurantiacus* J-10-fl, *Chloroflexus aggregans* DSM 9485, *Citrobacter koseri* ATCCBAA-895, *Clostridium acetobutylicum, Clostridium acetobutylicum* ATCC 824, *Clostridium acidurici, Clostridium aminobutyricum, Clostridium beijerinckii, Clostridium beijerinckii* NRRL B593, *Clostridium carboxidivorans* P7, *Clostridium cellulolyticum* H10, *Clostridium difficile, Clostridium kluyveri, Clostridium kluyveri* DSM 555, *Clostridium ljungdahli, Clostridium ljungdahlii* DSM 13528, *Clostridium pasteurianum, Clostridium pasteurianum* DSM 525, *Clostridium perfringens, Clostridium perfringens* ATCC 13124, *Clostridium perfringens* str. 13, *Clostridium propionicum, Clostridium saccharoperbutylacetonicum, Clostridium sporogens, Clostridum symbiosum, Clostridium tetani, Comamonas* sp. CNB-1, *Corynebacterium* sp. U-96, *Corynebacterium glutamicum, Corynebacterium glutamicum* ATCC 13032, *Corynebacterium glutamicum* R, *Corynebacterium glutamicum* ATCC 14067, *Corynebacterium variabile, Cupriavidus necator, Cupriavidus necator* N-1, *Cupriavidus taiwanensis, Cyanobium* PCC7001, *Deinococcus radiodurans* R1, *Desulfovibrio africanus* str. Walvis Bay, *Desulfovibrio fructosovorans* JJ, *Desulfatibacillum alkenivorans* AK-O1, *Desulfitobacterium hafniense, Desulfovibrio desulfuricans* subsp. *desulfuricans* str. ATCC 27774, *Desulfitobacterium metallireducens* DSM 15288, *Desulfotomaculum reducens* MI-1, *Dictyostelium discoideum* AX4, *Elizabethkingia meningoseptica, Erythrobacter* sp. NAP1, *Escherichia coli* C, *Escherichia coli* K12, *Escherichia coli* K-12 MG1655, *Escherichia coli* W, *Eubacterium barkeri, Flavobacterium frigoris, Fusobacterium nucleatum, Geobacter bemidjiensis* Bem, *Geobacter metallireducens* GS-15, *Geobacillus* sp. GHH01, *Geobacillus* sp. M10EXG, *Geobacillus* sp. Y4.1MC1, *Geobacillus stearothermophilus, Geobacillus thermoglucosidasius, Geobacillus themodenitrificans* NG80-2, *Geobacillus* sp. Y4.1MC1, *Geobacter sulfurreducens, Geobacter sulfurreducens* PCA, *Gibberella zeae, Haemophilus influenza, Haloarcula marismortui, Haloarcula marismortui* ATCC 43049, *Haloferax mediterranei* ATCC 33500, *Helicobacter pylori, Homo sapiens*, Human gut metagenome, *Hydrogenobacter thermophilus, Hydrogenobacter thermophilus* TK-6, *Hyphomicrobium denitrificans* ATCC 51888, *Hyphomicrobium zavarzinii, Kineococcus radiotolerans, Klebsiella oxytoca, Klebsiella pneumonia, Klebsiella pneumoniae* subsp. *pneumoniae* MGH 78578, *Kluyveromyces lactis, Lactobacillus acidophilus, Lactobacillus brevis* ATCC 367, *Lactobacillus paraplantarum, Lactobacillus plantarum, Lactobacillus reuteri, Lactobacillus* sp. 30a, *Leuconostoc mesenteroides, Lysinibacillus fusiformis*, Marine metagenome JCVI SCAF 1096627185304, *Marinobacter aquaeolei*, Marine gamma proteobacterium HTCC2080, *Mesorhizobium loti* MAFF303099, *Methanosarcina acetivorans* C2A, *Metallosphaera sedula, Methanocaldococcus jannaschii, Methanothermobacter thermautotrophicus, Methanosarcina mazei* Tuc01, *Methylomonas aminofaciens, Methylobacterium extorquens, Methylobacterium extorquens* AM1, *Methylobacillus flagellates, Methylobacillus flagellatus* KT, *Methylovorus glucosetrophus SIP3-4, *Methylobacter marinus, Methylococcus capsulatis, Methylomicrobium album* BG8, *Microlunatus phosphovorus* NM-1, *Methylovorus* sp. MP688, *Methylovorus glucosetrophus* SIP3-4, *Moorella thermoacetica, Mus musculus, Mycobacterium avium, Mycobacterium avium* subsp., *Mycobacterium avium* subsp. paratuberculosis K-10, *Mycobacterium bovis* BCG, *Mycobacterium gastri, Mycobacterium marinum* M, *Mycobacterium smegmatis, Mycobacterium smegmatis* MC2 155, *Mycobacter* sp. strain JC1 DSM 3803, *Mycobacterium tuberculosis, Natranaerobius thermophilus, Neosartorya fischeri, Nicotiana glutinosa, Nitrososphaera gargensis* Ga9.2, *Nocardia farcinica* IFM 10152, *Nocardia iowensis* (sp. NRRL 5646), *Nostoc* sp. PCC7120, *Ogataea parapolymorpha* DL-1 (*Hansenula polymorpha* DL-1), *Oryctolagus cuniculus, Oxalobacter formigenes, Paenibacillus peoriae* KCTC 3763, *Paracoccus denitrificans, Pediococcus pentosaceus, Pelobacter carbinolicus* DSM2380, *Pelotomaculum thermopropionicum, Penicillium chrysogenum, Photobacterium phosphoreum,* Photobacterium *profundum* 3TCK, *Pichia pastoris, Pichia stipitis, Picrophilus torridus* DSM9790, *Porphyromonas gingivalis, Porphyromonas gingivalis* W83, Pratuberculosis, *Propionibacterium acidipropionici* ATCC 4875, *Propionibacterium acnes* KPA171202, *Pseudomonas aeruginosa, Pseudomonas aeruginosa* PA01, *Pseudomonas aeruginosa* PAO1, *Pseudomonas fluorescens, Pseudomonas fluorescens* KU-7, *Pseudomonas knackmussii* (B13), *Pseudomonas mendocina, Pseudomonas putida, Pseudomonas putida* KT2440, *Pseudomonas* sp, *Pseudomonas* sp. CF600, *Pseudomonas* syringaepv. *syringae* B728a, *Psychroflexus torquis* ATCC 700755, *Pyrobaculum* aerophilum str. IM2, *Pyrococcus abyssi, Pyrococcus furiosus, Pyrococcus horikoshii* OT3, *Pyrobaculum islandicum* DSM 4184, *Ralstonia eutropha, Ralstonia eutropha* H16, *Ralstonia eutropha* JMP134, *Ralstonia metallidurans, Ralstonia pickettii, Rattus norvegicus, Rhizobium leguminosarum, Rhodobacter capsulatus, Rhodobacter sphaeroides, Rhodobacter sphaeroides* ATCC 17025, *Rhodococcus ruber, Rhodopseudomonas palustris, Rhodopseudomonas palustris* CGA009, *Rhodospirillum rubrum, Roseiflexus castenholzii, Saccharomyces cerevisae, Saccharomyces cerevisiae* S288c, *Salinispora arenicola, Salmonella enterica, Salmonella typhimurium, Salmonella typhimurium* LT2, *Salmonella enterica* subsp. *enterica* serovar *Typhimurium* str. LT2, *Schizosaccharomyces pombe, Selenomonas ruminantium, Shewanella oneidensis* MR-1, *Simmondsia chinensis, Sinorhizobium meliloti* 1021, *Streptomyces griseus* subsp. *griseus* NBRC 13350, *Streptococcus pyogenes* ATCC 10782, *Sulfolobus acidocalarius, Sulfolobus solfataricus, Sulfolobus solfataricus* P-2, *Sulfolobus tokodaii, Synechocystis* str. PCC 6803, *Syntrophobacter fumaroxidans, Syntrophus aciditrophicus, Thauera aromatic, Thermoanaerobacter brockii* HTD4, *Thermoanaerobacter* sp. X514, *Thermoanaerobacter tengcongensis* MB4, *Thermococcus kodakaraensis, Thermococcus litoralis, Thermoplasma acidophilum, Thermoproteus neutrophilus, Thermotoga maritima, Thermus thermophilus, Thiocapsa roseopersicina Trichomonas vaginalis* G3, *Trypanosoma brucei, Tsukamurella paurometabola* DSM 20162, *Vibrio cholera, Vibrio harveyi* ATCC BAA-1116, *Vibrio parahaemolyticus, Vibrio vulnificus, Xanthobacter autotrophicus* Py2, *Yarrowia lipolytica, Yersinia pestis, Zea mays, Zoogloea ramigera, Zymomonas mobilis,* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite butadiene or 2,4-pentadienoate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of butadiene or 2,4-pentadienoate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative butadiene or 2,4-pentadienoate biosynthetic pathway exists in an unrelated species, butadiene or 2,4-pentadienoate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize butadiene or 2,4-pentadienoate.

A nucleic acid molecule encoding a butadiene or 2,4-pentadienoate pathway enzyme or protein of the invention can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity, or be identical, to a nucleic acid described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5×Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding a butadiene or 2,4-pentadienoate pathway enzyme or protein of the invention can have at least a certain sequence identity to a nucleotide sequence disclosed herein. According, in some aspects of the invention, a nucleic acid molecule encoding a butadiene or 2,4-pentadienoate pathway enzyme or protein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity, or is identical, to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwisSProtein+SPupdate+PIR. Details of these programs can be found at the National Center for Biotechnology Information.

Methods for constructing and testing the expression levels of a non-naturally occurring butadiene or 2,4-pentadienoate—producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of butadiene or 2,4-pentadienoate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more butadiene or 2,4-pentadienoate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the present invention provides a method for producing butadiene including culturing a non-naturally occurring microbial organism disclosed herein under conditions and for a sufficient period of time to produce butadiene. In some aspects, the method further includes separating the butadiene from other components in the culture.

In some embodiments, the present invention provides a method for producing butadiene and hydrogen including culturing a non-naturally occurring microbial organism disclosed herein under conditions and for a sufficient period of time to produce butadiene and hydrogen. In some aspects, the method further includes separating the butadiene and hydrogen from other components in the culture. In some aspects, the hydrogen is separated by shaking.

In some embodiments, the present invention provides a method for producing 2,4-pentadienoate including culturing a non-naturally occurring microbial organism disclosed herein under conditions and for a sufficient period of time to produce 2,4-pentadienoate. In some aspects, the method further includes separating the 2,4-pentadienoate from other components in the culture.

In some embodiments, the present invention provides a method for producing 2,4-pentadienoate and hydrogen including culturing a non-naturally occurring microbial organism disclosed herein under conditions and for a sufficient period of time to produce 2,4-pentadienoate and hydrogen. In some aspects, the method further includes separating the 2,4-pentadienoate and hydrogen from other components in the culture. In some aspects, the hydrogen is separated by shaking.

Suitable purification and/or assays to test for the production of butadiene or 2,4-pentadienoate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. As described herein, Headspace GCMS analysis can be carried out on a 7890A GC with 5975C inert MSD using a GS-GASPRO column, 30m×0.32 mm (Agilent Technologies). Static headspace sample introduction can be performed on a CombiPAL autosampler (CTC Analytics) following 2 min incubation at 45° C.

The butadiene or 2,4-pentadienoate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art. Additionally, because butadiene can be a gas at fermentation temperatures, it can also be separated and capture accordingly. Exemplary methods to separate and capture gaseous butadiene are described herein.

Any of the non-naturally occurring microbial organisms described herein can be cultured to produce and/or secrete the biosynthetic products of the invention. For example, the butadiene or 2,4-pentadienoate producers can be cultured for the biosynthetic production of butadiene or 2,4-pentadienoate. Accordingly, in some embodiments, the invention provides culture medium containing the butadiene or 2,4-pentadienoate or butadiene or 2,4-pentadienoate pathway intermediate described herein. In some aspects, the culture medium can also be separated from the non-naturally occurring microbial organisms of the invention that produced the butadiene or 2,4-pentadienoate or butadiene or 2,4-pentadienoate pathway intermediate. Methods for separating a microbial organism from culture medium are well known in the art. Exemplary methods include filtration, flocculation, precipitation, centrifugation, sedimentation, and the like.

For the production of butadiene or 2,4-pentadienoate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high butadiene or 2,4-pentadienoate yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example: sugars such as glucose, xylose, arabinose, galactose, mannose, fructose, sucrose, starch, methanol, syngas, or glycerol, and it is understood that a carbon source can be used alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of butadiene or 2,4-pentadienoate.

In addition to the feedstocks, including the renewable feedstocks such as those exemplified above, the butadiene or 2,4-pentadienoate microbial organisms of the invention also can be modified for growth on syngas as its source of carbon or on methane. In this specific embodiment, one or more proteins or enzymes are expressed in the butadiene or 2,4-pentadienoate producing organisms to provide a metabolic pathway for utilization of syngas, methane or other gaseous carbon source. In the case of methane the organism can be a natural methanotroph including those mentioned herein, or a non-methanotroph such as *E. coli* that is genetically engineered to use methane such as by expression of methane monooxygenase (MMO), the methanol produced can be utilized as described herein.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $COH_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

$$2CO_2+4H_2+nADP+nPi \rightarrow CH_3COOH+2H_2O+nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a butadiene or 2,4-pentadienoate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the butadiene or 2,4-pentadienoate precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a butadiene or 2,4-pentadienoate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, butadiene or 2,4-pentadienoate and any of the intermediate metabolites in the butadiene or 2,4-pentadienoate pathway. All that is required is to engineer in one or more of the required enzyme or protein activities to achieve biosynthesis of the desired compound or intermediate including, for example, inclusion of some or all of the butadiene or 2,4-pentadienoate biosynthetic pathways. Accordingly, the invention provides a non-naturally occurring microbial organism that produces and/or secretes butadiene or 2,4-pentadienoate when grown on a carbohydrate or other carbon source and produces and/or secretes any of the intermediate metabolites shown in the butadiene or 2,4-pentadienoate pathway when grown on a carbohydrate or other carbon source. The butadiene or 2,4-pentadienoate producing microbial organisms of the invention can initiate synthesis from an intermediate, for example, 4-hydroxy-2-oxovalerate, 2-oxopentenoate, 2-oxopentenoyl-CoA, 2-hydroxypentenoyl-CoA, 2,4-Pentadienoyl-CoA, 2-hydroxypentenoate, malonyl-CoA, 3-Oxoglutaryl-CoA, 3-hydroxyglutaryl-CoA, 3-hydroxyglutaryl-phosphate, 3-hydroxy-5-oxopentanoate, 3,5-dihydroxypentanoate, 3,5-dihydroxypentanoyl-CoA, 5-hydroxypent-2-enoyl-CoA, 2,4-pentadienoyl-CoA, 3,5-dihydroxypentanoate, or 5-hydroxypent-2-enoate.

The non-naturally occurring microbial organisms of the invention are constructed using methods well known in the art as exemplified herein to exogenously express at least one nucleic acid encoding a butadiene or 2,4-pentadienoate pathway enzyme or protein in sufficient amounts to produce butadiene or 2,4-pentadienoate. It is understood that the microbial organisms of the invention are cultured under conditions sufficient to produce butadiene or 2,4-pentadienoate. Following the teachings and guidance provided herein, the non-naturally occurring microbial organisms of the invention can achieve biosynthesis of butadiene or 2,4-pentadienoate resulting in intracellular concentrations between about 0.01-200 mM or more. Generally, the intracellular concentration of butadiene or 2,4-pentadienoate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the butadiene or 2,4-pentadienoate producers can synthesize butadiene or 2,4-pentadienoate at intracellular concentrations of 5-10 mM or more as well as all other concentrations exemplified herein. It is understood that, even though the above description refers to intracellular concentrations, butadiene or 2,4-pentadienoate producing microbial organisms can produce butadiene or 2,4-pentadienoate intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of butadiene or 2,4-pentadienoate can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in butadiene or 2,4-pentadienoate or any butadiene or 2,4-pentadienoate pathway intermediate. The various carbon feedstock and other uptake sources enumerated above will be referred to herein, collectively, as "uptake sources." Uptake sources can provide isotopic enrichment for any atom present in the product butadiene or 2,4-pentadienoate or butadiene or 2,4-pentadienoate pathway intermediate, or for side products generated in reactions diverging away from a butadiene or 2,4-pentadienoate pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modem (Fm) is computed from the expression: Fm=(S−B)/(M−B), where B, S and M represent the $^{14}C/^{12}C$ ratios of the blank, the sample and the modem reference, respectively. Fraction Modem is a measurement of the deviation of the $^{14}C/^{12}C$ ratio of a sample from "Modem." Modem is defined as 95% of the radiocarbon concentration (in AD 1950) of National Bureau of Standards (NBS) Oxalic Acid I (i.e., standard reference materials (SRM) 4990b) normalized to $\delta^{13}CVP_{DB}=-19$ per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}=-19$ per mil. This is equivalent to an absolute (AD 1950) $^{14}C/^{12}C$ ratio of $1.176\pm0.010\times10^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is $1.2933\pm0.001$ (the weighted mean). The isotopic ratio of HOx II is -17.8 per mil. ASTM D6866-11 suggests use of the available Oxalic Acid II standard SRM 4990 C (Hox2) for the modem standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modem carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content of a compound or material and/or prepared downstream products that utilize a compound or material of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides butadiene or 2,4-pentadienoate or a butadiene or 2,4-pentadienoate pathway intermediate that has a carbon-12, carbon-13, and carbon-14 ratio that reflects an atmospheric carbon, also referred to as environmental carbon, uptake source. For example, in some aspects the butadiene or 2,4-pentadienoate or a butadiene or 2,4-pentadienoate pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides butadiene or 2,4-pentadienoate or a butadiene or 2,4-pentadienoate pathway intermediate that has a carbon-12, carbon-13, and carbon-14 ratio that reflects petroleum-based carbon uptake source. In this aspect, the butadiene or 2,4-pentadienoate or a butadiene or 2,4-pentadienoate pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides butadiene or 2,4-pentadienoate or a pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced butadiene or 2,4-pentadienoate or butadiene or 2,4-pentadienoate pathway intermediate as disclosed herein, and to the products derived therefrom, wherein the butadiene or 2,4-pentadienoate or a butadiene or 2,4-pentadienoate pathway intermediate has a carbon-12, carbon-13, and carbon-14 isotope ratio of about the same value as the $CO_2$ that occurs in the environment. For example, in some aspects the invention provides bioderived butadiene or 2,4-pentadienoate or a bioderived butadiene or 2,4-pentadienoate intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived butadiene or 2,4-pentadienoate or a bioderived butadiene or 2,4-pentadienoate pathway intermediate as disclosed herein, wherein the bioderived product is chemically modified to generate a final product. Methods of chemically modifying a bioderived product of butadiene or 2,4-pentadienoate, or an intermediate thereof, to generate a desired product are well known to those skilled in the art, as described herein. The invention further provides a polymer, a synthetic rubber, an ABS resin, a chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, a copolymer, an acrylonitrile 1,3-butadiene styrene (ABS), a styrene-1,3-butadiene rubber (styrene butadiene rubber; SBR), a styrene-1,3-butadiene latex, a styrene-butadiene latex (SB), a synthetic rubber article, a tire, an adhesive, a seal, a sealant, a coating, a hose, a shoe sole, a polybutadiene rubber, a gasket, a high impact polystyrene (HIPS), a paper coating, a carpet backing, a molded article, a pipe, a telephone, a computer casing, a mobile phone, a radio, an appliance, a foam mattress, a glove, footwear, styrene-butadiene block copolymers, an asphalt modifier, a toy, nylon, nylon-6,6, nylon-6,X, polychloroprene (neoprene), thermoplastic, polybutylene terephthalate (PBT), an automotive part, an electrical part, a water system part, polyurethane, a polyurethane-polyurea copolymer, a biodegradable polymer, PBAT (poly(butylene adipate-co-terephthalate)), PBS (poly(butylene succinate)), an elastic fiber, polytetramethylene ether glycol (PTMEG), a spandex fiber, elastane, an industrial solvent, a pharmaceutical, a thermoplastic elastomer (TPE), elastomer polyester, a copolyester ether (COPE), a thermoplastic polyurethane, packaging, a mold extruded product, methylmethacrylate butadiene styrene, a methacrylate butadiene styrene (MBS) resin, a clear resin, a transparent thermoplastic, polycarbonate (PC), polyvinyl carbonate (PVC), or polymethyl methacrylate (PMMA) having a carbon-12 versus carbon-13 versus carbon-14 isotope ratio of about the same value as the $CO_2$ that occurs in the environment, wherein the polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), a styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, asphalt modifier, toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) is generated directly from or in combination with bioderived butadiene or 2,4-pentadienoate or a bioderived butadiene or 2,4-pentadienoate pathway intermediate as disclosed herein.

The invention further provides a composition comprising bioderived butadiene or 2,4-pentadienoate, and a compound other than the bioderived butadiene or 2,4-pentadienoate. The compound other than the bioderived product can be a cellular portion, for example, a trace amount of a cellular portion of, or can be fermentation broth or culture medium or a purified or partially purified fraction thereof produced in the presence of, a non-naturally occurring microbial organism of the invention having a butadiene or 2,4-pentadienoate pathway. The composition can comprise, for example, a reduced level of a byproduct when produced by an organism having reduced byproduct formation, as disclosed herein. The composition can comprise, for example, bioderived butadiene or 2,4-pentadienoate, or a cell lysate or culture supernatant of a microbial organism of the invention. The compound can also be hydrogen.

Butadiene or 2,4-pentadienoate is a chemical used in commercial and industrial applications. Non-limiting examples of such applications include production of a polymer, a synthetic rubber, an ABS resin, a chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, a copolymer, an acrylonitrile 1,3-butadiene styrene (ABS), a styrene-1,3-butadiene rubber (styrene butadiene rubber; SBR), a styrene-1,3-butadiene latex, a styrene-butadiene latex (SB), a synthetic rubber article, a tire, an adhesive, a seal, a sealant, a coating, a hose, a shoe sole, a polybutadiene rubber, a gasket, a high impact polystyrene (HIPS), a paper coating, a carpet backing, a molded article, a pipe, a telephone, a computer casing, a mobile phone, a radio, an appliance, a foam mattress, a glove, footwear, styrene-butadiene block copolymers, an asphalt modifier, a toy, nylon, nylon-6,6, nylon-6,X, polychloroprene (neoprene), thermoplastic, polybutylene terephthalate (PBT), an automotive part, an electrical part, a water system part, polyurethane, a polyurethane-polyurea copolymer, a biodegradable polymer, PBAT (poly(butylene adipate-co-terephthalate)), PBS (poly(butylene succinate)), an elastic fiber, polytetramethylene ether glycol (PTMEG), a spandex fiber, elastane, an industrial solvent, a pharmaceutical, a thermoplastic elastomer (TPE), elastomer polyester, a copolyester ether (COPE), a thermoplastic polyurethane, packaging, a mold extruded product, methylmethacrylate butadiene styrene, a methacrylate butadiene styrene (MBS) resin, a clear resin, a transparent thermoplastic, polycarbonate (PC), polyvinyl carbonate (PVC), or polymethyl methacrylate (PMMA). Moreover, butadiene or 2,4-pentadienoate is also used as a raw material in the production of a wide range of products including a polymer, a synthetic rubber, an ABS resin, a chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, a copolymer, an acrylonitrile 1,3-butadiene styrene (ABS), a styrene-1,3-butadiene rubber (styrene butadiene rubber; SBR), a styrene-1,3-butadiene latex, a styrene-butadiene latex (SB), a synthetic rubber article, a tire, an adhesive, a seal, a sealant, a coating, a hose, a shoe sole, a polybutadiene rubber, a gasket, a high impact polystyrene (HIPS), a paper coating, a carpet backing, a molded article, a pipe, a telephone, a computer casing, a mobile phone, a radio, an appliance, a foam mattress, a glove, footwear, styrene-butadiene block copolymers, an asphalt modifier, a toy, nylon, nylon-6,6, nylon-6,X, polychloroprene (neoprene), thermoplastic, polybutylene terephthalate (PBT), an automotive part, an electrical part, a water system part, polyurethane, a polyurethane-polyurea copolymer, a biodegradable polymer, PBAT (poly(butylene adipate-co-terephthalate)), PBS (poly(butylene succinate)), an elastic fiber, polytetramethylene ether glycol (PTMEG), a spandex fiber, elastane, an industrial solvent, a pharmaceutical, a thermoplastic elastomer (TPE), elastomer polyester, a copolyester ether (COPE), a thermoplastic polyurethane, packaging, a mold extruded product, methylmethacrylate butadiene styrene, a methacrylate butadiene styrene (MBS) resin, a clear resin, a transparent thermoplastic, polycarbonate (PC), polyvinyl carbonate (PVC), or polymethyl methacrylate (PMMA). Accordingly, in some embodiments, the invention provides biobased polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly (butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) comprising one or more bioderived butadiene or 2,4-pentadienoate or bioderived pathway intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides a polymer, a synthetic rubber, an ABS resin, a chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, a copolymer, an acrylonitrile 1,3-butadiene styrene (ABS), a styrene-1,3-butadiene rubber (styrene butadiene rubber; SBR), a styrene-1,3-butadiene latex, a styrene-butadiene latex (SB), a synthetic rubber article, a tire, an adhesive, a seal, a sealant, a coating, a hose, a shoe sole, a polybutadiene rubber, a gasket, a high impact polystyrene (HIPS), a paper coating, a carpet backing, a molded article, a pipe, a telephone, a computer casing, a mobile phone, a radio, an appliance, a foam mattress, a glove, footwear, styrene-butadiene block copolymers, an asphalt modifier, a toy, nylon, nylon-6,6, nylon-6,X, polychloroprene (neoprene), thermoplastic, polybutylene terephthalate (PBT), an automotive part, an electrical part, a water system part, polyurethane, a polyurethane-polyurea copolymer, a biodegradable polymer, PBAT (poly(butylene adipate-co-terephthalate)), PBS (poly(butylene succinate)), an elastic fiber, polytetramethylene ether glycol (PTMEG), a spandex fiber, elastane, an industrial solvent, a pharmaceutical, a thermoplastic elastomer (TPE), elastomer polyester, a copolyester ether (COPE), a thermoplastic polyurethane, packaging, a mold extruded product, methylmethacrylate butadiene styrene, a methacrylate butadiene styrene (MBS) resin, a clear resin, a transparent thermoplastic, polycarbonate (PC), polyvinyl carbonate (PVC), or polymethyl methacrylate (PMMA) comprising bioderived butadiene or 2,4-pentadienoate or bioderived butadiene or 2,4-pentadienoate pathway intermediate, wherein the bioderived butadiene or 2,4-pentadienoate or bioderived butadiene or 2,4-pentadienoate pathway intermediate includes all or part of the butadiene or 2,4-pentadienoate or butadiene or 2,4-pentadienoate pathway intermediate used in the production of a polymer, a synthetic rubber, an ABS resin, a chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, a copolymer, an acrylonitrile 1,3-butadiene styrene (ABS), a styrene-1,3-butadiene rubber (styrene butadiene rubber; SBR), a styrene-1,3-butadiene latex, a styrene-butadiene latex (SB), a synthetic rubber article, a tire, an adhesive, a seal, a sealant, a coating, a hose, a shoe sole, a polybutadiene rubber, a gasket, a high impact polystyrene (HIPS), a paper coating, a carpet backing, a molded article, a pipe, a telephone, a computer casing, a mobile phone, a radio, an appliance, a foam mattress, a glove, footwear, styrene-butadiene block copolymers, an asphalt modifier, a toy, nylon, nylon-6,6, nylon-6,X, polychloroprene (neoprene), thermoplastic, polybutylene terephthalate (PBT), an automotive part, an electrical part, a water system part, polyurethane, a polyurethane-polyurea copolymer, a biodegradable polymer, PBAT (poly(butylene adipate-co-terephthalate)), PBS (poly(butylene succinate)), an elastic fiber, polytetramethylene ether glycol (PTMEG), a spandex fiber, elastane, an industrial solvent, a pharmaceutical, a thermoplastic elastomer (TPE), elastomer polyester, a copolyester ether (COPE), a thermoplastic polyurethane, packaging, a mold extruded product, methylmethacrylate butadiene styrene, a methacrylate butadiene styrene (MBS) resin, a clear resin, a transparent thermoplastic, polycarbonate (PC), polyvinyl carbonate (PVC), or polymethyl methacrylate (PMMA). For example, the final polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) can contain the bioderived butadiene or 2,4-pentadienoate, butadiene or 2,4-pentadienoate pathway intermediate, or a portion thereof that is the result of the manufacturing of a polymer, a synthetic rubber, an ABS resin, a chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, a copolymer, an acrylonitrile 1,3-butadiene styrene (ABS), a styrene-1,3-butadiene rubber (styrene butadiene rubber; SBR), a styrene-1,3-butadiene latex, a styrene-butadiene latex (SB), a synthetic rubber article, a tire, an adhesive, a seal, a sealant, a coating, a hose, a shoe sole, a polybutadiene rubber, a gasket, a high impact polystyrene (HIPS), a paper coating, a carpet backing, a molded article, a pipe, a telephone, a computer casing, a mobile phone, a radio, an appliance, a foam mattress, a glove, footwear, styrene-butadiene block copolymers, an asphalt modifier, a toy, nylon, nylon-6,6, nylon-6,X, polychloroprene (neoprene), thermoplastic, polybutylene terephthalate (PBT), an automotive part, an electrical part, a water system part, polyurethane, a polyurethane-polyurea copolymer, a biodegradable polymer, PBAT (poly(butylene adipate-co-terephthalate)), PBS (poly(butylene succinate)), an elastic fiber, polytetramethylene ether glycol (PTMEG), a spandex fiber, elastane, an industrial solvent, a pharmaceutical, a thermoplastic elastomer (TPE), elastomer polyester, a copolyester ether (COPE), a thermoplastic polyurethane, packaging, a mold extruded product, methylmethacrylate butadiene styrene, a methacrylate butadiene styrene (MBS) resin, a clear resin, a transparent thermoplastic, polycarbonate (PC), polyvinyl carbonate (PVC), or polymethyl methacrylate (PMMA). Such manufacturing can include chemically reacting the bioderived butadiene or 2,4-pentadienoate or bioderived butadiene or 2,4-pentadienoate pathway intermediate (e.g. chemical conversion, chemical functionalization, chemical coupling, oxidation, reduction, polymerization, copolymerization and the like) into the final polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA). Thus, in some aspects, the invention provides a biobased polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived butadiene or 2,4-pentadienoate or bioderived butadiene or 2,4-pentadienoate pathway intermediate as disclosed herein.

Additionally, in some embodiments, the invention provides a composition having a bioderived butadiene or 2,4-pentadienoate or butadiene or 2,4-pentadienoate pathway intermediate disclosed herein and a compound other than the bioderived butadiene or 2,4-pentadienoate or butadiene or 2,4-pentadienoate pathway intermediate. For example, in some aspects, the invention provides a biobased polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) wherein the butadiene or 2,4-pentadienoate or butadiene or 2,4-pentadienoate pathway intermediate used in its production is a combination of bioderived and petroleum derived butadiene or 2,4-pentadienoate or butadiene or 2,4-pentadienoate pathway intermediate. For example, a biobased polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) can be produced using 50% bioderived butadiene or 2,4-pentadienoate and 50% petroleum derived butadiene or 2,4-pentadienoate or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing polymer, synthetic rubber, ABS resin, chemical, hexamethylenediamine (HMDA), 1,4-butanediol, tetrahydrofuran (THF), adiponitrile, lauryl lactam, caprolactam, chloroprene, sulfalone, n-octanol, octene-1, polybutadiene, copolymer, acrylonitrile 1,3-butadiene styrene (ABS), styrene-1,3-butadiene rubber (styrene butadiene rubber; SBR), styrene-1,3-butadiene latex, styrene-butadiene latex (SB), synthetic rubber article, tire, adhesive, seal, sealant, coating, hose, shoe sole, polybutadiene rubber, gasket, high impact polystyrene (HIPS), paper coating, carpet backing, molded article, pipe, telephone, computer casing, mobile phone, radio, appliance, foam mattress, glove, footwear, styrene-butadiene block copolymers, an asphalt modifier, a toy, nylon, nylon-6,6, nylon-6,X, polychloroprene (neoprene), thermoplastic, polybutylene terephthalate (PBT), automotive part, electrical part, water system part, polyurethane, polyurethane-polyurea copolymer, biodegradable polymer, PBAT (poly(butylene adipate-co-terephthalate)), PBS (poly(butylene succinate)), elastic fiber, polytetramethylene ether glycol (PTMEG), spandex fiber, elastane, industrial solvent, pharmaceutical, thermoplastic elastomer (TPE), elastomer polyester, copolyester ether (COPE), thermoplastic polyurethane, packaging, mold extruded product, methylmethacrylate butadiene styrene, methacrylate butadiene styrene (MBS) resin, clear resin, transparent thermoplastic, polycarbonate (PC), polyvinyl carbonate (PVC), or polymethyl methacrylate (PMMA) using the bioderived butadiene or 2,4-pentadienoate or bioderived butadiene or 2,4-pentadienoate pathway intermediate of the invention are well known in the art.

The invention further provides bioderived hydrogen produced by culturing a non-naturally culturing microbial organism disclosed herein under conditions and for a sufficient period of time to produce hydrogen. In some embodiments, the invention provides a process for producing hydrogen including (a) culturing a non-naturally culturing microbial organism disclosed herein in a substantially anaerobic culture medium under a condition to produce hydrogen; (b) separating the produced hydrogen from the culture medium; and (c) collecting the separated hydrogen.

In some embodiments, the said condition allowing hydrogen production includes an aqueous environment and a gas phase. The said aqueous environment can contain a liquid feedstock. The liquid feedstock can include a carbon source selected from the group consisting of glucose, xylose, arabinose, galactose, mannose, fructose, sucrose, starch, methonal, and glycerol. In one aspect, the liquid feedstock is supplied continuously. In addition, the gas phase can be continuously flushed with a defined amount of an inert gas, or flushed at defined time points with a defined amount of an inert gas. The aqueous environment also can be continuously bubbled with defined amounts of an inert gas, or flushed at defined time points with a defined amount of an inert gas. In some aspects, the inert gas is nitrogen or argon. In some other embodiments, the produced hydrogen is separated from the culture medium by shaking.

Provided herein are exemplary methods to purify butadiene and hydrogen from the culture medium. In some embodiments, any of the methods or processes described herein further include recovering the co-produced compounds. In some embodiments, any of the methods or processes described herein further include recovering butadiene produced. In some embodiments, any of the methods or processes described herein further include recovering the hydrogen produced. Such methods or processes can include cryogenic membrane, adsorption matrix-based separation methods that are well-known in the art.

The butadiene and/or hydrogen produced using the compositions, methods and processes described herein can be recovered using standard techniques, such as gas stripping, membrane enhanced separation, fractionation, adsorption/desorption, pervaporation, thermal or vacuum desorption of butadiene from a solid phase, or extraction of butadiene immobilized or absorbed to a solid phase with a solvent (see, e.g., U.S. Pat. Nos. 4,703,007, 4,570,029, and 4,740,222, which are each hereby incorporated by reference in their entireties, particularly with respect to hydrogen recovery and purification methods ('222 patent)). Gas stripping involves the removal of butadiene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute butadiene vapor stream above the dew point of the vapor resulting in the condensation of liquid butadiene. In some embodiments, the butadiene is compressed and condensed.

The recovery of butadiene may involve one step or multiple steps. In some embodiments, the removal of butadiene vapor from the fermentation off-gas and the conversion of butadiene to a liquid phase are performed simultaneously. For example, butadiene can be directly condensed from the off-gas stream to form a liquid. In some embodiments, the removal of butadiene vapor from the fermentation off-gas and the conversion of butadiene to a liquid phase are performed sequentially. For example, butadiene may be adsorbed to a solid phase and then extracted from the solid phase with a solvent.

The recovery of hydrogen may involve one step or multiple steps. In some embodiments, the removal of hydrogen gas from the fermentation off-gas and the conversion of hydrogen to a liquid phase are performed simultaneously. In some embodiments, the removal of hydrogen gas from the fermentation off-gas and the conversion of hydrogen to a liquid phase are performed sequentially. For example, hydrogen may be adsorbed to a solid phase and then desorbed from the solid phase by a pressure swing. In some embodiments, recovered hydrogen gas is concentrated and compressed.

In some embodiments, any of the methods described herein further include purifying the hydrogen. For example, the hydrogen produced using the compositions and methods described herein can be purified using standard techniques. Purification refers to a process through which hydrogen is separated from one or more components that are present when the hydrogen is produced. In some embodiments, the hydrogen is obtained as a substantially pure gas. In some embodiments, the hydrogen is obtained as a substantially pure liquid. Examples of purification methods include (i) cryogenic condensation and (ii) solid matrix adsorption. As used herein, "purified hydrogen" means hydrogen that has been separated from one or more components that are present when the hydrogen is produced. In some embodiments, the hydrogen is at least about 20%, by weight, free from other components that are present when the hydrogen is produced. In various embodiments, the hydrogen is at least or about 25%, 30%, 40%, 50%, 60%, 70%, 75%, 80%, 90%, 95%, or 99%, by weight, pure. Purity can be assayed by any appropriate method, e.g., by column chromatography or GC-MS analysis.

In some embodiments, at least a portion of the gas phase remaining after one or more recovery steps for the removal of butadiene is recycled by introducing the gas phase into a cell culture system (such as a fermentor) for the production of butadiene.

A bioderived composition from a fermentor off-gas may contain butadiene with volatile impurities and bio-byproduct impurities. In some embodiments, butadiene from a fermentor off-gas can be purified using a method comprising: (a) contacting the fermentor off-gas with a solvent in a first column to form a butadiene-rich solution comprising the solvent, a major portion of the butadiene and a major portion of the bio-byproduct impurity; and a vapor comprising a major portion of the volatile impurity; (b) transferring the butadiene-rich solution from the first column to a second column; and (c) stripping butadiene from the butadiene-rich solution in the second column to form: an butadiene-lean solution comprising a major portion of the bio-byproduct impurity; and a purified butadiene.

Separation of hydrogen from other gaseous products such as butadiene, $CO_2$ can be accomplished by well-known methods such as pressure-swing adsorption and membrane-based methods. There are several types of membranes: gas-diffusion, ion conducting, and catalytic membranes. Apparatus and methods for separation of $H_2$ from $CO_2$ produced during fermentation is known in the art (see, e.g., US2010/02483181, which is incorporated herein by reference) and can be used in the methods and processes described herein.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of butadiene or 2,4-pentadienoate includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of butadiene or 2,4-pentadienoate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of butadiene or 2,4-pentadienoate. Generally, and as with non-continuous culture procedures, the continuous and/or near-continuous production of butadiene or 2,4-pentadienoate will include culturing a non-naturally occurring butadiene or 2,4-pentadienoate producing organism of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of butadiene or 2,4-pentadienoate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the butadiene or 2,4-pentadienoate producers of the invention for continuous production of substantial quantities of butadiene or 2,4-pentadienoate, the butadiene or 2,4-pentadienoate producers also can be, for example, simultaneously subjected to chemical synthesis and/or enzymatic procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of butadiene or 2,4-pentadienoate.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions.

Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

Employing the methods exemplified above, the methods of the invention allow the construction of cells and organisms that increase production of a desired product, for example, by coupling the production of a desired product to growth of the cell or organism engineered to harbor the identified genetic alterations. As disclosed herein, metabolic alterations have been identified that couple the production of butadiene or 2,4-pentadienoate to growth of the organism. Microbial organism strains constructed with the identified metabolic alterations produce elevated levels, relative to the absence of the metabolic alterations, of butadiene or 2,4-pentadienoate during the exponential growth phase. These strains can be beneficially used for the commercial production of butadiene or 2,4-pentadienoate in continuous fermentation process without being subjected to the negative selective pressures described previously. Although exemplified herein as metabolic alterations, in particular one or more gene disruptions, that confer growth coupled production of butadiene or 2,4-pentadienoate, it is understood that any gene disruption that increases the production of butadiene or 2,4-pentadienoate can be introduced into a host microbial organism, as desired.

Therefore, the methods of the invention provide a set of metabolic modifications that are identified by an in silico method such as OptKnock. The set of metabolic modifications can include functional disruption of one or more metabolic reactions including, for example, disruption by gene deletion. For butadiene or 2,4-pentadienoate production, metabolic modifications can be selected from the set of metabolic modifications listed in FIG. 3.

Also provided is a method of producing a non-naturally occurring microbial organisms having stable growth-coupled production of butadiene or 2,4-pentadienoate. The method can include identifying in silico a set of metabolic modifications that increase production of butadiene or 2,4-pentadienoate, for example, increase production during exponential growth; genetically modifying an organism to contain the set of metabolic modifications that increase production of butadiene or 2,4-pentadienoate, and culturing the genetically modified organism. If desired, culturing can include adaptively evolving the genetically modified organism under conditions requiring production of butadiene or 2,4-pentadienoate. The methods of the invention are applicable to bacterium, yeast and fungus as well as a variety of other cells and microorganism, as disclosed herein.

Thus, the invention provides a non-naturally occurring microbial organism comprising one or more gene disruptions that confer increased production of butadiene or 2,4-pentadienoate. In one embodiment, the one or more gene disruptions confer growth-coupled production of butadiene or 2,4-pentadienoate, and can, for example, confer stable growth-coupled production of butadiene or 2,4-pentadienoate. In another embodiment, the one or more gene disruptions can confer obligatory coupling of butadiene or 2,4-pentadienoate production to growth of the microbial organism. Such one or more gene disruptions reduce the activity of the respective one or more encoded enzymes.

The non-naturally occurring microbial organism can have one or more gene disruptions included in a metabolic modification listed in FIG. 3. As disclosed herein, the one or more gene disruptions can be a deletion. Such non-naturally occurring microbial organisms of the invention include bacteria, yeast, fungus, or any of a variety of other microorganisms applicable to fermentation processes, as disclosed herein.

Thus, the invention provides a non-naturally occurring microbial organism, comprising one or more gene disruptions, where the one or more gene disruptions occur in genes encoding proteins or enzymes where the one or more gene disruptions confer increased production of butadiene or 2,4-pentadienoate in the organism. The production of butadiene or 2,4-pentadienoate can be growth-coupled or not growth-coupled. In a particular embodiment, the production of butadiene or 2,4-pentadienoate can be obligatorily coupled to growth of the organism, as disclosed herein.

In some embodiments, the invention provides a non-naturally occurring microbial organism as described herein, wherein the microbial organism further includes attenuation of one or more endogenous enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. Accordingly, in some aspects, the attenuation is of the endogenous enzyme DHA kinase. In some aspects, the attenuation is of the endogenous enzyme methanol oxidase. In some aspects, the attenuation is of the endogenous enzyme PQQ-dependent methanol dehydrogenase. In some aspects, the attenuation is of the endogenous enzyme DHA synthase. The invention also provides a microbial organism wherein attenuation is of any combination of two or three endogenous enzymes described herein. For example, a microbial organism of the invention can include attenuation of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein attenuation is of all endogenous enzymes described herein. For example, in some aspects, a microbial organism described herein includes attenuation of DHA kinase, methanol oxidase, PQQ-dependent methanol dehydrogenase and DHA synthase.

In some embodiments, the invention provides a non-naturally occurring microbial organism as described herein, wherein the microbial organism further includes attenuation of one or more endogenous enzymes of a competing formaldehyde assimilation or dissimilation pathway. Examples of these endogenous enzymes are disclosed in FIG. 3. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes attenuation of one, two, three, four, five, six, seven, eight, nine, ten or more endogenous enzymes of a competing formaldehyde assimilation or dissimilation pathway.

In some embodiments, the invention provides a non-naturally occurring microbial organism as described herein, wherein the microbial organism further includes a gene disruption of one or more endogenous nucleic acids encoding enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. According, in some aspects, the gene disruptiondisruption is of an endogenous nucleic acid encoding the enzyme DHA kinase. In some aspects, the gene disruptiondisruption is of an endogenous nucleic acid encoding the enzyme methanol oxidase. In some aspects, the gene disruptiondisruption is of an endogenous nucleic acid encoding the enzyme PQQ-dependent methanol dehydrogenase. In some aspects, the gene disruption is of an endogenous nucleic acid encoding the enzyme DHA synthase. The invention also provides a microbial organism wherein the gene disruption is of any combination of two or three nucleic acids encoding endogenous enzymes described herein. For example, a microbial organism of the invention can include a gene disruption of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein all endogenous nucleic acids encoding enzymes described herein are disrupted. For example, in some aspects, a microbial organism described herein includes disruption of DHA kinase, methanol oxidase, PQQ-dependent methanol dehydrogenase and DHA synthase.

In some embodiments, the invention provides a non-naturally occurring microbial organism as described herein, wherein the microbial organism further includes a gene disruption of one or more endogenous enzymes of a competing formaldehyde assimilation or dissimilation pathway. Examples of these endogenous enzymes are disclosed in FIG. 3. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes a gene disruption of one, two, three, four, five, six, seven, eight, nine, ten or more endogenous nucleic acids encoding enzymes of a competing formaldehyde assimilation or dissimilation pathway.

The invention provides non naturally occurring microbial organisms having genetic alterations such as gene disruptions that increase production of butadiene or 2,4-pentadienoate, for example, growth-coupled production of butadiene or 2,4-pentadienoate. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Sets of metabolic alterations or transformations that result in increased production and elevated levels of butadiene or 2,4-pentadienoate biosynthesis are exemplified in FIG. 3. Each alteration within a set corresponds to the requisite metabolic reaction that should be functionally disrupted. Functional disruption of all reactions within each set can result in the increased production of butadiene or 2,4-pentadienoate by the engineered strain during the growth phase. The corresponding reactions to the referenced alterations can be found in FIG. 3, and the gene or genes that encode enzymes or proteins that carry out the reactions are set forth in FIG. 3.

For example, for each strain exemplified in FIG. 3, the metabolic alterations that can be generated for butadiene or 2,4-pentadienoate production are shown with "X" markings. These alterations include the functional disruption of the reactions shown in FIG. 3. Each of these non-naturally occurring alterations result in increased production and an enhanced level of butadiene or 2,4-pentadienoate production, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the increased production of butadiene or 2,4-pentadienoate or growth-coupled product production.

Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); and addition of drugs or other chemicals that reduce or disrupt enzymatic activity such as an enzyme inhibitor, an antibiotic or a target-specific drug.

One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., Genetics 120(4):875-885 (1988); Hayes, Annu. Rev. Genet. 37:3-29 (2003); in a diploid organism, deleting one allele resulting in loss of heterozygosity (Daigaku et al., *Mutation Research/Fundamental and Molecular Mechanisms of Mutagenesis* 600(1-2) 177-183 (2006)); introducing nucleic acids that increase RNA degradation (Houseley et al., *Cell*, 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2): 125-131 (2005); modifying regions outside the coding sequence, such as introducing secondary structure into an untranslated region (UTR) to block translation or reduce efficiency of translation (Ringnér et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5): 883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); or introducing translational regulatory elements involving RNA structure that can prevent or reduce translation that can be controlled by the presence or absence of small molecules (Araujo et al., *Comparative and Functional Genomics*, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911 (1992); and Russell et al., *J. Bact.* 189(21) 7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The butadiene or 2,4-pentadienoate-production strategies identified by the methods disclosed herein such as the OptKnock framework are generally ranked on the basis of their (i) theoretical yields, and (ii) growth-coupled butadiene or 2,4-pentadienoate formation characteristics. For the designs disclosed herein, the genes that can be disrupted to increase production of butadiene or 2,4-pentadienoate are shown in FIG. 3.

Accordingly, the invention also provides a non-naturally occurring microbial organism having a set of metabolic modifications coupling butadiene or 2,4-pentadienoate production to growth of the organism, where the set of metabolic modifications includes disruption of one or more genes selected from the set of genes encoding proteins as in FIG. 3.

Each of the strains can be supplemented with additional deletions if it is determined that the strain designs do not sufficiently increase the production of butadiene or 2,4-pentadienoate and/or couple the formation of the product with biomass formation. Alternatively, some other enzymes not known to possess significant activity under the growth conditions can become active due to adaptive evolution or random mutagenesis. Such activities can also be knocked out. However, the list of gene deletion sets disclosed herein allows the construction of strains exhibiting high-yield production of butadiene or 2,4-pentadienoate, including growth-coupled production of butadiene or 2,4-pentadienoate.

Butadiene or 2,4-pentadienoate can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of butadiene or 2,4-pentadienoate can be produced.

Therefore, the invention additionally provides a method for producing butadiene or 2,4-pentadienoate that includes culturing a non-naturally occurring microbial organism having one or more gene disruptions, as disclosed herein. The disruptions can occur in one or more genes encoding an enzyme that increases production of butadiene or 2,4-pentadienoate, including optionally coupling butadiene or 2,4-pentadienoate production to growth of the microorganism when the gene disruption reduces or eliminates an activity of the enzyme. For example, the disruptions can confer stable growth-coupled production of butadiene or 2,4-pentadienoate onto the non-naturally microbial organism.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational predictions are made of gene sets for disruption to increase production of butadiene or 2,4-pentadienoate, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth rates until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36:1056-1058 (2004)). The growth improvements brought about by adaptive evolution can be accompanied by enhanced rates of butadiene or 2,4-pentadienoate production. The strains are generally adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarra et al., *Nature* 420:186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields alongside the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

Adaptive evolution is a powerful technique that can be used to increase growth rates of mutant or engineered microbial strains, or of wild-type strains growing under unnatural environmental conditions. It is especially useful for strains designed via methods such as OptKnock, which results in growth-coupled product formation. Therefore, evolution toward optimal growing strains will indirectly optimize production as well. Unique strains of *E. coli* K-12 MG1655 were created through gene knockouts and adaptive evolution. (Fong and Palsson, *Nat. Genet.* 36:1056-1058 (2004)). In this work, all adaptive evolutionary cultures were maintained in prolonged exponential growth by serial passage of batch cultures into fresh medium before the stationary phase was reached, thus rendering growth rate as the primary selection pressure. Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (within 10%) at predicting the post-evolution growth rate of the knockout strains in 38 out of the 50 cases examined. Furthermore, a combination of OptKnock design with adaptive evolution has led to improved lactic acid production strains. (Fong et al., *Biotechnol. Bioeng.* 91:643-648 (2005)). Similar methods can be applied to the strains disclosed herein and applied to various host strains.

There are a number of developed technologies for carrying out adaptive evolution. Exemplary methods are disclosed herein. In some embodiments, optimization of a non-naturally occurring organism of the present invention includes utilizing adaptive evolution techniques to increase butadiene or 2,4-pentadienoate production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, *Proc. Natl. Acad Sci. USA* 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, *Methods Enzymol.* 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, *J. Gen. Microbiol* 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

Evolugator™ is a continuous culture device developed by Evolugate, LLC (Gainesville, Fla.) and exhibits significant time and effort savings over traditional evolution techniques (de Crecy et al., *Appl. Microbiol. Biotechnol.* 77:489-496 (2007)). The cells are maintained in prolonged exponential growth by the serial passage of batch cultures into fresh medium before the stationary phase is attained. By automating optical density measurement and liquid handling, the Evolugator™ can perform serial transfer at high rates using large culture volumes, thus approaching the efficiency of a chemostat in evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%. A drawback to this device is that it is large and costly, thus running large numbers of evolutions in parallel is not practical. Furthermore, gas addition is not well regulated, and strict anaerobic conditions are not maintained with the current device configuration. Nevertheless, this is an alternative method to adaptively evolve a production strain.

As disclosed herein, a nucleic acid encoding a desired activity of a butadiene or 2,4-pentadienoate pathway can be introduced into a host organism. In some cases, it can be desirable to modify an activity of a butadiene or 2,4-pentadienoate pathway enzyme or protein to increase production of butadiene or 2,4-pentadienoate. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a butadiene or 2,4-pentadionate pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., Methods Enzymol. 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, Methods Mol. Biol 352:191-204 (2007); Bergquist et al., Biomol. Eng 22:63-72 (2005); Gibbs et al., Gene 271:13-20 (2001)); Incremental Truncation for the Creation of Hybrid Enzymes (ITCHY), which creates a combinatorial library with 1 base pair deletions of a gene or gene fragment of interest (Ostermeier et al., Proc. Natl. Acad. Sci. USA 96:3562-3567 (1999); and Ostermeier et al., Nat. Biotechnol. 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., Nucleic Acids Res 29:E16 (2001)); SCRATCHY, which combines two methods for recombining genes, ITCHY and DNA shuffling (Lutz et al., Proc. Natl. Acad. Sci. USA 98:11248-11253 (2001)); Random Drift Mutagenesis (RNDM), in which mutations made via epPCR are followed by screening/selection for those retaining usable activity (Bergquist et al., Biomol. Eng. 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., Biotechnol. J. 3:74-82 (2008); Wong et al., Nucleic Acids Res. 32:e26 (2004); and Wong et al., Anal. Biochem. 341:187-189 (2005)); Synthetic Shuffling, which uses overlapping oligonucleotides designed to encode "all genetic diversity in targets" and allows a very high diversity for the shuffled progeny (Ness et al., Nat. Biotechnol. 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., Nucleic Acids Res. 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., Nat. Biotechnol. 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., Methods Enzymol. 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. Methods Enzymol. 208:564-586 (1991); and Reidhaar-Olson et al. Science 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., Angew. Chem. Int. Ed Engl. 40:3589-3591 (2001)); the Mutator Strains technique, in which conditional ts mutator plasmids, utilizing the mutD5 gene, which encodes a mutant subunit of DNA polymerase III, to allow increases of 20 to 4000-× in random and natural mutation frequency during selection and block accumulation of deleterious mutations when selection is not required (Selifonova et al., Appl. Environ. Microbiol. 67:3645-3649 (2001)); Low et al., J Mol. Biol. 260:359-3680 (1996)).

Additional exemplary methods include Look-Through Mutagenesis (LTM), which is a multidimensional mutagenesis method that assesses and optimizes combinatorial mutations of selected amino acids (Rajpal et al., Proc. Natl. Acad. Sci. USA 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., Proc. Natl. Acad. Sci. USA 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., Nat. Protoc. 2:891-903 (2007); and Reetz et al., Angew. Chem. Int. Ed Engl. 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Example I

Production of Butadiene or 2,4-Pentadienoate Via 4-Hydroxy-2-Oxovalerate

Pathways to butadiene and 2,4-pentadienoate are shown in FIG. 1. These pathways start with intermediates of central metabolism, pyruvate and acetyl-CoA. Acetyl-CoA is reduced to acetaldehyde by an acylating acetaldehyde dehydrogenase followed by an aldolase combining pyruvate and acetaldehyde to form 4-hydroxy-2-oxovalerate (Steps A and B). In several organisms, as described in more detail below, a bifunctional enzyme can carry out these two steps and the toxic intermediate, acetaldehyde, is not released but is rather channeled within the enzyme. 4-hydroxy 2-oxovalerate can then dehydrated to form 2-oxopentenoate (Step C). Subsequently, this metabolite can be reduced to form 2-hydroxypentenoate (Step D). 2-hydroxypentenoate can be dehydrated to form 2,4-pentadienoate that can be further decaboxylated to form butadiene (Steps E and F respectively).

Alternatively, 2-oxopentenoate can be activated to form 2-oxopentenoyl-CoA either by a ligase or a CoA transferase (Steps G and H) that can then be reduced to form 2-hydroxypentenoyl-CoA (Step I). The latter can be dehydrated to form 2,4-pentadienoyl-CoA (Step L) which is converted to 2,4-pentadienoate either by a CoA hydrolase or a CoA tranferase (Step M or N). 2-Hydroxypentenoate can also be activated to form 2-hydroxypentenoyl-CoA as shown in Steps J and K, which can then be converted to 2,4-pentadienoyl-CoA as discussed above. In all the pathway combinations outlined herein, the activation of the acid intermediate to its CoA form can also be enabled by a CoA synthetase. This enzyme requires 2 ATP equivalents for achieving this activation.

This set of pathways via 2,4-pentadienoate affords a theoretical maximum yield of 1 mol butadiene per mole glucose (0.3 g/g) as shown below:

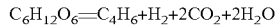

The pathway has a net excess redox of 1 mole/mole butadiene produced. The energetics of the pathway are quite favorable and the pathway through steps A-F has a net excess of 2 moles ATP/mole butadiene produced. If any other permutations of the pathway that activate the acid intermediates to CoA via a ligase or a transferase are used along with a CoA hydrolase, one ATP is required. This still keeps the pathway energetically favorable and brings the net ATP to 1 mole per mole butadiene produced. However, if a CoA transferase is used in Steps G or J along with a CoA transferase in Step N, the net ATP produced by the pathway still stays at 2 moles ATP/mole glucose.

One advantage of having a butadiene or 2,4-pentadienoate producing pathway that generates ATP is producing butadiene or 2,4-pentadienoate anaerobically. Anaerobic processes can be desirable due to the risk of explosion when oxygen is mixed with butadiene in a fermenter. Moreover, the presence of oxygen can be undesired because of its potential to cause polymerization of butadiene or 2,4-pentadienoate. Anaerobic production can be obtained by coproduction of succinate or other by products with butadiene as described previously (see, e.g., WO/2014/063156A3, WO/2014/063156A2, WO/2014/055649A1, WO/2013/192183A1). However, this can cause carbon from the substrate to be lost to other products and result in reduction of the theoretical yield of butadiene or 2,4-pentadienoate. A more preferred an anerobic process for butadiene or 2,4-pentadienoate production is where butadiede or 2,4-pentadienoate is produced either solely or with hydrogen such that no carbon is lost to other byproducts. For example, the pathways shown in FIG. 1 afford a maximum yield of 1 mole butadiene or 2,4-pentadienoate per mole glucose as shown below:

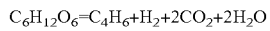

In this scenario, an excess of reducing equivalents is generated by the pathway. Since the pathway itself generates ATP, it is not required to donate the excess electrons to oxygen for oxidative phosphorylation and generation of ATP. Instead the reducing equivalent can be used for the formation of hydrogen via hydrogenases. Exemplary enzymes for these are described herein (Example XI). Further, the pathways shown in FIG. 1 proceed via acetyl-CoA and pyruvate and are amenable to carbon savings via the use of phospoketolase-dependent Acetyl-CoA synthesis pathway (Example VI). This will allow the theoretical yield of the pathway to be improved to 1.09 mole/mole as shown below and depicted in detail in FIG. 5:

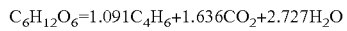

Step A, FIG. 1: Acetaldehyde Dehydrogenase

The reduction of acetyl-CoA to acetaldehyde can be catalyzed by NAD(P)+-dependent acetaldehyde dehydrogenase (EC 1.2.1.10). Acylating acetaldehyde dehydrogenases of *E. coli* are encoded by adhE and mhpF (Ferrandez et al, *J Bacteriol* 179:2573-81 (1997)). The *Pseudomonas* sp. CF600 enzyme, encoded by dmpF, participates in meta-cleavage pathways and forms a complex with 4-hydroxy-2-oxovalerate aldolase (Shingler et al, *J Bacteriol* 174:711-24 (1992)). BphJ, a nonphosphorylating acylating aldehyde dehydrogenase, catalyzes the conversion of aldehydes to form acyl-coenzyme A in the presence of NAD(+) and coenzyme A (CoA) (Baker et al., *Biochemistry*, 2012 Jun. 5; 51(22):4558-67. Epub 2012 May 21). Solventogenic organisms such as *Clostridium acetobutylicum* encode bifunctional enzymes with alcohol dehydrogenase and acetaldehyde dehydrogenase activities. The bifunctional *C. acetobutylicum* enzymes are encoded by bdh I and adhE2 (Walter, et al., *J. Bacteriol.* 174:7149-7158 (1992); Fontaine et al., *J. Bacteriol.* 184:821-830 (2002)). Yet another candidate for acylating acetaldehyde dehydrogenase is the ald gene from *Clostridium beijerinckii* (Toth, *Appl. Environ. Microbiol.* 65:4973-4980 (1999). This gene is very similar to the eutE acetaldehyde dehydrogenase genes of *Salmonella typhimurium* and *E. coli* (Toth, *Appl. Environ. Microbiol.* 65:4973-4980 (1999).

| Protein | GenBank ID | GI Number | Organism |
| --- | --- | --- | --- |
| adhE | NP_415757.1 | 16129202 | *Escherichia coli* |
| mhpF | NP_414885.1 | 16128336 | *Escherichia coli* |
| dmpF | CAA43226.1 | 45683 | *Pseudomonas* sp. CF600 |
| adhE2 | AAK09379.1 | 12958626 | *Clostridium acetobutylicum* |
| bdh I | NP_349892.1 | 15896543 | *Clostridium acetobutylicum* |
| Ald | AAT66436 | 49473535 | *Clostridium beijerinckii* |
| eutE | NP_416950 | 16130380 | *Escherichia coli* |
| eutE | AAA80209 | 687645 | *Salmonella typhimurium* |
| bphJ | CAA54035.1 | 520923 | *Burkholderia xenovorans* LB400 |

Other acyl-CoA dehydrogenases that reduce an acyl-CoA to its corresponding aldehyde include fatty acyl-CoA reductase (EC 1.2.1.42, 1.2.1.50), succinyl-CoA reductase (EC 1.2.1.76), acetyl-CoA reductase, butyryl-CoA reductase and propionyl-CoA reductase (EC 1.2.1.3). Aldehyde forming acyl-CoA reductase enzymes with demonstrated activity on acyl-CoA, 3-hydroxyacyl-CoA and 3-oxoacyl-CoA substrates are known in the literature. Several acyl-CoA reductase enzymes are active on 3-hydroxyacyl-CoA substrates. For example, some butyryl-CoA reductases from Clostridial organisms, are active on 3-hydroxybutyryl-CoA and propionyl-CoA reductase of *L. reuteri* is active on 3-hydroxypropionyl-CoA. An enzyme for converting 3-oxoacyl-CoA substrates to their corresponding aldehydes is malonyl-CoA reductase. Enzymes in this class can be refined using evolution or enzyme engineering methods known in the art to have activity on enoyl-CoA substrates.

Exemplary fatty acyl-CoA reductases enzymes are encoded by acr1 of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)). Two gene products from *Mycobacterium tuberculosis* accept longer chain fatty acyl-CoA substrates of length C16-C18 (Harminder Singh, U. Central Florida (2007)). Yet another fatty acyl-CoA reductase is LuxC of *Photobacterium phosphoreum* (Lee et al, *Biochim Biohys Acta* 1388:215-22 (1997)). Enzymes with succinyl-CoA reductase activity are encoded by sucD of *Clostridium kluyveri* (Sohling, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J. Bacteriol*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385

(1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., Biosci Biotechnol Biochem., 71:58-68 (2007)). Exemplary propionyl-CoA reductase enzymes include pduP of *Salmonella typhimurium* LT2 (Leal, Arch. Microbiol. 180:353-361 (2003)) and eutE from *E. coli* (Skraly, WO Patent No. 2004/024876). The propionyl-CoA reductase of *Salmonella typhimurium* LT2, which naturally converts propionyl-CoA to propionaldehyde, also catalyzes the reduction of 5-hydroxyvaleryl-CoA to 5-hydroxypentanal (WO 2010/068953A2). The propionaldehyde dehydrogenase of *Lactobacillus reuteri*, PduP, has a broad substrate range that includes butyraldehyde, valeraldehyde and 3-hydroxypropionaldehyde (Luo et al, *Appl Microbiol Biotech*, 89: 697-703 (2011)). Additionally, some acyl-ACP reductase enzymes such as the orf1594 gene product of *Synechococcus elongatus* PCC7942 also exhibit aldehyde-forming acyl-CoA reductase activity (Schirmer et al, *Science*, 329: 559-62 (2010)).

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, *Science* 318:1782-1786 (2007); and Thauer, *Science* 318:1732-1733 (2007)). The enzyme utilizes NADPH as a cofactor and has been characterized in *Metallosphaera* and *Sulfolobus* sp. (Alber et al., *J. Bacteriol.* 188:8551-8559 (2006); and Hugler, *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg, *Science* 318:1782-1786 (2007)). A gene encoding a malonyl-CoA reductase from *Sulfolobus tokodaii* was cloned and heterologously expressed in *E. coli* (Alber et al., *J. Bacteriol* 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity

| sProtein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| Rv1543 | NP_216059.1 | 15608681 | *Mycobacterium tuberculosis* |
| Rv3391 | NP_217908.1 | 15610527 | *Mycobacterium tuberculosis* |
| LUXC | AAT00788.1 | 46561111 | *Photobacterium phosphoreum* |
| MSED_0709 | YP_001190808.1 | 146303492 | *Metallosphaera sedula* |
| Tneu_0421 | ACB39369.1 | 170934108 | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| pduP | NP_460996 | 16765381 | *Salmonella typhimurium* LT2 |
| eutE | NP_416950 | 16130380 | *Escherichia coli* |
| pduP | CCC03595.1 | 337728491 | *Lactobacillus reuteri* |

Additionally, some acyl-ACP reductase enzymes such as the orf1594 gene product of *Synechococcus elongatus* PCC7942 also exhibit aldehyde-forming acyl-CoA reductase activity (Schirmer et al, Science, 329: 559-62 (2010)). The S. elongates PCC7942 acyl-ACP reductase is coexpressed with an aldehyde decarbonylase in an operon that appears to be conserved in a majority of cyanobacterial organisms. This enzyme, expressed in *E. coli* together with the aldehyde decarbonylase, conferred the ability to produce alkanes. The *P. marinus* AAR was also cloned into *E. coli* and, together with a decarbonylase, demonstrated production of alkanes (see, e.g., US Application 2011/0207203).

to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of

| Gene | GenBank ID | GI Number | Organism |
|---|---|---|---|
| orf1594 | YP_400611.1 | 81300403 | *Synechococcus elongatus* PCC7942 |
| PMT9312_0533 | YP_397030.1 | 78778918 | *Prochlorococcus marinus* MIT 9312 |
| syc0051_d | YP_170761.1 | 56750060 | *Synechococcus elongatus* PCC 6301 |
| Ava_2534 | YP_323044.1 | 75908748 | *Anabaena variabilis* ATCC 29413 |
| alr5284 | NP_489324.1 | 17232776 | *Nostoc* sp. PCC 7120 |
| Aazo_3370 | YP_003722151.1 | 298491974 | *Nostoc azollae* |
| Cyan7425_0399 | YP_002481152.1 | 220905841 | *Cyanothece* sp. PCC 7425 |
| N9414_21225 | ZP_01628095.1 | 119508943 | *Nodularia spumigena* CCY9414 |
| L8106_07064 | ZP_01619574.1 | 119485189 | *Lyngbya* sp. PCC 8106 |

*Salmonella typhimurium* and *E. coli* (Toth, *Appl. Environ. Microbiol.* 65:4973-4980 (1999)).

| Gene | GenBank ID | GI Number | Organism |
|---|---|---|---|
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |

Step B, FIG. 1: 4-hydroxy 2-oxovalerate aldolase

The condensation of pyruvate and acetaldehyde to 4-hydroxy-2-oxovalerate is catalyzed by 4-hydroxy-2-oxovalerate aldolase (EC 4.1.3.39). This enzyme participates in pathways for the degradation of phenols, cresols and catechols. The *E. coli* enzyme, encoded by mhpE, is highly specific for acetaldehyde as an acceptor but accepts the alternate substrates 2-ketobutyrate or phenylpyruvate as donors (Pollard et al., *Appl Environ Microbiol* 64:4093-4094 (1998)). Similar enzymes are encoded by the cmtG and todH genes of *Pseudomonas putida* (Lau et al., *Gene* 146:7-13 (1994); Eaton, *J. Bacteriol.* 178:1351-1362 (1996)). In *Pseudomonas* CF600, this enzyme is part of a bifunctional aldolase-dehydrogenase heterodimer encoded by dmpFG (Manjasetty et al., *Acta Crystallogr. D. Biol Crystallogr.* 57:582-585 (2001)). The dehydrogenase functionality interconverts acetaldehyde and acetyl-CoA, providing the advantage of reduced cellular concentrations of acetaldehyde, toxic to some cells. It has been shown recently that substrate channeling can occur within this enzyme in the presence of NAD and residues that could play an important role in channeling acetaldehyde into the DmpF site were also identified.

| Gene | GenBank ID | GI Number | Organism |
|---|---|---|---|
| mhpE | AAC73455.1 | 1786548 | *Escherichia coli* |
| cmtG | AAB62295.1 | 1263190 | *Pseudomonas putida* |
| todH | AAA61944.1 | 485740 | *Pseudomonas putida* |
| dmpG | CAA43227.1 | 45684 | *Pseudomonas* sp. CF600 |
| dmpF | CAA43226.1 | 45683 | *Pseudomonas* sp. CF600 |
| bphI | CAA54036.1 | 520924 | *Burkholderia xenovorans* LB400 |

Step C, FIG. 1: 4-hydroxy 2-oxovalerate Dehydratase

The dehydration of 4-hydroxy-2-oxovalerate to 2-oxopentenoate is catalyzed by 4-hydroxy-2-oxovalerate hydratase (EC 4.2.1.80). 4-Hydroxy-2-oxovalerate hydratase participates in aromatic degradation pathways and is typically co-transcribed with a gene encoding an enzyme with 4-hydroxy-2-oxovalerate aldolase activity. Exemplary gene products are encoded by mhpD of *E. coli* (Ferrandez et al., *J Bacteriol.* 179:2573-2581 (1997); Pollard et al., *Eur J Biochem.* 251:98-106 (1998)), todG and cmtF of *Pseudomonas putida* (Lau et al., *Gene* 146:7-13 (1994); Eaton, *J Bacteriol.* 178:1351-1362 (1996)), cnbE of *Comamonas* sp. CNB-1 (Ma et al., *Appl Environ Microbiol* 73:4477-4483 (2007)) and mhpD of *Burkholderia xenovorans* (Wang et al., *FEBS J* 272:966-974 (2005)). A closely related enzyme, 2-oxohepta-4-ene-1,7-dioate hydratase, participates in 4-hydroxyphenylacetic acid degradation, where it converts 2-oxo-hept-4-ene-1,7-dioate (OHED) to 2-oxo-4-hydroxy-hepta-1,7-dioate using magnesium as a cofactor (Burks et al., *J. Am. Chem. Soc.* 120: (1998)). OHED hydratase enzyme candidates have been identified and characterized in *E. coli* C (Roper et al., *Gene* 156:47-51 (1995); Izumi et al., *J Mol. Biol.* 370:899-911 (2007)) and *E. coli* W (Prieto et al., *J Bacteriol.* 178:111-120 (1996)). Sequence comparison reveals homologs in a wide range of bacteria, plants and animals. Enzymes with highly similar sequences are contained in *Klebsiella pneumonia* (91% identity, eval=2e-138) and *Salmonella enterica* (91% identity, eval=4e-138), among others.

| Gene | GenBank ID | GI Number | Organism |
|---|---|---|---|
| mhpD | AAC73453.2 | 87081722 | *Escherichia coli* |
| cmtF | AAB62293.1 | 1263188 | *Pseudomonas putida* |
| todG | AAA61942.1 | 485738 | *Pseudomonas putida* |
| cnbE | YP_001967714.1 | 190572008 | *Comamonas* sp. CNB-1 |
| mhpD | Q13VU0 | 123358582 | *Burkholderia xenovorans* |
| hpcG | CAA57202.1 | 556840 | *Escherichia coli* C |
| hpaH | CAA86044.1 | 757830 | *Escherichia coli* W |
| hpaH | ABR80130.1 | 150958100 | *Klebsiella pneumonia* |
| Sari_01896 | ABX21779.1 | 160865156 | *Salmonella enteric* |

2-(Hydroxymethyl)glutarate dehydratase is a [4Fe-4S]-containing enzyme that dehydrates 2-(hydroxymethyl)glutarate to 2-methylene-glutarate, studied for its role in nicontinate catabolism in *Eubacterium barkeri* (formerly *Clostridium barkeri*) (Alhapel et al., *Proc Natl Acad Sci* 103:12341-6 (2006)). Similar enzymes with high sequence homology are found in *Bacteroides capillosus*, *Anaerotruncus colihominis*, and *Natranaerobius thermophilius*. These enzymes are homologous to the alpha and beta subunits of [4Fe-4S]-containing bacterial serine dehydratases (e.g., *E. coli* enzymes encoded by tdcG, sdhB, and sdaA). An enzyme with similar functionality in *E. barkeri* is dimethylmaleate hydratase, a reversible $Fe^{2+}$-dependent and oxygen-sensitive enzyme in the aconitase family that hydrates dimethylmaeate to form (2R,3S)-2,3-dimethylmalate. This enzyme is encoded by dmdAB (Alhapel et al., *Proc Natl Acad Sci* USA 103:12341-6 (2006); Kollmann-Koch et al., *Hoppe Seylers. Z Physiol Chem.* 365:847-857 (1984)).

| Protein | GenBank ID | GI Number | Organism |
|---|---|---|---|
| hmd | ABC88407.1 | 86278275 | *Eubacterium barkeri* |
| BACCAP_02294 | ZP_02036683.1 | 154498305 | *Bacteroides capillosus* |
| ANACOL_02527 | ZP_02443222.1 | 167771169 | *Anaerotruncus colihominis* |
| NtherDRAFT_2368 | ZP_02852366.1 | 169192667 | *Natranaerobius thermophilus* |
| dmdA | ABC88408 | 86278276 | *Eubacterium barkeri* |
| dmdB | ABC88409 | 86278277 | *Eubacterium barkeri* |

Step D, FIG. 1: 2-oxopentenoate Reductase

The reduction of 2-oxopentenoate to 2-hydroxypentenoate is carried out by an alcohol dehydrogenase that reduces a ketone group. Several exemplary alcohol dehydrogenases can catalyze this transformation. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J Biochem.* 130:329-334 (1983)). Conversion of alpha-ketoadipate into alpha-hydroxyadipate is catalyzed by 2-ketoadipate reductase, an enzyme found in rat and in human placenta (Suda et al., *Arch. Biochem. Biophys.* 176:610-620 (1976); Suda et al., *Biochem. Biophys. Res. Commun.* 77:586-591 (1977)). An additional candidate oxidoreductase is the mitochondrial 3-hydroxybutyrate dehydrogenase (bdh) from the human heart which has been cloned and characterized (Marks et al., *J. Biol. Chem.* 267:15459-15463 (1992)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555 (1989)) convert acetone to isopropanol. Methyl ethyl ketone reductase catalyzes the reduction of MEK to 2-butanol. Exemplary MEK reductase enzymes can be found in *Rhodococcus ruber* (Kosjek et al., *Biotechnol Bioeng.* 86:55-62 (2004)) and *Pyrococcus furiosus* (van der et al., *Eur. J Biochem.* 268:3062-3068 (2001)).

| Gene | GenBank ID | GI Number | Organism |
| --- | --- | --- | --- |
| Mdh | AAC76268.1 | 1789632 | *Escherichia coli* |
| ldhA | NP_415898.1 | 16129341 | *Escherichia coli* |
| Ldh | YP_725182.1 | 113866693 | *Ralstonia eutropha* |
| Bdh | AAA58352.1 | 177198 | *Homo sapiens* |
| Adh | AAA23199.2 | 60592974 | *Clostridium beijerinckii* NRKL B593 |
| Adh | P14941.1 | 113443 | *Thermoanaerobacter brockii* HTD4 |
| Sadh | CAD36475 | 21615553 | *Rhodococcus ruber* |
| adhA | AAC25556 | 3288810 | *Pyrococcus furiosus* | substrates has not been described in the literature, a wealth of structural information is available for this enzyme and other researchers have successfully engineered the enzyme to alter activity, inhibition and localization (Weaver, *Acta Crystallogr D Biol Crystallogr,* 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., *J Bacteriol,* 183:461-467 (2001); Woods et al., 954:14-26 (1988); Guest et al., *J Gen Microbiol* 131:2971-2984 (1985)). Additional enzyme candidates are found in *Campylobacter jejuni* (Smith et al., *Int. J Biochem. Cell Biol* 31:961-975 (1999)), *Thermus thermophilus* (Mizobata et al., *Arch. Biochem. Biophys.* 355:49-55 (1998)) and *Rattus norvegicus* (Kobayashi et al., *J Biochem,* 89:1923-1931 (1981)). Similar enzymes with high sequence homology include fum1 from *Arabidopsis thaliana* and fumC from *Corynebacterium glutamicum*. The mmcBC fumarase from *Pelotomaculum thermopropionicum* is another class of fumarase with two subunits (Shimoyama et al., *FEMS Microbiol Lett,* 270:207-213 (2007)). Citramalate hydrolyase naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum, Morganella morganii, Citrobacter amalonaticus* where it is thought to participate in glutamate degradation (Kato et al., *Arch. Microbiol* 168:457-463 (1997)). The *M. jannaschii* protein sequence does not bear significant homology to genes in these organisms. Dimethylmaleate hydratase is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel et al., supra; Kollmann-Koch et al., *Hoppe Seylers. Z Physiol Chem.* 365:847-857 (1984)).

| Gene | GenBank ID | GI Number | Organism |
| --- | --- | --- | --- |
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| fumC | O69294 | 9789756 | *Campylobacter jejuni* |
| fumC | P84127 | 75427690 | *Thermus thermophilus* |
| fumH | P14408 | 120605 | *Rattus norvegicus* |
| fum1 | P93033 | 39931311 | *Arabidopsis thaliana* |
| fumC | Q8NRN8 | 39931596 | *Corynebacterium glutamicum* |
| mmcB | YP_001211906 | 147677691 | *Pelotomaculum thermopropionicum* |
| mmcC | YP_001211907 | 147677692 | *Pelotomaculum thermopropionicum* |
| leuD | Q58673.1 | 3122345 | *Methanocaldococcus jannaschii* |
| dmdA | ABC88408 | 86278276 | *Eubacterium barkeri* |
| dmdB | ABC88409.1 | 86278277 | *Eubacterium barkeri* |

Step E, FIG. 1: 2-hydroxypentenoate Dehydratase

Enzyme candidates for the dehydration of 2-hydroxypentenoate (FIG. 1, Step E) include fumarase (EC 4.2.1.2), citramalate hydratase (EC 4.2.1.34) and dimethylmaleate hydratase (EC 4.2.1.85). Fumarases naturally catalyze the reversible dehydration of malate to fumarate. Although the ability of fumarase to react with 2-hydroxypentenoate as Oleate hydratases catalyze the reversible hydration of non-activated alkenes to their corresponding alcohols. These enzymes represent additional suitable candidates as suggested in WO2011076691. Oleate hydratases from *Elizabethkingia meningoseptica* and *Streptococcus pyogenes* have been characterized (WO 2008/119735). Examples include the following proteins.

| Protein | GenBank ID | GI Number | Organism |
| --- | --- | --- | --- |
| OhyA | ACT54545.1 | 254031735 | *Elizabethkingia meningoseptica* |
| HMPREF0841_1446 | ZP_07461147.1 | 306827879 | *Streptococcus pyogenes* ATCC 10782 |
| P700755_13397 | ZP_01252267.1 | 91215295 | *Psychroflexus torquis* ATCC 700755 |
| RPB_2430 | YP_486046.1 | 86749550 | *Rhodopseudomonas palustris* |

Step F, FIG. 1: 2,4-pentadienoate Decarboxylase

The decarboxylation reactions of 2,4-pentadienoate to butadiene (step F of FIG. 1) are catalyzed by enoic acid decarboxylase enzymes. Exemplary enzymes are sorbic acid decarboxylase, aconitate decarboxylase, 4-oxalocrotonate decarboxylase and cinnamate decarboxylase. Sorbic acid decarboxylase converts sorbic acid to 1,3-pentadiene. Sorbic acid decarboxylation by *Aspergillus niger* requires three genes: padA1, ohbA1, and sdrA (Plumridge et al. *Fung. Genet. Bio,* 47:683-692 (2010). PadA1 is annotated as a phenylacrylic acid decarboxylase, ohbA1 is a putative 4-hydroxybenzoic acid decarboxylase, and sdrA is a sorbic acid decarboxylase regulator. Additional species have also been shown to decarboxylate sorbic acid including several fungal and yeast species (Kinderlerler and Hatton, *Food Addit Contam.,* 7(5):657-69 (1990); Casas et al., *Int J Food Micro.,* 94(1):93-96 (2004); Pinches and Apps, *Int. J Food Microbiol.* 116: 182-185 (2007)). For example, *Aspergillus oryzae* and *Neosartorya fischeri* have been shown to decarboxylate sorbic acid and have close homologs to padA1, ohbA1, and sdrA.

| Gene name | GenBankID | GI Number | Organism |
| --- | --- | --- | --- |
| padA1 | XP_001390532.1 | 145235767 | *Aspergillus niger* |
| ohbA1 | XP_001390534.1 | 145235771 | *Aspergillus niger* |
| sdrA | XP_001390533.1 | 145235769 | *Aspergillus niger* |
| padA1 | XP_001818651.1 | 169768362 | *Aspergillus oryzae* |
| ohbA1 | XP_001818650.1 | 169768360 | *Aspergillus oryzae* |
| sdrA | XP_001818649.1 | 169768358 | *Aspergillus oryzae* |
| padA1 | XP_001261423.1 | 119482790 | *Neosartorya fischeri* |
| ohbA1 | XP_001261424.1 | 119482792 | *Neosartorya fischeri* |
| sdrA | XP_001261422.1 | 119482788 | *Neosartorya fischeri* |

Aconitate decarboxylase (EC 4.1.1.6) catalyzes the final step in itaconate biosynthesis in a strain of *Candida* and also in the filamentous fungus *Aspergillus terreus* (Bonnarme et al. *J Bacteriol.* 177:3573-3578 (1995); Willke and Vorlop, *Appl Microbiol. Biotechnol* 56:289-295 (2001)). A cis-aconitate decarboxylase (CAD) (EC 4.1.16) has been purified and characterized from *Aspergillus terreus* (Dwiarti et al., *J Biosci. Bioeng.* 94(1): 29-33 (2002)). Recently, the gene has been cloned and functionally characterized (Kanamasa et al., *Appl. Microbiol Biotechnol* 80:223-229 (2008)) and (WO/2009/014437). Several close homologs of CAD are listed below (EP 2017344A1; WO 2009/014437 A1). The gene and protein sequence of CAD were reported previously (EP 2017344 A1; WO 2009/014437 A1), along with several close homologs listed in the table below.

| Gene name | GenBankID | GI Number | Organism |
| --- | --- | --- | --- |
| CAD | XP_001209273 | 115385453 | *Aspergillus terreus* |
|  | XP_001217495 | 115402837 | *Aspergillus terreus* |
|  | XP_001209946 | 115386810 | *Aspergillus terreus* |
|  | BAE66063 | 83775944 | *Aspergillus oryzae* |
|  | XP_001393934 | 145242722 | *Aspergillus niger* |
|  | XP_391316 | 46139251 | *Gibberella zeae* |

-continued

| Gene name | GenBankID | GI Number | Organism |
| --- | --- | --- | --- |
|  | XP_001389415 | 145230213 | *Aspergillus niger* |
|  | XP_001383451 | 126133853 | *Pichia stipitis* |
|  | YP_891060 | 118473159 | *Mycobacterium smegmatis* |
|  | NP_961187 | 41408351 | *Mycobacterium avium* subsp. *pratuberculosis* |
|  | YP_880968 | 118466464 | *Mycobacterium avium* |
|  | ZP_01648681 | 119882410 | *Salinispora arenicola* |

An additional class of decarboxylases has been characterized that catalyze the conversion of cinnamate (phenylacrylate) and substituted cinnamate derivatives to the corresponding styrene derivatives. These enzymes are common in a variety of organisms and specific genes encoding these enzymes that have been cloned and expressed in *E. coli* are: pad1 from *Saccharomyces cerevisae* (Clausen et al., *Gene* 142:107-112 (1994)), pdc from *Lactobacillus plantarum* (Barthelmebs et al., *Appl Environ Microbiol.* 67:1063-1069 (2001); Qi et al., *Metab Eng* 9:268-276 (2007); Rodriguez et al., *J. Agric. Food Chem.* 56:3068-3072 (2008)), pofK (pad) from *Klebsiella oxytoca* (Uchiyama et al., *Biosci. Biotechnol. Biochem.* 72:116-123 (2008); Hashidoko et al., *Biosci. Biotech. Biochem.* 58:217-218 (1994)), *Pediococcus pentosaceus* (Barthelmebs et al., *Appl Environ Microbiol.* 67:1063-1069 (2001)), and padC from *Bacillus subtilis* and *Bacillus pumilus* (Shingler et al., *J. Bacteriol.,* 174:711-724 (1992)). A ferulic acid decarboxylase from *Pseudomonas fluorescens* also has been purified and characterized (Huang et al., *J. Bacteriol.* 176:5912-5918 (1994)). Importantly, this class of enzymes have been shown to be stable and do not require either exogenous or internally bound co-factors, thus making these enzymes ideally suitable for biotransformations (Sariaslani, *Annu. Rev. Microbiol.* 61:51-69 (2007)).

| Protein | GenBank ID | GI Number | Organism |
| --- | --- | --- | --- |
| pad1 | AAB64980.1 | 1165293 | *Saccharomyces cerevisae* |
| ohbA1 | BAG32379.1 | 188496963 | *Saccharomyces cerevisiae* |
| pdc | AAC45282.1 | 1762616 | *Lactobacillus plantarum* |
| pad | BAF65031.1 | 149941608 | *Klebsiella oxytoca* |
| padC | NP_391320.1 | 16080493 | *Bacillus subtilis* |
| pad | YP_804027.1 | 116492292 | *Pedicoccus pentosaceus* |
| pad | CAC18719.1 | 11691810 | *Bacillus pumilus* |

4-Oxalocronate decarboxylase catalyzes the decarboxylation of 4-oxalocrotonate to 2-oxopentanoate. This enzyme has been isolated from numerous organisms and characterized. The decarboxylase typically functions in a complex with vinylpyruvate hydratase. Genes encoding this enzyme include dmpH and dmpE in *Pseudomonas* sp. (strain 600) (Shingler et al., *J. Bacteriol.,* 174:711-724 (1992)), xylII and xylIII from *Pseudomonas putida* (Kato et al., *Arch. Microbiol* 168:457-463 (1997); Stanley et al., *Biochemistry* 39:3514 (2000); Lian et al., *J. Am. Chem. Soc.* 116:10403-10411 (1994)) and Reut_B5691 and Reut_B5692 from *Ralstonia eutropha* JMP134 (Hughes et al., *J Bacteriol,* 158:

79-83 (1984)). The genes encoding the enzyme from *Pseudomonas* sp. (strain 600) have been cloned and expressed in *E. coli* (Shingler et al., *J. Bacteriol.* 174:711-724 (1992)). The 4-oxalocrotonate decarboxylase encoded by xyII in *Pseudomonas putida* functions in a complex with vinylpyruvate hydratase. A recombinant form of this enzyme devoid of the hydratase activity and retaining wild type decarboxylase activity has been characterized (Stanley et al., *Biochem.* 39:718-26 (2000)). A similar enzyme is found in *Ralstonia pickettii* (formerly *Pseudomonas pickettii*) (Kukor et al., *J. Bacteriol.* 173:4587-94 (1991)).

| Gene | GenBank | GI Number | Organism |
| --- | --- | --- | --- |
| dmpH | CAA43228.1 | 45685 | *Pseudomonas* sp. CF600 |
| dmpE | CAA43225.1 | 45682 | *Pseudomonas* sp. CF600 |
| xylII | YP_709328.1 | 111116444 | *Pseudomonas putida* |
| xylIII | YP_709353.1 | 111116469 | *Pseudomonas putida* |
| Reut_B5691 | YP_299880.1 | 73539513 | *Ralstonia eutropha* JMP134 |
| Reut_B5692 | YP_299881.1 | 73539514 | *Ralstonia eutropha* JMP134 |
| xylI | P49155.1 | 1351446 | *Pseudomonas putida* |
| tbuI | YP_002983475.1 | 241665116 | *Ralstonia pickettii* |
| nbaG | BAC65309.1 | 28971626 | *Pseudomonas fluorescens* KU-7 |

Numerous characterized enzymes decarboxylate amino acids and similar compounds, including aspartate decarboxylase, lysine decarboxylase and ornithine decarboxylase. Aspartate decarboxylase (EC 4.1.1.11) decarboxylates aspartate to form beta-alanine. This enzyme participates in pantothenate biosynthesis and is encoded by gene panD in *Escherichia coli* (Dusch et al., *Appl. Environ. Microbiol* 65:1530-1539 (1999); Ramjee et al., *Biochem. J* 323 (Pt 3):661-669 (1997); Merkel et al., *FEMS Microbiol Lett.* 143:247-252 (1996); Schmitzberger et al., *EMBO J* 22:6193-6204 (2003)). The enzymes from *Mycobacterium tuberculosis* (Chopra et al., *Protein Expr. Purif.* 25:533-540 (2002)) and *Corynebacterium glutanicum* (Dusch et al., *Appl. Environ. Microbiol* 65:1530-1539 (1999)) have been expressed and characterized in *E. coli*.

| Protein | GenBank ID | GI Number | Organism |
| --- | --- | --- | --- |
| panD | P0A790 | 67470411 | *Escherichia coli* K12 |
| panD | Q9X4N0 | 18203593 | *Corynebacterium glutanicum* |
| panD | P65660.1 | 54041701 | *Mycobacterium tuberculosis* |

Lysine decarboxylase (EC 4.1.1.18) catalyzes the decarboxylation of lysine to cadaverine. Two isozymes of this enzyme are encoded in the *E. coli* genome by genes cadA and ldcC. CadA is involved in acid resistance and is subject to positive regulation by the cadC gene product (Lemonnier et al., *Microbiology* 144 (Pt 3):751-760 (1998)). CadC accepts hydroxylysine and S-aminoethylcysteine as alternate substrates, and 2-aminopimelate and 6-aminocaproate act as competitive inhibitors to this enzyme (Sabo et al., *Biochemistry* 13:662-670 (1974)). The constitutively expressed ldc gene product is less active than CadA (Lemonnier and Lane, *Microbiology* 144 (Pt 3):751-760 (1998)). A lysine decarboxylase analogous to CadA was recently identified in *Vibrio parahaemolyticus* (Tanaka et al., *J Appl Microbiol* 104:1283-1293 (2008)). The lysine decarboxylase from *Selenomonas ruminantium*, encoded by ldc, bears sequence similarity to eukaryotic ornithine decarboxylases, and accepts both L-lysine and L-ornithine as substrates (Takatsuka et al., *Biosci. Biotechnol Biochem.* 63:1843-1846 (1999)). Active site residues were identified and engineered to alter the substrate specificity of the enzyme (Takatsuka et al., *J. Bacteriol.* 182:6732-6741 (2000)). Several ornithine decarboxylase enzymes (EC 4.1.1.17) also exhibit activity on lysine and other similar compounds. Such enzymes are found in *Nicotiana glutinosa* (Lee et al., *Biochem. J* 360:657-665 (2001)), *Lactobacillus* sp. 30a (Guirard et al., *J Biol. Chem.* 255:5960-5964 (1980)) and *Vibrio vulnificus* (Lee et al., *J Biol. Chem.* 282:27115-27125 (2007)). The enzymes from *Lactobacillus* sp. 30a (Momany et al., *J Mol. Biol.* 252:643-655 (1995)) and *V. vulnificus* have been crystallized. The *V. vulnificus* enzyme efficiently catalyzes lysine decarboxylation and the residues involved in substrate specificity have been elucidated (Lee et al., *J Biol. Chem.* 282:27115-27125 (2007)). A similar enzyme has been characterized in *Trichomonas vaginalis*. (Yarlett et al., *Biochem. J* 293 (Pt 2):487-493 (1993)).

| Protein | GenBank ID | GI Number | Organism |
| --- | --- | --- | --- |
| cadA | AAA23536.1 | 145458 | *Escherichia coli* |
| ldcC | AAC73297.1 | 1786384 | *Escherichia coli* |
| Ldc | O50657.1 | 13124043 | *Selenomonas ruminantium* |
| cadA | AB124819.1 | 44886078 | *Vibrio parahaemolyticus* |
| AF323910.1:1 ... 1299 | AAG45222.1 | 12007488 | *Nicotiana glutinosa* |
| odc1 | P43099.2 | 1169251 | *Lactobacillus* sp. 30a |
| VV2_1235 | NP_763142.1 | 27367615 | *Vibrio vulnificus* |

Steps G and J. FIG. 1: 2-oxopentenoate Ligase and 2-hydroxypentenoate Ligase

ADP and AMP-forming CoA ligases (6.2.1) with broad substrate specificities have been described in the literature. The ADP-forming acetyl-CoA synthetase (ACD, EC 6.2.1.13) from *Archaeoglobus fulgidus*, encoded by AF1211, was shown to operate on a variety of linear and branched-chain substrates including isobutyrate, isopentanoate, and fumarate (Musfeldt et al., *J. Bacteriol.* 184:636-644 (2002)). A second reversible ACD in *Archaeoglobus fulgidus*, encoded by AF1983, was also indicated to have a broad substrate range (Musfeldt et al., supra). The enzyme from *Haloarcula marismortui*, annotated as a succinyl-CoA synthetase, accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, *Arch. Microbiol* 182:277-287 (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, *Arch. Microbiol* 182:277-287 (2004); Musfeldt and Schonheit, *J. Bacteriol.* 184:636-644 (2002)). An additional enzyme is encoded by sucCD in *E. coli*, which naturally catalyzes the formation of succinyl-CoA from succinate with the concomitant consumption of one ATP, a reaction which is reversible in vivo (Buck et al., *Biochemistry* 24:6245-6252 (1985)). The acyl CoA ligase from *Pseudomonas putida* has been indicated to work on several aliphatic substrates including acetic, propionic, butyric, valeric, hexanoic, heptanoic, and octanoic acids and on aromatic compounds such as phenylacetic and phenoxyacetic acids (Femandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)). Recently, a CoA dependent acetyl-CoA ligase was also identified in *Propionibacterium acidipropionici* ATCC 4875 (Parizzi et al., *BMC Genomics.* 2012; 13: 562). This enzyme is distinct from the AMP-dependent acetyl-CoA synthetase and is instead related to the ADP-forming succinyl-CoA synthetase complex (SCSC). Genes related to the SCSC (α and β subunits) complex were also found in *Propionibacterium acnes* KPA171202 and *Microlunatus phophovorus* NM-1.

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol* 102:327-336 (1977)), *Ralstonia eutropha* (Priefert et al., *J. Bacteriol* 174:6590-6599 (1992)), *Methanothermobacter thermautotrophicus* (Ingram-Smith et al., *Archaea.* 2:95-107 (2007)), *Salmonella enterica* (Gulick et al., *Biochemistry* 42:2866-2873 (2003)) and *Saccharomyces cerevisiae* (Jogl et al., *Biochemistry*, 43:1425-1431 (2004)).

Methylmalonyl-CoA synthetase from *Rhodopseudomonas palustris* (MatB) converts methylmalonate and malonate to methylmalonyl-CoA and malonyl-CoA, respectively. Structure-based mutagenesis of this enzyme improved CoA synthetase activity with the alternate substrates ethylmalonate and butylmalonate (Crosby et al, AEM, in press (2012)).

| Gene | GenBank Accession No. | GI No. | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| Scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |
| matB | AAC83455.1 | 3982573 | *Rhizobium leguminosarum* |
| Acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| LSC1 | NP_014785 | 6324716 | *Saccharomyces cerevisiae* |
| LSC2 | NP_011760 | 6321683 | *Saccharomyces cerevisiae* |
| bioW | NP_390902.2 | 50812281 | *Bacillus subtilis* |
| bioW | CAA10043.1 | 3850837 | *Pseudomonas mendocina* |
| bioW | P22822.1 | 115012 | *Bacillus sphaericus* |
| PhI | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| PACID_02150 | YP_006979420.1 | 410864809 | *Propionibacterium acidipropionici* ATCC 4875 |
| PPA1754 | AAT83483.1 | 50840816 | *Propionibacterium acnes* KPA171202 |
| PPA1755 | AAT83484.1 | 50840817 | *Propionibacterium acnes* KPA171202 |
| Subunit alpha | YP_004571669.1 | 336116902 | *Microlunatus phoshovorus* NM-1 |
| Subunit beta | YP_004571668.1 | 336116901 | *Microlunatus phoshovorus* NM-1 |
| AACS | NP_084486.1 | 21313520 | *Mus musculus* |
| AACS | NP_076417.2 | 31982927 | *Homo sapiens* |

4HB-CoA synthetase catalyzes the ATP-dependent conversion of 4-hydroxybutyrate to 4-hydroxybutyryl-CoA. AMP-forming 4-HB-CoA synthetase enzymes are found in organisms that assimilate carbon via the dicarboxylate/hydroxybutyrate cycle or the 3-hydroxypropionate/4-hydroxybutyrate cycle. Enzymes with this activity have been characterized in *Thermoproteus neutrophilus* and *Metallosphaera sedula* (Ramos-Vera et al, *J. Bacteriol* 192:5329-40(2010); Berg et al, *Science* 318:1782-6 (2007)). Others can be inferred by sequence homology.

| Protein | GenBank ID | GI Number | Organism |
|---|---|---|---|
| Tneu_0420 | ACB39368.1 | 170934107 | *Thermoproteus neutrophilus* |
| Caur_0002 | YP_001633649.1 | 163845605 | *Chloroflexus aurantiacus* J-10-fl |
| Cagg_3790 | YP_002465062 | 219850629 | *Chloroflexus aggregans* DSM 9485 |
| Acs | YP_003431745 | 288817398 | *Hydrogenobacter thermophilus* TK-6 |
| PisI_0250 | YP_929773.1 | 119871766 | *Pyrobaculum islandicum* DSM 4184 |
| Msed_1422 | ABP95580.1 | 145702438 | *Metallosphaera sedula* |

Step I, FIG. 1: 2-oxopentenoyl-CoA Reductase 77

The reduction of 2-oxopentenoyl CoA to 2-hydroxypentanoyl-CoA can be accomplished by 3-oxoacyl-CoA reductase enzymes (EC 1.1.1.35) that typically convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Given the proximity in *E. coli* of paaH to other genes in the phenylacetate degradation operon (Nogales et al., *Microbiology*, 153:357-365 (2007)) and the fact that paaH mutants cannot grow on phenylacetate (Ismail et al., *Eur. J Biochem.* 270: 3047-3054 (2003)), it is expected that the *E. coli* paaH gene also encodes a 3-hydroxyacyl-CoA dehydrogenase. Additional 3-oxoacyl-CoA enzymes include the gene products of phaC in *Pseudomonas putida* (Olivera et al., *Proc. Natl.*

Acad. Sci U.S.A 95:6419-6424 (1998)) and paaC in Pseudomonas fluorescens (Di et al., Arch. Microbiol 188: 117-125 (2007)). These enzymes catalyze the reversible oxidation of 3-hydroxyadipyl-CoA to 3-oxoadipyl-CoA during the catabolism of phenylacetate or styrene.

Acetoacetyl-CoA reductase participates in the acetyl-CoA fermentation pathway to butyrate in several species of Clostridia and has been studied in detail (Jones et al., Microbiol Rev. 50:484-524 (1986)). The enzyme from Clostridium acetobutylicum, encoded by hbd, has been cloned and functionally expressed in E. coli (Youngleson et al., J. Bacteriol. 171:6800-6807 (1989)). Yet other genes demonstrated to reduce acetoacetyl-CoA to 3-hydroxybutyryl-CoA are phbB from Zoogloea ramigera (Ploux et al., Eur. J Biochem. 174:177-182 (1988)) and phaB from Rhodobacter sphaeroides (Alber et al., Mol. Microbiol 61:297-309 (2006)). The former gene is NADPH-dependent, its nucleotide sequence has been determined (Peoples et al., Mol. Microbiol 3:349-357 (1989)) and the gene has been expressed in E. coli. Substrate specificity studies on the gene led to the conclusion that it could accept 3-oxopropionyl-CoA as a substrate besides acetoacetyl-CoA (Ploux et al., Eur. J Biochem. 174:177-182 (1988)). Additional genes include phaB in Paracoccus denitrificans, Hbd1 (C-terminal domain) and Hbd2 (N-terminal domain) in Clostridium kluyveri (Hillmer and Gottschalk, Biochim. Biophys. Acta 3334:12-23 (1974)) and HSD17B10 in Bos taurus (Wakil et al., J Biol. Chem. 207:631-638 (1954)). The enzyme from Paracoccus denitrificans has been functionally expressed and characterized in E. coli (Yabutani et al., FEMS Microbiol Lett. 133:85-90 (1995)). A number of similar enzymes have been found in other species of Clostridia and in Metallosphaera sedula (Berg et al., Science. 318:1782-1786 (2007)). The enzyme from Candida tropicalis is a component of the peroxisomal fatty acid beta-oxidation multifunctional enzyme type 2 (MFE-2). The dehydrogenase B domain of this protein is catalytically active on acetoacetyl-CoA. The domain has been functionally expressed in E. coli, a crystal structure is available, and the catalytic mechanism is well-understood (Ylianttila et al., Biochem Biophys Res Commun 324:25-30 (2004); Ylianttila et al., J Mol Biol 358:1286-1295 (2006)). 3-Hydroxyacyl-CoA dehydrogenases that accept longer acyl-CoA substrates (eg. EC 1.1.1.35) are typically involved in beta-oxidation. An example is HSD17B10 in Bos taurus (WAKIL et al., J Biol. Chem. 207:631-638 (1954)). phbB from Cupriavidus necatar codes for a 3-hydroxyvaleryl-CoA dehydrogenase activity.

| Protein | GENBANK ID | GI NUMBER | ORGANISM |
|---|---|---|---|
| fadB | P21177.2 | 119811 | Escherichia coli |
| fadJ | P77399.1 | 3334437 | Escherichia coli |
| paaH | NP_415913.1 | 16129356 | Escherichia coli |
| Hbd2 | EDK34807.1 | 146348271 | Clostridium kluyveri |
| Hbd1 | EDK32512.1 | 146345976 | Clostridium kluyveri |
| phaC | NP_745425.1 | 26990000 | Pseudomonas putida |
| paaC | ABF82235.1 | 106636095 | Pseudomonas fluorescens |
| HSD17B10 | O02691.3 | 3183024 | Bos Taurus |
| phbB | P23238.1 | 130017 | Zoogloea ramigera |
| phaB | YP_353825.1 | 77464321 | Rhodobacter sphaeroides |
| phaB | BAA08358 | 675524 | Paracoccus denitrificans |
| phbB | AEI82198.1 | 338171145 | Cupriavidus necator |
| Hbd | NP_349314.1 | 15895965 | Clostridium acetobutylicum |
| Hbd | AAM14586.1 | 20162442 | Clostridium beijerinckii |
| Msed_1423 | YP_001191505 | 146304189 | Metallosphaera sedula |
| Msed_0399 | YP_001190500 | 146303184 | Metallosphaera sedula |
| Msed_0389 | YP_001190490 | 146303174 | Metallosphaera sedula |
| Msed_1993 | YP_001192057 | 146304741 | Metallosphaera sedula |
| Fox2 | Q02207 | 399508 | Candida tropicalis |
| HSD17B10 | O02691.3 | 3183024 | Bos Taurus |

Other exemplary enzymes that can carry this reaction are 2-hydroxyacid dehydrogenases. Such an enzyme, characterized from the halophilic archaeon Haloferax mediterranei catalyses a reversible stereospecific reduction of 2-ketocarboxylic acids into the corresponding D-2-hydroxycarboxylic acids. The enzyme is strictly NAD-dependent and prefers substrates with a main chain of 3-4 carbons (pyruvate and 2-oxobutanoate). Activity with 4-methyl-2-oxopentanoate is 10-fold lower. Two such enzymes from E. coli are encoded by malate dehydrogenase (mdh) and lactate dehydrogenase (ldhA). In addition, lactate dehydrogenase from Ralstonia eutropha has been shown to demonstrate high activities on 2-ketoacids of various chain lengths includings lactate, 2-oxobutyrate, 2-oxopentanoate and 2-oxoglutarate (Steinbuchel et al., Eur. J Biochem. 130:329-334 (1983)). Conversion of alpha-ketoadipate into alpha-hydroxyadipate can be catalyzed by 2-ketoadipate reductase, an enzyme reported to be found in rat and in human placenta (Suda et al., Arch. Biochem. Biophys. 176:610-620 (1976); Suda et al., Biochem. Biophys. Res. Commun. 77:586-591 (1977)). An additional oxidoreductase is the mitochondrial 3-hydroxybutyrate dehydrogenase (bdh) from the human heart which has been cloned and characterized (Marks et al., J. Biol. Chem. 267:15459-15463 (1992)). Alcohol dehydrogenase enzymes of C. beijerinckii (Ismaiel et al., J. Bacteriol. 175:5097-5105 (1993)) and T. brockii (Lamed et al., Biochem. J. 195:183-190 (1981); Peretz et al., Biochemistry. 28:6549-6555 (1989)) convert acetone to isopropanol. Methyl ethyl ketone reductase catalyzes the reduction of MEK to 2-butanol. Exemplary MEK reductase enzymes can be found in Rhodococcus ruber (Kosjek et al., Biotechnol Bioeng. 86:55-62 (2004)) and Pyrococcus furiosus (van der et al., Eur. J. Biochem. 268:3062-3068 (2001)).

| Gene | GenBank Accession No. | GI No. | Organism |
|---|---|---|---|
| mdh | AAC76268.1 | 1789632 | Escherichia coli |
| ldhA | NP_415898.1 | 16129341 | Escherichia coli |
| ldh | YP_725182.1 | 113866693 | Ralstonia eutropha |
| bdh | AAA58352.1 | 177198 | Homo sapiens |
| adh | AAA23199.2 | 60592974 | Clostridium beijerinckii NRRL B593 |
| adh | P14941.1 | 113443 | Thermoanaerobacter brockii HTD4 |
| sadh | CAD36475 | 21615553 | Rhodococcus ruber |
| adhA | AAC25556 | 3288810 | Pyrococcus furiosus |
| BM92_14160 | AHZ23715.1 | 631806019 | Haloferax mediterranei ATCC 33500 |

Step M, FIG. 1: 2,4-pentadienoyl-CoA Hydrolase

CoA hydrolysis of 2,4-pentadienoyl CoA can be catalyzed by CoA hydrolases or thioesterases in the EC class 3.1.2. Several CoA hydrolases with broad substrate ranges are suitable enzymes for hydrolyzing these intermediates. For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280: 38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, yciA, and ybdB (Kuznetsova, et al., *FEMS Microbiol Rev,* 2005, 29(2):263-279; Song et al., *J Biol Chem,* 2006, 281(16): 11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)) The acetyl-CoA hydrolase, ACH1, from *S. cerevisiae* represents another candidate hydrolase (Buu et al., *J. Biol. Chem.* 278:17203-17209 (2003)).

| Gene name | GenBank Accession # | GI# | Organism |
| --- | --- | --- | --- |
| acot12 | NP_570103.1 | 18543355 | Rattus norvegicus |
| tesB | NP_414986 | 16128437 | Escherichia coli |
| acot8 | CAA15502 | 3191970 | Homo sapiens |
| acot8 | NP_570112 | 51036669 | Rattus norvegicus |
| tesA | NP_415027 | 16128478 | Escherichia coli |
| ybgC | NP_415264 | 16128711 | Escherichia coli |
| paaI | NP_415914 | 16129357 | Escherichia coli |
| ybdB | NP_415129 | 16128580 | Escherichia coli |
| ACH1 | NP_009538 | 6319456 | Saccharomyces cerevisiae |
| yciA | NP_415769.1 | 16129214 | Escherichia coli |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA: acetyl-CoA transferases may also serve as candidates for this reaction step but would require certain mutations to change their function.

| Gene name | GenBank Accession # | GI# | Organism |
| --- | --- | --- | --- |
| gctA | CAA57199 | 559392 | Acidaminococcus fermentans |
| gctB | CAA57200 | 559393 | Acidaminococcus fermentans |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC 2292 of *Bacillus cereus*.

| Gene name | GenBank Accession # | GI# | Organism |
| --- | --- | --- | --- |
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

Methylmalonyl-CoA is converted to methylmalonate by methylmalonyl-CoA hydrolase (EC 3.1.2.7). This enzyme, isolated from *Rattus norvegicus* liver, is also active on malonyl-CoA and propionyl-CoA as alternative substrates (Kovachy et al., *J. Biol. Chem.,* 258: 11415-11421 (1983)).

Steps H, K and N, FIG. 1: 2-oxopentenoate:acetyl CoA Transferase, 2-hydroxypentenoate:acetyl-CoA CoA Transferase, 2,4-pentadienoyl-CoA:acetyl CoA CoA Transferase Several transformations require a CoA transferase to activate carboxylic acids to their corresponding acyl-CoA derivatives. CoA transferase enzymes have been described in the open literature and represent suitable candidates for these steps. These are described below.

The gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *J Bacteriol.* 178:871-880 (1996)). Similar CoA transferase activities are also present in *Trichomonas vaginalis, Trypanosoma brucei, Clostridium aminobutyricum* and *Porphyromonas gingivalis* (Riviere et al., *J. Biol. Chem.* 279:45337-45346 (2004); van Grinsven et al., *J. Biol. Chem.* 283:1411-1418 (2008)).

| Protein | GenBank ID | GI Number | Organism |
| --- | --- | --- | --- |
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| cat2 | CAB60036.1 | 6249316 | Clostridium aminobutyricum |
| cat2 | NP_906037.1 | 34541558 | Porphyromonas gingivalis W83 |

A fatty acyl-CoA transferase that utilizes acetyl-CoA as the CoA donor is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., 33:902-908 (1968)). This enzyme has a broad substrate range on substrates of chain length C3-C6 (Sramek et al., *Arch Biochem Biophys* 171:14-26 (1975)) and has been shown to transfer the CoA moiety to acetate from a variety of branched and linear 3-oxo and acyl-CoA substrates, including isobutyrate (Matthies et al., *Appl Environ. Microbiol* 58:1435-1439 (1992)), valerate (Vanderwinkel et al., *Biochem. Biophys. Res. Commun.* 33:902-908 (1968)) and butanoate (Vanderwinkel et al., *Biochem. Biophys. Res. Commun.* 33:902-908 (1968)). This enzyme is induced at the transcriptional level by acetoacetate, so modification of regulatory control may be necessary for engineering this enzyme into a pathway (Pauli et al., *Eur. J Biochem.* 29:553-562 (1972)). Similar enzymes exist in *Corynebacterium glutamicum* ATCC 13032 (Duncan et al., *Appl Environ Microbiol,* 68:5186-

5190 (2002)), *Clostridium acetobutylicum* (Cary et al., *Appl Environ Microbiol* 56:1576-1583 (1990); Wiesenbom et al., *Appl Environ Microbiol* 55:323-329 (1989)), and *Clostridium saccharoperbutylacetonicum* (Kosaka et al., *Biosci. Biotechnol Biochem.* 71:58-68 (2007)).

| Gene | GI # | Accession No. | Organism |
|---|---|---|---|
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

Step L, FIG. 1: 2-hydroxypentenoyl-CoA Dehydratase

The dehydration of 2-hydroxypentenoyl-CoA can be catalyzed by a special class of oxygen-sensitive enzymes that dehydrate 2-hydroxyacyl-CoA derivatives by a radical-mechanism (Buckel and Golding, *Annu. Rev. Microbiol.* 60:27-49 (2006); Buckel et al., *Curr. Opin. Chem. Biol.* 8:462-467 (2004); Buckel et al., *Biol. Chem.* 386:951-959 (2005); Kim et al., *FEBS J.* 272:550-561 (2005); Kim et al., *FEMS Microbiol. Rev.* 28:455-468 (2004); Zhang et al., *Microbiology* 145 (Pt 9):2323-2334 (1999)). One example of such an enzyme is the lactyl-CoA dehydratase from *Clostridium propionicum*, which catalyzes the dehydration of lactoyl-CoA to form acryloyl-CoA (Kuchta and Abeles, *J. Biol. Chem.* 260:13181-13189 (1985); Hofmeister and Buckel, *Eur. J. Biochem.* 206:547-552 (1992)). An additional example is 2-hydroxyglutaryl-CoA dehydratase encoded by hgdABC from *Acidaminococcus fermentans* (Mueller and Buckel, *Eur. J Biochem.* 230:698-704 (1995); Schweiger et al., *Eur. J Biochem.* 169:441-448 (1987)). Purification of the dehydratase from *A. fermentans* yielded two components, A and D. Component A (HgdC) acts as an activator or initiator of dehydration. Component D is the actual dehydratase and is encoded by HgdAB. Variations of this enzyme have been found in *Clostridum symbiosum* and *Fusobacterium nucleatum*. Component A, the activator, from *A. fermentans* is active with the actual dehydratse (component D) from *C. symbiosum* and is reported to have a specific activity of 60 per second, as compared to 10 per second with the component D from *A. fermentans*. Yet another example is the 2-hydroxyisocaproyl-CoA dehydratase from *Clostridium difficile* catalyzed by hadBC and activated by hadI (Darley et al., *FEBS J.* 272:550-61 (2005)). The sequence of the complete *C. propionicium* lactoyl-CoA dehydratase is not yet listed in publicly available databases. However, the sequence of the beta-subunit corresponds to the GenBank accession number AJ276553 (Selmer et al, *Eur J Biochem*, 269:372-80 (2002)). The dehydratase from *Clostridium sporogens* that dehydrates phenyllactyl-CoA to cinnamoyl-CoA is also a potential candidate for this step. This enzyme is composed of three subunits, one of which is a CoA transferase. The first step comprises of a CoA transfer from cinnamoyl-CoA to phenyllactate leading to the formation of phenyllactyl-CoA and cinnamate. The product cinnamate is released. The dehydratase then converts phenyllactyl-CoA into cinnamoyl-CoA. FldA is the CoA transferase and FldBC are related to the alpha and beta subunits of the dehydratase, component D, from *A. fermentans*.

| Gene | GenBank Accession No. | GI No. | Organism |
|---|---|---|---|
| hgdA | P11569 | 296439332 | *Acidaminococcus fermentans* |
| hgdB | P11570 | 296439333 | *Acidaminococcus fermentans* |
| hgdC | P11568 | 2506909 | *Acidaminococcus fermentans* |
| hgdA | AAD31676.1 | 4883832 | *Clostridum symbiosum* |
| hgdB | AAD31677.1 | 4883833 | *Clostridum symbiosum* |
| hgdC | AAD31675.1 | 4883831 | *Clostridum symbiosum* |
| hgdA | EDK88042.1 | 148322792 | *Fusobacterium nucleatum* |
| hgdB | EDK88043.1 | 148322793 | *Fusobacterium nucleatum* |
| hgdC | EDK88041.1 | 148322791 | *Fusobacterium nucleatum* |
| FldB | Q93AL9.1 | 75406928 | *Clostridium sporogens* |
| FldC | Q93AL8.1 | 75406927 | *Clostridium sporogens* |
| hadB | YP_001086863 | 126697966 | *Clostridium difficile* |
| hadC | YP_001086864 | 126697967 | *Clostridium difficile* |
| hadI | YP_001086862 | 126697965 | *Clostridium difficile* |
| lcdB | AJ276553 | 7242547 | *Clostridium propionicum* |

Another dehydratase that can potentially conduct such a biotransformation is the enoyl-CoA hydratase (4.2.1.17) of *Pseudomonas putida*, encoded by ech that catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., *Eur. J Biochem.* 270:3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J Biochem.* 270:3047-3054 (2003); Park and Lee, *Appl. Biochem. Biotechnol* 113-116:335-346 (2004); Park and Yup, *Biotechnol Bioeng* 86:681-686 (2004)).

| Gene | GenBank Accession No. | GI No. | Organism |
|---|---|---|---|
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | NP_745427.1 | 26990002 | *Pseudomonas putida* KT2440 |
| phaB | NP_745426.1 | 26990001 | *Pseudomonas putida* KT2440 |
| paaA | ABF82233.1 | 106636093 | *Pseudomonas fluorescens* |
| paaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Yang et al., *Biochemistry* 30:6788-6795 (1991); Yang, *J Bacteriol.* 173:7405-7406 (1991); Nakahigashi et al., *Nucleic Acids*

Res. 18:4937 (1990)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Protein | GenBank ID | GI Number | Organism |
|---|---|---|---|
| fadA | YP_026272.1 | 49176430 | Escherichia coli |
| fadB | NP_418288.1 | 16131692 | Escherichia coli |
| fadI | NP_416844.1 | 16130275 | Escherichia coli |
| fadJ | NP_416843.1 | 16130274 | Escherichia coli |
| fadR | NP_415705.1 | 16129150 | Escherichia coli |

Example II

Production of Butadiene or 2,4-Pentadienoate Via 3-Oxoglutaryl-CoA

Pathways to butadiene or 2,4-pentadienoate production as depicted in FIG. 2 starts with combining acetyl-CoA and malonyl-CoA via a thiolase (Step B). Acetyl-CoA can be carboxylated to form malonyl-CoA via an acetyl-CoA carboxylase (Step A). The product of the thiolase transformation in Step B is 3-oxoglutaryl-CoA. This can be reduced to form 3-hydroxyglutaryl-CoA(Step C). The latter can then be reduced to form 3-hydroxy 5-oxopentanoate and then 3,5-dihydroxypentanoate via an aldehyde forming 3-hydroxyglutaryl-CoA reductase and 3-hydroxy-5-oxopentanoate reductase respectively (Steps D and E). Alternatively, 3-hydroxyglutaryl-CoA can be reduced by an alcohol-forming 3-hydroxyglutaryl-CoA reductase to form 3,5-dihydroxypentanoate (Step F). Steps G and H in the pathway are two dehydration steps that dehydrate 3,5-dihydroxypentanoate to 5-hydroxy pent-2-enoate and to pent-2,4-dienoate respectively. This is eventually decarboxylated to form butadiene (Step I). 3-Hydroxy-5-oxopentanoate can also be formed from 3-oxoglutaryl-CoA via phosphate-3-hydroxyglutaryl transferase and 3-hydroxy-5-oxopentanoate synthase as shown in Steps R and S.

Alternatively, 3,5-dihydroxypentanoate can be activated to form 3,5-dihydroxypentanoyl-CoA (Step J or K), which is then dehydrated to form 5-hydroxypent-2-enoyl-CoA (Step L). Further dehydration of the latter leads to the formation of penta-2,4-dienoyl-CoA (Step O). This metabolite is then hydrolyzed to form 2,4-pentadienoate (Step P or Q). A CoA transferase can also be used for this effect. 2,4-pentadienoate is then decarboxylated to form butadiene (Step I). The intermediate 5-hydroxypent-2-enoate can also be converted to form 5-hydroxypent-2-enoyl-CoA either by a CoA ligase or a CoA transferase (Step M or N). This CoA intermediate is then dehydrated to form 2,4-pentadienoyl-CoA as shown in Step O.

These pathways afford a maximum theoretical yield of 1 mol butadiene/mol glucose with a net excess of one mole NAD(P)H per mole butadiene formed. These pathway can also make up to one mole of ATP per mole of butadiene formed. Some combinations of these pathways will proceed through Steps A through I. Certain combinations of these pathways will be ATP neutral. For example, when a CoA ligase is used to activate one of the acid intermediates in the pathway and then CoA hydrolysis is used to form 2,4-pentadienoate, ATP production is neutral. The ATP-generating pathways also therefore provide an opportunity to produce butadiene anaerobically with coproduction of hydrogen. As described for the pathways described in FIG. 1, this set of pathways also allows for accomplishing a yield increase in butadiene with the use of a phosphoketolase-dependent acetyl-CoA synthesis pathway (See Example VI below).

Step A, FIG. 2: Acetyl-CoA Carboxylase

Acetyl-CoA carboxylase (EC 6.4.1.2) catalyzes the ATP-dependent carboxylation of acetyl-CoA to malonyl-CoA. This enzyme is biotin dependent and is the first reaction of fatty acid biosynthesis initiation in several organisms. Exemplary enzymes are encoded by accABCD of *E. coli* (Davis et al, *J Biol Chem* 275:28593-8 (2000)), ACC1 of *Saccharomyces cerevisiae* and homologs (Sumper et al, *Methods Enzym* 71:34-7 (1981)). The mitochondrial acetyl-CoA carboxylase of *S. cerevisiae* is encoded by HFA1. Acetyl-CoA carboxylase holoenzyme formation requires attachment of biotin by a biotin:apoprotein ligase such as BPL1 of *S. cerevisiae*. These and additional ACC enzymes are listed in the table below.

| Protein | GenBank ID | GI Number | Organism |
|---|---|---|---|
| ACC1 | CAA96294.1 | 1302498 | Saccharomyces cerevisiae |
| KLLA0F06072g | XP_455355.1 | 50310667 | Kluyveromyces lactis |
| ACC1 | XP_718624.1 | 68474502 | Candida albicans |
| YALI0C11407p | XP_501721.1 | 50548503 | Yarrowia lipolytica |
| ANI_1_1724104 | XP_001395476.1 | 145246454 | Aspergillus niger |
| accA | AAC73296.1 | 1786382 | Escherichia coli |
| accB | AAC76287.1 | 1789653 | Escherichia coli |
| accC | AAC76288.1 | 1789654 | Escherichia coli |
| accD | AAC75376.1 | 1788655 | Escherichia coli |
| accA | CAD08690.1 | 16501513 | Salmonella enterica |
| accB | CAD07894.1 | 16504441 | Salmonella enterica |
| accC | CAD07895.1 | 16504442 | Salmonella enterica |
| accD | CAD07598.1 | 16503590 | Salmonella enterica |
| HFA1 | NP_013934.1 | 6323863 | Saccharomyces cerevisiae |
| BPL1 | NP_010140.1 | 6320060 | Saccharomyces cerevisiae |
| YMR207C | NP_013934.1 | 6323863 | Saccharomyces cerevisiae |
| YNR016C | NP_014413.1 | 6324343 | Saccharomyces cerevisiae |
| YGR037C | NP_011551.1 | 6321474 | Saccharomyces cerevisiae |
| YKL182W | NP_012739.1 | 6322666 | Saccharomyces cerevisiae |
| YPL231W | NP_015093.1 | 6325025 | Saccharomyces cerevisiae |
| accA | ZP_00618306.1 | 69288468 | Kineococcus radiotolerans |

-continued

| Protein | GenBank ID | GI Number | Organism |
|---|---|---|---|
| accB | ZP_00618387.1 | 69288621 | Kineococcus radiotolerans |
| accC | ZP_00618040.1/ ZP_00618387.1 | 69287824/ 69288621 | Kineococcus radiotolerans |
| accD | ZP_00618306.1 | 69288468 | Kineococcus radiotolerans |

Malonyl-CoA can also be produced from malonate, produced either intracellularly or from exogenously fed malonate. Organisms are known to convert malonate into malonyl-CoA either by a synthetase or via a CoA transferase. Additionally, the ability to uptake malonate can be conferred upon an organism by introducing a malonate transporter as described in Chen and Tan (Appl Biochem Biotechnol. 2013 September; 171(1):44-62). In this paper, a malonate transporter encoded by mae1 was cloned from *Schizosaccharomyces pombe* into *Saccharomyces cerevesiae*.

Malonyl-CoA synthetase converts malonate into malonyl-CoA while converting ATP into AMP. This enzyme was first discovered in bacteroids, *Bradyrhizobium japonicum*, of soyabean nodules (Kim and Chae, 1990). Free malonate is known to occur in legumes and its levels increase under symbiotic conditions. The enzyme has been purified from *B. japonicum* and from *Rhizobium leguminosarium* by *trifolii* (kim et al., 1993). In the latter, a mat operon is described that comprises of a malonate carrier (matC), a malonyl-CoA synthetase (matB), a malonyl-CoA decarboxylase (matA) and the regulator of the operon, matR.

| Protein | GenBank ID | GI Number | Organism |
|---|---|---|---|
| Mae1 | CAC37422.1 | 13810233 | Schizosaccharomyces pombe |
| matA | AAC83456.1 | 3982574 | Rhizobium leguminosarium |
| matB | AAC83455.1 | 3982573 | Rhizobium leguminosarium |
| matC | AAC83457.1 | 3982575 | Rhizobium leguminosarium |

Step B: FIG. 2: Malonyl-CoA:Acetyl-CoA Acyltransferase

Beta-ketothiolase enzymes catalyzing the formation of beta-ketovalerate from acetyl-CoA and propionyl-CoA are suitable candidates for catalyzing the condensation of acetyl-CoA and malonyl-CoA. *Zoogloea ramigera* possesses two ketothiolases that can form 3-ketovaleryl-CoA from propionyl-CoA and acetyl-CoA and *R. eutropha* has a beta-oxidation ketothiolase that is also capable of catalyzing this transformation (Gruys et al., U.S. Pat. No. 5,958,745 (1999)). The sequences of these genes or their translated proteins have not been reported, but several candidates in *R. eutropha, Z. ramigera*, or other organisms can be identified based on sequence homology to bktB from *R. eutropha*. These include:

| Protein | GenBank ID | GI Number | Organism |
|---|---|---|---|
| phaA | YP_725941.1 | 113867452 | Ralstonia eutropha |
| h16_A1713 | YP_726205.1 | 113867716 | Ralstonia eutropha |
| pcaF | YP_728366.1 | 116694155 | Ralstonia eutropha |
| h16_B1369 | YP_840888.1 | 116695312 | Ralstonia eutropha |
| h16_A0170 | YP_724690.1 | 113866201 | Ralstonia eutropha |
| h16_A0462 | YP_724980.1 | 113866491 | Ralstonia eutropha |
| h16_A1528 | YP_726028.1 | 113867539 | Ralstonia eutropha |

-continued

| Protein | GenBank ID | GI Number | Organism |
|---|---|---|---|
| h16_B0381 | YP_728545.1 | 116694334 | Ralstonia eutropha |
| h16_B0662 | YP_728824.1 | 116694613 | Ralstonia eutropha |
| h16_B0759 | YP_728921.1 | 116694710 | Ralstonia eutropha |
| h16_B0668 | YP_728830.1 | 116694619 | Ralstonia eutropha |
| h16_A1720 | YP_726212.1 | 113867723 | Ralstonia eutropha |
| h16_A1887 | YP_726356.1 | 113867867 | Ralstonia eutropha |
| phbA | P07097.4 | 135759 | Zoogloea ramigera |
| bktB | YP_002005382.1 | 194289475 | Cupriavidus taiwanensis |
| Rmet_1362 | YP_583514.1 | 94310304 | Ralstonia metallidurans |
| Bphy_0975 | YP_001857210.1 | 186475740 | Burkholderia phymatum |

Another suitable candidate is 3-oxoadipyl-CoA thiolase (EC 2.3.1.174), which converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., *J Bacteriol.* 176:6479-6488 (1994)) and *Acinetobacter calcoaceticus* (Doten et al., *J Bacteriol.* 169:3168-3174 (1987)). The gene products encoded by pcaF in *Pseudomonas* strain B13 (Kaschabek et al., *J Bacteriol.* 184:207-215 (2002)), phaD in *Pseudomonas putida* U (Olivera et al., *Proc. Natl. Acad. Sci U.S.A* 95:6419-6424 (1998)), paaE in *Pseudomonas fluorescens* ST (Di et al., *Arch. Microbiol* 188:117-125 (2007)), and paaJ from *E. coli* (Nogales et al., *Microbiology* 153: 357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*.

| Gene name | GI# | GenBank Accession # | Organism |
|---|---|---|---|
| paaJ | 16129358 | NP_415915.1 | Escherichia coli |
| pcaF | 17736947 | AAL02407 | Pseudomonas knackmussii (B13) |
| phaD | 3253200 | AAC24332.1 | Pseudomonas putida |
| pcaF | 506695 | AAA85138.1 | Pseudomonas putida |
| pcaF | 141777 | AAC37148.1 | Acinetobacter calcoaceticus |
| paaE | 106636097 | ABF82237.1 | Pseudomonas fluorescens |
| bkt | 115360515 | YP_777652.1 | Burkholderia ambifaria AMMD |
| bkt | 9949744 | AAG06977.1 | Pseudomonas aeruginosa PAO1 |
| pcaF | 9946065 | AAG03617.1 | Pseudomonas aeruginosa PAO1 |

3-Oxopimeloyl-CoA thiolase catalyzes the condensation of glutaryl-CoA and acetyl-CoA into 3-oxopimeloyl-CoA (EC 2.3.1.16). An enzyme catalyzing this transformation is encoded by genes bktB and bktC in *Ralstonia eutropha* (formerly known as *Alcaligenes eutrophus*) (Slater et al., *J. Bacteriol.* 180:1979-1987 (1998); Haywood et al., *FEMS Microbiology Letters* 52:91-96 (1988)). The sequence of the BktB protein is known. The pim operon of *Rhodopseudomonas palustris* also encodes a beta-ketothiolase, encoded by pimB, predicted to catalyze this transformation in the degradative direction during benzoyl-CoA degradation (Harrison et al., *Microbiology* 151:727-736 (2005)). A beta-ketothiolase enzyme in *S. aciditrophicus* was identified by sequence homology to bktB (43% identity, evalue=1e-93).

| Gene name | GI# | GenBank Accession # | Organism |
|---|---|---|---|
| bktB | 11386745 | YP_725948 | *Ralstonia eutropha* |
| pimB | 39650633 | CAE29156 | *Rhodopseudomonas palustris* |
| syn_02642 | 85860483 | YP_462685.1 | *Syntrophus aciditrophicus* |

Additional enzymes include beta-ketothiolases that are known to convert two molecules of acetyl-CoA into acetoacetyl-CoA (EC 2.1.3.9). Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J Mol. Microbiol Biotechnol* 2:531-541 (2000)), and ERG10 from *S. cerevisiae* (Hiser et al., *J. Biol. Chem.* 269:31383-31389 (1994)).

| Gene name | GI# | GenBank Accession # | Organism |
|---|---|---|---|
| atoB | 16130161 | NP_416728 | *Escherichia coli* |
| thlA | 15896127 | NP_349476.1 | *Clostridium acetobutylicum* |
| thlB | 15004782 | NP_149242.1 | *Clostridium acetobutylicum* |
| ERG10 | 6325229 | NP_015297 | *Saccharomyces cerevisiae* |

Step C, FIG. 2: 3-oxoglutaryl-CoA Reductase (Ketone-Reducing)

Exemplary genes and gene products for catalyzing the 3-oxoglutaryl-CoA reductase steps that converted 3-oxoglutaryl-CoA to 3-hydroxyglutaryl-CoA are described above in Example I, step I.

Step D: FIG. 2: 3-Hydroxyglutaryl-CoA Reductase (Aldehyde Forming)

Acyl-CoA dehydrogenases that reduce an acyl-CoA to its corresponding aldehyde include fatty acyl-CoA reductase (EC 1.2.1.42, 1.2.1.50), succinyl-CoA reductase (EC 1.2.1.76), acetyl-CoA reductase, butyryl-CoA reductase and propionyl-CoA reductase (EC 1.2.1.3). Aldehyde forming acyl-CoA reductase enzymes with demonstrated activity on acyl-CoA, 3-hydroxyacyl-CoA and 3-oxoacyl-CoA substrates are known in the literature. Several acyl-CoA reductase enzymes are active on 3-hydroxyacyl-CoA substrates. For example, some butyryl-CoA reductases from Clostridial organisms, are active on 3-hydroxybutyryl-CoA and propionyl-CoA reductase of *L. reuteri* is active on 3-hydroxypropionyl-CoA. An enzyme for converting 3-oxoacyl-CoA substrates to their corresponding aldehydes is malonyl-CoA reductase. Enzymes in this class can be refined using evolution or enzyme engineering methods known in the art to have activity on enoyl-CoA substrates.

Exemplary fatty acyl-CoA reductases enzymes are encoded by acr1 of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)). Two gene products from *Mycobacterium tuberculosis* accept longer chain fatty acyl-CoA substrates of length C16-C18 (Harminder Singh, U. Central Florida (2007)). Yet another fatty acyl-CoA reductase is LuxC of *Photobacterium phosphoreum* (Lee et al, *Biochim Biohys Acta* 1388:215-22 (1997)). Enzymes with succinyl-CoA reductase activity are encoded by sucD of *Clostridium kluyveri* (Sohling, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., Biosci Biotechnol Biochem., 71:58-68 (2007)). Exemplary propionyl-CoA reductase enzymes include pduP of *Salmonella typhimurium* LT2 (Leal, *Arch. Microbiol.* 180:353-361 (2003)) and eutE from *E. coli* (Skraly, WO Patent No. 2004/024876). The propionyl-CoA reductase of *Salmonella typhimurium* LT2, which naturally converts propionyl-CoA to propionaldehyde, also catalyzes the reduction of 5-hydroxyvaleryl-CoA to 5-hydroxypentanal (WO 2010/068953A2). The propionaldehyde dehydrogenase of *Lactobacillus reuteri*, PduP, has a broad substrate range that includes butyraldehyde, valeraldehyde and 3-hydroxypropionaldehyde (Luo et al, Appl Microbiol Biotech, 89: 697-703 (2011). Additionally, some acyl-ACP reductase enzymes such as the orf1594 gene product of *Synechococcus elongatus* PCC7942 also exhibit aldehyde-forming acyl-CoA reductase activity (Schirmer et al, *Science*, 329: 559-62 (2010)).

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| Rv1543 | NP_216059.1 | 15608681 | *Mycobacterium tuberculosis* |
| Rv3391 | NP_217908.1 | 15610527 | *Mycobacterium tuberculosis* |
| LUXC | AAT00788.1 | 46561111 | *Photobacterium phosphoreum* |
| MSED_0709 | YP_001190808.1 | 146303492 | *Metallosphaera sedula* |
| Tneu_0421 | ACB39369.1 | 170934108 | *Thermoproteus neutrophilus* |

| Protein | GenBank ID | GI Number | Organism |
|---|---|---|---|
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| bld | AAP42563.1 | 31075383 | Clostridium saccharoperbutylacetonicum |
| pduP | NP_460996 | 16765381 | Salmonella typhimurium LT2 |
| eutE | NP_416950 | 16130380 | Escherichia coli |
| pduP | CCC03595.1 | 337728491 | Lactobacillus reuteri |

Additionally, some acyl-ACP reductase enzymes such as the orf1594 gene product of *Synechococcus elongatus* PCC7942 also exhibit aldehyde-forming acyl-CoA reductase activity (Schirmer et al, Science, 329: 559-62 (2010)). The S. elongates PCC7942 acyl-ACP reductase is coexpressed with an aldehyde decarbonylase in an operon that appears to be conserved in a majority of cyanobacterial organisms. This enzyme, expressed in *E. coli* together with the aldehyde decarbonylase, conferred the ability to produce alkanes. The *P. marinus* AAR was also cloned into *E. coli* and, together with a decarbonylase, demonstrated production of alkanes (see, e.g., US Application 2011/0207203).

gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the aid gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999).

| Gene | GenBank ID | GI Number | Organism |
|---|---|---|---|
| orf1594 | YP_400611.1 | 81300403 | Synechococcus elongatus PCC7942 |
| PMT9312_0533 | YP_397030.1 | 78778918 | Prochlorococcus marinus MIT 9312 |
| syc0051_d | YP_170761.1 | 56750060 | Synechococcus elongatus PCC 6301 |
| Ava_2534 | YP_323044.1 | 75908748 | Anabaena variabilis ATCC 29413 |
| alr5284 | NP_489324.1 | 17232776 | Nostoc sp. PCC 7120 |
| Aazo_3370 | YP_003722151.1 | 298491974 | Nostoc azollae |
| Cyan7425_0399 | YP_002481152.1 | 220905841 | Cyanothece sp. PCC 7425 |
| N9414_21225 | ZP_01628095.1 | 119508943 | Nodularia spumigena CCY9414 |
| L8106_07064 | ZP_01619574.1 | 119485189 | Lyngbya sp. PCC 8106 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, *Science* 318:1782-1786 (2007); and Thauer, *Science* 318:1732-1733 (2007)). The enzyme utilizes NADPH as a cofactor and has been characterized in *Metallosphaera* and *Sulfolobus* sp. (Alber et al., *J. Bacteriol.* 188:8551-8559 (2006); and Hugler, *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg, *Science* 318:1782-1786 (2007)). A gene encoding a malonyl-CoA reductase from *Sulfolobus tokodaii* was cloned and heterologously expressed in *E. coli* (Alber et al., *J. Bacteriol* 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional

| Gene | GenBank ID | GI Number | Organism |
|---|---|---|---|
| Msed_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | NP_416950 | 16130380 | Escherichia coli |

Step E, FIG. 2: 3-hydroxy-5-oxopentanoate Reductase

The reduction of 3-hydroxy 5-oxopentenoate to 3,5-dihydroxypentanoate can be catalyzed by an aldehyde reductase.

Exemplary genes encoding enzymes that catalyze the conversion of an aldehyde to alcohol (e.g., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), ADH2 from *Saccharomyces cerevisiae* (Atsumi et al., *Nature* 451:86-89 (2008)), yqhD from *E. coli* which has preference for molecules longer than C(3) (Sulzenbacher et al., *J Mol Biol* 342:489-502 (2004)), and bdh I and bdh II from *C. acetobutylicum* which converts butyryaldehyde into butanol (Walter et al., 174:7149-7158 (1992)). The gene product of yqhD catalyzes the reduction of acetaldehyde, malondialdehyde, propionaldehyde, butyraldehyde, and acrolein using NADPH as the cofactor (Perez et al., 283: 7346-7353 (2008); Perez et al., *J Biol. Chem.* 283:7346-7353 (2008)). The adhA gene product from *Zymomonas mobilisE* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). Additional aldehyde reductase candidates are encoded by bdh in *C. saccharoperbutylacetonicum* and Cbei_1722, Cbei_2181 and Cbei_2421 in *C. beijerinckii*.

| Protein | GENBANK ID | GI NUMBER | ORGANISM |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| bdh | BAF45463.1 | 124221917 | *Clostridium saccharoperbutylacetonicum* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |

Enzymes exhibiting 4-hydroxybutyrate dehydrogenase activity (EC 1.1.1.61) also fall into this category. Such enzymes have been characterized in *Ralstonia eutropha* (Bravo et al., 49:379-387 (2004)), *Clostridium kluyveri* (Wolff et al., *Protein Expr. Purif* 6:206-212 (1995)) and *Arabidopsis thaliana* (Breitkreuz et al., 278:41552-41556 (2003)). The *A. thaliana* enzyme was cloned and characterized in yeast (Breitkreuz et al., *J. Biol. Chem.* 278:41552-41556 (2003)). Yet another gene is the alcohol dehydrogenase adhI from *Geobacillus thermoglucosidasius* (Jeon et al., *J Biotechnol* 135:127-133 (2008)).

| Protein | GenBank ID | GI number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |
| adhI | AAR91477.1 | 40795502 | *Geobacillus thermoglucosidasius* |

Another exemplary enzyme is 3-hydroxyisobutyrate dehydrogenase (EC 1.1.1.31) which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., 352:905-17 (2005)). The reversibility of the human 3-hydroxyisobutyrate dehydrogenase was demonstrated using isotopically-labeled substrate (Manning et al., 231:481-4 (1985)). Additional genes encoding this enzyme include 3hidh in *Homo sapiens* (Hawes et al., 324:218-228 (2000)) and *Oryctolagus cuniculus* (Hawes et al., *Methods Enzymol.* 324:218-228 (2000); Chowdhury et al., *Biosci. Biotechnol Biochem.* 60:2043-2047 (1996)), mmsB in *Pseudomonas aeruginosa* and *Pseudomonas putida*, and dhat in *Pseudomonas putida* (Aberhart et al., *J Chem. Soc. [Perkin 1]* 6:1404-1406 (1979); Chowdhury et al., *Biosci. Biotechnol Biochem.* 60:2043-2047 (1996); Chowdhury et al., *Biosci. Biotechnol Biochem.* 67:438-441 (2003)). Several 3-hydroxyisobutyrate dehydrogenase enzymes have been characterized in the reductive direction, including mmsB from *Pseudomonas aeruginosa* (Gokarn et al., (2008)) and mmsB from *Pseudomonas putida*.

| Protein | GenBank ID | GI number | Organism |
|---|---|---|---|
| P84067 | P84067 | 75345323 | *Thermus thermophilus* |
| 3hidh | P31937.2 | 12643395 | *Homo sapiens* |
| 3hidh | P32185.1 | 416872 | *Oryctolagus cuniculus* |
| mmsB | NP_746775.1 | 26991350 | *Pseudomonas putida* |

-continued

| Protein | GenBank ID | GI number | Organism |
|---|---|---|---|
| mmsB | P28811.1 | 127211 | *Pseudomonas aeruginosa* |
| dhat | Q59477.1 | 2842618 | *Pseudomonas putida* |

3-Hydroxypropionate dehydrogenase, also known as malonate semialdehyde reductase, catalyzes the reversible conversion of malonic semialdehyde to 3-HP. An NADH-dependent 3-hydroxypropionate dehydrogenase is thought to participate in beta-alanine biosynthesis pathways from propionate in bacteria and plants (Rathinasabapathi B., 159:671-674 (2002); Stadtman, *J. Am. Chem. Soc.* 77:5765-5766 (1955)). An NADPH-dependent malonate semialdehyde reductase catalyzes the reverse reaction in autotrophic $CO_2$-fixing bacteria. The enzyme activity has been detected in *Metallosphaera sedula*. (Alber et al., 188:8551-8559 (2006)). Several 3-hydroxyisobutyrate dehydrogenase enzymes exhibit 3-hydroxypropionate dehydrogenase activity. Three genes exhibiting this activity are mmsB from *Pseudomonas aeruginosa* PAO1 (Gokarn et al., (2008)), mmsB from *Pseudomonas putida* KT2440 and mmsB from *Pseudomonas putida* E23 (Chowdhury et al., 60:2043-2047 (1996)).

| Protein | GenBank ID | GI number | Organism |
|---|---|---|---|
| mmsB | NP_252259.1 | 15598765 | *Pseudomonas putida* |
| mmsB | NP_746775.1 | 26991350 | *Pseudomonas aeruginosa* |
| mmsB | JC7926 | 60729613 | *Pseudomonas putida* |

Homoserine dehydrogenase (EC 1.1.1.13) catalyzes the NAD(P)H-dependent reduction of aspartate semialdehyde to homoserine. In many organisms, including *E. coli*, homoserine dehydrogenase is a bifunctional enzyme that also catalyzes the ATP-dependent conversion of aspartate to aspartyl-4-phosphate (Starnes et al., 11:677-687 (1972) 1973)). The functional domains are catalytically independent and connected by a linker region (Sibilli et al., 256: 10228-10230 (1981)) and both domains are subject to allosteric inhibition by threonine. The homoserine dehydrogenase domain of the *E. coli* enzyme, encoded by thrA, was separated from the aspartate kinase domain, characterized, and found to exhibit high catalytic activity and reduced inhibition by threonine (James et al., 41:3720-3725 (2002)). This can be applied to other bifunctional threonine kinases including, for example, hom1 of *Lactobacillus plantarum* (Cahyanto et al., 152:105-112 (2006)) and *Arabidopsis thaliana*. The monofunctional homoserine dehydrogenases encoded by hom6 in *S. cerevisiae* (Jacques et al., 1544:28-41 (2001)) and hom2 in *Lactobacillus plantarum* (Cahyanto et al., *Microbiology* 152:105-112 (2006)) have been functionally expressed and characterized in *E. coli*.

| Protein | GenBank ID | GI number | Organism |
|---|---|---|---|
| thrA | AAC73113.1 | 1786183 | *Escherichia coli* K12 |
| akthr2 | O81852 | 75100442 | *Arabidopsis thaliana* |
| hom6 | CAA89671 | 1015880 | *Saccharomyces cerevisiae* |
| hom1 | CAD64819 | 28271914 | *Lactobacillus plantarum* |
| hom2 | CAD63186 | 28270285 | *Lactobacillus plantarum* |

Step F, FIG. 2: 3-Hydroxyglutaryl-CoA Reductase (Alcohol Forming)

Bifunctional oxidoreductases convert an acyl-CoA to its corresponding alcohol. Enzymes with this activity are required to convert 3-hydroxygloutaryl-CoA to 3,5-dihydroxypentanoate.

Exemplary bifunctional oxidoreductases that convert an acyl-CoA to alcohol include those that transform substrates such as acetyl-CoA to ethanol (e.g., adhE from *E. coli* (Kessler et al., *FEBS. Lett.* 281:59-63 (1991))) and butyryl-CoA to butanol (e.g. adhE2 from *C. acetobutylicum* (Fontaine et al., *J. Bacteriol.* 184:821-830 (2002))). The *C. acetobutylicum* enzymes encoded by bdh I and bdh II (Walter, et al., *J. Bacteriol.* 174:7149-7158 (1992)), reduce acetyl-CoA and butyryl-CoA to ethanol and butanol, respectively. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett*, 27:505-510 (2005)). Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol*, 184:2404-2410 (2002); Strauss et al., *Eur J Biochem*, 215:633-643 (1993)). This enzyme, with a mass of 300 kDa, is highly substrate-specific and shows little sequence similarity to other known oxidoreductases (Hugler et al., supra). No enzymes in other organisms have been shown to catalyze this specific reaction; however there is bioinformatic evidence that other organisms may have similar pathways (Klatt et al., *Env Microbiol*, 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leuconostoc mesenteroides* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced to their corresponding alcohols by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiol*, 122:635-644 (2000)). Bifunctional prokaryotic FAR enzymes are found in *Marinobacter aquaeolei* VT8 (Hofvander et al, FEBS Lett 3538-43 (2011)), *Marinobacter algicola* and *Oceanobacter* strain RED65 (US Pat Appl 20110000125).

| Protein | GenBank ID | GI Number | Organism |
|---|---|---|---|
| FAR | AAD38039.1 | 5020215 | *Simmondsia chinensis* |
| FAR | YP_959486.1 | 120555135 | *Marinobacter aquaeolei* |

Another candidate for catalyzing these steps is 3-hydroxy-3-methylglutaryl-CoA reductase (or HMG-CoA reductase). This enzyme naturally reduces the CoA group in 3-hydroxy-3-methylglutaryl-CoA to an alcohol forming mevalonate. The hmgA gene of *Sulfolobus solfataricus*, encoding 3-hydroxy-3-methylglutaryl-CoA reductase, has been cloned, sequenced, and expressed in *E. coli* (Bochar et al., *J. Bacteriol.* 179:3632-3638 (1997)). *S. cerevisiae* also has two HMG-CoA reductases in it (Basson et al., *Proc. Natl. Acad. Sci. U.S.A* 83:5563-5567 (1986)). The gene has also been isolated from *Arabidopsis thaliana* and has been shown to complement the HMG-COA reductase activity in *S. cerevisiae* (Learned et al., *Proc. Natl. Acad. Sci. U.S.A* 86:2779-2783 (1989)).

| Protein | GenBank ID | GI Number | Organism |
|---|---|---|---|
| HMG1 | CAA86503.1 | 587536 | *Saccharomyces cerevisiae* |
| HMG2 | NP_013555 | 6323483 | *Saccharomyces cerevisiae* |
| HMG1 | CAA70691.1 | 1694976 | *Arabidopsis thaliana* |
| hmgA | AAC45370.1 | 2130564 | *Sulfolobus solfataricus* |

4-Hydroxybutyryl-CoA reductase (alcohol forming) enzymes are bifunctional oxidoreductases that convert an 4-hydroxybutyryl-CoA to 1,4-butanediol. Enzymes with this activity include adhE from *E. coli*, adhE2 from *C. acetobutylicum* (Fontaine et al., *J. Bacteriol.* 184:821-830 (2002)) and the *C. acetobutylicum* enzymes encoded by bdh I and bdh II (Walter, et al., *J. Bacteriol.* 174:7149-7158 (1992)). In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett*, 27:505-510 (2005)).

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leuconostoc mesenteroides* |
| adhE | NP_781989.1 | 28211045 | *Clostridium tetani* |
| adhE | NP_563447.1 | 18311513 | *Clostridium perfringens* |
| adhE | YP_001089483.1 | 126700586 | *Clostridium difficile* |

Steps J. M. FIG. 2: 3,5-dihydroxypentanoate Ligase, 5-hydroxypent-2-enoate Ligase Exemplary genes and gene products for catalyzing the CoA ligase steps that convert 3,5-dihydroxypentanoate to 3,5-dihdyroxypentannoyl-CoA and 5-hydroxypent-2-enoyl-CoA are described above in Example I, step G and step J.

Steps K, N, and O: FIG. 2: 3,5-dihydroxnentanoate:acetyl-CoA CoA Transferase, 5-hydroxypent-2-enoate:acetyl-CoA CoA Transferase, 2,4-pentadienoyl-CoA:acetyl-CoA CoA Transferase Exemplary genes and gene products for catalyzing the CoA transferase steps that convert the substrates and products of Steps K, N, and Q in FIG. 2 are described above in Example I, Steps H, K and N.

Step P, FIG. 2: 2,4-pentadienoyl-CoA CoA Hydrolase

Exemplary genes and gene products for catalyzing the CoA hydrolase steps that convert 2,4-pentadienoyl-CoA into 2,4-pentadienoate are described above in Example I, step M.

Step I, FIG. 2: 2,4-pentadienoate Decarboxylase

Exemplary genes and gene products for catalyzing the decarboxylase steps that convert penta-2,4-dienoate to butadiene are described above in Example I, step F.

Step L, FIG. 2: 3,5-dihydroxypentanoyl-CoA dehydratase

Exemplary genes and gene products for catalyzing the dehydratase steps that convert 3,5-dihydroxypentanoyl-CoA into 5-hydroxyoent-2-enoyl-CoA belong to the category of 3-hydroxyacyl-CoA dehydratases, which are described in Example I, step L.

Step O, FIG. 2: 5-hydroxypent-2-enoyl-CoA Hydrolase

Acyl CoA dehydratases can catalyze the dehydration of 5-hydroxypent-2-enoyl-CoA into 2,4-pentadienoyl-CoA. Specifically, an enzyme that can catalyze this transformation has been described in Buckel, Appl Microbiol Biotechnol. 2001 October; 57(3):263-7. 5-hydroxyvaleryl-CoA dehydrogenase/dehydratase has been described from *Clostridium viride*, previously called *Clostridium aminovalericum*. This enzyme can first oxidize 5-hydroxyvaleryl-CoA to 5-hy-droxypentenoyl-CoA. This is subsequently dehydrated to form 2,4-pentadienoyl-CoA. The crystal structure of the dehydratase has been solved to 2.2 A° resolution. Eikmanns et al., *Proteins*. 1994 July; 19(3):269-71, Eikmanns and Buckel, *Eur J Biochem*, 1991 May 8; 197(3):661-8.

Other gene candidates in the enzyme class 4.2.1 can catalyze this transformation. Several candidates are listed in Example I, step L.

Steps G and H, FIG. 2: 3,5-dihydroxypentanoate Dehydratase and 5-hydroxypent-2-enoate Dehydratase Exemplary dehydratase that can catalyze dehydration of 3,5-dihydroxypentanoate to 5-hydroxy pent-2-enoate and of 5-hydroxy pent-2-enoate to pent-2,4-dienoate are described in Example I, step E.

Step S, FIG. 2: 3-hydroxy-5-oxopentanoate Synthase

The reduction of 3-hydroxyglutarylphosphate to 3-hydroxy-5-oxopentanoate can be catalyzed by an oxidoreductase or phosphate reductase in the EC class 1.2.1. Exemplary phosphonate reductase enzymes include glyceraldehyde-3-phosphate dehydrogenase (EC 1.2.1.12), aspartate-semialdehyde dehydrogenase (EC 1.2.1.11) acetylglutamylphosphate reductase (EC 1.2.1.38) and glutamate-5-semialdehyde dehydrogenase (EC 1.2.1.-). Aspartate semialdehyde dehydrogenase (ASD, EC 1.2.1.11) catalyzes the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J Mol. Biol.* 289:991-1002 (1999)) and the enzyme has been shown to accept the alternate substrate beta-3-methylaspartyl phosphate (Shames et al., *J Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); Blanco et al., *Acta Crystallogr. D. Biol. Crystallogr.* 60:1808-1815 (2004)). Other ASD candidates are found in *Mycobacterium tuberculosis* (Shafiani et al., *J Appl Microbiol* 98:832-838 (2005)), *Methanococcus jannaschii* (Faehnle et al., *J Mol. Biol.* 353:1055-1068 (2005)), and the infectious microorganisms *Vibrio cholera* and *Heliobacter pylori* (Moore et al., *Protein Expr. Purif* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly et al., *Microbiology* 140 (Pt 5):1023-1025 (1994)), *E. coli* (Parsot et al., *Gene.* 68:275-283 (1988)), and other organisms. Additional phosphate reductase enzymes of *E. coli* include glyceraldehyde 3-phosphate dehydrogenase (gapA (Branlant et al., *Eur. J Biochem.* 150:61-66 (1985))) and glutamate-5-semialdehyde dehydrogenase (proA (Smith et al., *J. Bacteriol.* 157:545-551 (1984))). Genes encoding glutamate-5-semialdehyde dehydrogenase enzymes from *Salmonella typhimurium* (Mahan et al., *J. Bacteriol.* 156: 1249-1262 (1983)) and *Campylobacter jejuni* (Louie et al., *Mol. Gen. Genet.* 240:29-35 (1993)) were cloned and expressed in *E. coli*.

| Protein | GenBank ID | GI Number | Organism |
|---|---|---|---|
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Heliobacter pylori* |
| ARG5,6 | NP_010992.1 | 6320913 | *Saccharomyces cerevisiae* |
| argC | NP_389001.1 | 16078184 | *Bacillus subtilis* |
| argC | NP_418393.1 | 16131796 | *Escherichia coli* |
| gapA | P0A9B2.2 | 71159358 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

Step R, FIG. 2: Phosphate-3-hydroxyglutaryl Transferase

Exemplary phosphate-transferring acyltransferases that can convert 3-hydroxyglutaryl-CoA into 3-hydroxyglutaryl phosphate include phosphotransacetylase (EC 2.3.1.8) and phosphotransbutyrylase (EC 2.3.1.19). The pta gene from *E. coli* encodes a phosphotransacetylase that reversibly converts acetyl-CoA into acetyl-phosphate (Suzuki, *Biochim. Biophys. Acta* 191:559-569 (1969)). This enzyme can also utilize propionyl-CoA as a substrate, forming propionate in the process (Hesslinger et al., *Mol. Microbiol* 27:477-492 (1998)). Other phosphate acetyltransferases that exhibit activity on propionyl-CoA are found in *Bacillus subtilis* (Rado et al., *Biochim. Biophys. Acta* 321:114-125 (1973)), *Clostridium kluyveri* (Stadtman, *Methods Enzymol* 1:596-599 (1955)), and *Thermotoga maritima* (Bock et al., *J Bacteriol.* 181:1861-1867 (1999)). Similarly, the ptb gene from *C. acetobutylicum* encodes phosphotransbutyrylase, an enzyme that reversibly converts butyryl-CoA into butyryl-phosphate (Wiesenbom et al., *Appl Environ. Microbiol* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004)) and *Bacillus megaterium* (Vazquez et al., *Curr. Microbiol* 42:345-349 (2001)).

| Protein | GenBank ID | GI Number | Organism |
|---|---|---|---|
| pta | NP_416800.1 | 71152910 | *Escherichia coli* |
| pta | P39646 | 730415 | *Bacillus subtilis* |
| pta | A5N801 | 146346896 | *Clostridium kluyveri* |
| pta | Q9X0L4 | 6685776 | *Thermotoga maritima* |
| ptb | NP_349676 | 34540484 | *Clostridium acetobutylicum* |
| ptb | AAR19757.1 | 38425288 | butyrate-producing bacterium L2-50 |
| ptb | CAC07932.1 | 10046659 | *Bacillus megaterium* |

Example III

Formate Assimilation Pathways

This example describes enzymatic pathways for converting pyruvate to formaldehyde, and optionally in combination with producing acetyl-CoA and/or reproducing pyruvate.

Step E, FIG. 3: Formate Reductase

The conversion of formate to formaldehyde can be carried out by a formate reductase (step E, FIG. 3). A suitable enzyme for these transformations is the aryl-aldehyde dehydrogenase, or equivalently a carboxylic acid reductase, from *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)). This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in Biocatalysis in the Pharmaceutical and Biotechnology Industries, ed. R.N. Patel, Chapter 15, pp. 425-440, CRC Press LLC, Boca Raton, Fla. (2006)). Information related to these proteins and genes is shown below.

| Protein | GenBank ID | GI number | Organism |
|---|---|---|---|
| Car | AAR91681.1 | 40796035 | *Nocardia iowensis* (sp. NRRL 5646) |
| Npt | ABI83656.1 | 114848891 | *Nocardia iowensis* (sp. NRRL 5646) |

Additional car and npt genes can be identified based on sequence homology.

| Protein | GenBank ID | GI number | Organism |
|---|---|---|---|
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |

| Protein | GenBank ID | GI number | Organism |
|---|---|---|---|
| TpauDRAFT_20920 | ZP_04026660.1 | 227979396 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial. Information related to these proteins and genes is shown below.

| Protein | GenBank ID | GI number | Organism |
|---|---|---|---|
| griC | YP_001825755.1 | 182438036 | Streptomyces griseus subsp. griseus NBRC 13350 |
| griD | YP_001825756.1 | 182438037 | Streptomyces griseus subsp. griseus NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., Curr. Genet. 28:131-137 (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). Information related to these proteins and genes is shown below.

| Protein | GenBank ID | GI number | Organism |
|---|---|---|---|
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Tani et al (Agric Biol Chem, 1978, 42: 63-68; Agric Biol Chem, 1974, 38: 2057-2058) showed that purified enzymes from *Escherichia coli* strain B could reduce the sodium salts of different organic acids (e.g. formate, glycolate, acetate, etc.) to their respective aldehydes (e.g. formaldehyde, glycoaldehyde, acetaldehyde, etc.). Of three purified enzymes examined by Tani et al (1978), only the "A" isozyme was shown to reduce formate to formaldehyde. Collectively, this group of enzymes was originally termed glycoaldehyde dehydrogenase; however, their novel reductase activity led the authors to propose the name glycolate reductase as being more appropriate (Morita et al, Agric Biol Chem, 1979, 43: 185-186). Morita et al (Agric Biol Chem, 1979, 43: 185-186) subsequently showed that glycolate reductase activity is relatively widespread among microorganisms, being found for example in: *Pseudomonas, Agrobacterium, Escherichia, Flavobacterium, Micrococcus, Staphylococcus, Bacillus*, and others. Without wishing to be bound by any particular theory, it is believed that some of these glycolate reductase enzymes are able to reduce formate to formaldehyde.

Any of these CAR or CAR-like enzymes can exhibit formate reductase activity or can be engineered to do so.

Step F, FIG. 3: Formate Ligase, Formate Transferase, Formate Synthetase

The acylation of formate to formyl-CoA is catalyzed by enzymes with formate transferase, synthetase, or ligase activity (Step F, FIG. 3). Formate transferase enzymes have been identified in several organisms including *Escherichia coli* (Toyota, et al., *J Bacteriol.* 2008 April; 190(7):2556-64), *Oxalobacter formigenes* (Toyota, et al., *J Bacteriol.* 2008 April; 190(7):2556-64; Baetz et al., *J Bacteriol.* 1990 July; 172(7):3537-40; Ricagno, et al., *EMBO J.* 2003 Jul. 1; 22(13):3210-9)), and *Lactobacillus acidophilus* (Azcarate-Peril, et al., *Appl. Environ. Microbiol.* 2006 72(3) 1891-1899). Homologs exist in several other organisms. Enzymes acting on the CoA-donor for formate transferase may also be expressed to ensure efficient regeneration of the CoA-donor. For example, if oxalyl-CoA is the CoA donor substrate for formate transferase, an additional transferase, synthetase, or ligase may be required to enable efficient regeneration of oxalyl-CoA from oxalate. Similarly, if succinyl-CoA or acetyl-CoA is the CoA donor substrate for formate transferase, an additional transferase, synthetase, or ligase may be required to enable efficient regeneration of succinyl-CoA from succinate or acetyl-CoA from acetate, respectively.

| Protein | GenBank ID | GI number | Organism |
|---|---|---|---|
| YfdW | NP_416875.1 | 16130306 | Escherichia coli |
| frc | O06644.3 | 21542067 | Oxalobacter formigenes |
| frc | ZP_04021099.1 | 227903294 | Lactobacillus acidophilus |

Suitable CoA-donor regeneration or formate transferase enzymes are encoded by the gene products of cat1, cat2, and cat3 of *Clostridium kluyveri*. These enzymes have been shown to exhibit succinyl-CoA, 4-hydroxybutyryl-CoA, and butyryl-CoA acetyltransferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.*

283:1411-1418 (2008)) and *Trypanosoma brucei* (Riviere et al., *J. Biol. Chem.* 279:45337-45346 (2004)). Yet another transferase capable of the desired conversions is butyryl-CoA:acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenbom et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below.

| Protein | GenBank ID | GI number | Organism |
| --- | --- | --- | --- |
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Additional transferase enzymes of interest include the gene products of atoAD from *E. coli* (Hanai et al., *Appl Environ Microbiol* 73:7814-7818 (2007)), ctfAB from *C. acetobutylicum* (Jojima et al., *Appl Microbiol Biotechnol* 77:1219-1224 (2008)), and ctfAB from *Clostridium saccharoperbutylacetonicum* (Kosaka et al., *Biosci. Biotechnol Biochem.* 71:58-68 (2007)). Information related to these proteins and genes is shown below.

| Protein | GenBank ID | GI number | Organism |
| --- | --- | --- | --- |
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3-ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif* 53:396-403 (2007)), and *Homo sapiens* (Fukao et al., *Genomics* 68:144-151 (2000); Tanaka et al., *Mol. Hum. Reprod.* 8:16-23 (2002)). Information related to these proteins and genes is shown below.

| Protein | GenBank ID | GI number | Organism |
| --- | --- | --- | --- |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Two additional enzymes that catalyze the activation of formate to formyl-CoA reaction are AMP-forming formyl-CoA synthetase and ADP-forming formyl-CoA synthetase. Exemplary enzymes, known to function on acetate, are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (24). Such enzymes may also acylate formate naturally or can be engineered to do so.

| Protein | GenBank ID | GI Number | Organism |
| --- | --- | --- | --- |
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic cren-archaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus*, *H. marismortui* and *P. aerophilum* have all been cloned, functionally expressed, and characterized in *E. coli* (Musfeldt et al., supra; Brasen et al., supra (2004)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). Such enzymes may also acylate formate naturally or can be engineered to do so. Information related to these proteins and genes is shown below.

| Protein | GenBank ID | GI number | Organism |
|---|---|---|---|
| AF1211 | NP_070039.1 | 11498810 | *Archaeoglobus fulgidus* DSM 4304 |
| AF1983 | NP_070807.1 | 11499565 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

An alternative method for adding the CoA moiety to formate is to apply a pair of enzymes such as a phosphate-transferring acyltransferase and a kinase. These activities enable the net formation of formyl-CoA with the simultaneous consumption of ATP. An exemplary phosphate-transferring acyltransferase is phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Homologs exist in several other organisms including *Salmonella enterica* and *Chlamydomonas reinhardtii*. Such enzymes may also phosphorylate formate naturally or can be engineered to do so.

| Protein | GenBank ID | GI number | Organism |
|---|---|---|---|
| Pta | NP_416800.1 | 16130232 | *Escherichia coli* |
| Pta | NP_461280.1 | 16765665 | *Salmonella enterica* subsp. *enterica* serovar Typhimurium str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

An exemplary acetate kinase is the *E. coli* acetate kinase, encoded by ackA (Skarstedt and Silverstein *J. Biol. Chem.* 251:6775-6783 (1976)). Homologs exist in several other organisms including *Salmonella enterica* and *Chlamydomonas reinhardtii*. It is likely that such enzymes naturally possess formate kinase activity or can be engineered to have this activity. Information related to these proteins and genes is shown below:

| Protein | GenBank ID | GI number | Organism |
|---|---|---|---|
| AckA | NP_416799.1 | 16130231 | *Escherichia coli* |
| AckA | NP_461279.1 | 16765664 | *Salmonella enterica* subsp. *enterica* serovar Typhimurium str. LT2 |
| ACK1 | XP_001694505.1 | 159472745 | *Chlamydomonas reinhardtii* |
| ACK2 | XP_001691682.1 | 159466992 | *Chlamydomonas reinhardtii* |

The acylation of formate to formyl-CoA can also be carried out by a formate ligase. For example, the product of the LSC1 and LSC2 genes of *S. cerevisiae* and the sucC and sucD genes of *E. coli* naturally form a succinyl-CoA ligase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Such enzymes may also acylate formate naturally or can be engineered to do so. Information related to these proteins and genes is shown below.

| Protein | GenBank ID | GI number | Organism |
|---|---|---|---|
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178(14):4122-4130 (1996)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependent conversion of acetoacetate into acetoacetyl-CoA. 4-Hydroxybutyryl-CoA synthetase activity has been demonstrated in *Metallosphaera sedula* (Berg et al., *Science* 318:1782-1786 (2007)). This function has been tentatively assigned to the Msed_1422 gene. Such enzymes may also acylate formate naturally or can be engineered to do so. Information related to these proteins and genes is shown below.

| Protein | GenBank ID | GI number | Organism |
|---|---|---|---|
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed_1422 | YP_001191504 | 146304188 | *Metallosphaera sedula* |

Step G, FIG. 3: Formyl-CoA Reductase

Several acyl-CoA dehydrogenases are capable of reducing an acyl-CoA (e.g., formyl-CoA) to its corresponding aldehyde (e.g., formaldehyde) (Steps F, FIG. 3). Exemplary genes that encode such enzymes include the *Acinetobacter calcoaceticus* acr1 encoding a fatty acyl-CoA reductase (Reiser and Somerville, *J. Bacteriol.* 179:2969-2975 (1997), the *Acinetobacter* sp. M-1 fatty acyl-CoA reductase (Ishige et al., *Appl. Environ. Microbiol.* 68:1192-1195 (2002), and a CoA- and NADP-dependent succinate semialdehyde dehydrogenase encoded by the sucD gene in *Clostridium kluyveri* (Sohling and Gottschalk, *J. Bacteriol.* 178:871-880 (1996); Sohling and Gottschalk, *J. Bacteriol.* 1778:871-880 (1996)). SucD of *P. gingivalis* is another succinate semialdehyde dehydrogenase (Takahashi et al., *J. Bacteriol.* 182:4704-4710 (2000). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:45-55 (1972); Koo et al., *Biotechnol. Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.* 71:58-68 (2007)). Additional aldehyde dehydrogenase enzyme candidates are found in *Desulfatibacillum alkenivorans, Citrobacter koseri, Salmonella enterica, Lactobacillus brevis* and *Bacillus selenitireducens*. Such enzymes may be capable of naturally converting formyl-CoA to formaldehyde or can be engineered to do so.

(2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra). Such enzymes may be capable of naturally converting formyl-CoA to formaldehyde or can be engineered to do so.

| Protein   | GenBank ID     | GI number | Organism                    |
|-----------|----------------|-----------|-----------------------------|
| Msed_0709 | YP_001190808.1 | 146303492 | *Metallosphaera sedula*     |
| Mcr       | NP_378167.1    | 15922498  | *Sulfolobus tokodaii*       |
| asd-2     | NP_343563.1    | 15898958  | *Sulfolobus solfataricus*   |
| Saci_2370 | YP_256941.1    | 70608071  | *Sulfolobus acidocaldarius* |
| Ald       | AAT66436       | 9473535   | *Clostridium beijerinckii*  |
| eutE      | AAA80209       | 687645    | *Salmonella typhimurium*    |
| eutE      | P77445         | 2498347   | *Escherichia coli*          |

| Protein        | GenBank ID   | GI number | Organism                                  |
|----------------|--------------|-----------|-------------------------------------------|
| acr1           | YP_047869.1  | 50086355  | *Acinetobacter calcoaceticus*             |
| acr1           | AAC45217     | 1684886   | *Acinetobacter baylyi*                    |
| acr1           | BAB85476.1   | 18857901  | *Acinetobacter* sp. Strain M-1            |
| sucD           | P38947.1     | 172046062 | *Clostridium kluyveri*                    |
| sucD           | NP_904963.1  | 34540484  | *Porphyromonas gingivalis*                |
| bphG           | BAA03892.1   | 425213    | *Pseudomonas* sp                          |
| adhE           | AAV66076.1   | 55818563  | *Leuconostoc mesenteroides*               |
| Bld            | AAP42563.1   | 31075383  | *Clostridium saccharoperbutylacetonicum*  |
| Ald            | ACL06658.1   | 218764192 | *Desulfatibacillum alkenivorans* AK-01    |
| Ald            | YP_001452373 | 157145054 | *Citrobacter koseri* ATCC BAA-895         |
| pduP           | NP_460996.1  | 16765381  | *Salmonella enterica* Typhimurium         |
| pduP           | ABJ64680.1   | 116099531 | *Lactobacillus brevis* ATCC 367           |
| BselDRAFT_1651 | ZP_02169447  | 163762382 | *Bacillus selenitireducens* MLS10         |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); Thauer, *Science* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); Hugler et al., *J. Bacteriol.* 184:2404-2410 (2002)). The enzyme is encoded by Msed_0709 in *Metallosphaera sedula* (Alber et al., supra (2006); Berg et al., *Science* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). This enzyme has also been shown to catalyze the conversion of methylmalonyl-CoA to its corresponding aldehyde (WO 2007/141208

Step H, FIG. 3: Formyltetrahydrofolate Synthetase

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY 2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
| --- | --- | --- | --- |
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| fhs | YP_001393842.1 | 153953077 | *Clostridium kluyveri* DSM 555 |
| fhs | YP_003781893.1 | 300856909 | *Clostridium ljungdahlii* DSM 13528 |
| MGA3_08300 | EIJ83208.1 | 387590889 | *Bacillus methanolicus* MGA3 |
| PB1_13509 | ZP_10132113.1 | 387929436 | *Bacillus methanolicus* PB1 |

Steps I and J. FIG. 3: Formyltetrahydrofolate Synthetase and Methylenetetrahydrofolate Dehydrogenase In *M. thermoacetica*, *E. coli*, and *C. hydrogenoformans*, methenyltetrahydrofolate cyclohydrolase and methylenetetrahydrofolate dehydrogenase are carried out by the bifunctional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
| --- | --- | --- | --- |
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonia eutropha* H16 |
| folD | NP_348702.1 | 15895353 | *Clostridium acetobutylicum* ATCC 824 |
| folD | YP_696506.1 | 110800457 | *Clostridium perfringens* |
| MGA3_09460 | EIJ83438.1 | 387591119 | *Bacillus methanolicus* MGA3 |
| PB1_14689 | ZP_10132349.1 | 387929672 | *Bacillus methanolicus* PB1 |

| Protein | GenBank ID | GI number | Organism |
| --- | --- | --- | --- |
| dmgo | ZP_09278452.1 | 359775109 | *Arthrobacter globiformis* |
| dmgo | YP_002778684.1 | 226360906 | *Rhodococcus opacus* B4 |
| dmgo | EFY87157.1 | 322695347 | *Metarhizium acridum* CQMa 102 |
| shd | AAD53398.2 | 5902974 | *Homo sapiens* |
| shd | NP_446116.1 | GI: 25742657 | *Rattus norvegicus* |
| dmgdh | NP_037523.2 | 24797151 | *Homo sapiens* |
| dmgdh | Q63342.1 | 2498527 | *Rattus norvegicus* |

Steps K, FIG. 3: Formaldehyde-Forming Enzyme or Spontaneous

Methylene-THF, or active formaldehyde, will spontaneously decompose to formaldehyde and THF (Thorndike and Beck, *Cancer Res.* 1977, 37(4) 1125-32; Ordonez and Caraballo, *Psychopharmacol Commun.* 1975 1(3) 253-60; Kallen and Jencks, 1966, *J Biol Chem* 241(24) 5851-63). To achieve higher rates, a formaldehyde-forming enzyme can be applied. Such an activity can be obtained by engineering an enzyme that reversibly forms methylene-THF from THF and a formaldehyde donor, to release free formaldehyde. Such enzymes include glycine cleavage system enzymes which naturally transfer a formaldehyde group from methylene-THF to glycine (see Step L, FIG. 3 for candidate enzymes). Additional enzymes include serine hydroxymethyltransferase (see Step M, FIG. 3 for candidate enzymes), dimethylglycine dehydrogenase (Porter, et al., *Arch Biochem Biophys.* 1985, 243(2) 396-407; Brizio et al., 2004, (37) 2, 434-442), sarcosine dehydrogenase (Porter, et al., *Arch Biochem Biophys.* 1985, 243(2) 396-407), and dimethylglycine oxidase (Leys, et al., 2003, The EMBO Journal 22(16) 4038-4048).

Step L, FIG. 3: Glycine Cleavage System

The reversible NAD(P)H-dependent conversion of 5,10-methylenetetrahydrofolate and $CO_2$ to glycine is catalyzed by the glycine cleavage complex, also called glycine cleavage system, composed of four protein components; P, H, T and L. The glycine cleavage complex is involved in glycine catabolism in organisms such as *E. coli* and glycine biosynthesis in eukaryotes (Kikuchi et al, *Proc Jpn Acad Ser* 84:246 (2008)). The glycine cleavage system of *E. coli* is encoded by four genes: gcvPHT and lpdA (Okamura et al, *Eur J Biochem* 216:539-48 (1993); Heil et al, *Microbiol* 148:2203-14 (2002)). Activity of the glycine cleavage system in the direction of glycine biosynthesis has been demonstrated in vivo in *Saccharomyces cerevisiae* (Maaheimo et al, *Eur J Biochem* 268:2464-79 (2001)). The yeast GCV is encoded by GCV1, GCV2, GCV3 and LPD1.

| Protein | GenBank ID | GI Number | Organism |
| --- | --- | --- | --- |
| gcvP | AAC75941.1 | 1789269 | *Escherichia coli* |
| gcvT | AAC75943.1 | 1789272 | *Escherichia coli* |
| gcvH | AAC75942.1 | 1789271 | *Escherichia coli* |
| lpdA | AAC73227.1 | 1786307 | *Escherichia coli* |
| GCV1 | NP_010302.1 | 6320222 | *Saccharomyces cerevisiae* |

| Protein | GenBank ID | GI Number | Organism |
| --- | --- | --- | --- |
| GCV2 | NP_013914.1 | 6323843 | *Saccharomyces cerevisiae* |
| GCV3 | NP_009355.3 | 269970294 | *Saccharomyces cerevisiae* |
| LPD1 | NP_116635.1 | 14318501 | *Saccharomyces cerevisiae* |

Step M, FIG. 3: Serine Hydroxymethyltransferase

Conversion of glycine to serine is catalyzed by serine hydroxymethyltransferase, also called glycine hydroxymethyltranferase. This enzyme reversibly converts glycine and 5,10-methylenetetrahydrofolate to serine and THF. Serine methyltransferase has several side reactions including the reversible cleavage of 3-hydroxyacids to glycine and an aldehyde, and the hydrolysis of 5,10-methenyl-THF to 5-formyl-THF. This enzyme is encoded by glyA of *E. coli* (Plamann et al, *Gene* 22:9-18 (1983)). Serine hydroxymethyltranferase enzymes of *S. cerevisiae* include SHM1 (mitochondrial) and SHM2 (cytosolic) (McNeil et al, *J Biol Chem* 269:9155-65 (1994)). Similar enzymes have been studied in *Corynebacterium glutamicum* and *Methylobacterium extorquens* (Chistoserdova et al, *J. Bacteriol* 176:6759-62 (1994); Schweitzer et al, *J Biotechnol* 139:214-21 (2009)).

| Protein | GenBank ID | GI Number | Organism |
| --- | --- | --- | --- |
| glyA | AAC75604.1 | 1788902 | *Escherichia coli* |
| SHM1 | NP_009822.2 | 37362622 | *Saccharomyces cerevisiae* |
| SHM2 | NP_013159.1 | 6323087 | *Saccharomyces cerevisiae* |
| glyA | AAA64456.1 | 496116 | *Methylobacterium extorquens* |
| glyA | AAK60516.1 | 14334055 | *Corynebacterium glutamicum* |

Step N, FIG. 3: Serine Deaminase

Serine can be deaminated to pyruvate by serine deaminase. Serine deaminase enzymes are present in several organisms including *Clostridium acidurici* (Carter, et al., 1972, *J. Bacteriol.*, 109(2) 757-763), *Escherichia coli* (Cicchillo et al., 2004, *J Biol Chem.*, 279(31) 32418-25), and *Corneybacterium* sp. (Netzer et al., *Appl Environ Microbiol.* 2004 December; 70(12):7148-55).

| Protein | GenBank ID | GI Number | Organism |
| --- | --- | --- | --- |
| sdaA | YP_490075.1 | 388477887 | *Escherichia coli* |
| sdaB | YP_491005.1 | 388478813 | *Escherichia coli* |
| tdcG | YP_491301.1 | 388479109 | *Escherichia coli* |
| tdcB | YP_491307.1 | 388479115 | *Escherichia coli* |
| sdaA | YP_225930.1 | 62390528 | *Corynebacterium* sp. |

Step O, FIG. 3: Methylenetetrahydrofolate Reductase

In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, PLoS One. 7:e33439). Homologs of RnfC are found in other organisms by blast search. The Rnf complex is known to be a reversible complex (Fuchs (2011) *Annu. Rev. Microbiol.* 65:631-658).

| Protein | GenBank ID | GI number | Organism |
| --- | --- | --- | --- |
| Moth_1191 | YP_430048.1 | 83590039 | *Moorella thermoacetica* |
| Moth_1192 | YP_430049.1 | 83590040 | *Moorella thermoacetica* |
| metF | NP_418376.1 | 16131779 | *Escherichia coli* |
| CHY_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans* P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

Step P, FIG. 3: Acetyl-CoA Synthase

Acetyl-CoA synthase is the central enzyme of the carbonyl branch of the Wood-Ljungdahl pathway. It catalyzes the synthesis of acetyl-CoA from carbon monoxide, coenzyme A, and the methyl group from a methylated corrinoid-iron-sulfur protein. The corrinoid-iron-sulfur-protein is methylated by methyltetrahydrofolate via a methyltransferase. Expression in a foreign host entails introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes used for carbon-monoxide dehydrogenase/acetyl-CoA synthase activity typically reside in a limited region of the native genome that can be an extended operon (Ragsdale, S. W., *Crit. Rev. Biochem. Mol. Biol.* 39:165-195 (2004); Morton et al., *J. Biol. Chem.* 266:23824-23828 (1991); Roberts et al., *Proc. Natl. Acad. Sci. U.S.A.* 86:32-36 (1989). Each of the genes in this operon from the acetogen, *M. thermoacetica*, has already been cloned and expressed actively in *E. coli* (Morton et al. supra; Roberts et al. supra; Lu et al., *J. Biol. Chem.* 268:5605-5614 (1993). The protein sequences of these genes can be identified by the following GenBank accession numbers.

| Protein | GenBank ID | GI number | Organism |
| --- | --- | --- | --- |
| AcsE | YP_430054 | 83590045 | *Moorella thermoacetica* |
| AcsD | YP_430055 | 83590046 | *Moorella thermoacetica* |

| Protein | GenBank ID | GI number | Organism |
| --- | --- | --- | --- |
| AcsF | YP_430056 | 83590047 | Moorella thermoacetica |
| Orf7 | YP_430057 | 83590048 | Moorella thermoacetica |
| AcsC | YP_430058 | 83590049 | Moorella thermoacetica |
| AcsB | YP_430059 | 83590050 | Moorella thermoacetica |
| AcsA | YP_430060 | 83590051 | Moorella thermoacetica |
| CooC | YP_430061 | 83590052 | Moorella thermoacetica |

The hydrogenic bacterium, *Carboxydothermus hydrogenoformans*, can utilize carbon monoxide as a growth substrate by means of acetyl-CoA synthase (Wu et al., *PLoS Genet.* 1:e65 (2005)). In strain Z-2901, the acetyl-CoA synthase enzyme complex lacks carbon monoxide dehydrogenase due to a frameshift mutation (Wu et al. supra (2005)), whereas in strain DSM 6008, a functional unframeshifted full-length version of this protein has been purified (Svetlitchnyi et al., *Proc. Natl. Acad. Sci. U.S.A.* 101:446-451 (2004)). The protein sequences of the *C. hydrogenoformans* genes from strain Z-2901 can be identified by the following GenBank accession numbers.

| Protein | GenBank ID | GI number | Organism |
| --- | --- | --- | --- |
| AcsE | YP_360065 | 78044202 | Carboxydothermus hydrogenoformans |
| AcsD | YP_360064 | 78042962 | Carboxydothermus hydrogenoformans |
| AcsF | YP_360063 | 78044060 | Carboxydothermus hydrogenoformans |
| Orf7 | YP_360062 | 78044449 | Carboxydothermus hydrogenoformans |
| AcsC | YP_360061 | 78043584 | Carboxydothermus hydrogenoformans |
| AcsB | YP_360060 | 78042742 | Carboxydothermus hydrogenoformans |
| CooC | YP_360059 | 78044249 | Carboxydothermus hydrogenoformans |

Homologous ACS/CODH genes can also be found in the draft genome assembly of *Clostridium carboxidivorans* P7.

| Protein | GenBank ID | GI Number | Organism |
| --- | --- | --- | --- |
| AcsA | ZP_05392944.1 | 255526020 | Clostridium carboxidivorans P7 |
| CooC | ZP_05392945.1 | 255526021 | Clostridium carboxidivorans P7 |
| AcsF | ZP_05392952.1 | 255526028 | Clostridium carboxidivorans P7 |
| AcsD | ZP_05392953.1 | 255526029 | Clostridium carboxidivorans P7 |
| AcsC | ZP_05392954.1 | 255526030 | Clostridium carboxidivorans P7 |
| AcsE | ZP_05392955.1 | 255526031 | Clostridium carboxidivorans P7 |
| AcsB | ZP_05392956.1 | 255526032 | Clostridium carboxidivorans P7 |
| Orf7 | ZP_05392958.1 | 255526034 | Clostridium carboxidivorans P7 |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. U.S.A.* 103:17921-17926 (2006)). This organism contains two sets of genes that encode ACS/CODH activity (Rother and Metcalf, *Proc. Natl. Acad Sci. U.S.A.* 101:16929-16934 (2004)). The protein sequences of both sets of *M. acetivorans* genes are identified by the following GenBank accession numbers.

| Protein | GenBank ID | GI number | Organism |
| --- | --- | --- | --- |
| AcsC | NP_618736 | 20092661 | Methanosarcina acetivorans |
| AcsD | NP_618735 | 20092660 | Methanosarcina acetivorans |
| AcsF, CooC | NP_618734 | 20092659 | Methanosarcina acetivorans |
| AcsB | NP_618733 | 20092658 | Methanosarcina acetivorans |
| AcsEps | NP_618732 | 20092657 | Methanosarcina acetivorans |
| AcsA | NP_618731 | 20092656 | Methanosarcina acetivorans |
| AcsC | NP_615961 | 20089886 | Methanosarcina acetivorans |
| AcsD | NP_615962 | 20089887 | Methanosarcina acetivorans |
| AcsF, CooC | NP_615963 | 20089888 | Methanosarcina acetivorans |
| AcsB | NP_615964 | 20089889 | Methanosarcina acetivorans |
| AcsEps | NP_615965 | 20089890 | Methanosarcina acetivorans |
| AcsA | NP_615966 | 20089891 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (i.e., $K_m$, $V_m$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

Step Y, FIG. 3: Glyceraldehydes-3-phosphate Dehydrogenase and Enzymes of Lower Glycolysis Enzymes comprising Step Y, G3P to PYR include: Glyceraldehyde-3-phosphate dehydrogenase; Phosphoglycerate kinase; Phosphoglyceromutase; Enolase; Pyruvate kinase or PTS-dependent substrate import.

Glyceraldehyde-3-phosphate dehydrogenase enzymes include:

NADP-dependent glyceraldehyde-3-phosphate dehydrogenase, exemplary enzymes are:

| Protein | GenBank ID | GI Number | Organism |
| --- | --- | --- | --- |
| gapN | AAA91091.1 | 642667 | Streptococcus mutans |
| NP-GAPDH | AEC07555.1 | 330252461 | Arabidopsis thaliana |
| GAPN | AAM77679.2 | 82469904 | Triticum aestivum |
| gapN | CAI56300.1 | 87298962 | Clostridium acetobutylicum |
| NADP-GAPDH | 2D2I_A | 112490271 | Synechococcus elongatus PCC 7942 |
| NADP-GAPDH | CAA62619.1 | 4741714 | Synechococcus elongatus PCC 7942 |
| GDP1 | XP_455496.1 | 50310947 | Kluyveromyces lactis NRRL Y-1140 |
| HP1346 | NP_208138.1 | 15645959 | Helicobacter pylori 26695 | and NAD-dependent glyceraldehyde-3-phosphate dehydrogenase, exemplary enzymes are:

| Protein | GenBank ID | GI Number | Organism |
| --- | --- | --- | --- |
| TDH1 | NP_012483.1 | 6322409 | Saccharomyces cerevisiae s288c |
| TDH2 | NP_012542.1 | 6322468 | Saccharomyces cerevisiae s288c |
| TDH3 | NP_011708.1 | 632163 | Saccharomyces cerevisiae s288c |

-continued

| Protein | GenBank ID | GI Number | Organism |
|---|---|---|---|
| KLLA0A11858g | XP_451516.1 | 50303157 | Kluyveromyces lactis NRRL Y-1140 |
| KLLA0F20988g | XP_456022.1 | 50311981 | Kluyveromyces lactis NRRL Y-1140 |
| ANI_1_256144 | XP_001397496.1 | 145251966 | Aspergillus niger CBS 513.88 |
| YALI0C06369g | XP_501515.1 | 50548091 | Yarrowia lipolytica |
| CTRG_05666 | XP_002551368.1 | 255732890 | Candida tropicalis MYA-3404 |
| HPODL_1089 | EFW97311.1 | 320583095 | Hansenula polymorpha DL-1 |
| gapA | YP_490040.1 | 388477852 | Escherichia coli |

Phosphoglycerate kinase enzymes include:

| Protein | GenBank ID | GI Number | Organism |
|---|---|---|---|
| PGK1 | NP_009938.2 | 10383781 | Saccharomyces cerevisiae s288c |
| PGK | BAD83658.1 | 57157302 | Candida boidinii |
| PGK | EFW98395.1 | 320584184 | Hansenula polymorpha DL-1 |
| pgk | EIJ77825.1 | 387585500 | Bacillus methanolicus MGA3 |
| pgk | YP_491126.1 | 388478934 | Escherichia coli |

Phosphoglyceromutase (aka phosphoglycerate mutase) enzymes include;

| Protein | GenBank ID | GI Number | Organism |
|---|---|---|---|
| GPM1 | NP_012770.1 | 6322697 | Saccharomyces cerevisiae s288c |
| GPM2 | NP_010263.1 | 6320183 | Saccharomyces cerevisiae s288c |
| GPM3 | NP_014585.1 | 6324516 | Saccharomyces cerevisiae s288c |
| HPODL_1391 | EFW96681.1 | 320582464 | Hansenula polymorpha DL-1 |
| HPODL_0376 | EFW97746.1 | 320583533 | Hansenula polymorpha DL-1 |
| gpmI | EIJ77827.1 | 387585502 | Bacillus methanolicus MGA3 |
| gpmA | YP_489028.1 | 388476840 | Escherichia coli |
| gpmM | AAC76636.1 | 1790041 | Escherichia coli |

Enolase (also known as phosphopyruvate hydratase and 2-phosphoglycerate dehydratase) enzymes include:

| Protein | GenBank ID | GI Number | Organism |
|---|---|---|---|
| ENO1 | NP_011770.3 | 398366315 | Saccharomyces cerevisiae s288c |
| ENO2 | AAB68019.1 | 458897 | Saccharomyces cerevisiae s288c |
| HPODL_2596 | EFW95743.1 | 320581523 | Hansenula polymorpha DL-1 |
| eno | EIJ77828.1 | 387585503 | Bacillus methanolicus MGA3 |
| eno | AAC75821.1 | 1789141 | Escherichia coli |

Pyruvate kinase (also known as phosphoenolpyruvate kinase and phosphoenolpyruvate kinase) or PTS-dependent substrate import enzymes include those below. Pyruvate kinase, also known as phosphoenolpyruvate synthase (EC 2.7.9.2), converts pyruvate and ATP to PEP and AMP. This enzyme is encoded by the PYK1 (Burke et al., J. Biol. Chem. 258:2193-2201 (1983)) and PYK2 (Boles et al., J. Bacteriol. 179:2987-2993 (1997)) genes in S. cerevisiae. In E. coli, this activity is catalyzed by the gene products of pykF and pykA. Note that pykA and pykF are genes encoding separate enzymes potentially capable of carrying out the PYK reaction. Selected homologs of the S. cerevisiae enzymes are also shown in the table below.

| Protein | GenBank ID | GI Number | Organism |
|---|---|---|---|
| PYK1 | NP_009362 | 6319279 | Saccharomyces cerevisiae |
| PYK2 | NP_014992 | 6324923 | Saccharomyces cerevisiae |
| pykF | NP_416191.1 | 16129632 | Escherichia coli |
| pykA | NP_416368.1 | 16129807 | Escherichia coli |
| KLLA0F23397g | XP_456122.1 | 50312181 | Kluyveromyces lactis |
| CaO19.3575 | XP_714934.1 | 68482353 | Candida albicans |
| CaO19.11059 | XP_714997.1 | 68482226 | Candida albicans |
| YALI0F09185p | XP_505195 | 210075987 | Yarrowia lipolytica |
| ANI_1_1126064 | XP_001391973 | 145238652 | Aspergillus niger |
| MGA3_03005 | EIJ84220.1 | 387591903 | Bacillus methanolicus MGA3 |
| HPODL_1539 | EFW96829.1 | 320582612 | Hansenula polymorpha DL-1 |

PTS-dependent substrate uptake systems catalyze a phosphotransfer cascade that couples conversion of PEP to pyruvate with the transport and phosphorylation of carbon substrates. For example, the glucose PTS system transports glucose, releasing glucose-6-phosphate into the cytoplasm and concomitantly converting phosphoenolpyruvate to pyruvate. PTS systems are comprised of substrate-specific and non-substrate-specific components. In E. coli the two non-specific components are encoded by ptsI (Enzyme I) and ptsH (HPr). The sugar-dependent components are encoded by crr and ptsG. Pts systems have been extensively studied and are reviewed, for example in Postma et al, Microbiol Rev 57: 543-94 (1993).

| Protein | GenBank ID | GI Number | Organism |
|---|---|---|---|
| ptsG | AC74185.1 | 1787343 | Escherichia coli |
| ptsI | AAC75469.1 | 1788756 | Escherichia coli |
| ptsH | AAC75468.1 | 1788755 | Escherichia coli |
| crr | AAC75470.1 | 1788757 | Escherichia coli |

The IIA[Glc] component mediates the transfer of the phosphoryl group from histidine protein Hpr (ptsH) to the IIB[Glc] (ptsG) component. A truncated variant of the crr gene was introduced into 1,4-butanediol producing strains.

Alternatively, Phosphoenolpyruvate phosphatase (EC 3.1.3.60) catalyzes the hydrolysis of PEP to pyruvate and phosphate. Numerous phosphatase enzymes catalyze this activity, including alkaline phosphatase (EC 3.1.3.1), acid phosphatase (EC 3.1.3.2), phosphoglycerate phosphatase (EC 3.1.3.20) and PEP phosphatase (EC 3.1.3.60). PEP phosphatase enzymes have been characterized in plants such as Virginia radiate, Bruguiera sexangula and Brassica nigra. The phytase from Aspergillus fumigates, the acid phosphatase from Homo sapiens and the alkaline phosphatase of E. coli also catalyze the hydrolysis of PEP to pyruvate (Brugger et al, Appl Microbiol Biotech 63:383-9 (2004); Hayman et al, Biochem J 261:601-9 (1989); et al, The Enzymes 3rd Ed. 4:373-415 (1971))). Similar enzymes have been characterized in Campylobacter jejuni (van Mourik et al., Microbiol. 154:584-92 (2008)), Saccharomyces cerevisiae (Oshima et al., Gene 179:171-7 (1996)) and Staphylococcus aureus (Shah and Blobel, J. Bacteriol. 94:780-1

(1967)). Enzyme engineering and/or removal of targeting sequences may be required for alkaline phosphatase enzymes to function in the cytoplasm.

| Protein | GenBank ID | GI Number | Organism |
|---|---|---|---|
| phyA | O00092.1 | 41017447 | Aspergillus fumigatus |
| Acp5 | P13686.3 | 56757583 | Homo sapiens |
| phoA | NP_414917.2 | 49176017 | Escherichia coli |
| phoX | ZP_01072054.1 | 86153851 | Campylobacter jejuni |
| PHO8 | AAA34871.1 | 172164 | Saccharomyces cerevisiae |
| SaurJH1_2706 | YP_001317815.1 | 150395140 | Staphylococcus aureus |

Step Q, FIG. 3: Pyruvate Formate Lyase

Pyruvate formate-lyase (PFL, EC 2.3.1.54), encoded by pflB in *E. coli*, can convert pyruvate into acetyl-CoA and formate. The activity of PFL can be enhanced by an activating enzyme encoded by pflA (Knappe et al., *Proc. Natl. Acad. Sci U.S.A* 81:1332-1335 (1984); Wong et al., *Biochemistry* 32:14102-14110 (1993)). Keto-acid formate-lyase (EC 2.3.1.-), also known as 2-ketobutyrate formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J Biosci.* 32:1195-1206 (2007)). The enzyme is oxygen-sensitive and, like PflB, can require post-translational modification by PFL-AE to activate a glycyl radical in the active site (Hesslinger et al., *Mol. Microbiol* 27:477-492 (1998)). A pyruvate formate-lyase from *Archaeglubus fulgidus* encoded by pflD has been cloned, expressed in *E. coli* and characterized (Lehtio et al., *Protein Eng Des Sel* 17:545-552 (2004)). The crystal structures of the *A. fulgidus* and *E. coli* enzymes have been resolved (Lehtio et al., *J Mol. Biol.* 357:221-235 (2006); Leppanen et al., Structure. 7:733-744 (1999)). Additional PFL and PFL-AE candidates are found in *Lactococcus lactis* (Melchiorsen et al., *Appl Microbiol Biotechnol* 58:338-344 (2002)), and *Streptococcus mutans* (Takahashi-Abbe et al., *Oral. Microbiol Immunol.* 18:293-297 (2003)), *Chlamydomonas reinhardtii* (Hemschemeier et al., *Eukaryot. Cell* 7:518-526 (2008b); Atteia et al., *J. Biol. Chem.* 281:9909-9918 (2006)) and *Clostridium pasteurianum* (Weidner et al., *J Bacteriol.* 178:2440-2444 (1996)).

| Protein | GenBank ID | GI Number | Organism |
|---|---|---|---|
| pflB | NP_415423 | 16128870 | Escherichia coli |
| pflA | NP_415422.1 | 16128869 | Escherichia coli |
| tdcE | AAT48170.1 | 48994926 | Escherichia coli |
| pflD | NP_070278.1 | 11499044 | Archaeglubus fulgidus |
| Pfl | CAA03993 | 2407931 | Lactococcus lactis |
| Pfl | BAA09085 | 1129082 | Streptococcus mutans |
| PFL1 | XP_001689719.1 | 159462978 | Chlamydomonas reinhardtii |
| pflA1 | XP_001700657.1 | 159485246 | Chlamydomonas reinhardtii |
| Pfl | Q46266.1 | 2500058 | Clostridium pasteurianum |
| Act | CAA63749.1 | 1072362 | Clostridium pasteurianum |

Step R, FIG. 3: Pyruvate Dehydrogenase, Pyruvate Ferredoxin Oxidoreductase, Pyruvate:NADP+ Oxidoreductase The pyruvate dehydrogenase (PDH) complex catalyzes the conversion of pyruvate to acetyl-CoA (FIG. 3R). The *E. coli* PDH complex is encoded by the genes aceEF and lpdA. Enzyme engineering efforts have improved the *E. coli* PDH enzyme activity under anaerobic conditions (Kim et al., *J. Bacteriol.* 190:3851-3858 (2008); Kim et al., *Appl. Environ. Microbiol.* 73:1766-1771 (2007); Zhou et al., *Biotechnol. Lett.* 30:335-342 (2008)). In contrast to the *E. coli* PDH, the *B. subtilis* complex is active and required for growth under anaerobic conditions (Nakano et al., 179:6749-6755 (1997)). The *Klebsiella pneumoniae* PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate. Comparative kinetics of *Rattus norvegicus* PDH and BCKAD indicate that BCKAD has higher activity on 2-oxobutanoate as a substrate (Paxton et al., *Biochem. J* 234:295-303 (1986)). The *S. cerevisiae* PDH complex can consist of an E2 (LA T) core that binds E1 (PDA1, PDB1), E3 (LPD1), and Protein X (PDX1) components (Pronk et al., Yeast 12:1607-1633 (1996)). The PDH complex of *S. cerevisiae* is regulated by phosphorylation of E1 involving PKP1 (PDH kinase I), PTC5 (PDH phosphatase I), PKP2 and PTC6. Modification of these regulators may also enhance PDH activity. Coexpression of lipoyl ligase (LplA of *E. coli* and AIM22 in *S. cerevisiae*) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
|---|---|---|---|
| aceE | NP_414656.1 | 16128107 | Escherichia coli |
| aceF | NP_414657.1 | 16128108 | Escherichia coli |
| lpd | NP_414658.1 | 16128109 | Escherichia coli |
| lplA | NP_418803.1 | 16132203 | Escherichia coli |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumoniae |
| aceF | YP_001333809.1 | 152968700 | Klebsiella pneumoniae |
| lpdA | YP_001333810.1 | 152968701 | Klebsiella pneumoniae |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| AIM22 | NP_012489.2 | 83578101 | Saccharomyces cerevisiae |

As an alternative to the large multienzyme PDH complexes described above, some organisms utilize enzymes in the 2-ketoacid oxidoreductase family (OFOR) to catalyze acylating oxidative decarboxylation of 2-keto-acids. Unlike the PDH complexes, PFOR enzymes contain iron-sulfur clusters, utilize different cofactors and use ferredoxin or flavodixin as electron acceptors in lieu of NAD(P)H. Pyruvate ferredoxin oxidoreductase (PFOR) can catalyze the oxidation of pyruvate to form acetyl-CoA (FIG. 3R). The PFOR from *Desulfovibrio africanus* has been cloned and expressed in *E. coli* resulting in an active recombinant enzyme that was stable for several days in the presence of oxygen (Pieulle et al., *J Bacteriol.* 179:5684-5692 (1997)).

Oxygen stability is relatively uncommon in PFORs and is believed to be conferred by a 60 residue extension in the polypeptide chain of the *D. africanus* enzyme. The *M. thermoacetica* PFOR is also well characterized (Menon et al., *Biochemistry* 36:8484-8494 (1997)) and was even shown to have high activity in the direction of pyruvate synthesis during autotrophic growth (Furdui et al., *J. Biol Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J Biochem.* 123: 563-569 (1982)). Several additional PFOR enzymes are described in Ragsdale, *Chem. Rev.* 103:2333-2346 (2003). Finally, flavodoxin reductases (e.g., fqrB from *Helicobacter pylori* or *Campylobacter jejuni* (St Maurice et al., *J. Bacteriol.* 189:4764-4773 (2007))) or Rnf-type proteins (Seedorf et al., *Proc. Natl. Acad. Sci. U.S.A.* 105:2128-2133 (2008); Herrmann et al., *J. Bacteriol.* 190:784-791 (2008)) provide a means to generate NADH or NADPH from the reduced ferredoxin generated by PFOR These proteins are identified below.

| Protein | GenBank ID | GI Number | Organism |
|---|---|---|---|
| Por | CAA70873.1 | 1770208 | *Desulfovibrio africanus* |
| Por | YP_428946.1 | 83588937 | *Moorella thermoacetica* |
| ydbK | NP_415896.1 | 16129339 | *Escherichia coli* |
| fqrB | NP_207955.1 | 15645778 | *Helicobacter pylori* |
| fqrB | YP_001482096.1 | 157414840 | *Campylobacter jejuni* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

Pyruvate:NADP oxidoreductase (PNO) catalyzes the conversion of pyruvate to acetyl-CoA. This enzyme is encoded by a single gene and the active enzyme is a homodimer, in contrast to the multi-subunit PDH enzyme complexes described above. The enzyme from *Euglena gracilis* is stabilized by its cofactor, thiamin pyrophosphate (Nakazawa et al, *Arch Biochem Biophys* 411:183-8 (2003)). The mitochondrial targeting sequence of this enzyme should be removed for expression in the cytosol. The PNO protein of *E. gracilis* and other NADP-dependent pyruvate:NADP+ oxidoreductase enzymes are listed in the table below.

| Protein | GenBank ID | GI Number | Organism |
|---|---|---|---|
| PNO | Q94IN5.1 | 33112418 | *Euglena gracilis* |
| cgd4_690 | XP_625673.1 | 66356990 | *Cryptosporidium parvum* Iowa II |
| TPP_PFOR_PNO | XP_002765111.11 | 294867463 | *Perkinsus marinus* ATCC 50983 |

Step S, FIG. 3: Formate Dehydrogenase

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Moorella thermoacetica* (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)). Formate dehydrogenases are also found many additional organisms including *C. carboxidivorans* P7, *Bacillus methanolicus*, *Burkholderia stabilis*, *Moorella thermoacetica* ATCC 39073, *Candida boidinii*, *Candida methylica*, and *Saccharomyces cerevisiae* S288c. The soluble formate dehydrogenase from *Ralstonia eutropha* reduces NAD+(fdsG, -B, -A, -C, -D) (Oh and Bowien, 1998)

Several EM8 enzymes have been identified that have higher specificity for NADP as the cofactor as compared to NAD. This enzyme has been deemed as the NADP-dependent formate dehydrogenase and has been reported from 5 species of the *Burkholderia cepacia* complex. It was tested and verified in multiple strains of *Burkholderia multivorans*, *Burkholderia stabilis*, *Burkholderia pyrrocinia*, and *Burkholderia cenocepacia* (Hatrongjit et al., *Enzyme and Microbial Tech.*, 46: 557-561 (2010)). The enzyme from *Burkholderia stabilis* has been characterized and the apparent $K_m$ of the enzyme were reported to be 55.5 mM, 0.16 mM and 1.43 mM for formate, NADP, and NAD respectively. More gene candidates can be identified using sequence homology of proteins deposited in Public databases such as NCBI, JGI and the metagenomic databases.

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |

| Protein | GenBank ID | GI Number | Organism |
| --- | --- | --- | --- |
| fdhA, PB1_11719 | ZP_10131761.1 | 387929084 | Bacillus methanolicus PB1 |
| fdhD, MGA3_06630 | EIJ82880.1 | 387590561 | Bacillus methanolicus MGA3 |
| fdhD, PB1_11724 | ZP_10131762.1 | 387929085 | Bacillus methanolicus PB1 |
| fdh | ACF35003.1 | 194220249 | Burkholderia stabilis |
| fdh | ACF35004.1 | 194220251 | Burkholderia pyrrocinia |
| fdh | ACF35002.1 | 194220247 | Burkholderia cenocepacia |
| fdh | ACF35001.1 | 194220245 | Burkholderia multivorans |
| fdh | ACF35000.1 | 194220243 | Burkholderia cepacia |
| FDH1 | AAC49766.1 | 2276465 | Candida boidinii |
| fdh | CAA57036.1 | 1181204 | Candida methylica |
| FDH2 | P0CF35.1 | 294956522 | Saccharomyces cerevisiae S288c |
| FDH1 | NP_015033.1 | 6324964 | Saccharomyces cerevisiae S288c |
| fdsG | YP_725156.1 | 113866667 | Ralstonia eutropha |
| fdsB | YP_725157.1 | 113866668 | Ralstonia eutropha |
| fdsA | YP_725158.1 | 113866669 | Ralstonia eutropha |
| fdsC | YP_725159.1 | 113866670 | Ralstonia eutropha |
| fdsD | YP_725160.1 | 113866671 | Ralstonia eutropha |

Example IV

Production of Reducing Equivalents and Formaldehyde from Methnal

This example describes methanol metabolic pathways and other additional enzymes for generating reducing equivalents as shown in FIG. 4 and for production of formaldehyde as shown in FIG. 3.

FIG. 4, Step A—Methanol Methyltransferase

A complex of 3-methyltransferase proteins, denoted MtaA, MtaB, and MtaC, perform the desired methanol methyltransferase activity (Sauer et al., Eur. J. Biochem. 243:670-677 (1997); Naidu and Ragsdale, J. Bacteriol. 183:3276-3281 (2001); Tallant and Krzycki, J. Biol. Chem. 276:4485-4493 (2001); Tallant and Krzycki, J. Bacteriol. 179:6902-6911 (1997); Tallant and Krzycki, J. Bacteriol. 178:1295-1301 (1996); Ragsdale, S. W., Crit. Rev. Biochem. Mol. Biol. 39:165-195 (2004)).

MtaB is a zinc protein that can catalyze the transfer of a methyl group from methanol to MtaC, a corrinoid protein. Exemplary genes encoding MtaB and MtaC can be found in methanogenic archaea such as Methanosarcina barkeri (Maeder et al., J. Bacteriol. 188:7922-7931 (2006) and Methanosarcina acetivorans (Galagan et al., Genome Res. 12:532-542 (2002), as well as the acetogen, Moorella thermoacetica (Das et al., Proteins 67:167-176 (2007). In general, the MtaB and MtaC genes are adjacent to one another on the chromosome as their activities are tightly interdependent. The protein sequences of various MtaB and MtaC encoding genes in M. barkeri, M. acetivorans, and M. thermoaceticum can be identified by their following GenBank accession numbers.

| Protein | GenBank ID | GI Number | Organism |
| --- | --- | --- | --- |
| MtaB1 | YP_304299 | 73668284 | Methanosarcina barkeri |
| MtaC1 | YP_304298 | 73668283 | Methanosarcina barkeri |
| MtaB2 | YP_307082 | 73671067 | Methanosarcina barkeri |
| MtaC2 | YP_307081 | 73671066 | Methanosarcina barkeri |
| MtaB3 | YP_304612 | 73668597 | Methanosarcina barkeri |
| MtaC3 | YP_304611 | 73668596 | Methanosarcina barkeri |
| MtaB1 | NP_615421 | 20089346 | Methanosarcina acetivorans |
| MtaB1 | NP_615422 | 20089347 | Methanosarcina acetivorans |
| MtaB2 | NP_619254 | 20093179 | Methanosarcina acetivorans |
| MtaC2 | NP_619253 | 20093178 | Methanosarcina acetivorans |
| MtaB3 | NP_616549 | 20090474 | Methanosarcina acetivorans |
| MtaC3 | NP_616550 | 20090475 | Methanosarcina acetivorans |
| MtaB | YP_430066 | 83590057 | Moorella thermoacetica |
| MtaC | YP_430065 | 83590056 | Moorella thermoacetica |
| MtaA | YP_430064 | 83590056 | Moorella thermoacetica |

The MtaB1 and MtaC1 genes, YP_304299 and YP_304298, from M. barkeri were cloned into E. coli and sequenced (Sauer et al., Eur. J. Biochem. 243:670-677 (1997)). The crystal structure of this methanol-cobalamin methyltransferase complex is also available (Hagemeier et al., Proc. Natl. Acad. Sci. USA. 103:18917-18922 (2006)). The MtaB genes, YP_307082 and YP_304612, in M. barkeri were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611 were identified based on their proximity to the MtaB genes and also their homology to YP_304298. The three sets of MtaB and MtaC genes from M. acetivorans have been genetically, physiologically, and biochemically characterized (Pritchett and Metcalf, Mol. Microbiol. 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The M. thermoacetica MtaB gene was identified based on homology to the methanogenic MtaB genes and also by its adjacent chromosomal proximity to the methanol-induced corrinoid protein, MtaC, which has been crystallized (Zhou et al., Acta Crystallogr. Sect. F. Struct. Biol. Cryst. Commun. 61:537-540 (2005) and further characterized by Northern hybridization and Western Blotting ((Das et al., Proteins 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as Methanosarcina barkeri (Maeder et al., J.

Bacteriol. 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$—MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---|---|---|---|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$—MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers

| Protein | GenBank ID | GI number | Organism |
|---|---|---|---|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |
| MtaA | YP_430064 | 83590056 | *Moorella thermoacetica* |

FIG. 4, Step B—Methylenetetrahydrofolate Reductase

The conversion of methyl-THF to methylenetetrahydrofolate is catalyzed by methylenetetrahydrofolate reductase. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, PLoS One. 7:e33439). Homologs of RnfC are found in other organisms by blast search. The Rnf complex is known to be a reversible complex (Fuchs (2011) Annu. Rev. Microbiol. 65:631-658).

| Protein | GenBank ID | GI number | Organism |
|---|---|---|---|
| Moth_1191 | YP_430048.1 | 83590039 | *Moorella thermoacetica* |
| Moth_1192 | YP_430049.1 | 83590040 | *Moorella thermoacetica* |
| metF | NP_418376.1 | 16131779 | *Escherichia coli* |
| CHY_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans* P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

FIG. 4, Steps C and D—Methylenetetrahydrofolate Dehydrogenase, Methenyltetrahydrofolate Cyclohydrolase In *M. thermoacetica*, *E. coli*, and *C. hydrogenoformans*, methenyltetrahydrofolate cyclohydrolase and methylenetetrahydrofolate dehydrogenase are carried out by the bifunctional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
|---|---|---|---|
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonia eutropha* H16 |

| Protein | GenBank ID | GI number | Organism |
| --- | --- | --- | --- |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

FIG. 4, Step E—Formyltetrahydrofolate Deformylase

This enzyme catalyzes the hydrolysis of 10-formyltetrahydrofolate (formyl-THF) to THF and formate. In E. coli, this enzyme is encoded by purU and has been overproduced, purified, and characterized (Nagy, et al., J. Bacteriol. 3:1292-1298 (1995)). Homologs exist in Corynebacterium sp. U-96 (Suzuki, et al., Biosci. Biotechnol. Biochem. 69(5): 952-956 (2005)), Corynebacterium glutamicum ATCC 14067, Salmonella enterica, and several additional organisms.

| Protein | GenBank ID | GI number | Organism |
| --- | --- | --- | --- |
| purU | AAC74314.1 | 1787483 | Escherichia coli K-12 MG1655 |
| purU | BAD97821.1 | 63002616 | Corynebacterium sp. U-96 |
| purU | EHE84645.1 | 354511740 | Corynebacterium glutamicum ATCC 14067 |
| purU | NP_460715.1 | 16765100 | Salmonella enterica subsp. enterica serovar Typhimurium str. LT2 |

FIG. 4, Step F—Formyltetrahydrofolate Synthetase

Formyltetrahydrofolate synthetase ligates formate to tetrahydrofolate at the expense of one ATP. This reaction is catalyzed by the gene product of Moth_0109 in M. thermoacetica (O'brien et al., Experientia Suppl. 26:249-262 (1976); Lovell et al., Arch. Microbiol. 149:280-285 (1988); Lovell et al., Biochemistry 29:5687-5694 (1990)), FHS in Clostridium acidurici (Whitehead and Rabinowitz, J. Bacteriol. 167:203-209 (1986); Whitehead and Rabinowitz, J. Bacteriol. 170:3255-3261 (1988), and CHY_2385 in C. hydrogenoformans (Wu et al., PLoS Genet. 1:e65 (2005). Homologs exist in C. carboxidivorans P7. This enzyme is found in several other organisms as listed below.

| Protein | GenBank ID | GI number | Organism |
| --- | --- | --- | --- |
| Moth_0109 | YP_428991.1 | 83588982 | Moorella thermoacetica |
| CHY_2385 | YP_361182.1 | 78045024 | Carboxydothermus hydrogenoformans |
| FHS | P13419.1 | 120562 | Clostridium acidurici |
| CcarbDRAFT_1913 | ZP_05391913.1 | 255524966 | Clostridium carboxidivorans P7 |
| CcarbDRAFT_2946 | ZP_05392946.1 | 255526022 | Clostridium carboxidivorans P7 |
| Dhaf_0555 | ACL18622.1 | 219536883 | Desulfitobacterium hafniense |
| fhs | YP_001393842.1 | 153953077 | Clostridium kluyveri DSM 555 |
| fhs | YP_003781893.1 | 300856909 | Clostridium ljungdahlii DSM 13528 |
| MGA3_08300 | EIJ83208.1 | 387590889 | Bacillus methanolicus MGA3 |
| PB1_13509 | ZP_10132113.1 | 387929436 | Bacillus methanolicus PB1 |

FIG. 4, Step G—Formate Hydrogen Lyase

A formate hydrogen lyase enzyme can be employed to convert formate to carbon dioxide and hydrogen. An exemplary formate hydrogen lyase enzyme can be found in Escherichia coli. The E. coli formate hydrogen lyase consists of hydrogenase 3 and formate dehydrogenase-H (Maeda et al., Appl Microbiol Biotechnol 77:879-890 (2007)). It is activated by the gene product of fhlA. (Maeda et al., Appl Microbiol Biotechnol 77:879-890 (2007)). The addition of the trace elements, selenium, nickel and molybdenum, to a fermentation broth has been shown to enhance formate hydrogen lyase activity (Soini et al., Microb. Cell Fact. 7:26 (2008)). Various hydrogenase 3, formate dehydrogenase and transcriptional activator genes are shown below.

| Protein | GenBank ID | GI number | Organism |
| --- | --- | --- | --- |
| hycA | NP_417205 | 16130632 | Escherichia coli K-12 MG1655 |
| hycB | NP_417204 | 16130631 | Escherichia coli K-12 MG1655 |
| hycC | NP_417203 | 16130630 | Escherichia coli K-12 MG1655 |
| hycD | NP_417202 | 16130629 | Escherichia coli K-12 MG1655 |
| hycE | NP_417201 | 16130628 | Escherichia coli K-12 MG1655 |
| hycF | NP_417200 | 16130627 | Escherichia coli K-12 MG1655 |
| hycG | NP_417199 | 16130626 | Escherichia coli K-12 MG1655 |
| hycH | NP_417198 | 16130625 | Escherichia coli K-12 MG1655 |
| hycI | NP_417197 | 16130624 | Escherichia coli K-12 MG1655 |
| fdhF | NP_418503 | 16131905 | Escherichia coli K-12 MG1655 |
| fhlA | NP_417211 | 16130638 | Escherichia coli K-12 MG1655 |

A formate hydrogen lyase enzyme also exists in the hyperthermophilic archaeon, Thermococcus litoralis (Takacs et al., BMC. Microbiol 8:88 (2008)).

| Protein | GenBank ID | GI number | Organism |
| --- | --- | --- | --- |
| mhyC | ABW05543 | 157954626 | Thermococcus litoralis |
| mhyD | ABW05544 | 157954627 | Thermococcus litoralis |
| mhyE | ABW05545 | 157954628 | Thermococcus litoralis |
| myhF | ABW05546 | 157954629 | Thermococcus litoralis |
| myhG | ABW05547 | 157954630 | Thermococcus litoralis |
| myhH | ABW05548 | 157954631 | Thermococcus litoralis |
| fdhA | AAB94932 | 2746736 | Thermococcus litoralis |
| fdhB | AAB94931 | 157954625 | Thermococcus litoralis |

Additional formate hydrogen lyase systems have been found in Salmonella typhimurium, Klebsiella pneumoniae, Rhodospirillum rubrum, Methanobacterium formicicum (Vardar-Schara et al., Microbial Biotechnology 1:107-125 (2008)).

FIG. 4, Step H—Hydrogenase

Hydrogenase enzymes can convert hydrogen gas to protons and transfer electrons to acceptors such as ferredoxins, NAD+, or NADP+. Ralstonia eutropha H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, Biochim. Biophys. Acta, 567, 315-324 (1979); Bernhard et al., Eur. J. Biochem. 248, 179-186 (1997)). R. eutropha also contains an $O_2$-tolerant soluble hydrogenase encoded by the Hox operon which is cytoplasmic and directly reduces NAD+ at the expense of hydrogen (Schneider and Schlegel, Biochim. Biophys. Acta 452, 66-80 (1976); Burgdorf, J. Bact. 187(9) 3122-3132(2005)). Soluble hydrogenase enzymes are additionally present in several other organisms including Geobacter sulfurreducens (Coppi, Microbiology 151, 1239-1254 (2005)), Synechocystis str. PCC 6803 (Germer, J. Biol. Chem., 284(52), 36462-36472 (2009)), and Thiocapsa roseopersicina (Rakhely, Appl. Environ. Microbiol. 70(2) 722-728 (2004)). The Synechocystis enzyme is capable of generating NADPH from hydrogen. Overexpression of both the Hox operon from Synechocystis str. PCC 6803 and the accessory genes encoded by the Hyp operon from Nostoc sp. PCC 7120 led to increased hydrogenase activity compared to expression of the Hox genes alone (Germer, J. Biol. Chem. 284(52), 36462-36472 (2009)).

| Protein | GenBank ID | GI Number | Organism |
|---|---|---|---|
| HoxF | NP_942727.1 | 38637753 | Ralstonia eutropha H16 |
| HoxU | NP_942728.1 | 38637754 | Ralstonia eutropha H16 |
| HoxY | NP_942729.1 | 38637755 | Ralstonia eutropha H16 |
| HoxH | NP_942730.1 | 38637756 | Ralstonia eutropha H16 |
| HoxW | NP_942731.1 | 38637757 | Ralstonia eutropha H16 |
| HoxI | NP_942732.1 | 38637758 | Ralstonia eutropha H16 |
| HoxE | NP_953767.1 | 39997816 | Geobacter sulfurreducens |
| HoxF | NP_953766.1 | 39997815 | Geobacter sulfurreducens |
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypB | NP_484743.1 | 17228195 | Nostoc sp. PCC 7120 |
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

The genomes of E. coli and other enteric bacteria encode up to four hydrogenase enzymes (Sawers, G., Antonie Van Leeuwenhoek 66:57-88 (1994); Sawers et al., J Bacteriol. 164:1324-1331 (1985); Sawers and Boxer, Eur. J Biochem. 156:265-275 (1986); Sawers et al., J Bacteriol. 168:398-404 (1986)). Given the multiplicity of enzyme activities E. coli or another host organism can provide sufficient hydrogenase activity to split incoming molecular hydrogen and reduce the corresponding acceptor. Endogenous hydrogen-lyase enzymes of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase activity in E. coli is also dependent upon the expression of the hyp genes whose corresponding proteins are involved in the assembly of the hydrogenase complexes (Jacobi et al., Arch. Microbiol 158: 444-451 (1992); Rangarajan et al., J Bacteriol. 190:1447-1458 (2008)). The endogenous hydrogenase genes can be modified to increase the expression. For example, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. The M. thermoacetica and Clostridium ljungdahli hydrogenases are suitable for a host that lacks sufficient endogenous hydrogenase activity. M. thermoacetica and C. ljungdahli can grow with $CO_2$ as the exclusive carbon source indicating that reducing equivalents are extracted from $H_2$ to enable acetyl-CoA synthesis via the Wood-Ljungdahl pathway (Drake, H. L., J Bacteriol. 150:702-709 (1982); Drake and Daniel, Res Microbiol 155: 869-883 (2004); Kellum and Drake, J Bacteriol. 160:466-469 (1984)). M. thermoacetica has homologs to several hyp, hyc, and hyf genes from E. coli. These protein sequences encoded for by these genes are identified by the following GenBank accession numbers. In addition, several gene clusters encoding hydrogenase functionality are present in M. thermoacetica and C. ljungdahli (see for example US 2012/0003652).

| Protein | GenBank ID | GI Number | Organism |
|---|---|---|---|
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

Proteins in M. thermoacetica whose genes are homologous to the E. coli hydrogenase genes are shown below.

| Protein | GenBank ID | GI Number | Organism |
|---|---|---|---|
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | Clostridium ljungdahli |
| CLJU_c07030 | ADK13773.1 | 300434006 | Clostridium ljungdahli |
| CLJU_c07040 | ADK13774.1 | 300434007 | Clostridium ljungdahli |
| CLJU_c07050 | ADK13775.1 | 300434008 | Clostridium ljungdahli |
| CLJU_c07060 | ADK13776.1 | 300434009 | Clostridium ljungdahli |
| CLJU_c07070 | ADK13777.1 | 300434010 | Clostridium ljungdahli |
| CLJU_c07080 | ADK13778.1 | 300434011 | Clostridium ljungdahli |
| CLJU_c14730 | ADK14541.1 | 300434774 | Clostridium ljungdahli |
| CLJU_c14720 | ADK14540.1 | 300434773 | Clostridium ljungdahli |
| CLJU_c14710 | ADK14539.1 | 300434772 | Clostridium ljungdahli |
| CLJU_c14700 | ADK14538.1 | 300434771 | Clostridium ljungdahli |
| CLJU_c28670 | ADK15915.1 | 300436148 | Clostridium ljungdahli |
| CLJU_c28660 | ADK15914.1 | 300436147 | Clostridium ljungdahli |
| CLJU_c28650 | ADK15913.1 | 300436146 | Clostridium ljungdahli |
| CLJU_c28640 | ADK15912.1 | 300436145 | Clostridium ljungdahli |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J. Am. Chem. Soc.* 129:10328-10329 (2007)).

| Protein | GenBank ID | GI Number | Organism |
|---|---|---|---|
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |

Some hydrogenase and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. *J Biochem Mol Biol.* 2006 Jan. 31; 39(1):46-54.). The N-terminal domain of the protein shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, *J Biochem.* 1999 November; 126(5):917-26). Additional ferredoxin proteins have been characterized in *Helicobacter pylori* (Mukhopadhyay et al. *J Bacteriol.* 2003 May; 185(9):2927-35) and *Campylobacter jejuni* (van Vliet et al. *FEMS Microbiol Lett.* 2001 Mar. 15; 196(2):189-93). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans* P7, *Clostridium ljungdahli* and *Rhodospirillum rubrum* are predicted to encode several ferredoxins, listed below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| cooF | AAG29808.1 | 11095245 | *Carboxydothermus hydrogenoformans* |
| fdxN | CAA35699.1 | 46143 | *Rhodobacter capsulatus* |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |
| cooF | AAC45122.1 | 1498747 | *Rhodospirillum rubrum* |
| fdxN | AAA26460.1 | 152605 | *Rhodospirillum rubrum* |
| Alvin_2884 | ADC63789.1 | 288897953 | *Allochromatium vinosum* DSM 180 |
| Fdx | YP_002801146.1 | 226946073 | *Azotobacter vinelandii* DJ |
| CKL_3790 | YP_001397146.1 | 153956381 | *Clostridium kluyveri* DSM 555 |
| fer1 | NP_949965.1 | 39937689 | *Rhodopseudomonas palustris* CGA009 |
| Fdx | CAA12251.1 | 3724172 | *Thauera aromatica* |
| CHY_2405 | YP_361202.1 | 78044690 | *Carboxydothermus hydrogenoformans* |
| Fer | YP_359966.1 | 78045103 | *Carboxydothermus hydrogenoformans* |
| Fer | AAC83945.1 | 1146198 | *Bacillus subtilis* |
| fdx1 | NP_249053.1 | 15595559 | *Pseudomonas aeruginosa* PA01 |
| yfhL | AP_003148.1 | 89109368 | *Escherichia coli* K-12 |
| CLJU_c00930 | ADK13195.1 | 300433428 | *Clostridium ljungdahli* |
| CLJU_c00010 | ADK13115.1 | 300433348 | *Clostridium ljungdahli* |
| CLJU_c01820 | ADK13272.1 | 300433505 | *Clostridium ljungdahli* |
| CLJU_c17980 | ADK14861.1 | 300435094 | *Clostridium ljungdahli* |
| CLJU_c17970 | ADK14860.1 | 300435093 | *Clostridium ljungdahli* |
| CLJU_c22510 | ADK15311.1 | 300435544 | *Clostridium ljungdahli* |
| CLJU_c26680 | ADK15726.1 | 300435959 | *Clostridium ljungdahli* |
| CLJU_c29400 | ADK15988.1 | 300436221 | *Clostridium ljungdahli* |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., *Biochemistry.* 1997 Feb. 11; 36(6): 1505-13). The *Helicobacter pylori* FNR, encoded by HP1164 (fqrB), is coupled to the activity of pyruvate: ferredoxin oxidoreductase (PFOR) resulting in the pyruvate-dependent production of NADPH (St Maurice et al., *J. Bacteriol.* 189:4764-4773 (2007)). An analogous enzyme is found in *Campylobacter jejuni* (St Maurice et al., *J. Bacteriol.* 189:4764-4773 (2007)). A ferredoxin:NADP+ oxidoreductase enzyme is encoded in the *E. coli* genome by fpr (Bianchi et al. *J Bacteriol.* 1993 March; 175(6):1590-5). Ferredoxin:NAD+ oxidoreductase utilizes reduced ferredoxin to generate NADH from NAD+. In several organisms, including *E. coli*, this enzyme is a component of multifunctional dioxygenase enzyme complexes. The ferredoxin: NAD+ oxidoreductase of *E. coli*, encoded by hcaD, is a component of the 3-phenylproppionate dioxygenase system involved in involved in aromatic acid utilization (Diaz et al. *J Bacteriol.* 1998 June; 180(11):2915-23). NADH:ferredoxin reductase activity was detected in cell extracts of *Hydrogenobacter thermophilus*, although a gene with this activity has not yet been indicated (Yoon et al. Arch Microbiol. 1997 May; 167(5):275-9). Additional ferredoxin:NAD (P)+ oxidoreductases have been annotated in *Clostridium carboxydivorans* P7. The NADH-dependent reduced ferredoxin: NADP oxidoreductase of *C. kluyveri*, encoded by nfnAB, catalyzes the concomitant reduction of ferredoxin and NAD+ with two equivalents of NADPH (Wang et al, *J Bacteriol* 192: 5115-5123 (2010)). Finally, the energy-conserving membrane-associated Rnf-type proteins (Seedorf et al, *PNAS* 105:2128-2133 (2008); and Herrmann, *J. Bacteriol* 190:784-791 (2008)) provide a means to generate NADH or NADPH from reduced ferredoxin.

| Protein | GenBank ID | GI Number | Organism |
|---|---|---|---|
| fqrB | NP_207955.1 | 15645778 | *Helicobacter pylori* |
| fqrB | YP_001482096.1 | 157414840 | *Campylobacter jejuni* |
| RPA3954 | CAE29395.1 | 39650872 | *Rhodopseudomonas palustris* |
| Fpr | BAH29712.1 | 225320633 | *Hydrogenobacter thermophilus* |
| yumC | NP_391091.2 | 255767736 | *Bacillus subtilis* |
| Fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| NfnA | YP_001393861.1 | 153953096 | *Clostridium kluyveri* |
| NfnB | YP_001393862.1 | 153953097 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CLJU_c11410 (RnfB) | ADK14209.1 | 300434442 | *Clostridium ljungdahlii* |
| CLJU_c11400 (RnfA) | ADK14208.1 | 300434441 | *Clostridium ljungdahlii* |
| CLJU_c11390 (RnfE) | ADK14207.1 | 300434440 | *Clostridium ljungdahlii* |
| CLJU_c11380 (RnfG) | ADK14206.1 | 300434439 | *Clostridium ljungdahlii* |
| CLJU_c11370 (RnfD) | ADK14205.1 | 300434438 | *Clostridium ljungdahlii* |
| CLJU_c11360 (RnfC) | ADK14204.1 | 300434437 | *Clostridium ljungdahlii* |
| MOTH_1518 (NfnA) | YP_430370.1 | 83590361 | *Moorella thermoacetica* |
| MOTH_1517(NfnB) | YP_430369.1 | 83590360 | *Moorella thermoacetica* |
| CHY_1992 (NfnA) | YP_360811.1 | 78045020 | *Carboxydothermus hydrogenoformans* |
| CHY_1993 (NfnB) | YP_360812.1 | 78044266 | *Carboxydothermus hydrogenoformans* |
| CLJU_c37220 (NfnAB) | YP_003781850.1 | 300856866 | *Clostridium ljungdahlii* |

FIG. 4, Step I—Formate Dehydrogenase

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Moorella thermoacetica* (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)). Formate dehydrogenases are also found many additional organisms including *C. carboxidivorans* P7, *Bacillus methanolicus, Burkholderia stabilis, Moorella thermoacetica* ATCC 39073, *Candida boidinii, Candida methylica*, and *Saccharomyces cerevisiae* S288c. The soluble formate dehydrogenase from *Ralstonia eutropha* reduces $NAD^+$ (fdsG, -B, -A, -D) (Oh and Bowien, 1998)

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003. | 194220249 | *Burkholderia stabilis* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |

| Protein | GenBank ID | GI Number | Organism |
|---|---|---|---|
| fdsG | YP_725156.1 | 113866667 | Ralstonia eutropha |
| fdsB | YP_725157.1 | 113866668 | Ralstonia eutropha |
| fdsA | YP_725158.1 | 113866669 | Ralstonia eutropha |
| fdsC | YP_725159.1 | 113866670 | Ralstonia eutropha |
| fdsD | YP_725160.1 | 113866671 | Ralstonia eutropha |

FIG. 4, Step J, FIG. 3, Step A—Methanol Dehydrogenase

NAD+ dependent methanol dehydrogenase enzymes (EC 1.1.1.244) catalyze the conversion of methanol and NAD+ to formaldehyde and NADH. An enzyme with this activity was first characterized in *Bacillus methanolicus* (Heggeset et al., *Applied and Environmental Microbiology*, 78(15):5170-5181 (2012)). This enzyme is zinc and magnesium dependent, and activity of the enzyme is enhanced by the activating enzyme encoded by act (Kloosterman et al *J Biol Chem* 277:34785-92 (2002)). The act is a Nudix hydrolase. Several of these candidates have been identified and shown to have activity on methanol. Additional NAD(P)+ dependent enzymes can be identified by sequence homology. Methanol dehydrogenase enzymes utilizing different electron acceptors are also known in the art. Examples include cytochrome dependent enzymes such as mxaIF of the methylotroph *Methylobacterium extorquens* (Nunn et al, *Nucl Acid Res* 16:7722 (1988)). Methanol dehydrogenase enzymes of methanotrophs such as *Methylococcus capsulatis* function in a complex with methane monooxygenase (MMO) (Myronova et al, *Biochem* 45:11905-14 (2006)). Methanol can also be oxidized to formaldehyde by alcohol oxidase enzymes such as methanol oxidase (EC 1.1.3.13) of *Candida boidinii* (Sakai et al, *Gene* 114: 67-73 (1992)).

| Protein | GenBank ID | GI Number | Organism |
|---|---|---|---|
| mdh, MGA3_17392 | EIJ77596.1 | 387585261 | Bacillus methanolicus MGA3 |
| mdh2, MGA3_07340 | EIJ83020.1 | 387590701 | Bacillus methanolicus MGA3 |
| mdh3, MGA3_10725 | EIJ80770.1 | 387588449 | Bacillus methanolicus MGA3 |
| act, MGA3_09170 | EIJ83380.1 | 387591061 | Bacillus methanolicus MGA3 |
| mdh, PB1_17533 | ZP_10132907.1 | 387930234 | Bacillus methanolicus PB1 |
| mdh1, PB1_14569 | ZP_10132325.1 | 387929648 | Bacillus methanolicus PB1 |
| mdh2, PB1_12584 | ZP_10131932.1 | 387929255 | Bacillus methanolicus PB1 |
| act, PB1_14394 | ZP_10132290.1 | 387929613 | Bacillus methanolicus PB1 |
| BFZC1_05383 | ZP_07048751.1 | 299535429 | Lysinibacillus fusiformis |
| BFZC1_20163 | ZP_07051637.1 | 299538354 | Lysinibacillus fusiformis |
| Bsph_4187 | YP_001699778.1 | 169829620 | Lysinibacillus sphaericus |
| Bsph_1706 | YP_001697432.1 | 169827274 | Lysinibacillus sphaericus |
| mdh2 | YP_004681552.1 | 339322658 | Cupriavidus necator N-1 |
| nudF1 | YP_004684845.1 | 339325152 | Cupriavidus necator N-1 |
| BthaA_010200007655 | ZP_05587334.1 | 257139072 | Burkholderia thailandensis E264 |
| BTH_I1076 (MutT/NUDIX NTP pyrophosphatase) | YP_441629.1 | 83721454 | Burkholderia thailandensis E264 |
| BalcAV_11743 | ZP_10819291.1 | 402299711 | Bacillus alcalophilus ATCC 27647 |
| BalcAV_05251 | ZP_10818002.1 | 402298299 | Bacillus alcalophilus ATCC 27647 |
| alcohol dehydrogenase | YP_001447544 | 156976638 | Vibrio harveyi ATCC BAA-1116 |
| P3TCK_27679 | ZP_01220157.1 | 90412151 | Photobacterium profundum 3TCK |
| alcohol dehydrogenase | YP_694908 | 110799824 | Clostridium perfringens ATCC 13124 |
| adhB | NP_717107 | 24373064 | Shewanella oneidensis MR-1 |
| alcohol dehydrogenase | YP_237055 | 66047214 | Pseudomonas syringae pv. syringae B728a |
| alcohol dehydrogenase | YP_359772 | 78043360 | Carboxydothermus hydrogenoformans Z-2901 |
| alcohol dehydrogenase | YP_003990729 | 312112413 | Geobacillus sp. Y4.1MC1 |
| PpeoK3_010100018471 | ZP_10241531.1 | 390456003 | Paenibacillus peoriae KCTC 3763 |
| OBE_12016 | EKC54576 | 406526935 | human gut metagenome |
| alcohol dehydrogenase | YP_001343716 | 152978087 | Actinobacillus succinogenes 130Z |
| dhaT | AAC45651 | 2393887 | Clostridium pasteurianum DSM 525 |
| alcohol dehydrogenase | NP_561852 | 18309918 | Clostridium perfringens str. 13 |
| BAZO_10081 | ZP_11313277.1 | 410459529 | Bacillus azotoformans LMG 9581 |
| alcohol dehydrogenase | YP_007491369 | 452211255 | Methanosarcina mazei Tuc01 |
| alcohol dehydrogenase | YP_004860127 | 347752562 | Bacillus coagulans 36D1 |
| alcohol dehydrogenase | YP_002138168 | 197117741 | Geobacter bemidjiensis Bem |
| DesmeDRAFT_1354 | ZP_08977641.1 | 354558386 | Desulfitobacterium metallireducens DSM 15288 |
| alcohol dehydrogenase | YP_001337153 | 152972007 | Klebsiella pneumoniae subsp. pneumoniae MGH 78578 |
| alcohol dehydrogenase | YP_001113612 | 134300116 | Desulfotomaculum reducens MI-1 |
| alcohol dehydrogenase | YP_001663549 | 167040564 | Thermoanaerobacter sp. X514 |
| ACINNAV82_2382 | ZP_16224338.1 | 421788018 | Acinetobacter baumannii Naval-82 |
| alcohol dehydrogenase | YP_005052855 | 374301216 | Desulfovibrio africanus str. Walvis Bay |
| alcohol dehydrogenase | AGF87161 | 451936849 | uncultured organism |
| DesfrDRAFT_3929 | ZP_07335453.1 | 303249216 | Desulfovibrio fructosovorans JJ |
| alcohol dehydrogenase | NP_617528 | 20091453 | Methanosarcina acetivorans C2A |

-continued

| Protein | GenBank ID | GI Number | Organism |
|---|---|---|---|
| alcohol dehydrogenase | NP_343875.1 | 15899270 | Sulfolobus solfataricus P-2 |
| adh4 | YP_006863258 | 408405275 | Nitrososphaera gargensis Ga9.2 |
| Ta0841 | NP_394301.1 | 16081897 | Thermoplasma acidophilum |
| PTO1151 | YP_023929.1 | 48478223 | Picrophilus torridus DSM9790 |
| alcohol dehydrogenase | ZP_10129817.1 | 387927138 | Bacillus methanolicus PB-1 |
| cgR_2695 | YP_001139613.1 | 145296792 | Corynebacterium glutamicum R |
| alcohol dehydrogenase | YP_004758576.1 | 340793113 | Corynebacterium variabile |
| HMPREF1015_01790 | ZP_09352758.1 | 365156443 | Bacillus smithii |
| ADH1 | NP_014555.1 | 6324486 | Saccharomyces cerevisiae |
| NADH-dependent butanol dehydrogenase A | YP_001126968.1 | 138896515 | Geobacillus themodenitrificans NG80-2 |
| alcohol dehydrogenase | WP_007139094.1 | 494231392 | Flavobacterium frigoris |
| methanol dehydrogenase | WP_003897664.1 | 489994607 | Mycobacterium smegmatis |
| ADH1B | NP_000659.2 | 34577061 | Homo sapiens |
| PMI01_01199 | ZP_10750164.1 | 399072070 | Caulobacter sp. AP07 |
| YiaY | YP_026233.1 | 49176377 | Escherichia coli |
| MCA0299 | YP_112833.1 | 53802410 | Methylococcus capsulatis |
| MCA0782 | YP_113284.1 | 53804880 | Methylococcus capsulatis |
| mxaI | YP_002965443.1 | 240140963 | Methylobacterium extorquens |
| mxaF | YP_002965446.1 | 240140966 | Methylobacterium extorquens |
| AOD1 | AAA34321.1 | 170820 | Candida boidinii |
| hypothetical protein GOS_1920437 | EDA87976.1 | 142827286 | Marine metagenome JCVI_SCAF_1096627185304 |
| alcohol dehydrogenase | CAA80989.1 | 580823 | Geobacillus stearothermophilus |

An in vivo assay was developed to determine the activity of methanol dehydrogenases. This assay relies on the detection of formaldehyde (HCHO), thus measuring the forward activity of the enzyme (oxidation of methanol). To this end, a strain comprising a BDOP and lacking fimA, firmB, firmR was created using Lambda Red recombinase technology (Datsenko and Wanner, Proc. Natl. Acad. Sci. USA, 6 97(12): 6640-5 (2000). Plasmids expressing methanol dehydrogenases were transformed into the strain, then grown to saturation in LB medium+antibiotic at 37° C. with shaking. Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DETECTX Formaldehyde Detection kit (Arbor Assays; Ann Arbor, Mich.) according to manufacturer's instructions. The fimA, fimB, fimR deletions resulted in the native formaldehyde utilization pathway to be deleted, which enables the formation of formaldehyde that can be used to detect methanol dehydrogenase activity in the non-naturally occurring microbial organism.

The activity of several enzymes was measured using the assay described above. The results of four independent experiments are provided in the Table below.

Results of In Vivo Assays Showing Formaldehyde (HCHO) Production by Various Non-Naturally Occurring Microbial Organism Comprising a Plasmid Expressing a Methanol Dehydrogenase.

| Accession number Experiment 1 | HCHO (µM) | Accession number Experiment 2 | HCHO (µM) | Accession number Experiment 3 | HCHO (µM) | Accession number Experiment 4 | HCHO (µM) |
|---|---|---|---|---|---|---|---|
| EIJ77596.1 | >50 | EIJ77596.1 | >50 | EIJ77596.1 | >50 | EIJ77596.1 | >20 |
| EIJ83020.1 | >20 | NP_00659.2 | >50 | NP_561852 | >50 | ZP_11313277.1 | >50 |
| EIJ80770.1 | >50 | YP_004758576.1 | >20 | YP_002138168 | >50 | YP_001113612 | >50 |
| ZP_10132907.1 | >20 | ZP_09352758.1 | >50 | YP_026233.1 | >50 | YP_001447544 | >20 |
| ZP_10132325.1 | >20 | ZP_10129817.1 | >20 | YP_001447544 | >50 | AGF87161 | >50 |
| ZP_10131932.1 | >50 | YP_001139613.1 | >20 | Metalibrary | >50 | EDA87976.1 | >20 |
| ZP_07048751.1 | >50 | NP_014555.1 | >10 | YP_359772 | >50 | Empty vector | −0.8 |
| YP_001699778.1 | >50 | WP_007139094.1 | >10 | ZP_01220157.1 | >50 | | |
| YP_004681552.1 | >10 | NP_343875.1 | >1 | ZP_07335453.1 | >20 | | |
| ZP_10819291.1 | <1 | YP_006863258 | >1 | YP_001337953 | >20 | | |
| Empty vector | 2.33 | NP_394301.1 | >1 | YP_694908 | >20 | | |
| | | ZP_10750164.1 | >1 | NP_717107 | >20 | | |
| | | YP_023929.1 | >1 | AAC45651 | >10 | | |
| | | ZP_08977641.1 | <1 | ZP_11313277.1 | >10 | | |
| | | ZP_10117398.1 | <1 | ZP_16224338.1 | >10 | | |
| | | YP_004108045.1 | <1 | YP_001113612 | >10 | | |
| | | ZP_09753449.1 | <1 | YP_004860127 | >10 | | |
| | | Empty vector | 0.17 | YP_003310546 | >10 | | |
| | | | | YP_001343716 | >10 | | |
| | | | | NP_717107 | >10 | | |
| | | | | YP_002434746 | >10 | | |
| | | | | Empty vector | 0.11 | | |

FIG. 4, Step K—Spontaneous or Formaldehyde Activating Enzyme

The conversion of formaldehyde and THF to methylenetetrahydrofolate can occur spontaneously. It is also possible that the rate of this reaction can be enhanced by a formaldehyde activating enzyme. A formaldehyde activating enzyme (Fae) has been identified in *Methylobacterium extorquens* AM1 which catalyzes the condensation of formaldehyde and tetrahydromethanopterin to methylene tetrahydromethanopterin (Vorholt, et al., *J. Bacteriol.*, 182(23), 6645-6650 (2000)). It is possible that a similar enzyme exists or can be engineered to catalyze the condensation of formaldehyde and tetrahydrofolate to methylenetetrahydrofolate. Homologs exist in several organisms including *Xanthobacter autotrophicus* Py2 and *Hyphomicrobium denitrificans* ATCC 51888.

| Protein | GenBank ID | GI Number | Organism |
|---|---|---|---|
| MexAM1_META1p1766 | Q9FA38.3 | 17366061 | *Methylobacterium extorquens* AM1 |
| Xaut_0032 | YP_001414948.1 | 154243990 | *Xanthobacter autotrophicus* Py2 |
| Hden_1474 | YP_003755607.1 | 300022996 | *Hyphomicrobium denitrificans* ATCC 51888 |

FIG. 4, Step L—Formaldehyde Dehydrogenase

Oxidation of formaldehyde to formate is catalyzed by formaldehyde dehydrogenase. An NAD+ dependent formaldehyde dehydrogenase enzyme is encoded by fdhA of *Pseudomonas putida* (Ito et al, *J Bacteriol* 176: 2483-2491 (1994)). Additional formaldehyde dehydrogenase enzymes include the NAD+ and glutathione independent formaldehyde dehydrogenase from *Hyphomicrobium zavarzinii* (Jerome et al, Appl Microbiol Biotechnol 77:779-88 (2007)), the glutathione dependent formaldehyde dehydrogenase of *Pichia pastoris* (Sunga et al, Gene 330:39-47 (2004)) and the NAD(P)+ dependent formaldehyde dehydrogenase of *Methylobacter marinus* (Speer et al, FEMS Microbiol Lett, 121(3):349-55 (1994)).

| Protein | GenBank ID | GI Number | Organism |
|---|---|---|---|
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| fdh | P47734.2 | 221222447 | *Methylobacter marinus* |

In addition to the formaldehyde dehydrogenase enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, *J Bacteriol* 182:6645-50 (2000)). The enzymes of this pathway are S-(hydroxymethyl)glutathione synthase (EC 4.4.1.22), glutathione-dependent formaldehyde dehydrogenase (EC 1.1.1.284) and S-formylglutathione hydrolase (EC 3.1.2.12).

FIG. 4, Step M—Spontaneous or S-(hydroxymethyl)glutathione Synthase

While conversion of formaldehyde to S-hydroxymethylglutathione can occur spontaneously in the presence of glutathione, it has been shown by Goenrich et al (Goenrich, et al., *J Biol Chem* 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for glutathione-dependent formaldehyde dehydrogenase, which catalyzes the subsequent oxidation of S-hydroxymethylglutathione. Putative proteins with sequence identity to Gfa from *P. denitrificans* are present also in *Rhodobacter sphaeroides*, *Sinorhizobium meliloti*, and *Mesorhizobium loti*.

| Protein | GenBank ID | GI Number | Organism |
|---|---|---|---|
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizobium loti* MAFF303099 |

FIG. 4, Step N—Glutathione-Dependent Formaldehyde Dehydrogenase

Glutathione-dependent formaldehyde dehydrogenase (GS-FDH) belongs to the family of class III alcohol dehydrogenases. Glutathione and formaldehyde combine non-enzymatically to form hydroxymethylglutathione, the true substrate of the GS-FDH catalyzed reaction. The product, S-formylglutathione, is further metabolized to formic acid.

| Protein | GenBank ID | GI Number | Organism |
|---|---|---|---|
| frmA | YP_488650.1 | 388476464 | *Escherichia coli* K-12 MG1655 |
| SFA1 | NP_010113.1 | 6320033 | *Saccharomyces cerevisiae* S288c |
| flhA | AAC44551.1 | 1002865 | *Paracoccus denitrificans* |
| adhI | AAB09774.1 | 986949 | *Rhodobacter sphaeroides* |

FIG. 4, Step O—S-Formylglutathione Hydrolase

S-formylglutathione hydrolase is a glutathione thiol esterase found in bacteria, plants and animals. It catalyzes conversion of S-formylglutathione to formate and glutathione. The fghA gene of *P. denitrificans* is located in the same operon with gfa and flhA, two genes involved in the oxidation of formaldehyde to formate in this organism. In *E. coli*, FrmB is encoded in an operon with FrmR and FrmA, which are proteins involved in the oxidation of formaldehyde. YeiG of *E. coli* is a promiscuous serine hydrolase; its highest specific activity is with the substrate S-formylglutathione.

| Protein | GenBank ID | GI Number | Organism |
|---|---|---|---|
| frmB | NP_414889.1 | 16128340 | Escherichia coli K-12 MG1655 |
| yeiG | AAC75215.1 | 1788477 | Escherichia coli K-12 MG1655 |
| fghA | AAC44554.1 | 1002868 | Paracoccus denitrificans | the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, *C. ljungdahli* and *Campylobacter curvus* 525.92.

| Protein | GenBank ID | GI Number | Organism |
|---|---|---|---|
| CODH (putative) | YP_430813 | 83590804 | Moorella thermoacetica |
| CODH-II (CooS-II) | YP_358957 | 78044574 | Carboxydothermus hydrogenoformans |
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |
| CLJU_c09110 | ADK13979.1 | 300434212 | Clostridium ljungdahli |
| CLJU_c09100 | ADK13978.1 | 300434211 | Clostridium ljungdahli |
| CLJU_c09090 | ADK13977.1 | 300434210 | Clostridium ljungdahli |

FIG. 4, Step P—Carbon Monoxide Dehydrogenase (CODH)

CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicolinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of Example V Methods for Formaldehyde Fixation Provided herein are exemplary pathways, which utilize formaldehyde produced from the oxidation of methanol (see, e.g., FIG. 3, step A, or FIG. 4, step J) or from formate assimilation pathways described in Example III (see, e.g., FIG. 3) in the formation of intermediates of certain central metabolic pathways that can be used for the production of compounds disclosed herein.

One exemplary pathway that can utilize formaldehyde produced from the oxidation of methanol is shown in FIG. 3, which involves condensation of formaldehyde and D-ribulose-5-phosphate to form hexulose-6-phosphate (h6p) by hexulose-6-phosphate synthase (FIG. 3, step B). The enzyme can use $Mg^{2+}$ or $Mn^{2+}$ for maximal activity, although other metal ions are useful, and even non-metal-ion-dependent mechanisms are contemplated. H6p is converted into fructose-6-phosphate by 6-phospho-3-hexuloisomerase (FIG. 3, step C).

Another exemplary pathway that involves the detoxification and assimilation of formaldehyde produced from the oxidation of methanol is shown in FIG. 3 and proceeds through dihydroxyacetone. Dihydroxyacetone synthase is a special transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis (FIG. 3). The DHA obtained from DHA synthase can be further phosphorylated to form DHA phosphate and assimilated into glycolysis and several other pathways (FIG. 3). Alternatively, or in addition, a fructose-6-phosphate aldolase can be used to catalyze the conversion of DHA and G3P to fructose-6-phosphate (FIG. 3, step Z).

FIG. 3, Steps B and C—Hexulose-6-phosphate Synthase (Step B) and 6-phospho-3-hexuloisomerase (Step C)

Both of the hexulose-6-phosphate synthase and 6-phospho-3-hexuloisomerase enzymes are found in several organisms, including methanotrophs and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasueda et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of formaldehyde (Orita et al., 2007, Appl Microbiol Biotechnol. 76:439-445). In some organisms, these two enzymes naturally exist as a fused version that is bifunctional.

Exemplary candidate genes for hexulose-6-phopshate synthase are:

| Protein | GenBank ID | GI number | Organism |
| --- | --- | --- | --- |
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |
| Hps | YP_544362.1 | 91774606 | *Methylobacillus flagellatus* |
| Hps | YP_545763.1 | 91776007 | *Methylobacillus flagellatus* |
| Hps | AAG29505.1 | 11093955 | *Aminomonas aminovorus* |
| SgbH | YP_004038706.1 | 313200048 | *Methylovorus* sp. MP688 |
| Hps | YP_003050044.1 | 253997981 | *Methylovorus glucosetrophus* SIP3-4 |
| Hps | YP_003990382.1 | 312112066 | *Geobacillus* sp. Y4.1MC1 |
| Hps | gb|AAR91478.1 | 40795504 | *Geobacillus* sp. M10EXG |
| Hps | YP_007402409.1 | 448238351 | *Geobacillus* sp. GHH01 |

Exemplary gene candidates for 6-phospho-3-hexuloisomerase are:

| Protein | GenBank ID | GI number | Organism |
| --- | --- | --- | --- |
| Phi | AAR39393.1 | 40074228 | *Bacillus methanolicus* MGA3 |
| Phi | EIJ81376.1 | 387589056 | *Bacillus methanolicus* PB1 |
| Phi | BAA83098.1 | 5706383 | *Methylomonas aminofaciens* |
| RmpB | BAA90545.1 | 6899860 | *Mycobacterium gastri* |
| Phi | YP_545762.1 | 91776006 | *Methylobacillus flagellatus* KT |
| Phi | YP_003051269.1 | 253999206 | *Methylovorus glucosetrophus* SIP3-4 |
| Phi | YP_003990383.1 | 312112067 | *Geobacillus* sp. Y4.1MC1 |
| Phi | YP_007402408.1 | 448238350 | *Geobacillus* sp. GHH01 |

Candidates for enzymes where both of these functions have been fused into a single open reading frame include the following.

| Protein | GenBank ID | GI number | Organism |
| --- | --- | --- | --- |
| PH1938 | NP_143767.1 | 14591680 | *Pyrococcus horikoshii* OT3 |
| PF0220 | NP_577949.1 | 18976592 | *Pyrococcus furiosus* |
| TK0475 | YP_182888.1 | 57640410 | *Thermococcus kodakaraensis* |
| PAB1222 | NP_127388.1 | 14521911 | *Pyrococcus abyssi* |
| MCA2738 | YP_115138.1 | 53803128 | *Methylococcus capsulatas* |
| Metal_3152 | EIC30826.1 | 380884949 | *Methylomicrobium album* BG8 |

FIG. 3, Step D—Dihydroxyacetone Synthase

The dihydroxyacetone synthase enzyme in *Candida boidinii* uses thiamine pyrophosphate and $Mg^{2+}$ as cofactors and is localized in the peroxisome. The enzyme from the methanol-growing carboxydobacterium, *Mycobacter* sp. strain JC1 DSM 3803, was also found to have DHA synthase and kinase activities (Ro et al., 1997, J Bac 179(19):6041-7). DHA synthase from this organism also has similar cofactor requirements as the enzyme from *C. boidinii*. The $K_m$s for formaldehyde and xylulose 5-phosphate were reported to be 1.86 mM and 33.3 microM, respectively. Several other mycobacteria, excluding only *Mycobacterium tuberculosis*, can use methanol as the sole source of carbon and energy and are reported to use dihydroxyacetone synthase (Part et al., 2003, JBac 185(1): 142-7.

| Protein | GenBank ID | GI number | Organism |
| --- | --- | --- | --- |
| DAS1 | AAC83349.1 | 3978466 | *Candida boidinii* |
| HPODL_2613 | EFW95760.1 | 320581540 | *Ogataea parapolymorpha* DL-1 (*Hansenula polymorpha* DL-1) |
| | AAG12171.2 | 18497328 | *Mycobacter* sp. strain JC1 DSM 3803 |

FIG. 3, Step Z—Fructose-6-phosphate Aldolase

Fructose-6-phosphate aldolase (F6P aldolase) can catalyze the combination of dihydroxyacetone (DHA) and glyceraldehyde-3-phosphate (G3P) to form fructose-6-phosphate. This activity was recently discovered in *E. coli* and the corresponding gene candidate has been termed fsa (Schurmann and Sprenger, *J. Biol. Chem.*, 2001, 276(14), 11055-11061). The enzyme has narrow substrate specificity and cannot utilize fructose, fructose 1-phosphate, fructose 1,6-bisphosphate, or dihydroxyacetone phosphate. It can however use hydroxybutanone and acetol instead of DHA. The purified enzyme displayed a $V_{max}$ of 7 units/mg of protein for fructose 6-phosphate cleavage (at 30 degrees C., pH 8.5 in 50 mm glycylglycine buffer). For the aldolization reaction a $V_{max}$ of 45 units/mg of protein was found; $K_m$ values for the substrates were 9 mM for fructose 6-phosphate, 35 mM for dihydroxyacetone, and 0.8 mM for glyceraldehyde 3-phosphate. The enzyme prefers the aldol formation over the cleavage reaction.

The selectivity of the *E. coli* enzyme towards DHA can be improved by introducing point mutations. For example, the mutation A129S improved reactivity towards DHA by over 17 fold in terms of $K_{cat}/K_m$ (Gutierrez et al., *Chem Commun (Camb)*, 2011, 47(20), 5762-5764). The same mutation reduced the catalytic efficiency on hydroxyacetone by more than 3 fold and reduced the affinity for glycoaldehyde by more than 3 fold compared to that of the wild type enzyme (Castillo et al., Advanced Synthesis & Catalysis, 352(6), 1039-1046). Genes similar to fsa have been found in other genomes by sequence homology. Some exemplary gene candidates have been listed below.

| Gene | Protein accession no. | GI number | Organism |
|---|---|---|---|
| fsa | AAC73912.2 | 87081788 | *Escherichia coli* K12 |
| talC | AAC76928.1 | 1790382 | *Escherichia coli* K12 |
| fsa | WP_017209835.1 | 515777235 | *Clostridium beijerinckii* |
| DR_1337 | AAF10909.1 | 6459090 | *Deinococcus radiodurans* R1 |
| talC | NP_213080.1 | 15605703 | *Aquifex aeolicus* VF5 |
| MJ_0960 | NP_247955.1 | 15669150 | *Methanocaldococcus janaschii* |
| mipB | NP_993370.2 | 161511381 | *Yersinia pestis* |

As Described Below, there is an Energetic Advantage to Using F6P Aldolase in the DHA Pathway.

The assimilation of formaldehyde formed by the oxidation of methanol can proceed either via the dihydroxyacetone (DHA) pathway (step D, FIG. 3) or the Ribulose monophosphate (RuMP) pathway (steps B and C, FIG. 3). In the RuMP pathway, formaldehyde combines with ribulose-5-phosphate to form F6P. F6P is then either metabolized via glycolysis or used for regeneration of ribulose-5-phosphate to enable further formaldehyde assimilation. Notably, ATP hydrolysis is not required to form F6P from formaldehyde and ribulose-5-phosphate via the RuMP pathway.

In contrast, in the DHA pathway, formaldehyde combines with xylulose-5-phosphate (X5P) to form dihydroxyacetone (DHA) and glyceraldehyde-3-phosphate (G3P). Some of the DHA and G3P must be metabolized to F6P to enable regeneration of xylulose-5-phosphate. In the standard DHA pathway, DHA and G3P are converted to F6P by three enzymes: DHA kinase, fructose bisphosphate aldolase, and fructose bisphosphatase. The net conversion of DHA and G3P to F6P requires ATP hydrolysis as described below. First, DHA is phosphorylated to form DHA phosphate (DHAP) by DHA kinase at the expense of an ATP. DHAP and G3P are then combined by fructose bisphosphate aldolase to form fructose-1,6-diphosphate (FDP). FDP is converted to F6P by fructose bisphosphatase, thus wasting a high energy phosphate bond.

A more ATP efficient sequence of reactions is enabled if DHA synthase functions in combination with F6P aldolase as opposed to in combination with DHA kinase, fructose bisphosphate aldolase, and fructose bisphosphatase. F6P aldolase enables direct conversion of DHA and G3P to F6P, bypassing the need for ATP hydrolysis. Overall, DHA synthase when combined with F6P aldolase is identical in energy demand to the RuMP pathway. Both of these formaldehyde assimilation options (i.e., RuMP pathway, DHA synthase+F6P aldolase) are superior to DHA synthase combined with DHA kinase, fructose bisphosphate aldolase, and fructose bisphosphatase in terms of ATP demand.

Example VI

Phosphoketolase-Dependent Acetyl-CoA Synthesis Enzymes

This Example provides genes that can be used for enhancing carbon flux through acetyl-CoA using phosphoketolase enzymes.

FIG. 3, Step T—Fructose-6-phosphate Phosphoketolase

Conversion of fructose-6-phosphate and phosphate to acetyl-phosphate and erythrose-5-phosphate can be carried out by fructose-6-phosphate phosphoketolase (EC 4.1.2.22). Conversion of fructose-6-phosphate and phosphate to acetyl-phosphate and erythrose-5-phosphate is one of the key reactions in the *Bifidobacterium* shunt. There is evidence for the existence of two distinct phosphoketolase enzymes in bifidobacteria (Sgorbati et al, 1976, Antonie Van Leeuwenhoek, 42(1-2) 49-57; Grill et al, 1995, Curr Microbiol, 31(1); 49-54). The enzyme from *Bifidobacterium dentium* appeared to be specific solely for fructose-6-phosphate (EC: 4.1.2.22) while the enzyme from *Bifidobacterium pseudolongum* subsp. *globosum* is able to utilize both fructose-6-phosphate and D-xylulose 5-phosphate (EC: 4.1.2.9) (Sgorbati et al, 1976, Antonie Van Leeuwenhoek, 42(1-2) 49-57). The enzyme encoded by the xfp gene, originally discovered in *Bifidobacterium animalis lactis*, is the dual-specificity enzyme (Meile et al., 2001, *J Bacteriol*, 183, 2929-2936; Yin et al, 2005, FEMS Microbiol Lett, 246(2); 251-257). Additional phosphoketolase enzymes can be found in *Leuconostoc mesenteroides* (Lee et al, Biotechnol Lett. 2005 June; 27(12):853-8), *Clostridium acetobutylicum* ATCC 824 (Servinsky et al, Journal of Industrial Microbiology & Biotechnology, 2012, 39, 1859-1867), *Aspergillus nidulans* (Kocharin et al, 2013, Biotechnol Bioeng, 110(8), 2216-2224; Papini, 2012, Appl Microbiol Biotechnol, 95 (4), 1001-1010), *Bifidobacterium breve* (Suziki et al, 2010, Acta Crystallogr Sect F Struct Biol Cryst Commun., 66 (Pt 8):941-3), *Lactobacillus paraplantarum* (Jeong et al, 2007, J Microbiol Biotechnol, 17(5), 822-9).

| Protein | GENBANK ID | GI NUMBER | Organism |
|---|---|---|---|
| xfp | YP_006280131.1 | 386867137 | *Bifidobacterium animalis lactis* |
| xfp | AAV66077.1 | 55818565 | *Leuconostoc mesenteroides* |
| CAC1343 | NP_347971.1 | 15894622 | *Clostridium acetobutylicum* ATCC 824 |
| xpkA | CBF76492.1 | 259482219 | *Aspergillus nidulans* |
| xfp | WP_003840380.1 | 489937073 | *Bifidobacterium dentium* ATCC 27678 |
| xfp | AAR98788.1 | 41056827 | *Bifidobacterium pseudolongum* subsp. *globosum* |
| xfp | WP_022857642.1 | 551237197 | *Bifidobacterium pseudolongum* subsp. *globosum* |
| xfp | ADF97524.1 | 295314695 | *Bifidobacterium breve* |
| xfp | AAQ64626.1 | 34333987 | *Lactobacillus paraplantarum* |

FIG. 3, Step U—Xylulose-5-phosphate Phosphoketolase

Conversion of xylulose-5-phosphate and phosphate to acetyl-phosphate and glyceraldehyde-3-phosphate can be carried out by xylulose-5-phosphate phosphoketolase (EC 4.1.2.9). There is evidence for the existence of two distinct phosphoketolase enzymes in bifidobacteria (Sgorbati et al, 1976, Antonie Van Leeuwenhoek, 42 (1-2) 49-57; Grill et al, 1995, Curr Microbiol, 31(1); 49-54). The enzyme from *Bifidobacterium dentium* appeared to be specific solely for fructose-6-phosphate (EC: 4.1.2.22) while the enzyme from

*Bifidobacterium pseudolongum* subsp. *globosum* is able to utilize both fructose-6-phosphate and D-xylulose 5-phosphate (EC: 4.1.2.9) (Sgorbati et al, 1976, Antonie Van Leeuwenhoek, 42(1-2) 49-57). Many characterized enzymes have dual-specificity for xylulose-5-phosphate and fructose-6-phosphate. The enzyme encoded by the xfp gene, originally discovered in *Bifidobacterium animalis lactis*, is the dual-specificity enzyme (Meile et al., 2001, J Bacteriol, 183, 2929-2936; Yin et al, 2005, FEMS Microbiol Lett, 246(2); 251-257). Additional phosphoketolase enzymes can be found in *Leuconostoc mesenteroides* (Lee et al, Biotechnol Lett. 2005 June; 27(12):853-8), *Clostridium acetobutylicum* ATCC 824 (Servinsky et al, Journal of Industrial Microbiology & Biotechnology, 2012, 39, 1859-1867), *Aspergillus nidulans* (Kocharin et al, 2013, Biotechnol Bioeng, 110(8), 2216-2224; Papini, 2012, Appl Microbiol Biotechnol, 95 (4), 1001-1010), *Bifidobacterium breve* (Suziki et al, 2010, Acta Crystallogr Sect F Struct Biol Cryst Commun., 66 (Pt 8):941-3), and *Lactobacillus paraplantarum* (Jeong et al, 2007, J Microbiol Biotechnol 17 (5), 822-9).

| Protein | GENBANK ID | GI NUMBER | Organism |
|---|---|---|---|
| xfp | YP_006280131.1 | 386867137 | *Bifidobacterium animalis lactis* |
| xfp | AAV66077.1 | 55818565 | *Leuconostoc mesenteroides* |
| CAC1343 | NP_347971.1 | 15894622 | *Clostridium acetobutylicum* ATCC 824 |
| xpkA | CBF76492.1 | 259482219 | *Aspergillus nidulans* |
| xfp | AAR98788.1 | 41056827 | *Bifidobacterium pseudolongum* subsp. *globosum* |
| xfp | WP_022857642.1 | 551237197 | *Bifidobacterium pseudolongum* subsp. *globosum* |
| xfp | ADF97524.1 | 295314695 | *Bifidobacterium breve* |
| xfp | AAQ64626.1 | 34333987 | *Lactobacillus paraplantarum* |

FIG. 3, Step V—Phosphotransacetylase

The formation of acetyl-CoA from acetyl-phosphate can be catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction can also be catalyzed by some phosphotransbutyrylase enzymes (EC 2.3.1.19), including the ptb gene products from *Clostridium acetobutylicum* (Wiesenbom et al., App. Environ. Microbiol. 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001). Homologs to the *E. coli* pta gene exist in several other organisms including *Salmonella enterica* and *Chlamydomonas reinhardtii*.

| Protein | GenBank ID | GI Number | Organism |
|---|---|---|---|
| Pta | NP_416800.1 | 71152910 | *Escherichia coli* |
| Pta | P39646 | 730415 | *Bacillus subtilis* |
| Pta | A5N801 | 146346896 | *Clostridium kluyveri* |
| Pta | Q9X0L4 | 6685776 | *Thermotoga maritime* |
| Ptb | NP_349676 | 34540484 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |
| Pta | NP_461280.1 | 16765665 | *Salmonella enterica* subsp. *enterica* serovar *Typhimurium* str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

FIG. 3, Step W—Acetate Kinase

Acetate kinase (EC 2.7.2.1) can catalyze the reversible ATP-dependent phosphorylation of acetate to acetylphosphate. Exemplary acetate kinase enzymes have been characterized in many organisms including *E. coli*, *Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)). Homologs exist in several other organisms including *Salmonella enterica* and *Chlamydomonas reinhardtii*.

| Protein | GenBank ID | GI Number | Organism |
|---|---|---|---|
| ackA | NP_416799.1 | 16130231 | *Escherichia coli* |
| Ack | AAB18301.1 | 1491790 | *Clostridium acetobutylicum* |
| Ack | AAA72042.1 | 349834 | *Methanosarcina thermophila* |
| purT | AAC74919.1 | 1788155 | *Escherichia coli* |
| buk1 | NP_349675 | 15896326 | *Clostridium acetobutylicum* |
| buk2 | Q97II1 | 20137415 | *Clostridium acetobutylicum* |
| ackA | NP_461279.1 | 16765664 | *Salmonella typhimurium* |
| ACK1 | XP_001694505.1 | 159472745 | *Chlamydomonas reinhardtii* |
| ACK2 | XP_001691682.1 | 159466992 | *Chlamydomonas reinhardtii* |

FIG. 3, Step X—Acetyl-CoA Transferase, Synthetase, or Ligase

The acylation of acetate to acetyl-CoA can be catalyzed by enzymes with acetyl-CoA synthetase, ligase or transferase activity. Two enzymes that can catalyze this reaction are AMP-forming acetyl-CoA synthetase or ligase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599

(1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184: 636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are shown below.

| Protein | GenBank ID | GI Number | Organism |
| --- | --- | --- | --- |
| Acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |
| Scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

An acetyl-CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosaka et al., *Biosci. Biotechnol Biochem.* 71:58-68 (2007)). These proteins are identified below.

| Protein | GenBank ID | GI Number | Organism |
| --- | --- | --- | --- |
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* ATCC 13032 |
| cg0592 | YP_224801.1 | 62389399 | *Corynebacterium glutamicum* ATCC 13032 |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

Additional exemplary acetyl-CoA transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J Biochem.* 212:121-127 (1993); Sohling et al., *J. Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These proteins are identified below.

| Protein | GenBank ID | GI Number | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

Example VII

Attenuation or Disruption of Endogenous Enzymes

This example provides endogenous enzyme targets for attenuation or disruption that can be used for enhancing carbon flux through acetyl-CoA.

DHA Kinase

Methylotrophic yeasts typically utilize a cytosolic DHA kinase to catalyze the ATP-dependent activation of DHA to DHAP. DHAP together with G3P is combined to form fructose-1,6-bisphosphate (FBP) by FBP aldolase. FBP is then hydrolyzed to F6P by fructose bisphosphatase. The net conversion of DHA and G3P to F6P by this route is energetically costly (1 ATP) in comparison to the F6P aldolase route, described above and shown in FIG. 3. DHA kinase also competes with F6P aldolase for the DHA substrate. Attenuation of endogenous DHA kinase activity will thus improve the energetics of formaldehyde assimilation pathways, and also increase the intracellular availability of DHA for DHA synthase. DHA kinases of *Saccharomyces cerevisiae*, encoded by DAK1 and DAK2, enable the organism to maintain low intracellular levels of DHA (Molin et al, *J Biol Chem* 278:1415-23 (2003)). In methylotrophic yeasts DHA kinase is essential for growth on methanol (Luers et al, *Yeast* 14:759-71 (1998)). The DHA kinase enzymes of *Hansenula polymorpha* and *Pichia pastoris* are encoded by DAK (van der Klei et al, *Curr Genet* 34:1-11 (1998); Luers et al, supra). DAK enzymes in other organisms can be identified by sequence similarity to known enzymes.

| Protein | GenBank ID | GI Number | Organism |
|---|---|---|---|
| DAK1 | NP_013641.1 | 6323570 | *Saccharomyces cerevisiae* |
| DAK2 | NP_116602.1 | 14318466 | *Saccharomyces cerevisiae* |
| DAK | AAC27705.1 | 3171001 | *Hansenula polymorpha* |
| DAK | AAC39490.1 | 3287486 | *Pichia pastoris* |
| DAK2 | XP_505199.1 | 50555582 | *Yarrowia lipolytica* |

Methanol Oxidase

Attenuation of redox-inefficient endogenous methanol oxidizing enzymes, combined with increased expression of a cytosolic NADH-dependent MeDH, will enable redox-efficient oxidation of methanol to formaldehyde in the cytosol. Methanol oxidase, also called alcohol oxidase (EC 1.1.3.13), catalyzes the oxygen-dependent oxidation of methanol to formaldehyde and hydrogen peroxide. In eukaryotic organisms, alcohol oxidase is localized in the peroxisome. Exemplary methanol oxidase enzymes are encoded by AOD of *Candida boidinii* (Sakai and Tani, *Gene* 114:67-73 (1992)); and AOX of *H. polymorpha, P. methanolica* and *P. pastoris* (Ledeboer et al, Nucl Ac Res 13:3063-82 (1985); Koutz et al, Yeast 5:167-77 (1989); Nakagawa et al, Yeast 15:1223-1230 (1999)).

| Protein | GenBank ID | GI Number | Organism |
|---|---|---|---|
| AOX2 | AAF02495.1 | 6049184 | *Pichia methanolica* |
| AOX1 | AAF02494.1 | 6049182 | *Pichia methanolica* |
| AOX1 | AAB57849.1 | 2104961 | *Pichia pastoris* |
| AOX2 | AAB57850.1 | 2104963 | *Pichia pastoris* |
| AOX | P04841.1 | 113652 | *Hansenula polymorpha* |
| AOD1 | Q00922.1 | 231528 | *Candida boidinii* |
| AOX1 | AAQ99151.1 | 37694459 | *Ogataea pini* |

PQQ-Dependent MeDH

PQQ-dependent MeDH from *M. extorquens* (mxaIF) uses cytochrome as an electron carrier (Nunn et al, Nucl Acid Res 16:7722 (1988)). MeDH enzymes of methanotrophs such as *Methylococcus capsulatis* function in a complex with methane monooxygenase (MMO) (Myronova et al, Biochem 45:11905-14 (2006)). Note that of accessory proteins, cytochrome CL and PQQ biosynthesis enzymes are needed for active MeDH. Attenuation of one or more of these required accessory proteins, or retargeting the enzyme to a different cellular compartment, would also have the effect of attenuating PQQ-dependent MeDH activity.

| Protein | GenBank ID | GI Number | Organism |
|---|---|---|---|
| MCA0299 | YP_112833.1 | 53802410 | *Methylococcus capsulatis* |
| MCA0782 | YP_113284.1 | 53804880 | *Methylococcus capsulatis* |
| mxaI | YP_002965443.1 | 240140963 | *Methylobacterium extorquens* |
| mxaF | YP_002965446.1 | 240140966 | *Methylobacterium extorquens* |

DHA Synthase and Other Competing Formaldehyde Assimilation and Dissimilation Pathways Carbon-efficient formaldehyde assimilation can be improved by attenuation of competing formaldehyde assimilation and dissimilation pathways. Exemplary competing assimilation pathways in eukaryotic organisms include the peroxisomal dissimilation of formaldehyde by DHA synthase, and the DHA kinase pathway for converting DHA to F6P, both described herein Exemplary competing endogenous dissimilation pathways include one or more of the enzymes shown in FIG. 3.

Methylotrophic yeasts normally target selected methanol assimilation and dissimilation enzymes to peroxisomes during growth on methanol, including methanol oxidase, DHA synthase and S-(hydroxymethyl)-glutathione synthase (see review by Yurimoto et al, supra). The peroxisomal targeting mechanism comprises an interaction between the peroxisomal targeting sequence and its corresponding peroxisomal receptor (Lametschwandtner et al, J Biol Chem 273:33635-43 (1998)). Peroxisomal methanol pathway enzymes in methylotrophic organisms contain a PTS1 targeting sequence which binds to a peroxisomal receptor, such as PexSp in *Candida boidinii* (Horiguchi et al, J Bacteriol 183:6372-83 (2001)). Disruption of the PTS1 targeting sequence, the PexSp receptor and/or genes involved in peroxisomal biogenesis would enable cytosolic expression of DHA synthase, S-(hydroxymethyl)-glutathione synthase or other methanol-inducible peroxisomal enzymes. PTS1 targeting sequences of methylotrophic yeast are known in the art (Horiguchi et al, supra). Identification of peroxisomal targeting sequences of unknown enzymes can be predicted using bioinformatic methods (eg. Neuberger et al, *J Mol Biol* 328:581-92 (2003))).

Example VIII

Methanol Assimilation Via MeDH and the Ribulose Monophosphate Pathway

This example shows that co-expression of an active MeDH(MeDH) and the enzymes of the Ribulose Monophosphate (RuMP) pathway can effectively assimilate methanol derived carbon.

An experimental system was designed to test the ability of a MeDH in conjunction with the enzymes H6P synthase (HPS) and 6P3HI (PHI) of the RuMP pathway to assimilate methanol carbon into the glycolytic pathway and the TCA cycle. *Escherichia coli* strain ECh-7150 (ΔlacIA, ΔpflB, ΔptsI, ΔPpckA(pckA), ΔPglk(glk), glk::glfB, ΔhycE, ΔfrmR, ΔfrmA, ΔfrmB) was constructed to remove the glutathione-dependent formaldehyde detoxification capability encoded by the FrmA and FrmB enzyme. This strain was then transformed with plasmid pZA23S variants that either contained or lacked gene 2616A encoding a fusion of the HPS and PHI enzymes. These two transformed strains were then each transformed with pZS*13S variants that contained gene 2315L (encoding an active MeDH), or gene 2315 RIP2 (encoding a catalytically inactive MeDH), or no gene insertion. Genes 2315 and 2616 are internal nomenclatures for NAD-dependent MeDH from *Bacillus methanolicus* MGA3 and 2616 is a fused phs-hpi constructs as described in Orita et al. (2007) *Appl Microbiol Biotechnol* 76:439-45.

The six resulting strains were aerobically cultured in quadruplicate, in 5 ml minimal medium containing 1% arabinose and 0.6 M 13C-methanol as well as 100 ug/ml carbenicillin and 25 µg/ml kanamycin to maintain selection of the plasmids, and 1 mM IPTG to induce expression of the MeDH and HPS-PHI fusion enzymes. After 18 hours incubation at 37° C., the cell density was measured spectrophotometrically at 600 nM wavelength and a clarified sample of each culture medium was submitted for analysis to detect evidence of incorporation of the labeled methanol carbon into TCA-cycle derived metabolites. The label can be further enriched by deleting the gene araD that competes with ribulose-5-phosphate.

$^{13}C$ carbon derived from labeled methanol provided in the experiment was found to be significantly enriched in the metabolites pyruvate, lactate, succinate, fumarate, malate, glutamate and citrate, but only in the strain expressing both catalytically active MeDH 2315L and the HPS-PHI fusion 2616A together (data not shown). Moreover, this strain grew significantly better than the strain expressing catalytically active MeDH but lacking expression of the HPS-PHI fusion (data not shown), suggesting that the HPS-PHI enzyme is capable of reducing growth inhibitory levels of formaldehyde that cannot be detoxified by other means in this strain background. These results show that co-expression of an active MeDH and the enzymes of the RuMP pathway can effectively assimilate methanol derived carbon and channel it into TCA-cycle derived products.

Example IX

Decarboxylation of 2,4-pentadienoate to Butadiene by a Phenylacrylate Decarboxylase PadA1 (GI number: 1165293) and OhbA1 (GI number: 188496963) encoding phenylacrylate decarboxylase from *S. cerevisiae* were codon optimized by DNA 2.0 and were cloned by DNA 2.0 into the following vectors suitable for expression in *E. coli*, pD424-NH and pD441-NH respectively (DNA 2.0 Inc.,). The genes were tested for decarboxylation of 2,4-pentadienoate and the enzymatic reactions were carried out under the following conditions: 100 mM Tris-HCL pH 7.2; 10 mM KCL; 10 mM NaCL; 5 mM DTT; 20 mM 2,4-Pentadienoate; 1.5 mg/ml lysate of *E. coli* DH5a cells containing decarboxylase from *S. cerevisiae*.

The control reactions with lysate in the absence of substrate were conducted in parallel. 100 μL reactions were incubated overnight with shaking (175 rpm) at 25° C. in 1.5 ml gas-tight vials. Headspace GCMS analysis was carried out on a 7890A GC with 5975C inert MSD using a GS-GASPRO column, 30 m×0.32 mm (Agilent Technologies). Static headspace sample introduction was performed on a CombiPAL autosampler (CTC Analytics) following 2 min incubation at 45 C. The presence of 1,3-butadiene was evaluated and the enzymatic reaction product was identified by direct comparison with a standard of 1,3-butadiene (Sigma). GC/MS analysis showed the production of 1,3-butadiene from the enzymatic samples but not from the lysate alone controls.

While no butadiene formation was detected with the no substrate-control, butadiene was measured when 2,4-PD was added as a substrate (data not shown).

Example X

Demonstration of acetyl-CoA Reductase, 4-hydroxy 2-oxovalerate Aldolase, 4-hydroxy 2-oxovalerate Decarboxylase in FIG. 1

Genes expressing acetyl-CoA reductase (bphJ from *Burkholderia xenovorans* LB400, GI no: 520923), 4-hydroxy 2-oxovalerate aldolase (bphI from *Burkholderia xenovorans* LB400, GI no: 520924), 4-hydroxy 2-oxovalerate decarboxylase (kdc from *Mycobacterium tuberculosis* BcG H37Rv, GI no: 614088617), and alcohol dehydrogenase (yjgB from *Chronobacter sakazakii*, GI no: 387852894) were cloned into a plasmid suitable for expression in *E. coli*, plasmid pZA23 S (kanamycin resistance marker, p 15A origin of replication) obtained from R. Lutz (Expressys, Germany) and are based on the pZ Expression System (Lutz, R. & Bujard, H. Nucleic Acids Res. 25, 1203-1210 (1997)).

*E. coli* (MG1655 variants) cells were transformed with the expression plasmid and selected and maintained using antibiotic selection with Kanamycin. Cells were grown in LB media with kanamycin. The formation of a 4-carbon diol from glucose was detected using LCMS while the empty vector control did not make any 4-carbon diol (data not shown).

Example XI

Hydrogen Synthesis

Reducing equivalents generated by degradation and metabolism of organic substrates can be harnessed to drive the synthesis of hydrogen ($H_2$) from protons by a hydrogenase or formate-hydrogen lyase. Reducing equivalents for hydrogen evolution can come in the form of NADH, NADPH, FADH, reduced quinones, reduced ferredoxins, reduced flavodoxins and reduced thioredoxins. The reducing equivalents, particularly quinones and ferredoxins, can directly serve as electron donors for the hydrogen-forming enzymes. For example, electrons from a menaquinol-forming enzyme such as formate dehydrogenase-O can be directly transferred to a menaquinol-utilizing hydrogenase such as hydrogenase-2 of *E. coli*. Alternately, reducing equivalents can be transferred indirectly via intermediate enzymes that interconvert donor/acceptor pairs to an appropriate reduced cofactor for the hydrogen-forming enzymes. As an example of an indirect electron transfer to hydrogen, electrons from NADH can be transferred to the quinone pool by an NADH dehydrogenase, and the resulting reduced quinones can drive conversion of protons to hydrogen by hydrogenase-2. Enzymes such as NAD(P)H:ferredoxin oxidoreductase are also useful for interconverting redox from NAD(P)H to ferredoxin.

Hydrogenase

Native to *E. coli* and other enteric bacteria are multiple genes encoding up to four hydrogenases (Sawers, G., Antonie Van Leeuwenhoek 66:57-88 (1994); Sawers et al., *J Bacteriol.* 164:1324-1331 (1985); Sawers and Boxer, *Eur. J Biochem.* 156:265-275 (1986); Sawers et al., *J Bacteriol.* 168:398-404 (1986)). Three of the four hydrogenases of *E. coli* are capable of evolving hydrogen: hydrogenases 2, 3 and 4. The oxygen-sensitive hydrogenase 2 (Hyd-2), encoded by the hybOABCDEFG gene cluster, is membrane-bound and can operate both as an uptake hydrogenase and also in the hydrogen-generating direction (Lukey et al, JBC 285(6):3928-38 (2010)). Hyd-2 transfers electrons to the periplasmic ferredoxin hybA which, in turn, transfers electrons to a quinone via the hybB integral membrane protein. Hydrogenase 3 (hyd-3) is a $H_2$-evolving, energy conserving, membrane-associated hydrogenase responsible for formate-dependent $H_2$ evolution (Hakobyan et al, *Biophys Chem* 115:55-61 (2005)). Active under anaerobic conditions in the absence of an external electron acceptor, this enzyme is associated with the formate hydrogen lyase complex which converts formate to $CO_2$ and $H_2$. The function of hydrogenase 4 (hyj) is unknown but is thought to catalyze a similar reaction to hydrogenase 3 based on sequence similarity and induction under similar conditions. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol* 158:444-451 (1992); Rangarajan et al., *J. Bacteriol.* 190:1447-1458 (2008)). The formate dehydrogenase component of the *E. coli* formate-hydrogen lyase consists of formate dehydrogenase-H (Maeda et al., *Appl Microbiol Biotechnol* 77:879-890

(2007)). FHL is activated by the gene product of fhlA (Maeda et al., Appl Microbiol Biotechnol 77:879-890 (2007)). The addition of the trace elements, selenium, nickel and molybdenum, to a fermentation broth has been shown to enhance formate hydrogen lyase activity (Soini et al., Microb. Cell Fact. 7:26 (2008)). These proteins are identified below.

| Protein | GenBank ID | GI Number | Organism |
|---|---|---|---|
| Hydrogenase-2 | | | |
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |
| Hydrogenase-3 | | | |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| Hydrogenase-4 | | | |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |
| Accessory/assembly proteins | | | |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |
| Formate dehydrogenases and activator | | | |
| fdhF | NP_418503 | 16131905 | Escherichia coli |
| fhlA | NP_417211 | 16130638 | Escherichia coli |
| fdnG | NP_415991.1 | 16129433 | Escherichia coli |
| fdnH | NP_415992.1 | 16129434 | Escherichia coli |
| fdnI | NP_415993.1 | 16129435 | Escherichia coli |
| fdoG | NP_418330.1 | 16131734 | Escherichia coli |
| fdoH | NP_418329.1 | 16131733 | Escherichia coli |
| fdoI | NP_418328.1 | 16131732 | Escherichia coli |

Formate-Hydrogen Lyase

A formate hydrogen lyase enzyme also exists in the hyperthermophilic archaeon, Thermococcus litoralis (Takacs et al., BMC. Microbiol 8:88 (2008)). Additional formate hydrogen lyase systems have been found in Salmonella typhimurium, Klebsiella pneumoniae, Rhodospirillum rubrum, Methanobacterium formicicum (Vardar-Schara et al., 1:107-125 (2008)). These proteins are identified below.

| Protein | GenBank ID | GI Number | Organism |
|---|---|---|---|
| mhyC | ABW05543 | 157954626 | Thermococcus litoralis |
| mhyD | ABW05544 | 157954627 | Thermococcus litoralis |
| mhyE | ABW05545 | 157954628 | Thermococcus litoralis |
| myhF | ABW05546 | 157954629 | Thermococcus litoralis |
| myhG | ABW05547 | 157954630 | Thermococcus litoralis |
| myhH | ABW05548 | 157954631 | Thermococcus litoralis |
| fdhA | AAB94932 | 2746736 | Thermococcus litoralis |
| fdhB | AAB94931 | 157954625 | Thermococcus litoralis |

Alternately, an NADH-dependent hydrogenase can be utilized. Bidirectional NADH-dependent hydrogenases have been characterized in cyanobacteria such as Synechocystis sp. PCC 6803 and proteobacteria such as Cupriavidus necator (Schmitz et al, Biochem Biophys Acta 1554:66-74 (2002)). The C. necator (R. eutropha H16) hydrogenase is $O_2$-tolerant, cytoplasmic and directly transfers electrons from NADH to hydrogen (Schneider and Schlegel, Biochim. Biophys. Acta 452, 66-80 (1976); Burgdorf, J. Bact. 187 (9) 3122-3132 (2005)). Soluble hydrogenase enzymes are additionally present in several other organisms including Geobacter sulfurreducens (Coppi, Microbiology 151, 1239-1254 (2005)), Synechocystis str. PCC 6803 (Germer, J. Biol. Chem., 284(52), 36462-36472 (2009)), and Thiocapsa roseopersicina (Rakhely, Appl. Environ. Microbiol. 70 (2) 722-728 (2004)). The Synechocystis enzyme is capable of generating NADPH from hydrogen. Overexpression of both the Hox operon from Synechocystis str. PCC 6803 and the accessory genes encoded by the Hyp operon from Nostoc sp. PCC 7120 led to increased hydrogenase activity compared to expression of the Hox genes alone (Germer, J. Biol. Chem. 284(52), 36462-36472 (2009)).

| Protein | GenBank ID | GI Number | Organism |
|---|---|---|---|
| HoxF | NP_942727.1 | 38637753 | Ralstonia eutropha H16 |
| HoxU | NP_942728.1 | 38637754 | Ralstonia eutropha H16 |
| HoxY | NP_942729.1 | 38637755 | Ralstonia eutropha H16 |
| HoxH | NP_942730.1 | 38637756 | Ralstonia eutropha H16 |
| HoxW | NP_942731.1 | 38637757 | Ralstonia eutropha H16 |
| HoxI | NP_942732.1 | 38637758 | Ralstonia eutropha H16 |
| HoxE | NP_953767.1 | 39997816 | Geobacter sulfurreducens |
| HoxF | NP_953766.1 | 39997815 | Geobacter sulfurreducens |
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypE | NP_484743.1 | 17228195 | Nostoc sp. PCC 7120 |
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

The *M. thermoacetica* hydrogenases are suitable for a host that lacks sufficient endogenous hydrogenase activity. *M. thermoacetica* can grow with $CO_2$ as the exclusive carbon source indicating that reducing equivalents are extracted from $H_2$ to enable acetyl-CoA synthesis via the Wood-Ljungdahl pathway (Drake, H. L., *J. Bacteriol.* 150: 702-709 (1982); Drake and Daniel, *Res. Microbiol.* 155: 869-883 (2004); Kellum and Drake, *J. Bacteriol.* 160:466-469 (1984)) (see FIG. 68). *M. thermoacetica* has homologs to several hyp, hyc, and hyf genes from *E. coli*. The protein sequences encoded for by these genes are identified by the following GenBank accession numbers.

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

Ferredoxin:NADP+ Oxidoreductase

For enzymes that use reducing equivalents in the form of NADH or NADPH, these reduced carriers can be generated by transferring electrons from reduced ferredoxin. Two enzymes catalyze the reversible transfer of electrons from reduced ferredoxins to NAD(P)$^+$, ferredoxin:NAD$^+$ oxidoreductase (EC 1.18.1.3) and ferredoxin:NADP oxidoreductase (FNR, EC 1.18.1.2). Ferredoxin:NADP$^+$ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J Biochem.* 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St Maurice et al., *J. Bacteriol.* 189:4764-4773 (2007)). An analogous enzyme is found in *Campylobacter jejuni* (St Maurice et al., *J. Bacteriol.* 189:4764-4773 (2007)). A ferredoxin:NADP$^+$ oxidoreductase enzyme is encoded in the *E. coli* genome by fpr (Bianchi et al. *J Bacteriol.* 1993 March; 175(6):1590-5). Ferredoxin:NAD$^+$ oxidoreductase utilizes reduced ferredoxin to generate NADH from NAD$^+$. In several organisms, including *E. coli*, this enzyme is a component of multifunctional dioxygenase enzyme complexes. The ferredoxin:NAD$^+$ oxidoreductase of *E. coli*, encoded by hcaD, is a component of the 3-phenylproppionate dioxygenase system involved in involved in aromatic acid utilization (Diaz et al. *J. Bacteriol.* 1998 June; 180(11):2915-23). NADH:ferredoxin reductase activity was detected in cell extracts of *Hydrogenobacter thermophilus* strain TK-6, although a gene with this activity has not yet been indicated (Yoon et al. Arch Microbiol. 1997 May; 167(5):275-9). NADP oxidoreductase of *C. kluyveri*, encoded by nfnAB, catalyzes the concomitant reduction of ferredoxin and NAD+ with two equivalents of NADPH (Wang et al, *J. Bacteriol* 192: 5115-5123 (2010)). Finally, the energy-conserving membrane-associated Rnf-type proteins (Seedorf et al., Proc. Natl. Acad. Sci. U.S.A. 105:2128-2133 (2008); Herrmann et al., *J. Bacteriol.* 190:784-791 (2008)) provide a means to generate NADH or NADPH from reduced ferredoxin. Additional ferredoxin:NAD(P)+ oxidoreductases have been annotated in *Clostridium carboxydivorans* P7 and *Clostridium ljungdahli*.

While the N-terminal domain of the protein shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, *J Biochem.* 1999

| Protein | GenBank ID | GI Number | Organism |
|---|---|---|---|
| HP1164 | NP_207955.1 | 15645778 | *Helicobacter pylori* |
| RPA3954 | CAE29395.1 | 39650872 | *Rhodopseudomonas palustris* |
| fpr | BAH29712.1 | 225320633 | *Hydrogenobacter thermophilus* |
| yumC | NP_391091.2 | 255767736 | *Bacillus subtilis* |
| CJE0663 | AAW35824.1 | 57167045 | *Campylobacter jejuni* |
| fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| NfnA | YP_001393861.1 | 153953096 | *Clostridium kluyveri* |
| NfnB | YP_001393862.1 | 153953097 | *Clostridium kluyveri* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |
| CLJU_c11410 (RnfB) | ADK14209.1 | 300434442 | *Clostridium ljungdahli* |
| CLJU_c11400 (RnfA) | ADK14208.1 | 300434441 | *Clostridium ljungdahli* |
| CLJU_c11390 (RnfE) | ADK14207.1 | 300434440 | *Clostridium ljungdahli* |
| CLJU_c11380 (RnfG) | ADK14206.1 | 300434439 | *Clostridium ljungdahli* |
| CLJU_c11370 (RnfD) | ADK14205.1 | 300434438 | *Clostridium ljungdahli* |
| CLJU_c11360 (RnfC) | ADK14204.1 | 300434437 | *Clostridium ljungdahli* |

Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S] [4Fe-4S] type ferredoxin (Park et al. *J Biochem Mol Biol.* 2006 Jan. 31; 39(1):46-54).

November; 126(5):917-26). Additional ferredoxin proteins have been characterized in *Helicobacter pylori* (Mukhopadhyay et al. *J. Bacteriol.* 2003 May; 185(9):2927-35) and *Campylobacter jejuni* (van Vliet et al. *FEMS Microbiol Lett.* 2001 Mar. 15; 196(2):189-93). A 2Fe-2S ferredoxin from *Clostridium pasteurianum* has been cloned and expressed in *E. coli* (Fujinaga and Meyer, Biochemical and Biophysical Research Communications, 192 (3): (1993)). Acetogenic bacteria such as *Moorella thermoacetica*, *Clostridium carboxidivorans* P7, *Clostridium ljungdahli* and *Rhodospirillum rubrum* are predicted to encode several ferredoxins, listed in the table below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| cooF | AAG29808.1 | 11095245 | *Carboxydothermus hydrogenoformans* |

-continued

| Protein | GenBank ID | GI Number | Organism |
|---|---|---|---|
| fdxN | CAA35699.1 | 46143 | *Rhodobacter capsulatus* |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |
| cooF | AAC45122.1 | 1498747 | *Rhodospirillum rubrum* |
| fdxN | AAA26460.1 | 152605 | *Rhodospirillum rubrum* |
| Alvin_2884 | ADC63789.1 | 288897953 | *Allochromatium vinosum* DSM 180 |
| fdx | YP_002801146.1 | 226946073 | *Azotobacter vinelandii* DJ |
| CKL_3790 | YP_001397146.1 | 153956381 | *Clostridium kluyveri* DSM 555 |
| fer1 | NP_949965.1 | 39937689 | *Rhodopseudomonas palustris* CGA009 |
| fdx | CAA12251.1 | 3724172 | *Thauera aromatica* |
| CHY_2405 | YP_361202.1 | 78044690 | *Carboxydothermus hydrogenoformans* |
| fer | YP_359966.1 | 78045103 | *Carboxydothermus hydrogenoformans* |
| fer | AAC83945.1 | 1146198 | *Bacillus subtilis* |
| fdx1 | NP_249053.1 | 15595559 | *Pseudomonas aeruginosa* PA01 |
| yfhL | AP_003148.1 | 89109368 | *Escherichia coli* K-12 |
| CLJU_c00930 | ADK13195.1 | 300433428 | *Clostridium ljungdahli* |
| CLJU_c00010 | ADK13115.1 | 300433348 | *Clostridium ljungdahli* |
| CLJU_c01820 | ADK13272.1 | 300433505 | *Clostridium ljungdahli* |
| CLJU_c17980 | ADK14861.1 | 300435094 | *Clostridium ljungdahli* |
| CLJU_c17970 | ADK14860.1 | 300435093 | *Clostridium ljungdahli* |
| CLJU_c22510 | ADK15311.1 | 300435544 | *Clostridium ljungdahli* |
| CLJU_c26680 | ADK15726.1 | 300435959 | *Clostridium ljungdahli* |
| CLJU_c29400 | ADK15988.1 | 300436221 | *Clostridium ljungdahli* |

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, said microbial organism having a butadiene pathway and comprising at least four exogenous nucleic acids encoding butadiene pathway enzymes expressed in a sufficient amount to produce butadiene, wherein said butadiene pathway comprises a pathway selected from:
   (1) 1A, 1B, 1C, 1G, 1I, 1L, 1M, and 1F;
   (2) 1A, 1B, 1C, 1G, 1I, 1L, 1N, and 1F;
   (3) 1A, 1B, 1C, 1H, 1I, 1L, 1M, and 1F;
   (4) 1A, 1B, 1C, 1H, 1I, 1L, 1N, and 1F;
   (5) 1A, 1B, 1C, 1D, 1J, 1L, 1M, and 1F;
   (6) 1A, 1B, 1C, 1D, 1J, 1L, 1N, and 1F;
   (7) 1A, 1B, 1C, 1D, 1K, 1L, 1M, and 1F; and
   (8) 1A, 1B, 1C, 1D, 1K, 1L, 1N, and 1F,
   wherein 1A is an acetaldehyde dehydrogenase, wherein 1B is a 4-hydroxy 2-oxovalerate aldolase, wherein 1C is a 4-hydroxy 2-oxovalerate dehydratase, wherein 1D is a 2-oxopentenoate reductase, wherein 1F is a 2,4-pentadienoate decarboxylase, wherein 1G is a 2-oxopentenoate ligase, wherein 1H is a 2-oxopentenoate: acetyl CoA transferase, wherein 1I is a 2-oxopentenoyl-CoA reductase, wherein 1J is a 2-hydroxypentenoate ligase, wherein 1K is a 2-hydroxypentenoate: acetyl-CoA CoA transferase, wherein 1L is a 2-hydroxypentenoyl-CoA dehydratase, wherein 1M is a 2,4-Pentadienoyl-CoA hydrolase, and wherein 1N is a 2,4-Pentadienoyl-CoA: acetyl CoA transferase.

2. The non-naturally occurring microbial organism of claim 1, wherein said microbial organism comprises four, five, six, seven, or eight, exogenous nucleic acids each encoding a butadiene pathway enzyme, or wherein said microbial organism comprises exogenous nucleic acids encoding each of the enzymes of at least one of the pathways selected from (1) to (8).

3. The non-naturally occurring microbial organism of claim 1 further comprising an acetyl-CoA pathway, wherein said acetyl-CoA pathway comprises a pathway selected from:
   (1) 3T and 3V;
   (2) 3T, 3W, and 3X;
   (3) 3U and 3V; and
   (4) 3U, 3W, and 3X,
   wherein 3T is a fructose-6-phosphate phosphoketolase, wherein 3U is a xylulose-5-phosphate phosphoketolase, wherein 3V is a phosphotransacetylase, wherein 3W is an acetate kinase, wherein 3X is an acetyl-CoA transferase, an acetyl-CoA synthetase, or an acetyl-CoA ligase.

4. The non-naturally occurring microbial organism of claim 1, wherein said microbial organism further comprises a formaldehyde fixation pathway, wherein said formaldehyde fixation pathway comprises:
   (1) 3D and 3Z;
   (2) 3D; or
   (3) 3B and 3C,
   wherein 3B is a 3-hexulose-6-phosphate synthase, wherein 3C is a 6-phospho-3-hexuloisomerase, wherein 3D is a dihydroxyacetone synthase, wherein 3Z is a fructose-6-phosphate aldolase.

5. The non-naturally occurring microbial organism of claim 1, wherein said microbial organism further comprises a methanol metabolic pathway, wherein said methanol metabolic pathway comprises a pathway selected from:
   (1) 4A and 4B;
   (2) 4A, 4B and 4C;
   (3) 4J;
   (4) 4J, 4K and 4C;
   (5) 4J, 4M, and 4N;
   (6) 4J and 4L;
   (7) 4J, 4L, and 4G;
   (8) 4J, 4L, and 4I;

(9) 4A, 4B, 4C, 4D, and 4E;
(10) 4A, 4B, 4C, 4D, and 4F;
(11) 4J, 4K, 4C, 4D, and 4E;
(12) 4J, 4K, 4C, 4D, and 4F;
(13) 4J, 4M, 4N, and 4O;
(14) 4A, 4B, 4C, 4D, 4E, and 4G;
(15) 4A, 4B, 4C, 4D, 4F, and 4G;
(16) 4J, 4K, 4C, 4D, 4E, and 4G;
(17) 4J, 4K, 4C, 4D, 4F, and 4G;
(18) 4J, 4M, 4N, 4O, and 4G;
(19) 4A, 4B, 4C, 4D, 4E, and 4I;
(20) 4A, 4B, 4C, 4D, 4F, and 4I;
(21) 4J, 4K, 4C, 4D, 4E, and 4I;
(22) 4J, 4K, 4C, 4D, 4F, and 4I; and
(23) 4J, 4M, 4N, 4O, and 4I,
wherein 4A is a methanol methyltransferase, wherein 4B is a methylenetetrahydrofolate reductase, wherein 4C is a methylenetetrahydrofolate dehydrogenase, wherein 4D is a methenyltetrahydrofolate cyclohydrolase, wherein 4E is a formyltetrahydrofolate deformylase, wherein 4F is a formyltetrahydrofolate synthetase, wherein 4G is a formate hydrogen lyase, wherein 4I is a formate dehydrogenase, wherein 4J is a methanol dehydrogenase, wherein 4K is a formaldehyde activating enzyme or spontaneous, wherein 4L is a formaldehyde dehydrogenase, wherein 4M is a S-(hydroxymethyl)glutathione synthase or spontaneous, wherein 4N is a glutathione-dependent formaldehyde dehydrogenase, wherein 4O is a S-formylglutathione hydrolase.

6. The non-naturally occurring microbial organism of claim 1, wherein said microbial organism further comprises a formate assimilation pathway, wherein said formate assimilation pathway comprises a pathway selected from:
(1) 3E;
(2) 3F, and 3G;
(3) 3H, 3I, 3J, and 3K;
(4) 3H, 3I, 3J, 3L, 3M, and 3N;
(5) 3E, 3H, 3I, 3J, 3L, 3M, and 3N;
(6) 3F, 3G, 3H, 3I, 3J, 3L, 3M, and 3N;
(7) 3K, 3H, 3I, 3J, 3L, 3M, and 3N; and
(8) 3H, 3I, 3J, 3O, and 3P,
wherein 3E is a formate reductase, 3F is a formate ligase, a formate transferase, or a formate synthetase, wherein 3G is a formyl-CoA reductase, wherein 3H is a formyltetrahydrofolate synthetase, wherein 3I is a methenyltetrahydrofolate cyclohydrolase, wherein 3J is a methylenetetrahydrofolate dehydrogenase, wherein 3K is a formaldehyde-forming enzyme or spontaneous, wherein 3L is a glycine cleavage system, wherein 3M is a serine hydroxymethyltransferase, wherein 3N is a serine deaminase, wherein 3O is a methylenetetrahydrofolate reductase, wherein 3P is an acetyl-CoA synthase.

7. The non-naturally occurring microbial organism of claim 6, wherein said formate assimilation pathway further comprises:
(1) 3Q;
(2) 3R and 3S;
(3) 3Y and 3Q; or
(4) 3Y, 3R, and 3S,
wherein 3Q is a pyruvate formate lyase, wherein 3R is a pyruvate dehydrogenase, a pyruvate ferredoxin oxidoreductase, or a pyruvate:NADP+oxidoreductase, wherein 3S is a formate dehydrogenase, wherein 3Y is a glyceraldehyde-3-phosphate dehydrogenase or an enzyme of lower glycolysis.

8. The non-naturally occurring microbial organism of claim 1, wherein said organism further comprises:
(a) a methanol oxidation pathway, wherein said methanol oxidation pathway comprises 3A, wherein 3A a methanol dehydrogenase;
(b) a carbon monoxide dehydrogenase;
(c) a hydrogenase;
(d) attenuation of one or more endogenous enzymes selected from DHA kinase, methanol oxidase, PQQ-dependent methanol dehydrogenase, DHA synthase or any combination thereof;
(e) attenuation of one or more endogenous enzymes of a competing formaldehyde assimilation or dissimilation pathway;
(f) a gene disruption of one or more endogenous nucleic acids encoding enzymes selected from DHA kinase, methanol oxidase, PQQ-dependent methanol dehydrogenase, DHA synthase or any combination thereof;
(g) a gene disruption of one or more endogenous nucleic acids encoding enzymes of a competing formaldehyde assimilation or dissimilation pathway; or
(h) a hydrogen synthesis pathway catalyzing the synthesis of hydrogen from a reducing equivalent, said hydrogen synthesis pathway comprising an enzyme selected from the group consisting of a hydrogenase, a formate-hydrogene lyase and ferredoxin: NADP+ oxidoreductase.

9. The non-naturally occurring microbial organism of claim 1, wherein said at least one exogenous nucleic acid is a heterologous nucleic acid.

10. The non-naturally occurring microbial organism of claim 1, wherein said non-naturally occurring microbial organism is in a substantially anaerobic culture medium.

11. The non-naturally occurring microbial organism of claim 1, wherein said microbial organism is a species of bacteria, yeast, or fungus.

12. The non-naturally occurring microbial organism of claim 1, wherein said butadiene pathway comprises 1A, 1B, 1C, 1G, 1I, 1L, 1M, and 1F.

13. The non-naturally occurring microbial organism of claim 1, wherein said butadiene pathway comprises 1A, 1B, 1C, 1G, 1I, 1L, 1N, and 1F.

14. The non-naturally occurring microbial organism of claim 1, wherein said butadiene pathway comprises 1A, 1B, 1C, 1H, 1I, 1L, 1M, and 1F.

15. The non-naturally occurring microbial organism of claim 1, wherein said butadiene pathway comprises 1A, 1B, 1C, 1H, 1I, 1L, 1N, and 1F.

16. The non-naturally occurring microbial organism of claim 1, wherein said butadiene pathway comprises 1A, 1B, 1C, 1D, 1J, 1L, 1M, and 1F.

17. The non-naturally occurring microbial organism of claim 1, wherein said butadiene pathway comprises 1A, 1B, 1C, 1D, 1J, 1L, 1N, and 1F.

18. The non-naturally occurring microbial organism of claim 1, wherein said butadiene pathway comprises 1A, 1B, 1C, 1D, 1K, 1L, 1M, and 1F.

19. The non-naturally occurring microbial organism of claim 1, wherein said butadiene pathway comprises 1A, 1B, 1C, 1D, 1K, 1L, 1N, and 1F.

20. A culture medium comprising bioderived butadiene, wherein said culture medium is separated from a non-naturally occurring microbial organism having the butadiene pathway in claim 1.

21. A method for producing (a) butadiene or (b) butadiene and hydrogen, comprising culturing the non-naturally occurring microbial organism of claim 1 under conditions and for a sufficient period of time to produce butadiene.

22. The method of claim 21, wherein said method further comprises separating the butadiene or the butadiene and hydrogen from other components in the culture.

23. The method of claim 22, wherein the separating comprises extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

* * * * *